(12) United States Patent
Koblish et al.

(10) Patent No.: US 6,917,834 B2
(45) Date of Patent: Jul. 12, 2005

(54) DEVICES AND METHODS FOR CREATING LESIONS IN ENDOCARDIAL AND SURROUNDING TISSUE TO ISOLATE FOCAL ARRHYTHMIA SUBSTRATES

(75) Inventors: Josef V. Koblish, Sunnyvale, CA (US); Russell B. Thompson, Los Altos, CA (US); James G. Whayne, Saratoga, CA (US); Yi Yang, San Francisco, CA (US); David K. Swanson, Mountain View, CA (US); Sidney D. Fleischman, Menlo Park, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 181 days.

(21) Appl. No.: 09/975,393

(22) Filed: Oct. 10, 2001

(65) Prior Publication Data

US 2002/0087208 A1 Jul. 4, 2002

Related U.S. Application Data

(63) Continuation of application No. 08/984,414, filed on Dec. 3, 1997, now abandoned.

(51) Int. Cl.$^7$ ................................................ A61N 1/00
(52) U.S. Cl. ..................... 607/122; 607/105; 607/106; 607/113; 606/41
(58) Field of Search ............................... 606/41; 607/99, 607/105, 106, 113, 122

(56) References Cited

U.S. PATENT DOCUMENTS

| | | |
|---|---|---|
| 1,207,479 A | 12/1916 | Bisgaard |
| 5,041,085 A | 8/1991 | Osborne et al. |
| 5,098,412 A | 3/1992 | Shiu |
| 5,263,493 A | 11/1993 | Avitall |
| 5,273,535 A | 12/1993 | Edwards et al. |
| 5,306,245 A | 4/1994 | Heaven |
| 5,370,675 A | 12/1994 | Edwards et al. |
| 5,439,006 A | 8/1995 | Brennen et al. |
| 5,482,037 A | 1/1996 | Borghi |
| 5,487,385 A | 1/1996 | Avitall |
| 5,637,090 A | 6/1997 | McGee et al. |
| 5,672,174 A | 9/1997 | Gough et al. |
| 5,702,438 A | 12/1997 | Avitall |
| 5,709,224 A | 1/1998 | Behl et al. |
| 5,730,127 A | 3/1998 | Avitall |
| 5,738,683 A | 4/1998 | Osypka |
| 5,827,273 A | 10/1998 | Edwards |
| 5,853,411 A * | 12/1998 | Whayne et al. ............... 606/41 |
| 5,908,445 A * | 6/1999 | Whayne et al. ............ 607/122 |
| 5,938,660 A | 8/1999 | Swartz et al. |
| 5,967,984 A | 10/1999 | Chu et al. |
| 6,012,457 A * | 1/2000 | Lesh .......................... 128/898 |
| 6,024,740 A | 2/2000 | Lesh et al. |
| 6,036,687 A | 3/2000 | Laufer et al. |
| 6,117,101 A | 9/2000 | Diederich et al. |
| 6,164,283 A | 12/2000 | Lesh |

* cited by examiner

Primary Examiner—Rosiland Rollins
(74) Attorney, Agent, or Firm—Bingham McCutchen LLP

(57) ABSTRACT

Devices and methods are provided for creating lesions in endocardial tissues surrounding a vessel opening to thereby isolate focal arrhythmia substrates, including an invasive catheter assembly comprising an elongate body having a longitudinal axis and first and second lumens, a first catheter having a distally mounted expandable anchor body disposed in the first lumen, and a second catheter having a distally mounted electrode disposed in the second lumen, the elongate body having a first distal opening accessing the first lumen through which the first catheter may be extended axially relative to the longitudinal axis of the elongate body and a second distal opening accessing the second lumen through which the second catheter may be extended at an angle relative to the longitudinal axis of the elongate body. The disclosed invention also includes an elongate catheter having an expandable electrode body mounted on one end, wherein the electrode body is configured to form an enlarged circumferential region when expanded, the enlarged circumferential region defining a distal facing surface of the electrode body, the distal facing surface including an area configured to emit radio frequency (RF) energy.

44 Claims, 96 Drawing Sheets

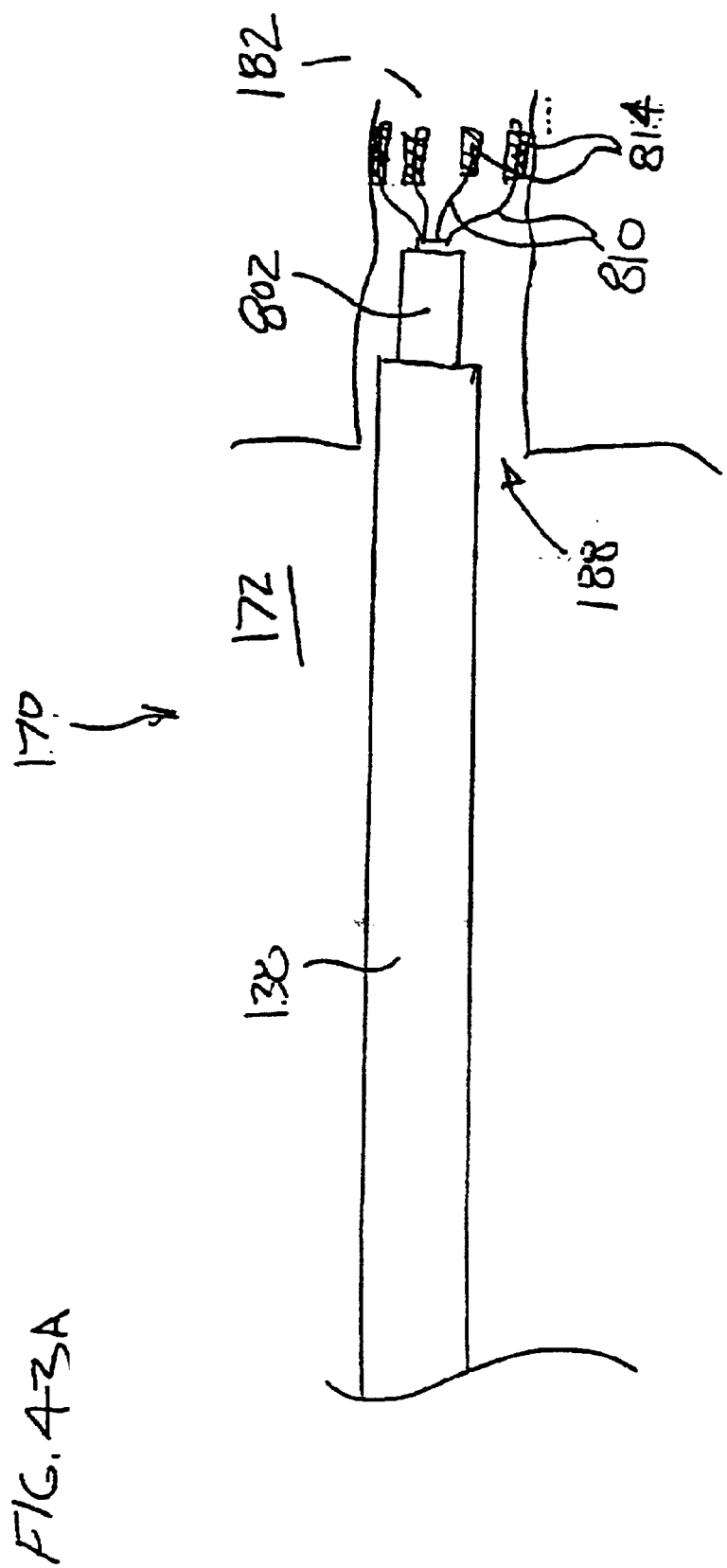

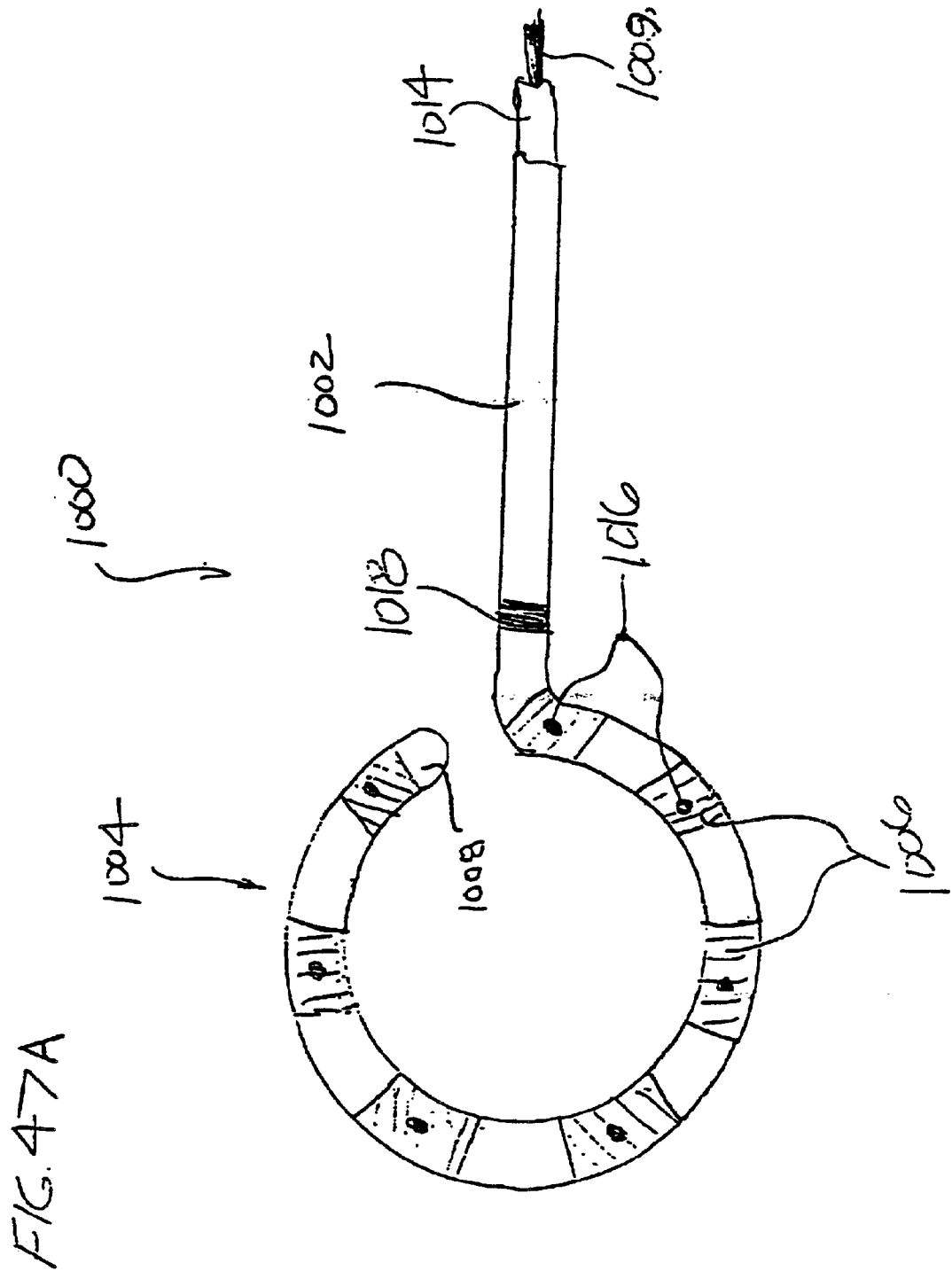

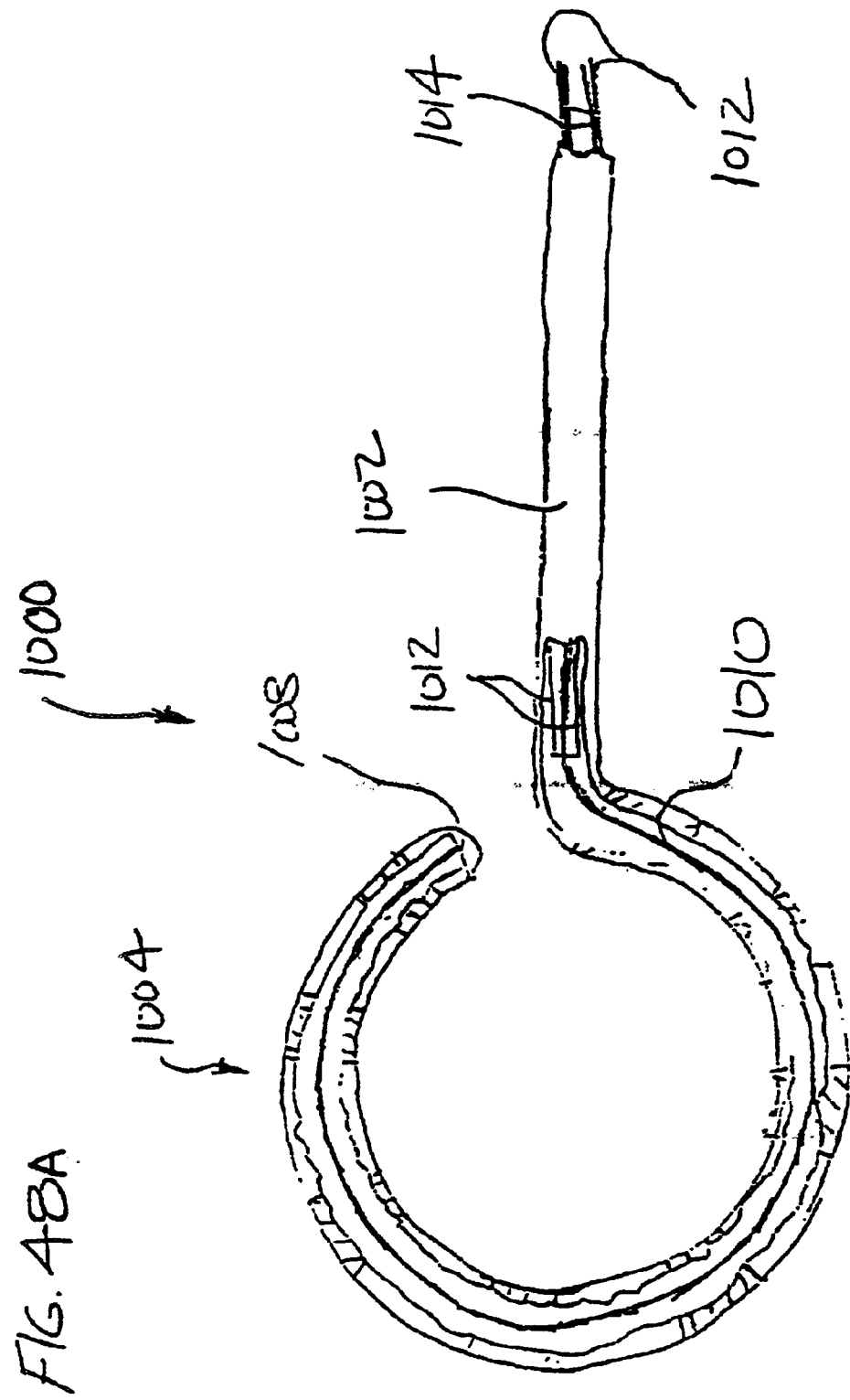

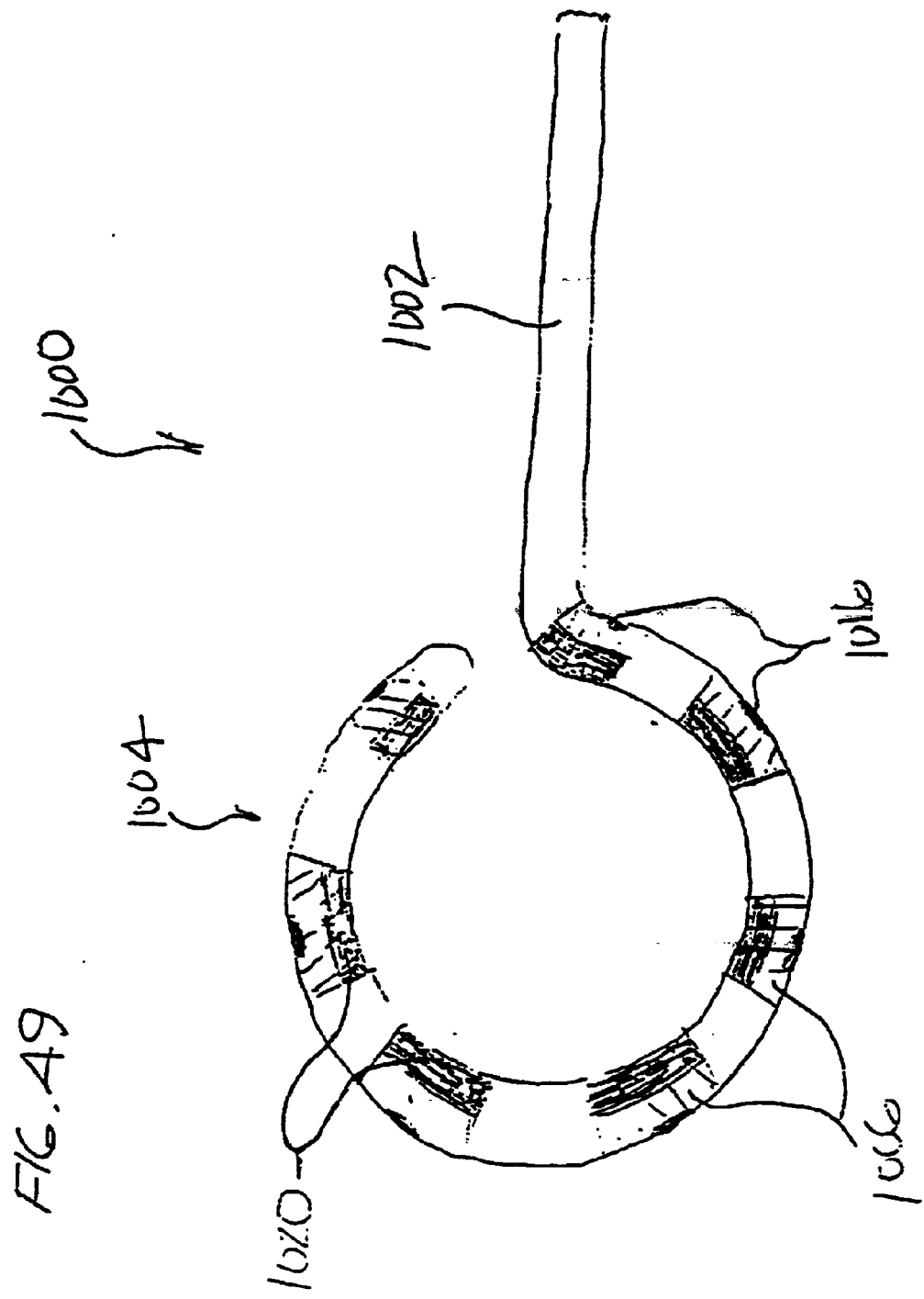

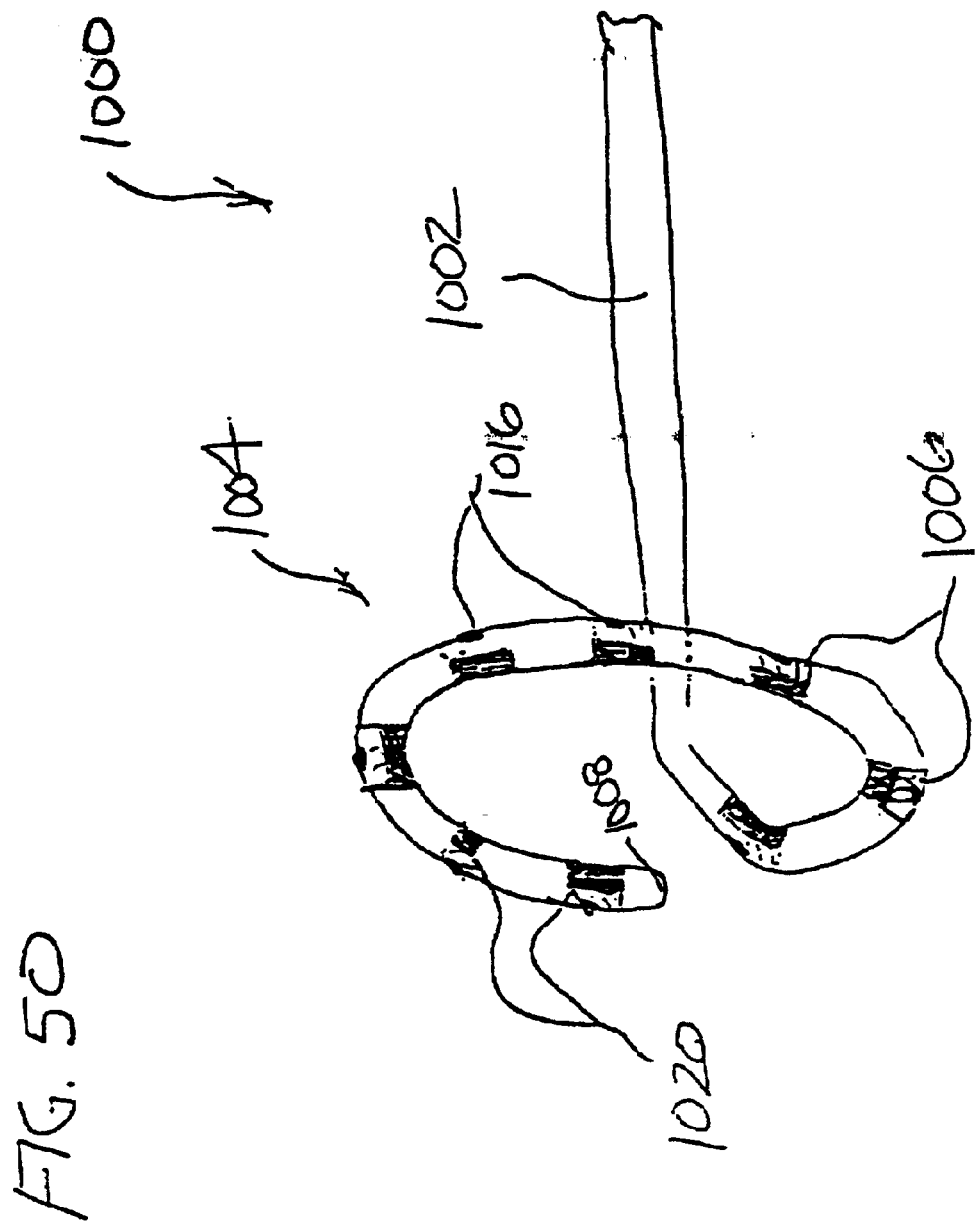

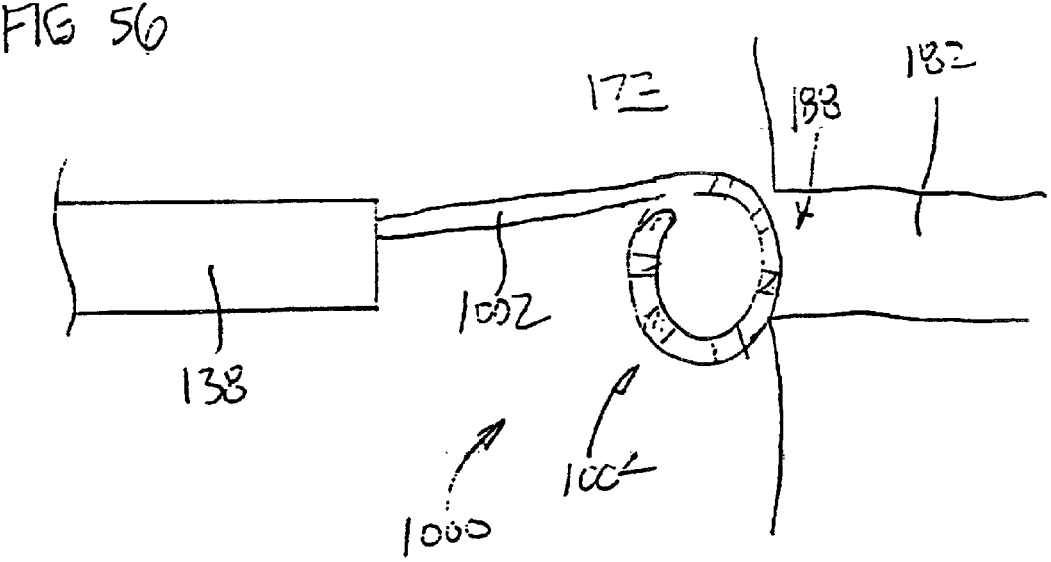
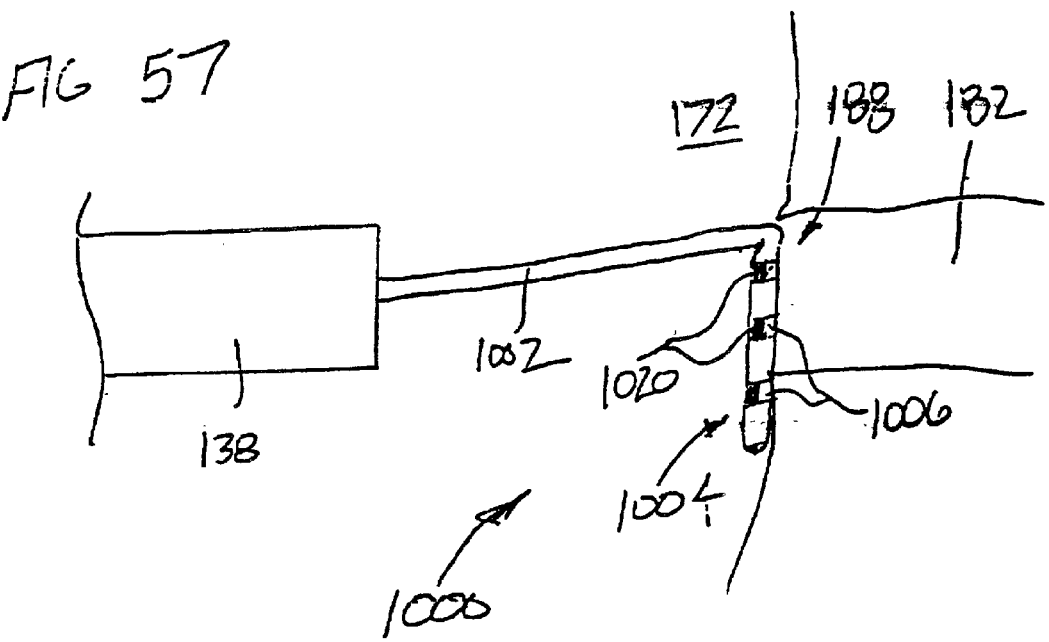

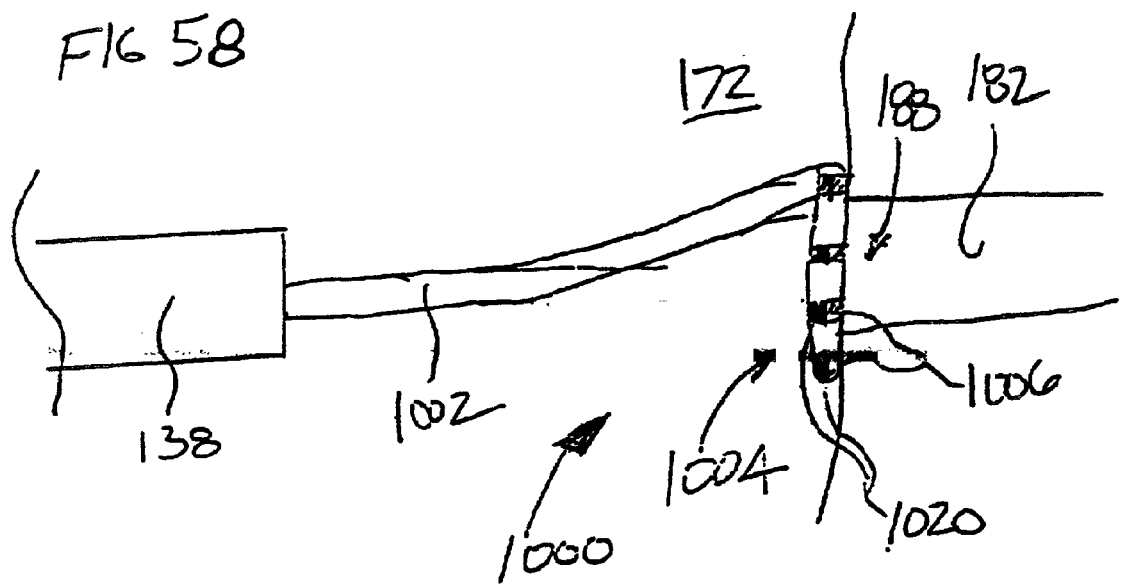

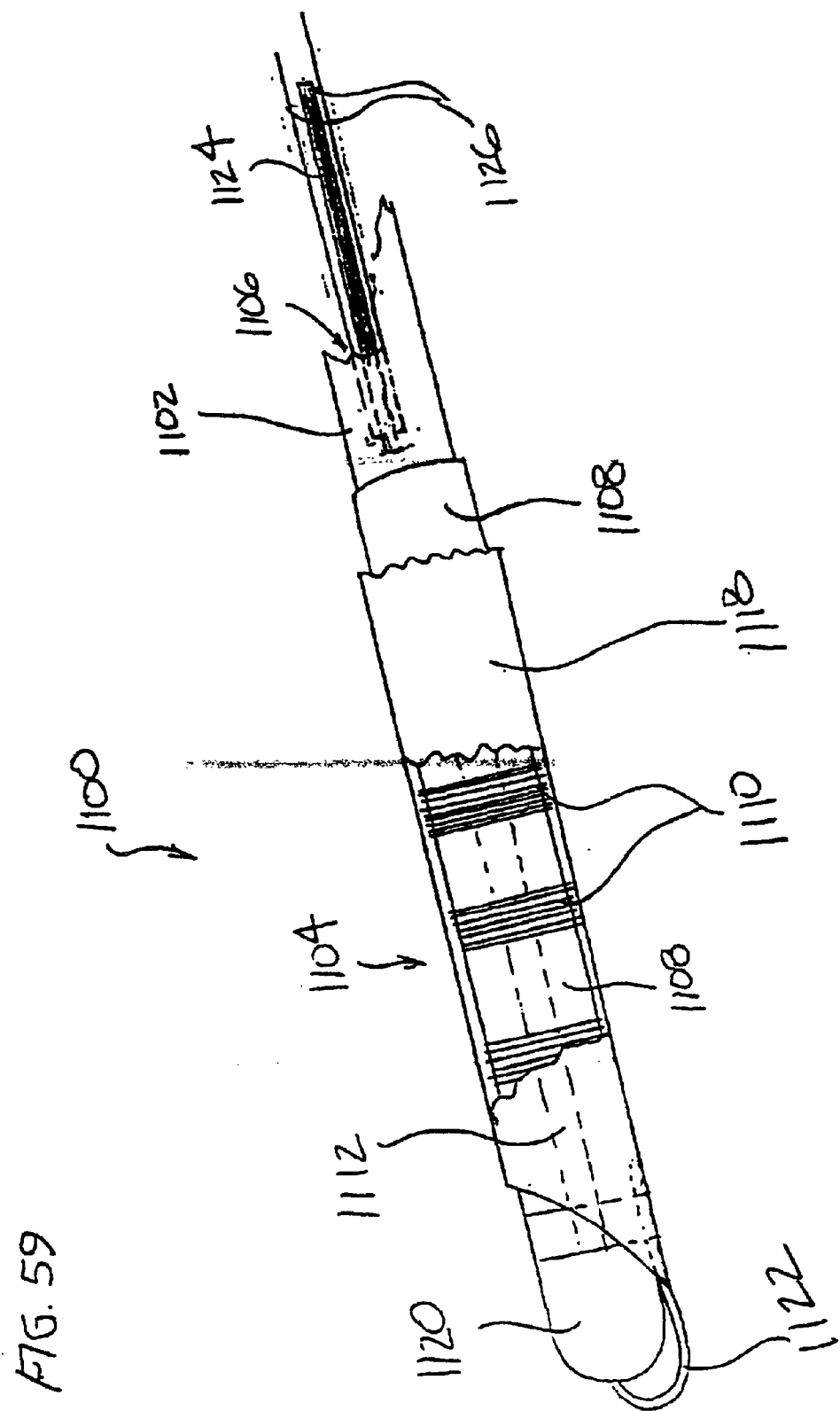

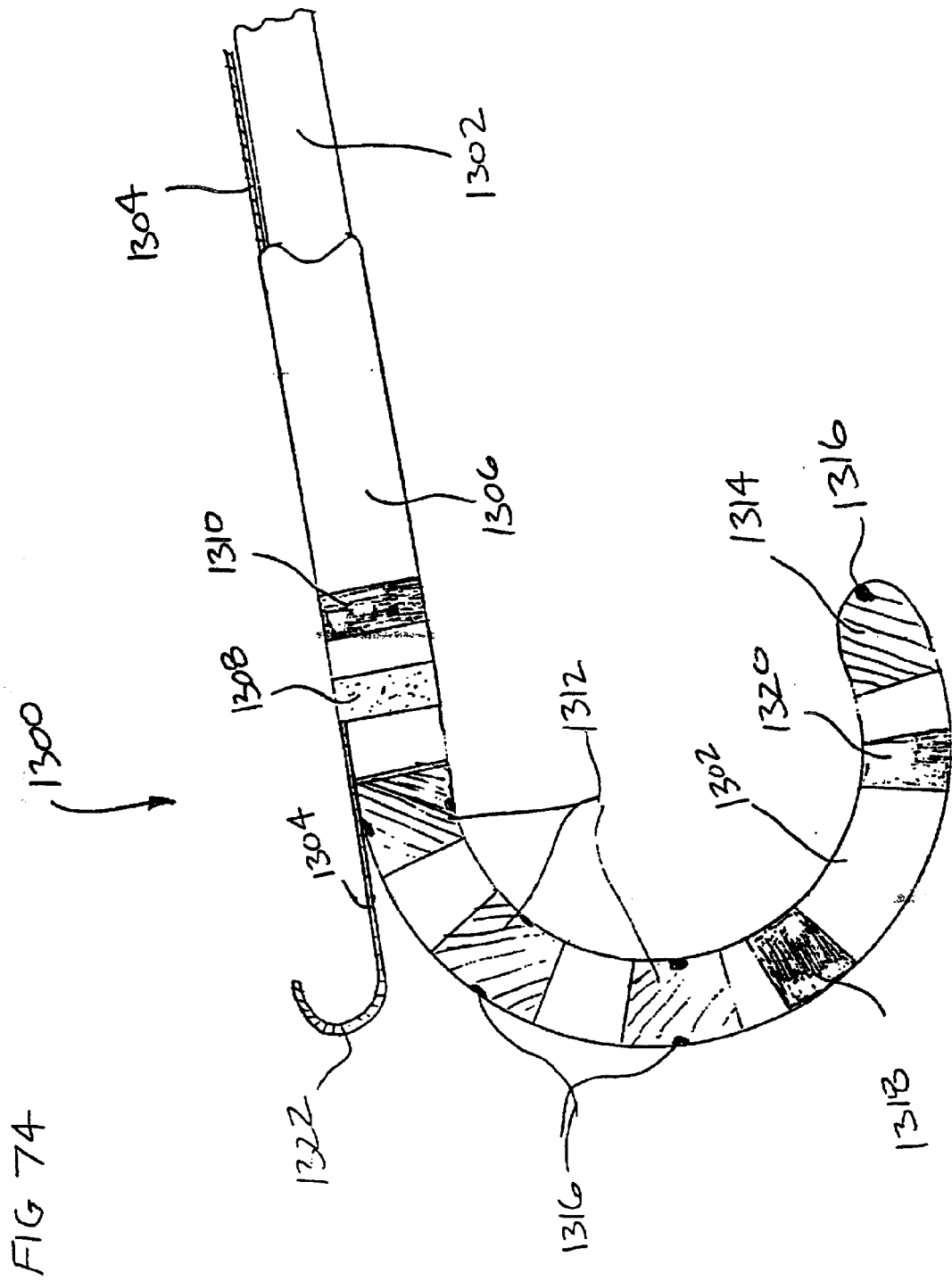

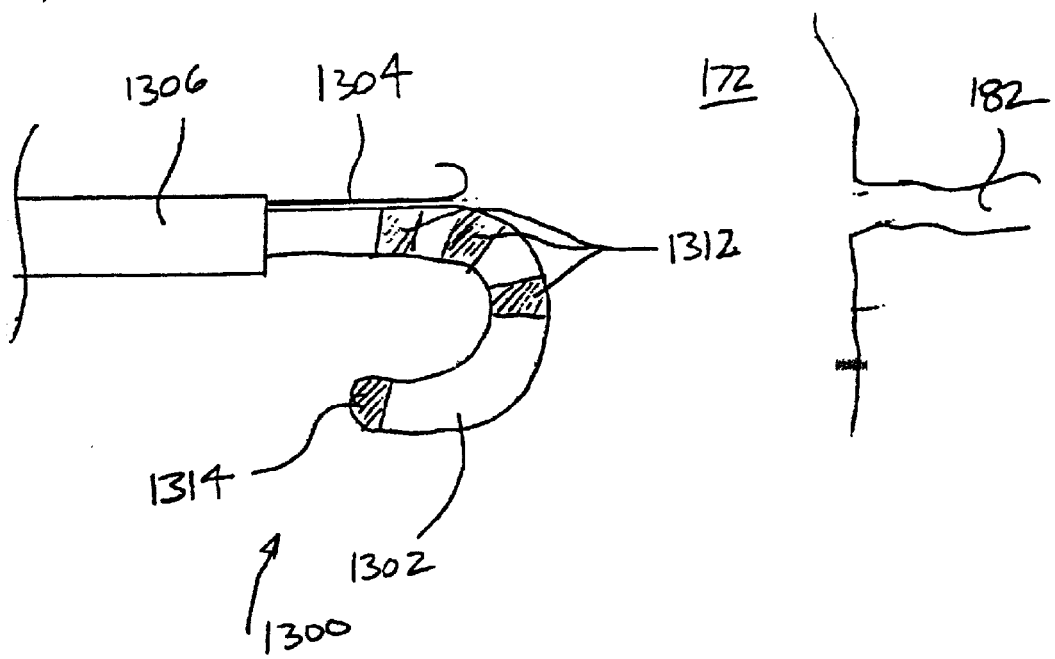
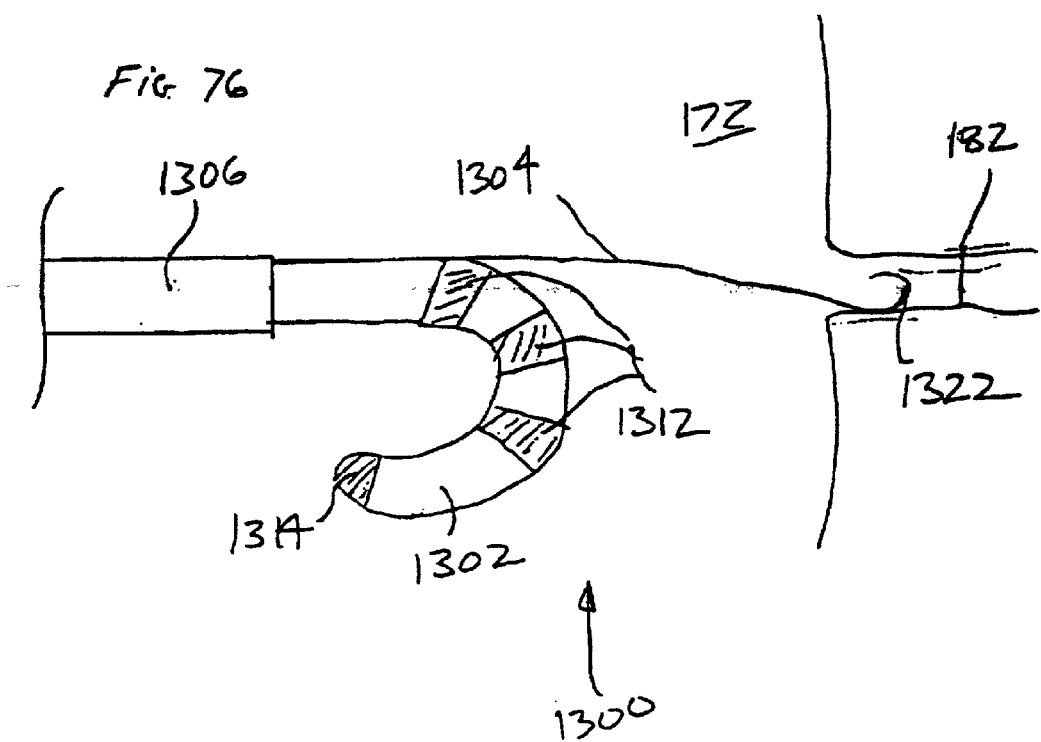

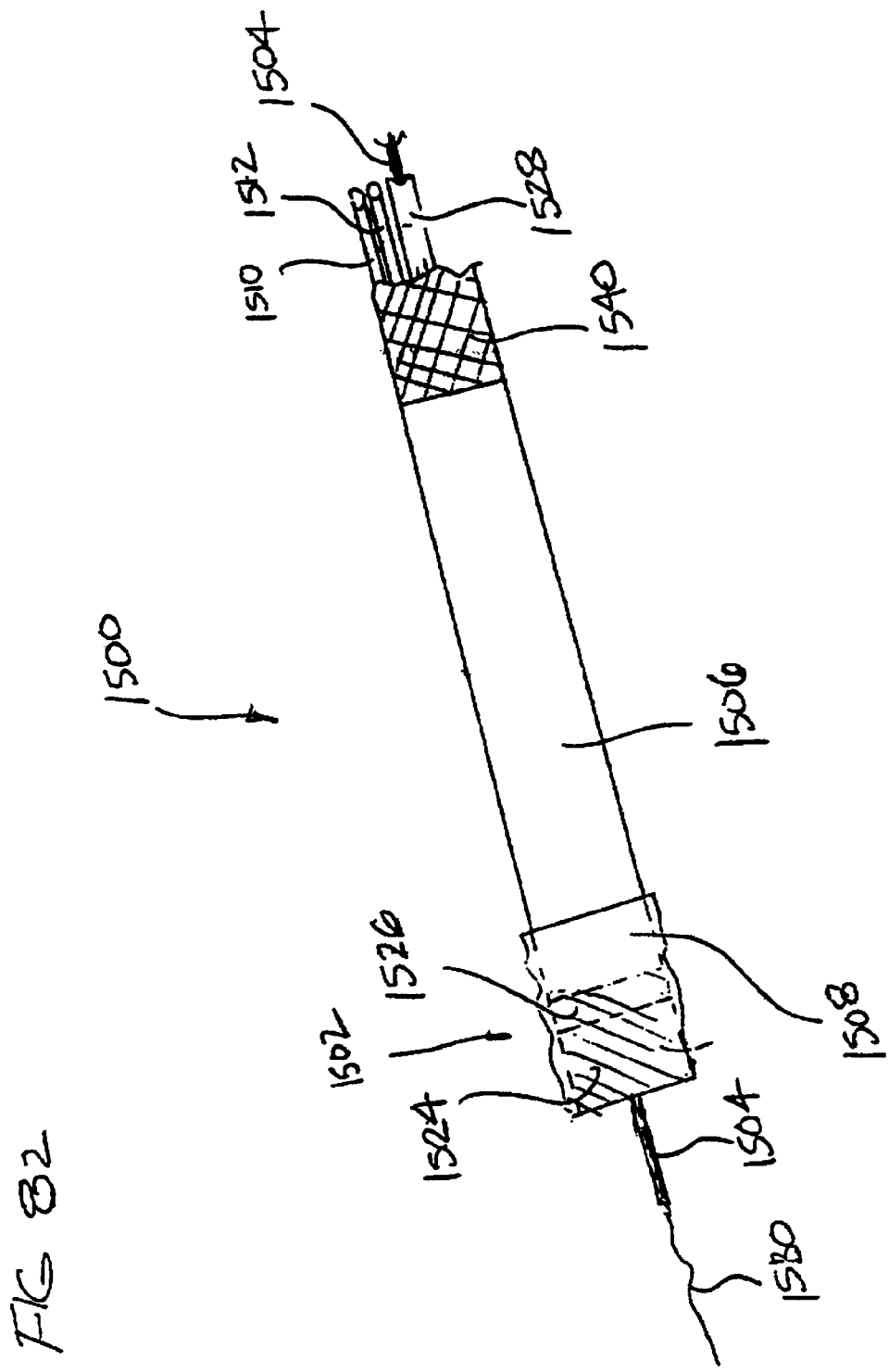

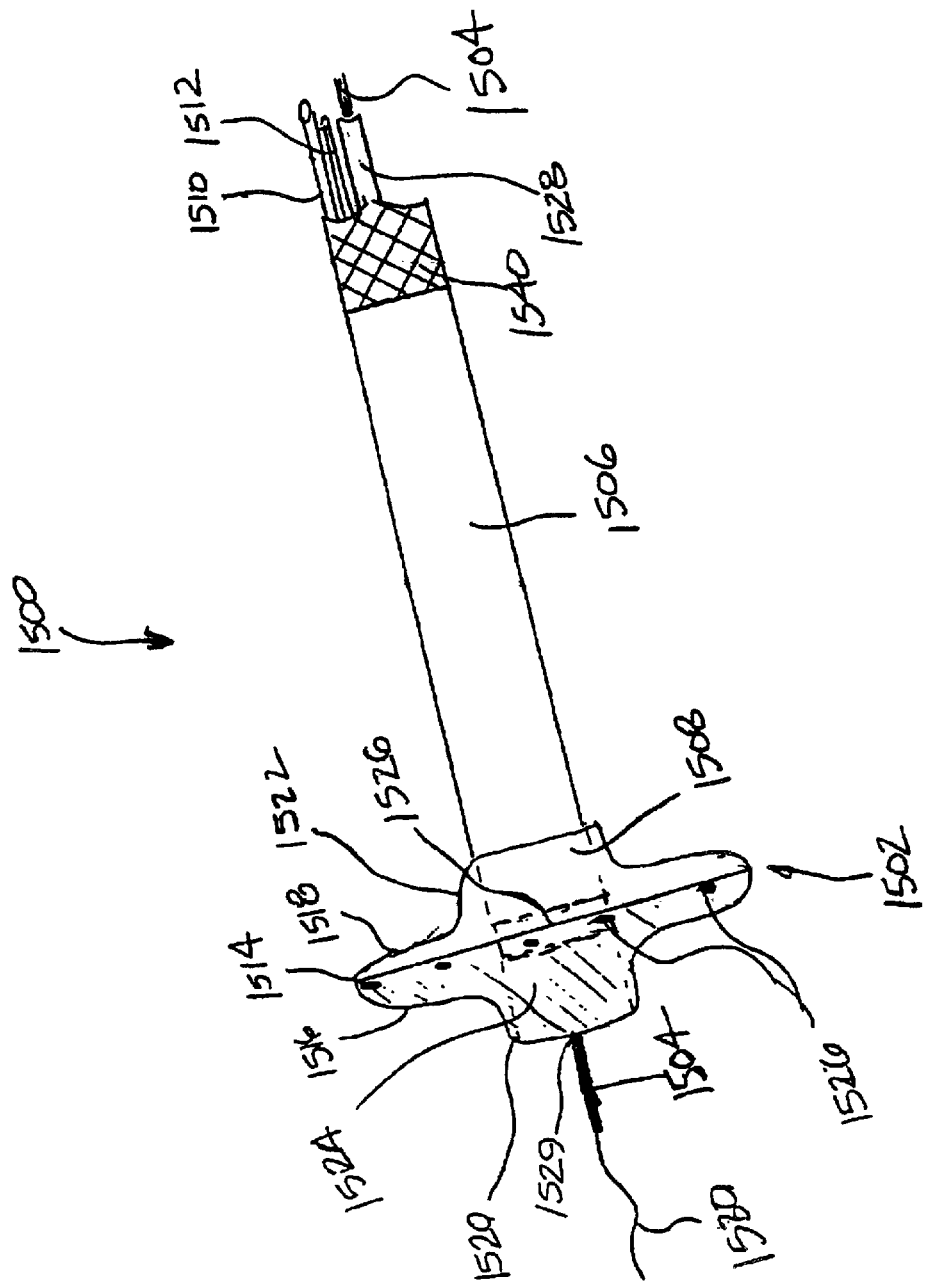

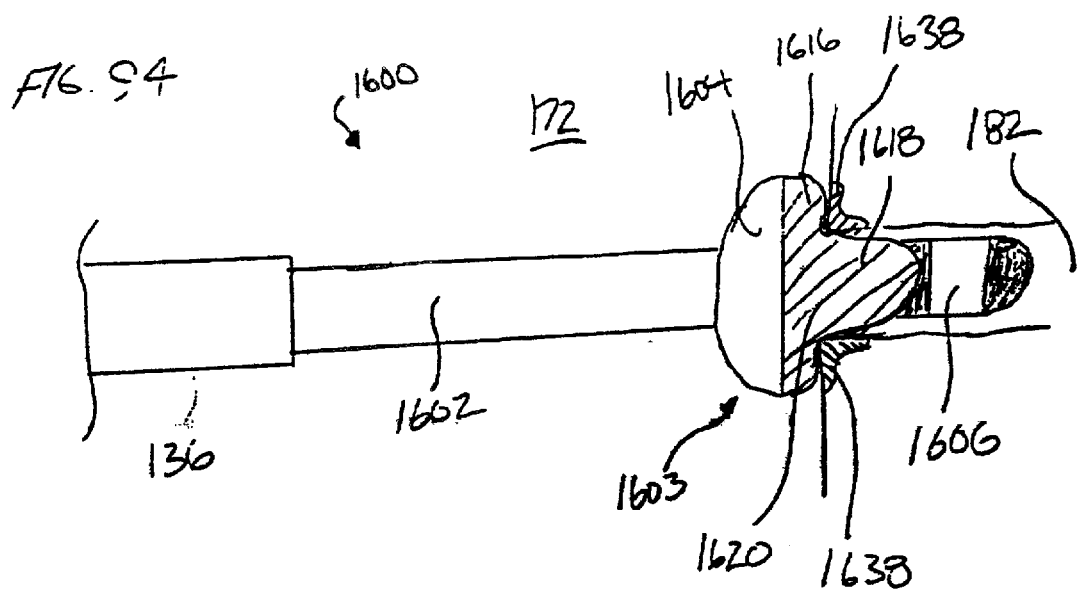
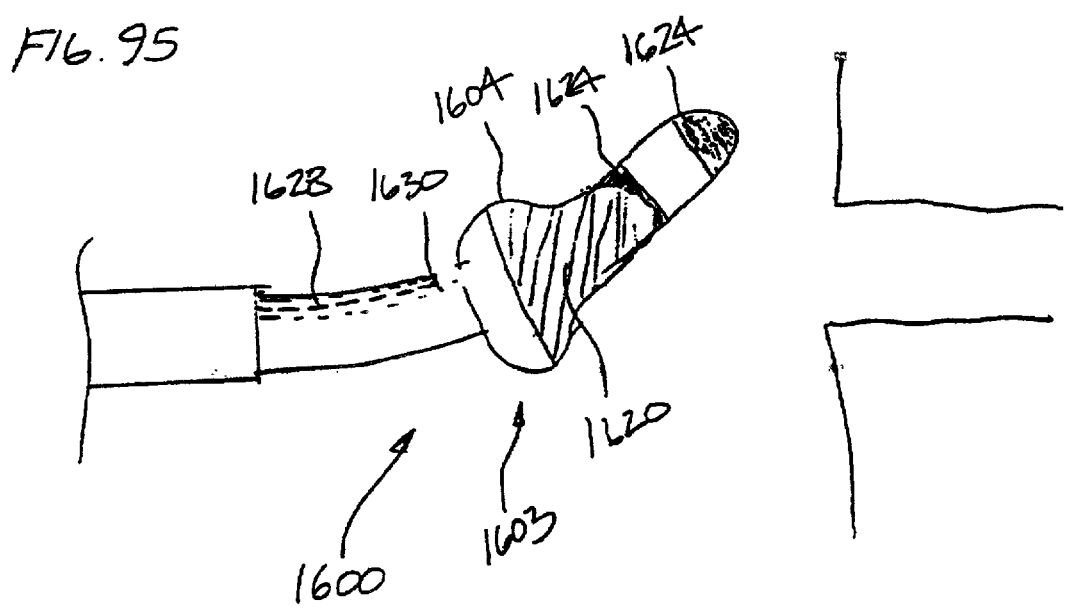

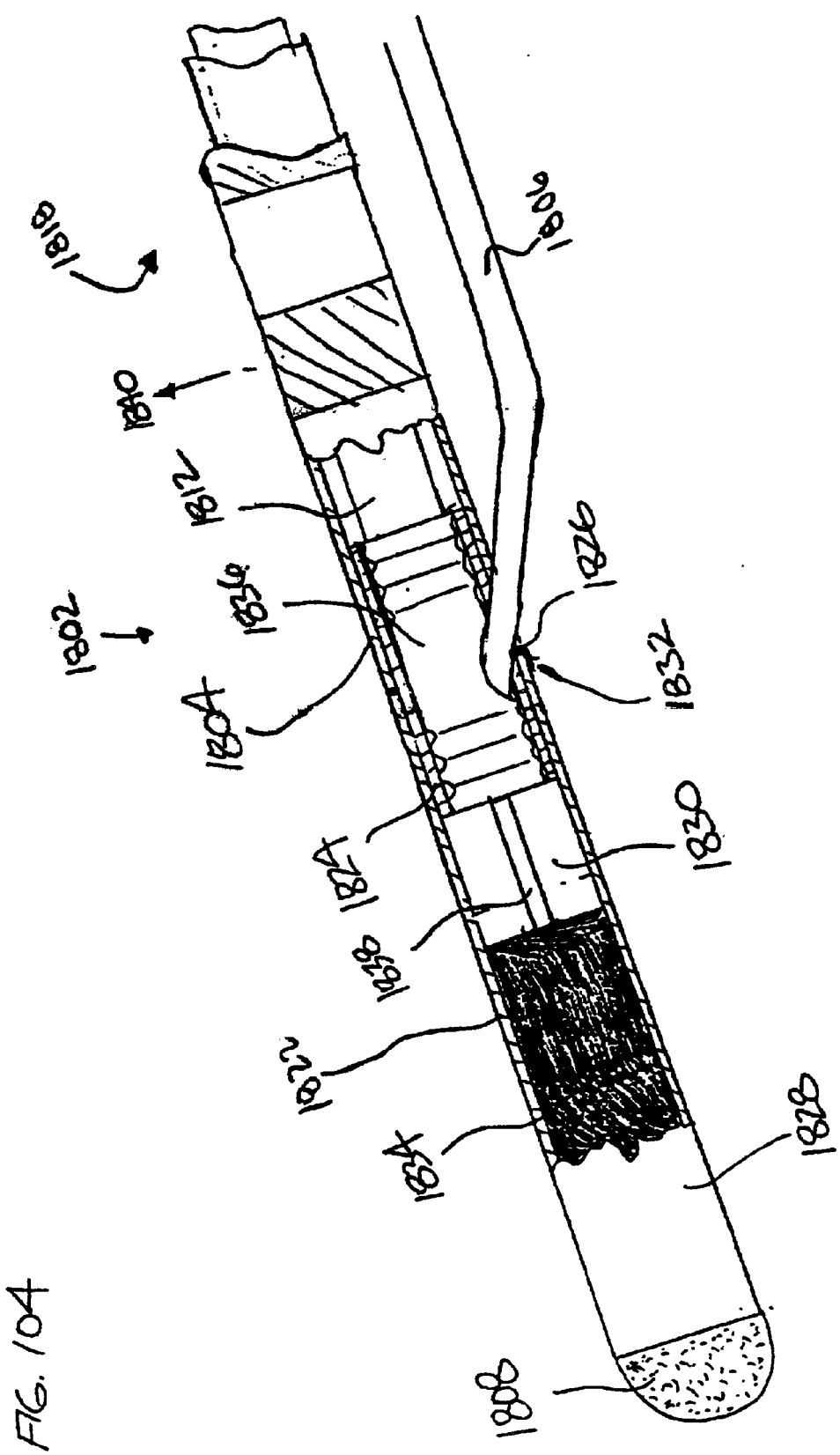

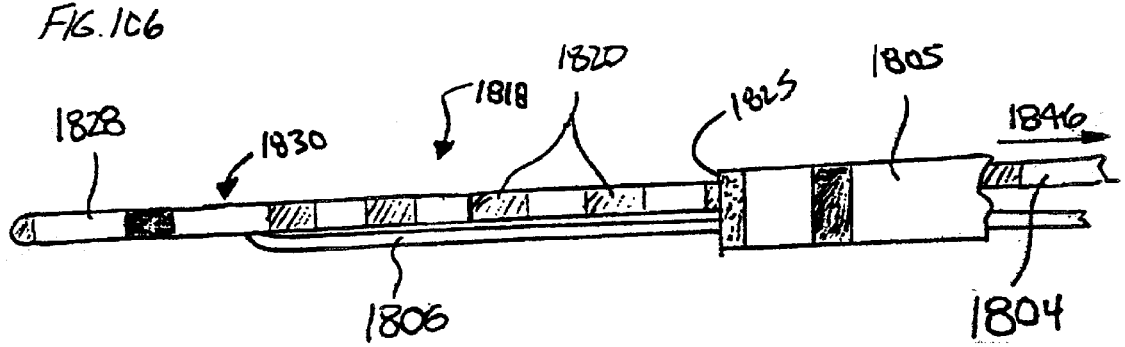
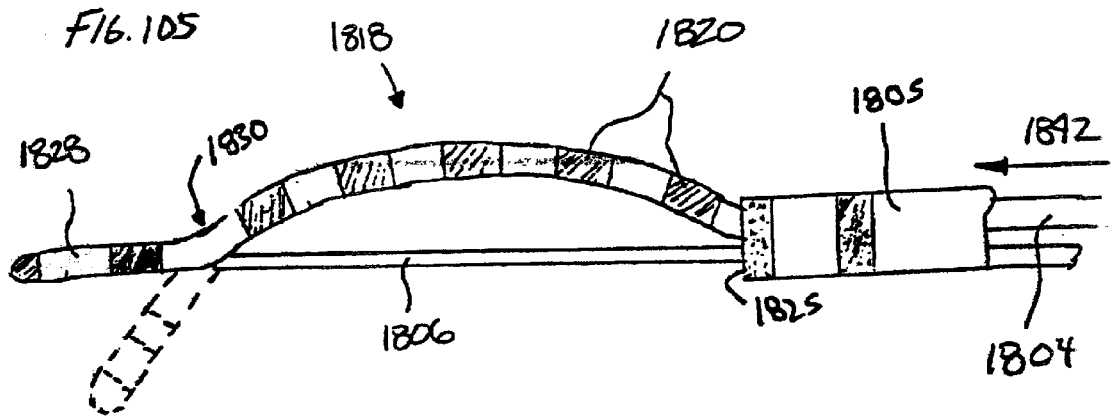
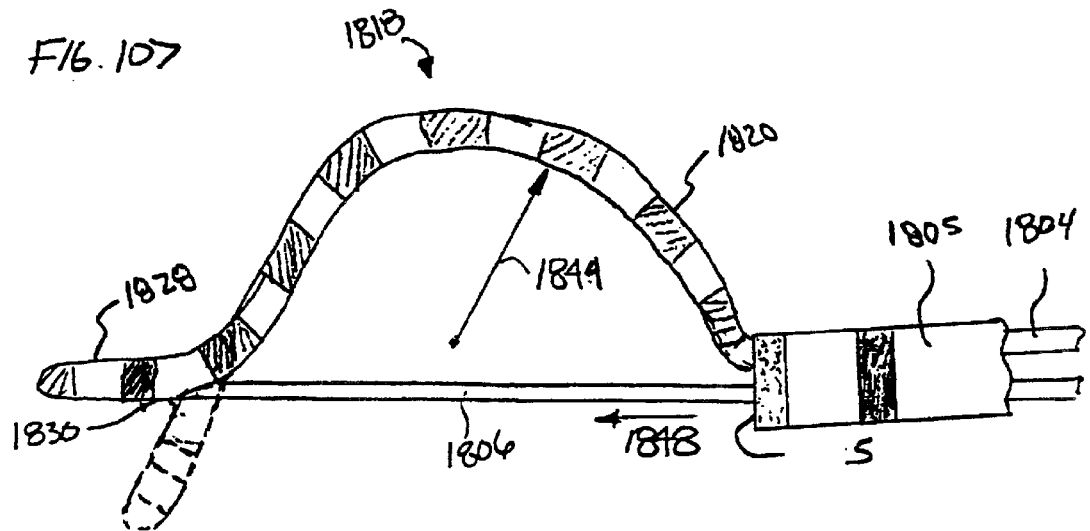

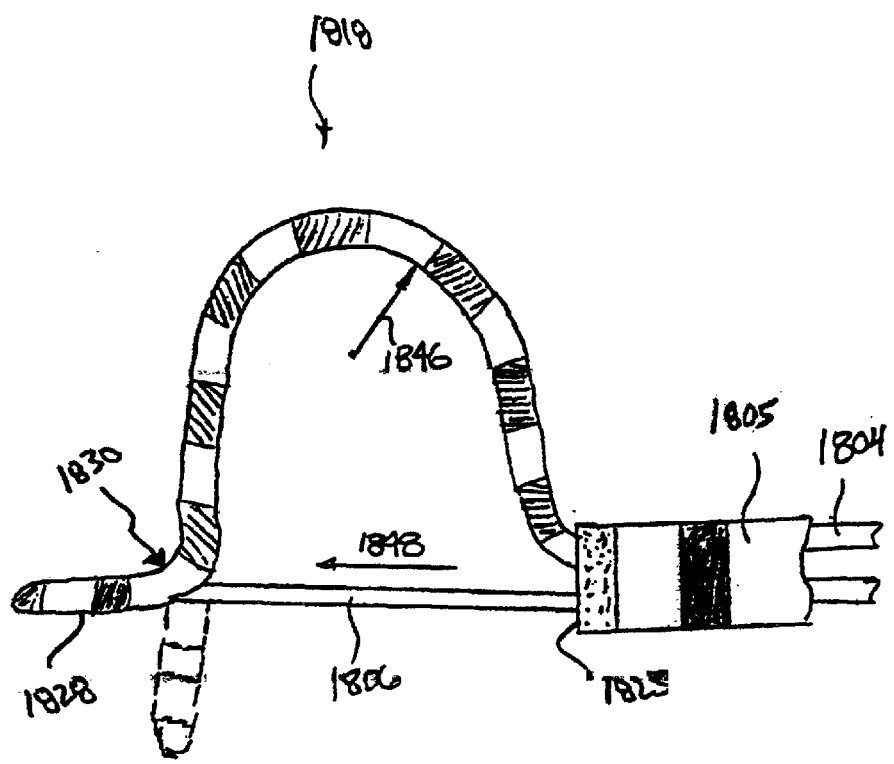

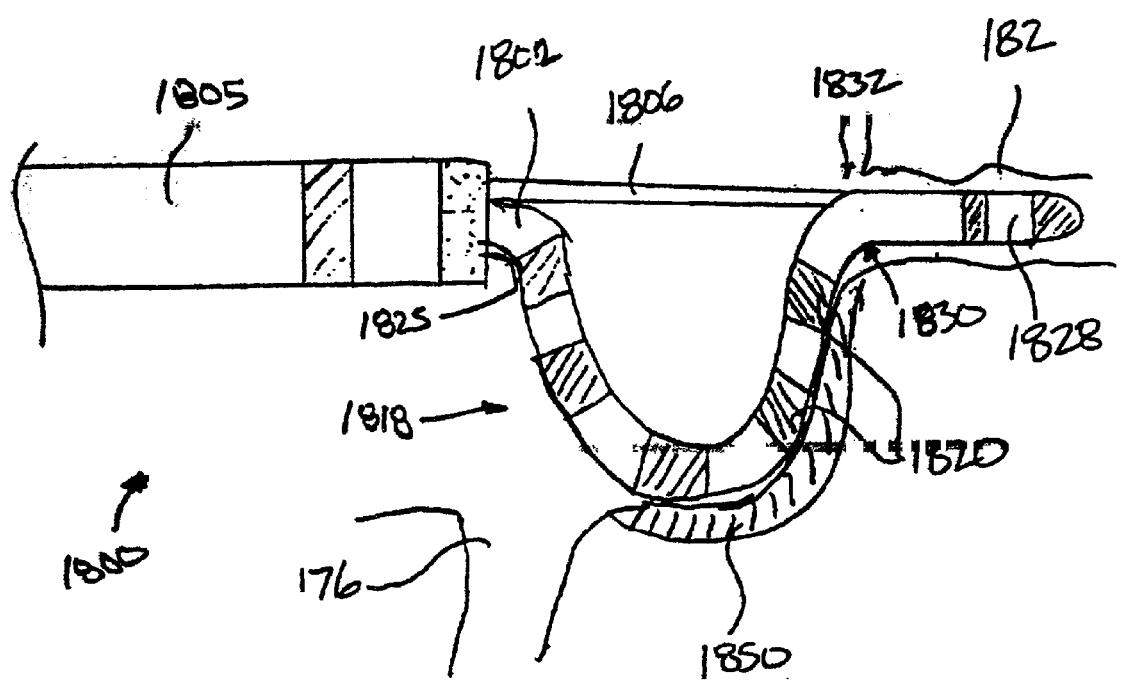

DEVICES AND METHODS FOR CREATING LESIONS IN ENDOCARDIAL AND SURROUNDING TISSUE TO ISOLATE FOCAL ARRHYTHMIA SUBSTRATES

This application is a continuation of U.S. Ser. No. 08/984,414, field Dec. 3, 1997, now abandoned.

FIELD OF THE INVENTION

The present invention pertains to the field of catheter systems and, more particularly to therapeutic catheters for the electrophysiological treatment of cardiac rhythm disturbances.

BACKGROUND

Normal sinus rhythm of the heart begins with the sinoatrial node (or "SA node") generating a depolarization wave front, or electrical impulse. This impulse causes adjacent myocardial tissue cells in the right and left atria to depolarize. The electrical impulse uniformly propagates across the right and left atria and the atrial septum to the atrioventricular node (or "AV node"), causing the atria to contract and empty blood from the atria into the ventricles. The electrical impulse propagates through the AV node to the atrioventricular bundle (or "HIS bundle"), where it further propagates across the ventricles, causing the ventricles to contract. The AV node regulates the propagation delay to the HIS bundle, so that atrial systole occurs during ventricular diastole. This coordination of the electrical activity results in the described, organized sequence of myocardial contraction leading to a normal heartbeat.

Sometimes aberrant conductive pathways develop in heart tissue, which disrupt the normal path of depolarization events. For example, anatomical obstacles, called "conduction blocks," can cause the electrical impulse to degenerate into several circular wavelets that circulate about the obstacles. These wavelets, called "reentry circuits," disrupt the normal activation of the atria or ventricles. As a further example, localized regions of ischemic myocardial tissue may propagate depolarization events slower than normal myocardial tissue. The ischemic region, also called a "slow conduction zone," creates errant, circular propagation patterns, called "circus motion." The circus motion also disrupts the normal depolarization patterns, thereby disrupting the normal contraction of the heart tissue.

The aberrant conductive pathways create abnormal, irregular, and sometimes life-threatening heart rhythms, called arrhythmias. An arrhythmia can take place in the atria, for example, as in atrial tachycardia (AT) or atrial flutter (AF). The arrhythmia can also take place in the ventricle, for example, as in ventricular tachycardia (VT).

In treating arrhythmias, it is sometimes essential that the location of the sources of the aberrant pathways (called focal arrhythmia substrates) be located. Once located, the focal arrhythmia substrate can be destroyed, or ablated, e.g., by surgical cutting, or the application of heat. In particular, ablation can remove the aberrant conductive pathway, thereby restoring normal myocardial contraction. An example of such an ablation procedure is described in U.S. Pat. No. 5,471,982, issued to Edwards et al.

Alternatively, arrhythmias may be treated by actively interrupting all of the potential pathways for atrial reentry circuits by creating complex lesion patterns on the myocardial tissue. An example of such a procedure is described in U.S. Pat. No. 5,575,810, issued to Swanson et al.

Frequently, a focal arrhythmia substrate resides at the base, or within, one or more pulmonary veins, wherein the atrial tissue extends. The automaticity created by these substrates results in ectopic atrial tachycardia. Although the effect caused by the depolarization wavefront propagating from the pulmonary vein containing the substrate resembles that caused by multiple focal arrhythmia substrates within the atria, the atrial fibrillation is actually caused by a single focal arrhythmia substrate within the pulmonary vein. Arrhythmia substrates residing at the base of, or within, a pulmonary vein may alternatively originate from a re-entrant circuit with the depolarization wavefront propagating around a signal vein or within a slow conduction zone residing near or within the vein.

Current techniques of eradicating these substrates include steering a conventional ablation catheter within the target pulmonary vein and mapping this region to pinpoint the substrate. However, this is a time consuming and difficult process. Either extensive mapping must be performed within the pulmonary vein to accurately locate the target ablation site, or multiple lesions must be created to, in effect, "carpet bomb" the substrate. Moreover, the substrate may be located deep within the pulmonary vein, thereby making the manipulations required to steer the catheter's distal tip to the target site difficult.

Thus, it would be beneficial to provide more simplistic and efficient apparatus and methods for eradicating focal arrhythmia substrates residing at the base of, or within, a pulmonary vein.

SUMMARY OF THE INVENTION

The present invention is directed to devices and methods for creating circumferential lesions in endocardial and surrounding tissues, such as, e.g., in and around pulmonary veins, in the inferior vena cava, the superior vena cava, and the sinus coronary, to thereby isolate focal arrhythmia substrates.

In accordance with one preferred embodiment, the present invention is directed to an invasive catheter assembly comprising an elongate body having a longitudinal axis and first and second lumens. A first catheter having a distally mounted anchor mechanism (e.g., an expandable body, or a j-shaped hook) is disposed in the first lumen, the elongate body having a first distal opening accessing the first lumen through which the first catheter may be extended axially relative to the longitudinal axis of the elongate body. A second catheter having a distally mounted electrode is disposed in the second lumen, the elongate body having a second distal opening accessing the second lumen through which the second catheter may be extended at an angle relative to the longitudinal axis of the elongate body.

In this instance, to create a lesion in endocardial tissue about a vessel opening, the distal end of the first catheter is extended through the first elongate body opening into a selected vessel, wherein the anchor body is used to rotatably secure the distal end of the first catheter within the vessel. The distal end of the second catheter is then extended through the second elongate body opening until the electrode comes into contact with endocardial wall tissue near the vessel opening. Electrical energy is then transmitted into the tissue via the electrode, wherein a circumferential lesion may be formed about the vessel opening by rotating the second catheter about the first catheter, while transmitting the energy into the tissue.

In accordance with another preferred embodiment, the present invention is directed to an invasive catheter assembly comprising an elongate catheter having an expandable electrode body mounted proximate on its distal end, the electrode body configured to form an enlarged circumferential region when expanded, the enlarged circumferential region defining a distal facing surface of the electrode body, wherein the distal facing surface is configured to emit radio frequency (RF) energy. The RF energy emitting area may comprise, by way of examples, a conductive substance disposed on an exterior surface of the electrode body, or a microporous section providing for the ionic transfer of RF energy from an electrode located within the electrode body, via an ionic medium filling the electrode body, to surrounding tissues.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which similar elements depicted in alternate embodiments are referred to by common reference numbers, wherein:

FIG. 43A is a side view of the electrode carrying structure of FIG. 37, wherein the catheter assembly employs the guide sheath to guide the electrode carrying structure into the pulmonary vein;

FIG. 47A is a partially cut-away perspective view of yet another preferred tissue ablation catheter assembly, including a preferred electrode carrying structure having a preformed circular shape at its distal end co-planar to its main body;

FIG. 48A is a partially cut-away perspective view of the electrode carrying structure of FIG. 47A, particularly illustrating a first preferred steering mechanism;

FIG. 49 is a partially cut-away perspective view of the electrode carrying structure of FIG. 47A, particularly illustrating temperature sensors and masked electrode areas;

FIG. 50 is a partially cut-away perspective view of the electrode carrying structure of FIG. 47A, wherein the electrode carrying structure is preformed into a circular shape orthogonal to the main body of the catheter assembly;

FIG. 56 depicts the electrode carrying structure of FIG. 51, wherein the preformed circular electrode carrying structure is butted up against the opening of the pulmonary vein;

FIG. 57 depicts the electrode carrying structure of FIG. 51, wherein the preformed circular electrode carrying structure is bent orthogonal to the portion of the catheter tube proximal thereto while the preformed portion is outside of the pulmonary vein;

FIG. 58 depicts the electrode carrying structure of FIG. 51, wherein the preformed circular electrode carrying structure is disposed around the opening of the pulmonary vein;

FIG. 59 is a partially cut-away perspective view of a still further preferred tissue ablation catheter assembly, including another preferred electrode carrying structure housed within a sheath and is mounted thereto by a wire;

FIG. 74 is a partially cut-away perspective view of the distal end of a still further preferred tissue ablation catheter assembly, including an ablation catheter and guide wire, both of which are disposed in guide sheath;

FIG. 75 is a side view of the catheter assembly of FIG. 74 disposed in the left atrium of the heart;

FIG. 76 depicts the guide wire of the catheter assembly of FIG. 75 disposed in the pulmonary vein;

FIG. 82 is a partially cut-away perspective view of the distal end of yet another preferred tissue ablation catheter assembly, including a catheter having conductive shell disposed over a balloon-like body depicted in a deflated geometry, wherein the catheter includes an internal lumen through which a guide wire is disposed;

FIG. 83 is a partially cut-away perspective view of the distal end of the catheter assembly of FIG. 82, wherein the balloon-like body is depicted in an expanded geometry;

FIG. 94 depicts the catheter assembly of FIG. 92 creating a lesion in and around the opening of the pulmonary vein.

FIG. 95 depicts the catheter assembly of FIG. 92 performing a steering maneuver within the left atrium of the heart.

FIG. 104 is a partially cut-away perspective view of a distal section of the ablation catheter assembly of FIG. 103;

FIG. 105 is a partially cut-away perspective view of the electrode carrying structure of FIG. 103, forming a loop with a first shape;

FIG. 106 is a partially cut-away perspective view of the electrode carrying structure of FIG. 103, deployed in a low profile geometry;

FIG. 107 is a partially cut-away perspective view of the electrode carrying structure of FIG. 103, forming a loop with a second shape;

FIG. 108 is a partially cut-away perspective view of the electrode carrying structure of FIG. 103, forming a loop with a third shape;

FIG. 111 depicts the electrode carrying structure of FIG. 107, wherein the electrode carrying structure is deployed in an exemplary geometry for creating a circumferential lesion between a pulmonary vein and the mitral valve.

DETAILED DESCRIPTION OF THE PREFERRED EMBODIMENTS

Figure 1:
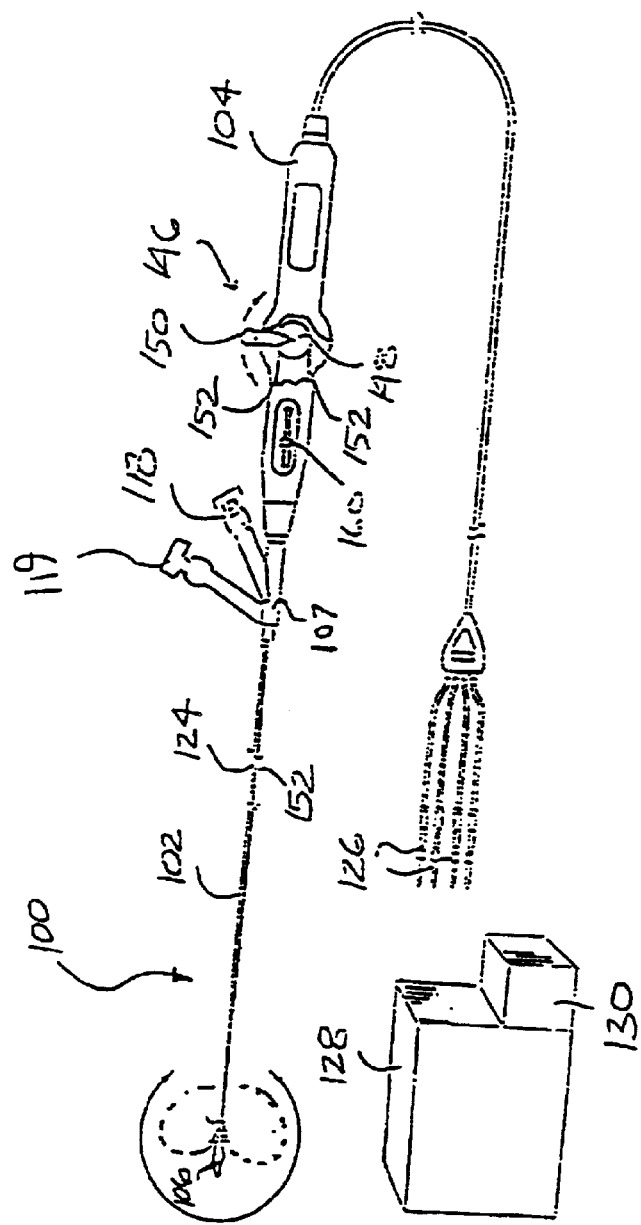
FIG. 1 is a perspective elevation view of a first preferred tissue ablation catheter assembly.
Figure 2:
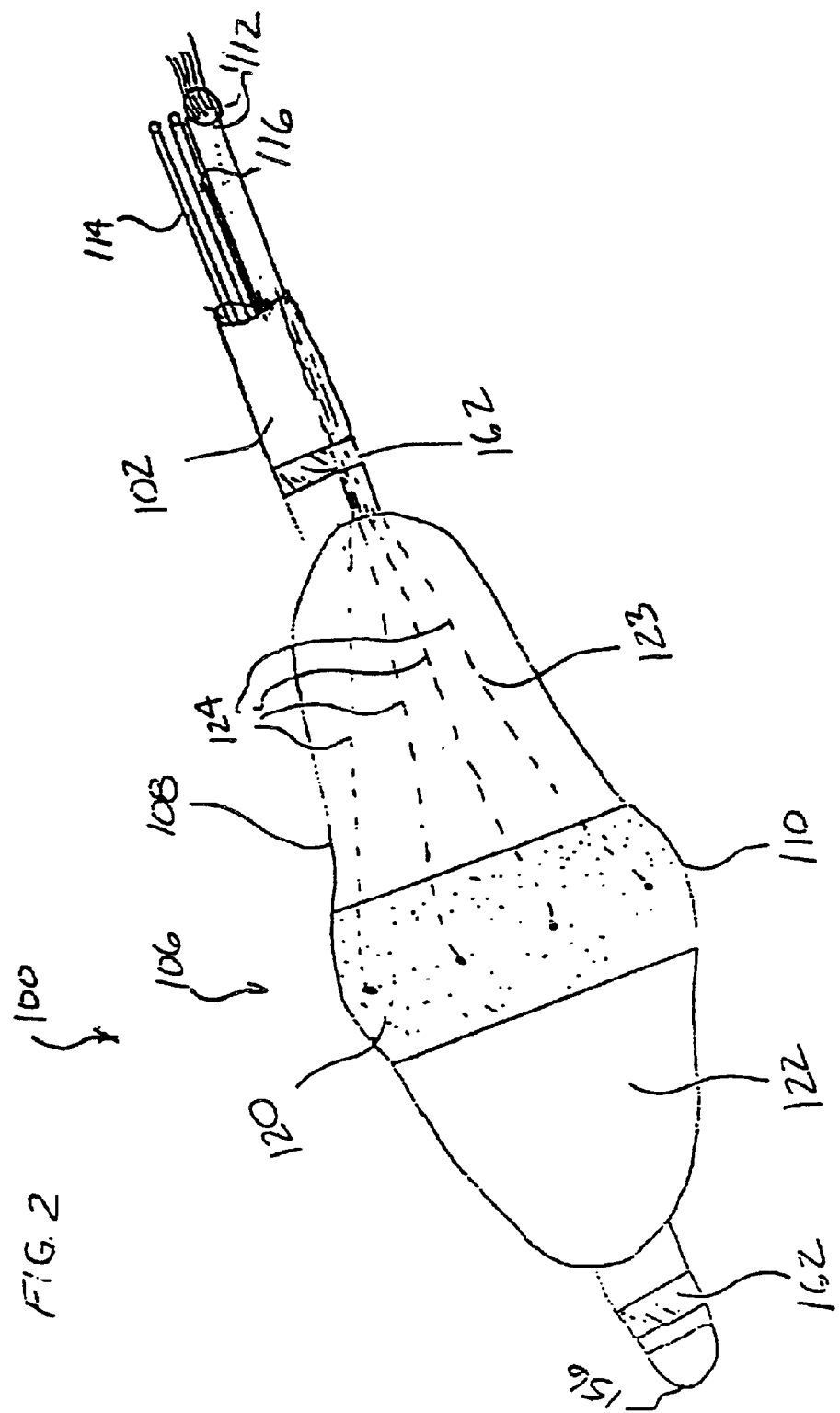
FIG. 2 is a partially cut-away perspective view of a first preferred electrode carrying structure for use with the catheter assembly of FIG. 1, wherein the electrode carrying structure includes a balloon-like body with a circumferentially disposed conductive shell depicted in an expanded geometry.
Figure 3:
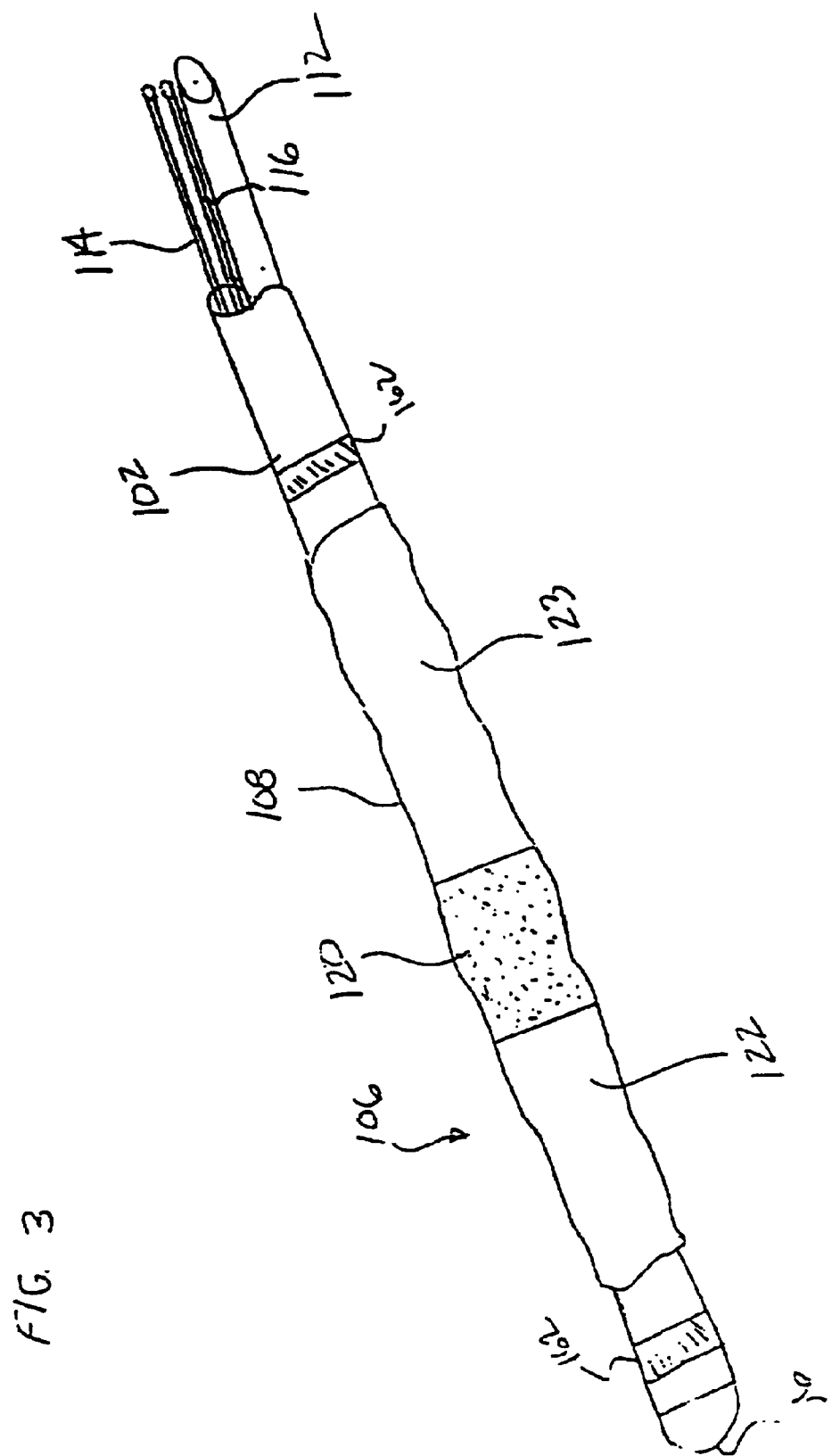
FIG. 3 is a partially cut-away perspective view of the electrode carrying structure of FIG. 2 depicted in a deflated geometry.

Referring to FIGS. 1–3, a first preferred embodiment of a tissue ablation catheter assembly 100 includes a flexible catheter tube 102 made of a polymeric, electrically nonconductive material, like polyethylene, polyurethane, or PEBAX® (i.e., polyether block amide). The catheter tube 102 has an open proximal end that is connected to a handle 104, and a distal end that is connected to a first preferred electrode carrying structure 106 configured to deliver ablation energy to the interior of the pulmonary veins of a patient, as is described in greater detail herein. The distal extremity of the catheter tube 102 is open and includes a closed distal tip 156 that is suitably bonded thereto.

As best seen in FIGS. 2 and 3, the electrode carrying structure 106 includes an expandable-collapsible electrode body 108 formed by a "balloon-like" wall suitably bonded to and disposed about the closed distal end of the catheter tube 102. In particular, such an arrangement provides axial support to the electrode body 108 during manipulation of the catheter assembly 100. The geometry of the electrode body 108 can be altered between a collapsed, low profile geometry (shown in FIG. 3), and an expanded, high profile geometry, (shown in FIG. 2).

The catheter tube 102 includes a main lumen 112 used to house non-fluid components, such as steering and ablation signal wires, along with respective inflation and venting lumens 114 and 116 employed to inflate the electrode body 108. In particular, the respective distal ends of the respective inflation and venting lumens 114 and 116 open into a hollow interior of the electrode body 108 (not shown), preferably at opposite ends thereof in order to facilitate the venting of the electrode body 108. The proximal ends of the lumens 114 and 116 communicate with ports 118 and 119, respectively, of a housing port 107 on the handle 104.

In order to inflate the electrode body 108, in accordance with methods known in the art, a liquid inflation medium, such as water, saline solution, or other bio-compatible fluid is conveyed under positive pressure through the port 118 and into the inflation lumen 114. The liquid medium fills the interior of the electrode body 108 and exerts pressure on the inside of the electrode body 108 to urge the electrode body 108 from its collapsed geometry (FIG. 3) to its expanded geometry (see FIG. 2). Constant exertion of pressure through the inflation lumen 114 maintains the electrode body 108 in its expanded geometry. The venting lumen 116 is used to vent any air or excess fluid from the electrode body 108. Alternatively, the inflating fluid medium can comprise a gaseous medium such as carbon dioxide.

Regardless of the type of inflating medium used, the inflation preferably occurs under relatively low pressures of no more than 30 psi. In particular, the pressure used depends upon the desired amount of inflation, the strength of material used for the electrode body 108, and the degree of flexibility required, i.e., higher pressure results in a harder, less flexible electrode body 108, when inflated.

Preferably, the electrode body 108 is less than 8 French diameter when in a collapsed geometry for ease of manipulation through the vasculature, and about 2.0 cm in circumference around its the largest portion when in its expanded geometry and located in a desired ablation region within the pulmonary vein. The electrode body 108 is preferably made of a suitable bio-compatible, thermoplastic or elastomeric material, and can be configured to have any one of many shapes in its expanded geometry, such as the ellipsoid shape shown in FIG. 2, depending on the desired resulting geometry.

Proximate the center of the electrode body 108 is a pronounced circumferential region 110 having a larger circumference than that of the rest of the electrode body 108. In this manner, expansion of the electrode body 108 within the pulmonary vein provides a force that is concentrated between the enlarged circumferential region 110 and the interior surface of a pulmonary vein in which the electrode body 108 is situated, thus enhancing the lesion creating characteristics of the electrode carrying structure 106, which will be described in further detail below. It should be noted that the exact location of the enlarged circumferential region 110 may be varied in alternate preferred embodiments, and not necessarily limited to the center of the electrode body 108.

A more detailed description of preferred structures and methods of manufacture of the balloon-like electrode body 108 is provided in co-pending U.S. application Ser. No. 08/630,719, filed Apr. 8, 1996, 1996, entitled "Expandable-Collapsible Electrode Carrying Structures With Electrically Conductive Walls," and in co-pending U.S. application Ser. No. 08/631,356, filed Apr. 12, 1996, entitled "Tissue Heating And Ablation Systems And Methods Using Electrode Structures with Distally Oriented Porous Regions," which are both fully incorporated herein by reference for all that they disclose and teach.

A conductive shell 120 made of a material having a relatively high electrical and thermal conductivity is suitably deposited on the outer surface of the balloon-like electrode body 108 over the enlarged circumferential region 110 using ion beam deposition or equivalent techniques. Materials possessing these characteristics include, among others, gold, platinum, platinum/iridium, conductive ink epoxy, or a combination thereof. In particular, noble metals are preferred. To enhance adherence between the electrode body 108 and conductive shell 120, an undercoating made of a material such as titanium, iridium, nickel, or combinations or alloys thereof is deposited on the enlarged circumferential region 110 prior to deposition of the conductive shell 120.

The area of the electrode body wall 108 located immediately proximal and distal to the enlarged area 110 is preferably masked prior to the deposition of the conductive material, so that resulting non-conductive regions 122 and 123 are formed on either side of the conductive shell 120. In particular, the masking of the regions on either side on the conductive region assures that the maximum current density will be distributed at the enlarged circumferential region 110 of the electrode body 108, thereby allowing the electrode carrying structure 106 to efficiently form annular lesions within the pulmonary vein. Alternatively, the conductive shell 120 can be formed of a thin electrically conductive metal foil, or may be co-extruded with the wall forming the electrode body 108, as is disclosed and described in the above-incorporated U.S. application Ser. No. 08/630,719.

As will be appreciated by those skilled in the art, the conductive shell 120 serves as the transmitter of energy that ablates tissue. While the type of ablation energy used can vary, in the illustrated preferred embodiment, the shell 120 serves to transmit radio frequency electromagnetic (RF) energy. Notably, the shell 120 is preferably sufficiently flexible to conform to the same range of geometries, (i.e., between collapsed to expanded), as the electrode body 108. However, the conductive shell 120 preferably resists stretching within this range, to thereby minimize "thinning." In particular, thinning of the shell 120 creates localized changes in the conductive surface, with attendant increases in resistance and "hot spots." For this reason, the elasticity of the electrode body 108 and shell 120 should be selected to fall within acceptable bounds, so that the ability to "fold" is retained, while still preserving stability during inflation and preventing creasing in the folds, which can cause open circuits.

In order to deliver current, the shell 120 is coupled to a plurality of insulated ablation signal wires 124 (shown in phantom in FIG. 2). Preferably, the ablation signal wires 124 are coupled at points uniformly distributed about the geometric center of the shell 120, in order to prevent inefficient RF energy delivery due to voltage drops. The ablation signal wires 124 extend from the shell 120, through the main lumen 112 of the catheter tube 102, to external connectors 126 on the handle 104 (seen in FIG. 1). The connectors 126 electrically couple the shell 120 to a RF generator 128. A controller 130 is associated with the generator 128, either as an integrated unit or as a separate box, and governs the delivery of RF ablation energy to the shell 120 according to preestablished criteria. A more detailed description concerning the electrical coupling of the conductive shell 120 to the RF generator 128 via ablation signal wires 124 is disclosed in the above-incorporated U.S. application Ser. No. 08/630,719.

As will also be appreciated by those skilled in the art, the electrical resistivity of the electrode body 108 has a significant influence on the lesion geometry and controllability. It has been discovered that ablation with devices that have a low-resistivity electrode body requires more RF power and results in deeper lesions. On the other hand, devices that have a high-resistivity electrode body generate more uniform heating, therefore, improving the controllability of the lesion. Because of the additional heat generated by the increased electrode body resistivity, less RF power is required to reach similar tissue temperatures after the same interval of time. Consequently, lesions generated with high-resistivity bodies usually have smaller depth. Thus, by adjusting the resistivity of the electrode body 108, the power level, time that the RF ablation energy is transmitted, and percentage-shell tissue contact, the electrode carrying structure 106 is able to create lesions of different sizes and depths. A more detailed description of this process is disclosed and described in the above-incorporated U.S. application Ser. No. 08/630,719.

Figure 4:
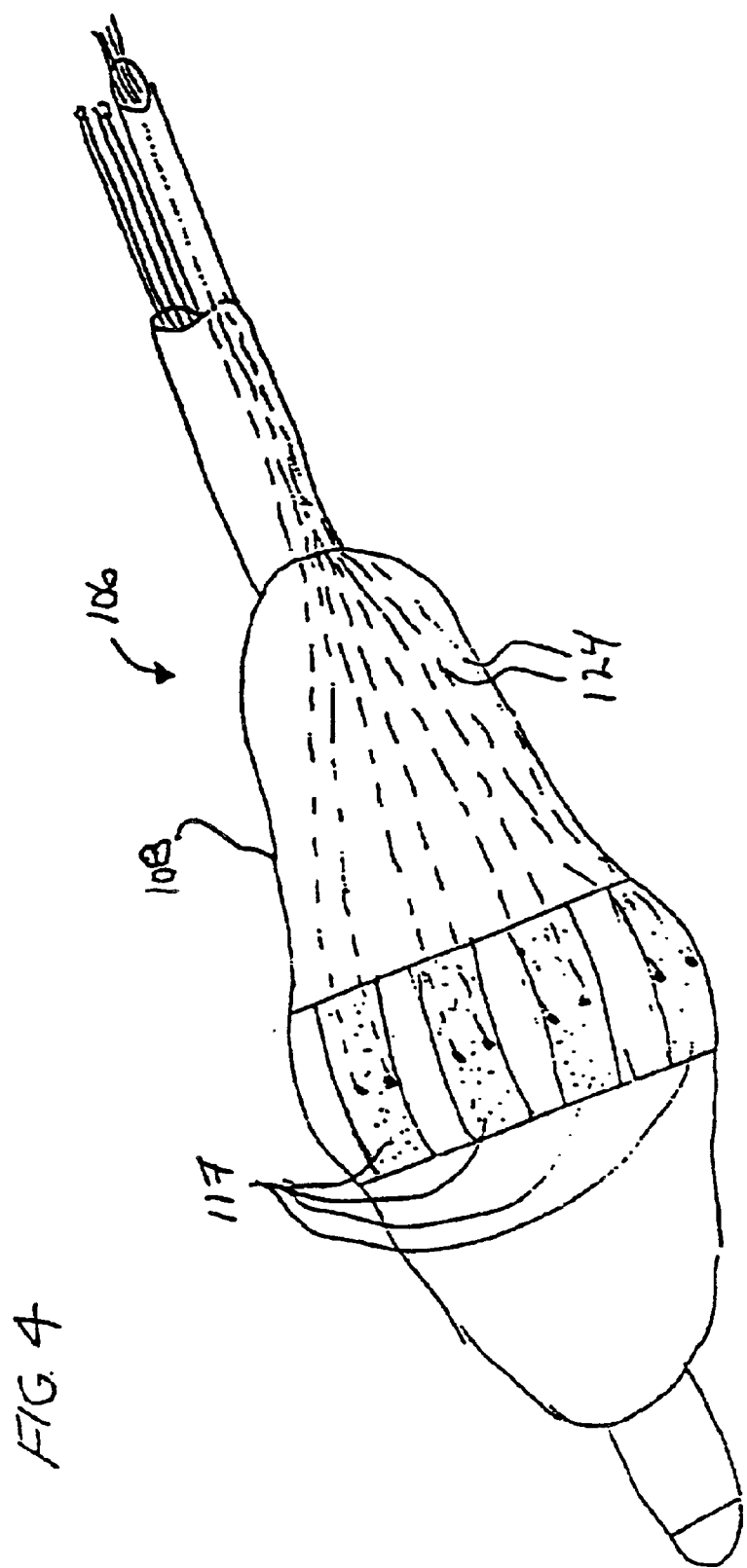
FIG. 4 is a partially cut-away perspective view of the electrode carrying structure of FIG. 2, particularly illustrating a circumferential conductive shell formed into segmented areas.

Referring to FIG. 4, the conductive shell 120 need not be formed of a continuous electrically conductive material, but may alternately be segmented—i.e., wherein the conductive shell is broken into a plurality of circumferentially displaced conductive segments 117. In accordance with this alternate arrangement, a respective pair of ablation signal wires 124 are electrically coupled in parallel to each segment 117. This alternate configuration decreases the effect of voltage gradients within the conductive shell 120, which in turn, improves the uniformity of the delivered current density.

The spacing between the conductive segments 117 is preferably sufficiently close to provide additive heating effects when ablating energy is delivered transmitted simultaneously to adjacent segments 117, as is more fully disclosed in described in U.S. Pat. No. 5,582,609, issued to Swanson et al., which is fully incorporated herein by reference for all its discloses and teaches. In particular, segmenting the conductive surface provides an additional advantage of allowing the electrode body 108 to circumferentially fold upon itself in a consistent, uniform fashion, as is described in greater detail herein.

Referring again to FIGS. 2–3, the characteristics of lesions created by the electrode carrying structure 106 can further be controlled by regulating the temperature of the electrode body wall 108 in order to cool the conductive shell 120. By way of preferred example, such a cooling effect can be accomplished by continuously or intermittently recycling the inflation medium within the electrode body 108, through the venting lumen 116 or, alternatively, another lumen (not shown). Such use of active cooling allows the shell 120 to form deep lesions while transmitting ablation energy. Further details concerning the use of active cooling to enhance lesion formation are disclosed and described in co-pending U.S. patent application Ser. No. 08/431,790, filed May 1, 1995, and entitled "Systems and Methods for Obtaining Desired Lesion Characteristics While Ablating Body Tissue," which is fully incorporated herein by reference for all it discloses and teaches.

Figure 5:
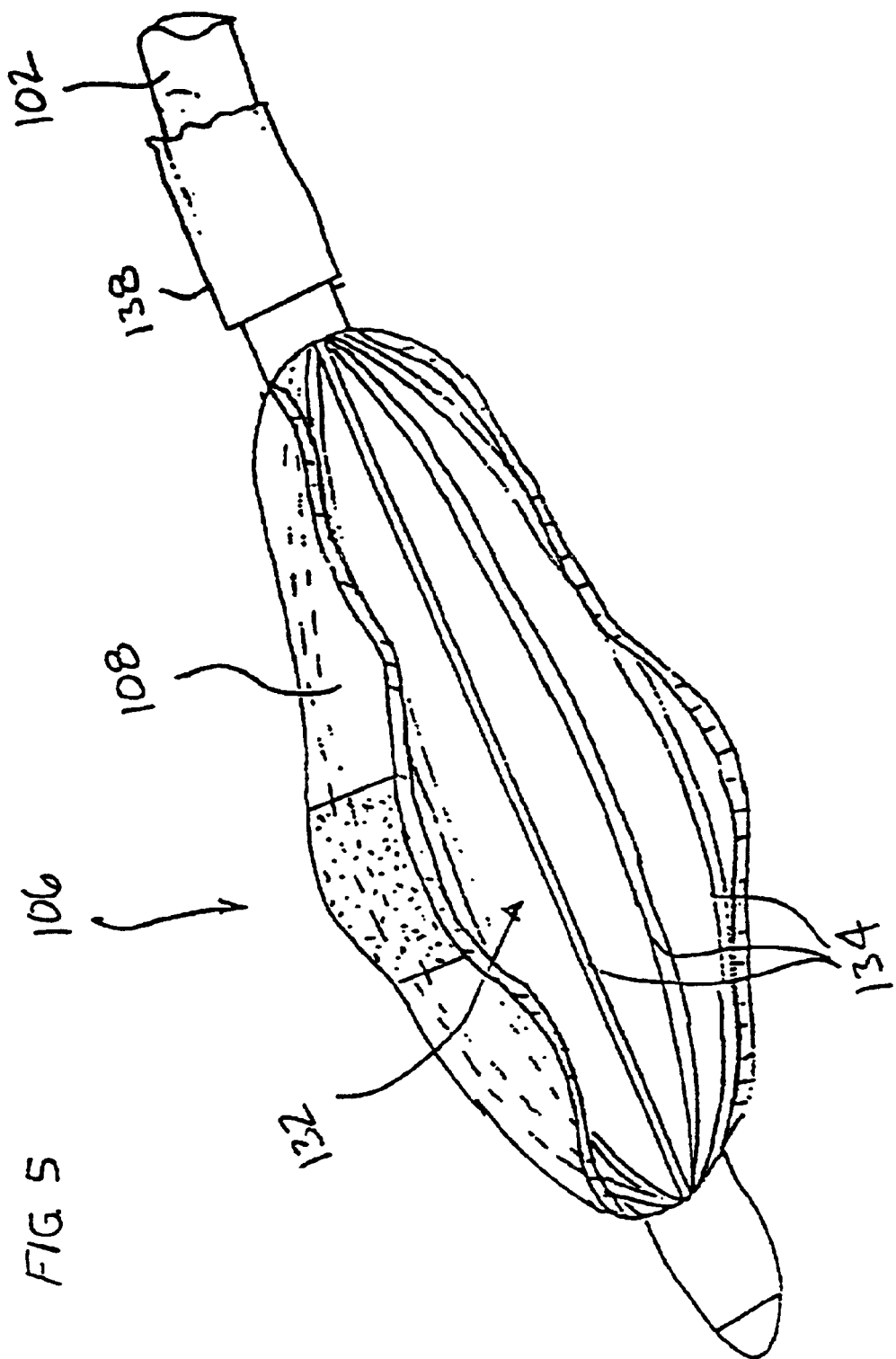
FIG. 5 is a partially cut-away perspective view of the electrode carrying structure of FIG. 2, particularly illustrating an internal support structure formed by a plurality of collapsible spline elements.
Figure 6:
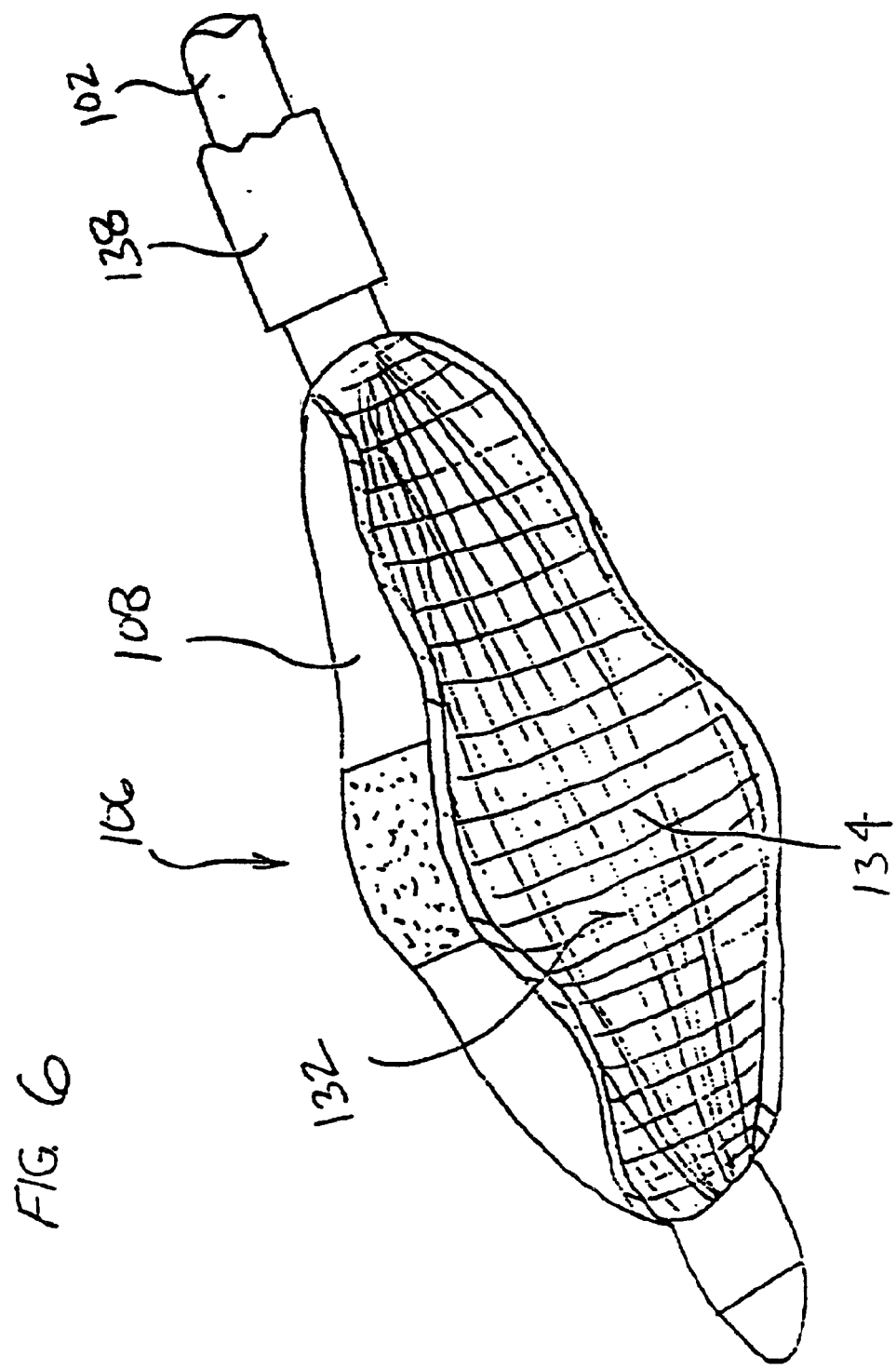
FIG. 6 is a partially cut-away perspective view of the electrode carrying structure of FIG. 2, particularly illustrating an internal support structure formed by a collapsible mesh.
Figure 7:
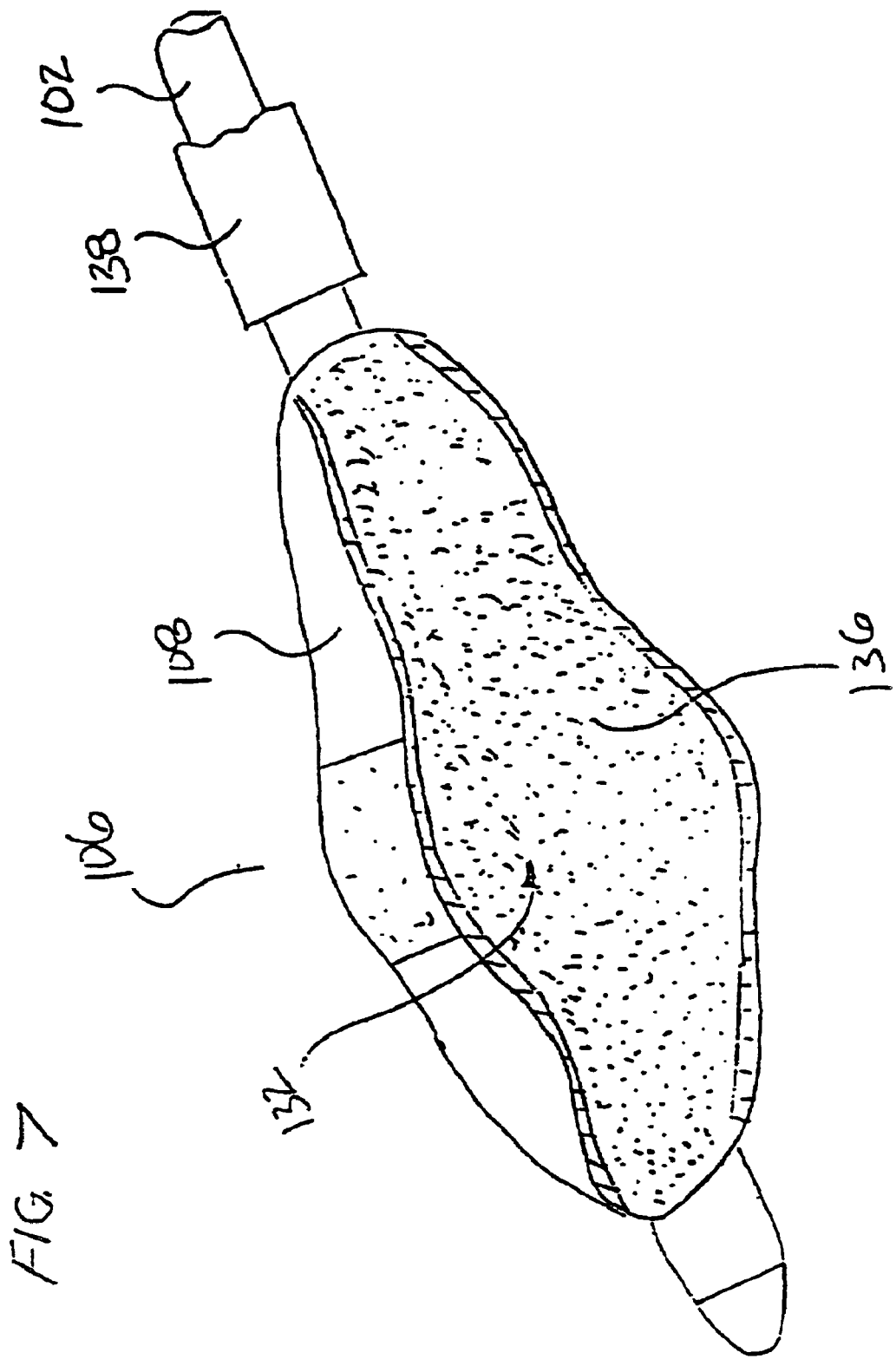
FIG. 7 is a partially cut-away perspective view of the electrode carrying structure of FIG. 2, particularly illustrating an internal support structure formed by a collapsible foam element.

Referring to FIGS. 5–7, the electrode carrying structure 106 may alternately include a collapsible, interior support structure 132 arranged to apply an outward force against the electrode body wall 108 to augment, or replace, the outward force caused by a pressurized liquid medium to maintain the electrode body 108 in its expanded geometry. As will be appreciated by those skilled in the art, the form of the interior support structure 132 can vary. It can, for example, comprise an assemblage of flexible spline elements 134 made from a resilient, inert wire, such as nickel titanium (commercially available as Nitinol material), stainless steel 17-7, or thermoplastic material, as shown in FIG. 5; a three dimensional structure formed by a resilient mesh 134, as shown in FIG. 6; or a foam substance 136 molded to normally assume the shape of the expanded geometry of the electrode body 108, as shown in FIG. 7, respectively.

In each of these alternate configurations, the internal support structure must be collapsible, (i.e., after the removal of any inflation medium), by outside compression, such as that applied by a conventional introducer guide sheath 138 disposed about the catheter tube 102.

Figure 8:
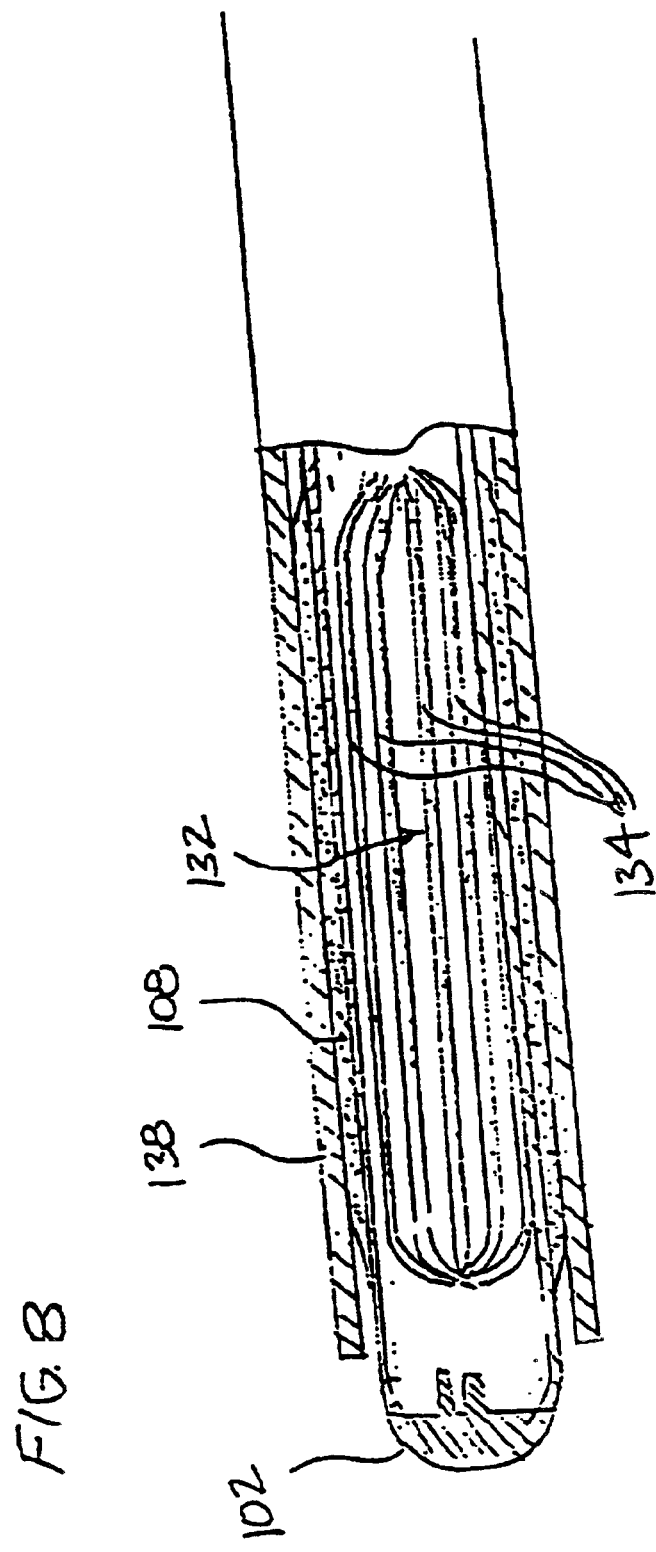
FIG. 8 is a partially cut-away side view of the electrode carrying structure of FIG. 5, particularly illustrating the plurality of internal support splines in a collapsed geometry.

For example, referring to the preferred embodiments of FIGS. 5 and 8 for purposes of illustration, the guide sheath 138 is used to introduce the catheter assembly 100 into a heart chamber, wherein the electrode carrying structure 106 is passed through the guide sheath 138 until it is in a desired position relative to the patient's anatomy. So long as the electrode assembly is retained within the guide sheath 138, the internal support spline elements 134 remain in a collapsed position (shown in FIG. 8). The attending physician then withdraws the guide sheath 138 relative to the catheter tube 102, thereby causing the spline elements 134 to return to an expanded geometry (shown in FIG. 5), and causing the electrode body 108 to assume its expanded position.

After use, the catheter structure with the expanded electrode body 108 is withdrawn back into the guide sheath 138, causing the flexible spine elements 134 to collapse into a low profile geometry within the sheath 138. Further details concerning the structure, form, and manufacture of preferred interior electrode body structures for use in the catheter assembly 100 are disclosed and described in the above-incorporated U.S. application Ser. No. 08/630,719.

Figure 9:
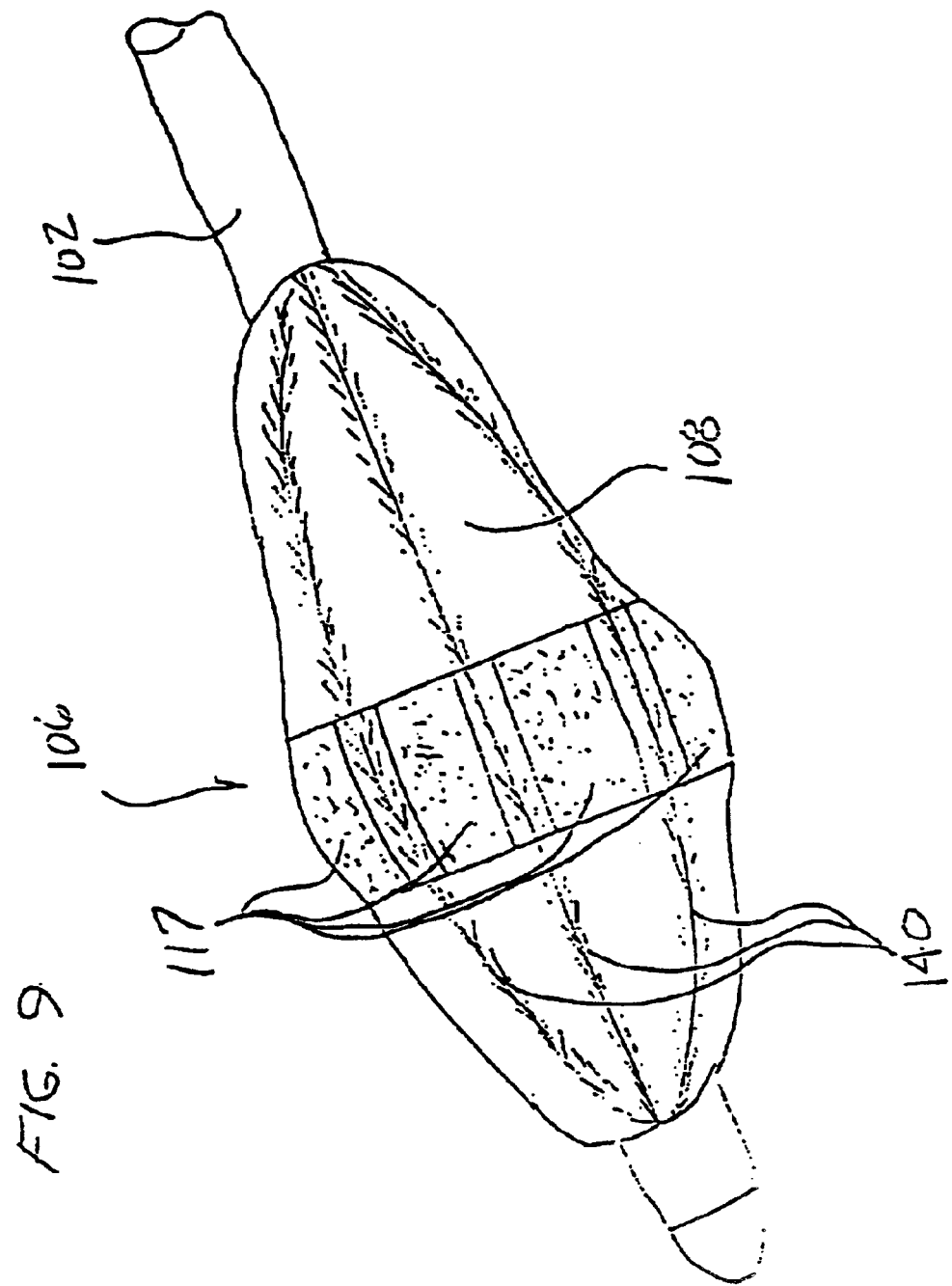
FIG. 9 is a partially cut-away perspective view of the electrode carrying structure of FIG. 2, particularly illustrating a creased construction and shown in an expanded geometry.
Figure 10:
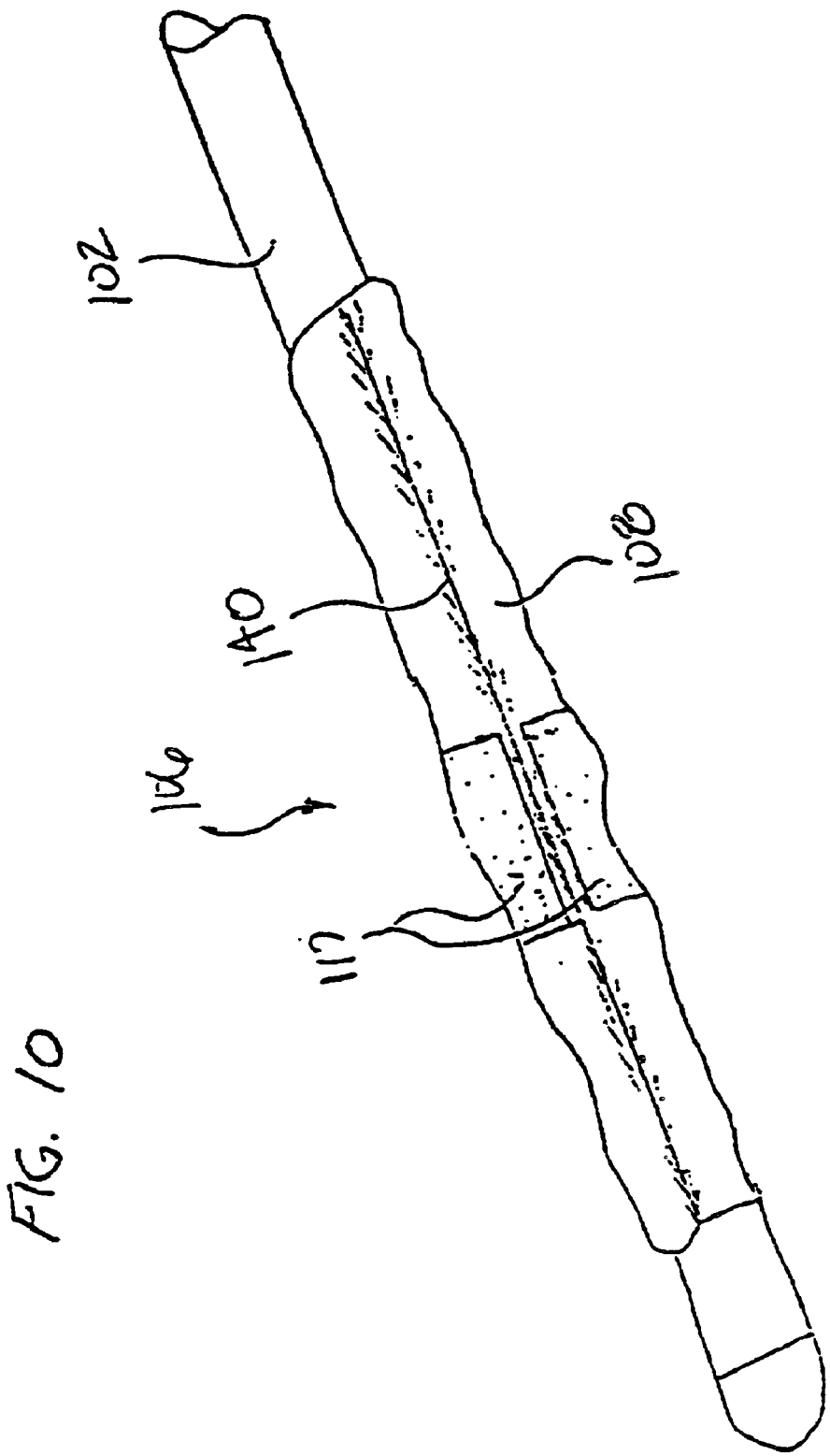
FIG. 10 is a partially cut-away perspective view of the electrode carrying structure of FIG. 9, shown in a "folded" (i.e., deflated) geometry.
Figure 11:
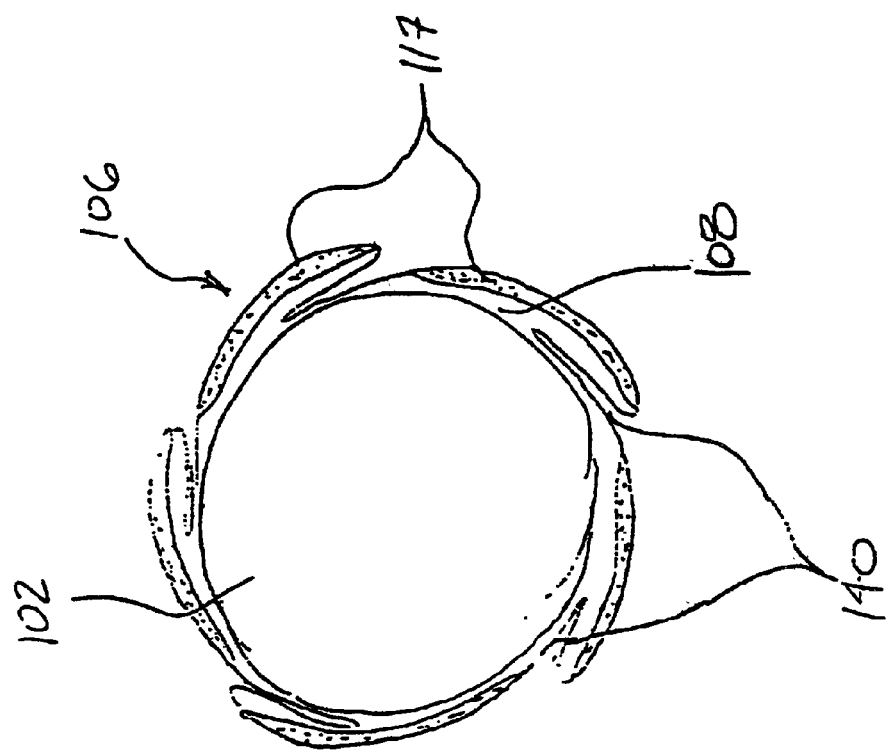
FIG. 11 is a cross-sectional view of the electrode carrying structure of FIG. 10.

Referring to FIGS. 9–11, the electrode body 108 can alternately be molded with preformed regions 140 of reduced thickness, causing the formation of longitudinal creases. In particular, in order to create these creased regions 140, a mold having a preformed surface geometry is employed such that the electrode body material is formed slightly thinner, indented, or ribbed along the desired regions 140. As FIGS. 10 and 11 show, the electrode body 108 will collapse about the creased regions 140 when returning to a collapsed geometry, causing the electrode body 108 to circumferentially fold upon itself in a consistent, uniform fashion. The resulting collapsed geometry can thus be made more uniform and compact.

In further accord with this alternate configuration, the creased regions 140 are preferably masked before deposition of the electrical conductive material, thereby creating segmented conductive areas 117. In this way, the conductive regions 117 are not subject to folding and collapse of the electrode body 108, and are thus protected against folding and stretching forces, which could otherwise cause creasing and current interruptions, or increases in resistance, thereby affecting local current densities and temperature conditions during operation. In fact, the selective segmented deposition of the conductive areas 117 can itself establish predefined creased regions 140 on the electrode body 108, without special molding of preformed regions of the electrode body 108. Further details concerning preferred techniques for folding the electrode body 108 using segmented conductive areas 117 are disclosed and described in the above-incorporated U.S. application Ser. No. 08/630,719.

Figure 12:
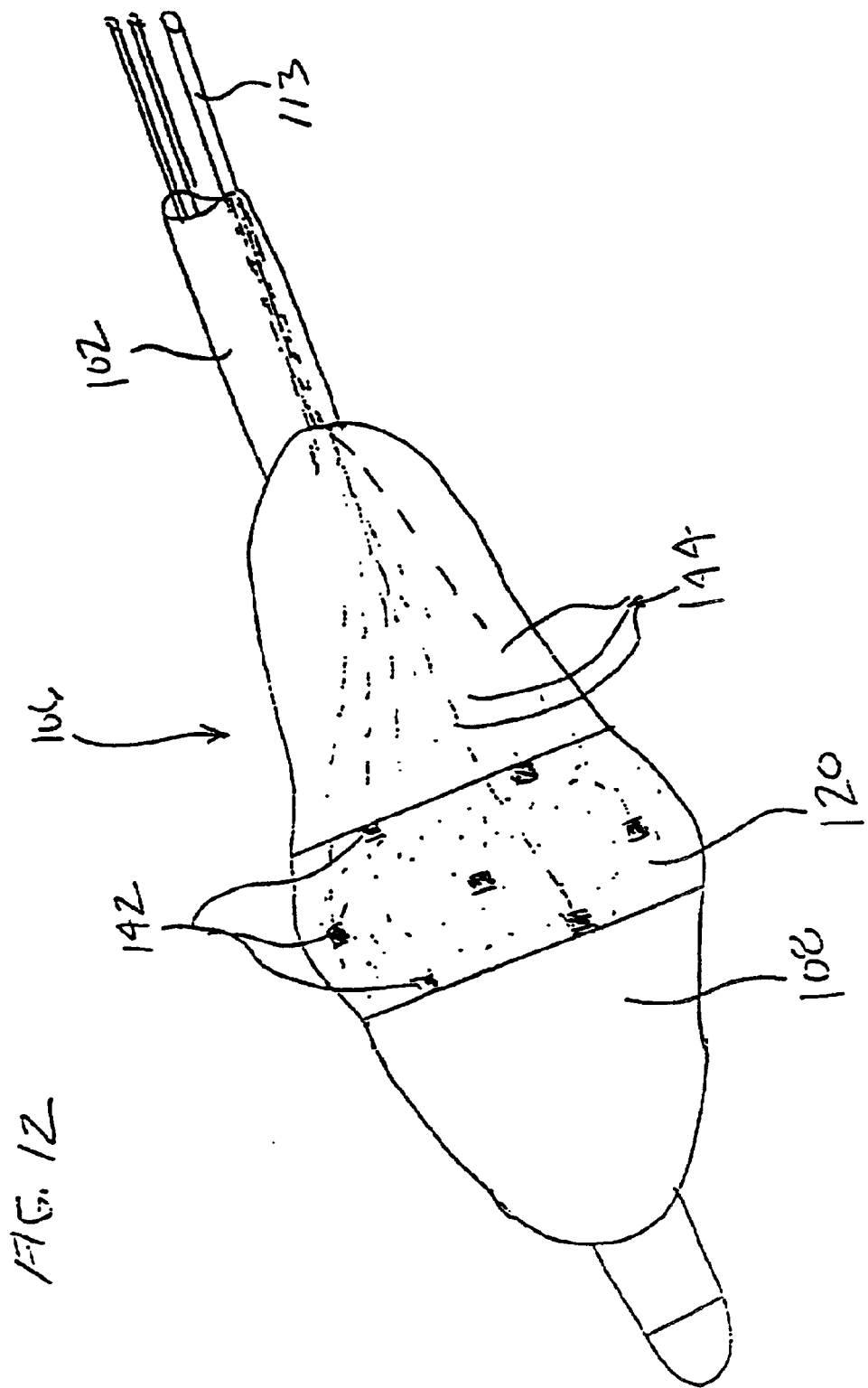
FIG. 12 is a partially cut-away perspective view of the electrode carrying structure of FIG. 2, particularly illustrating a plurality of temperature sensing elements.

Referring to FIG. 12, the electrode carrying structure 106 preferably includes a plurality of temperature sensing elements 142, which are coupled to the controller 130 through a plurality of corresponding temperature sensing element wires 144 (shown in phantom) extending through a temperature sensing element wire lumen 113 carried within the catheter tube 102. Preferably, the temperature sensing element wires 144 are shielded to block RF interference emitted by the ablation signal wires 124. Temperatures sensed by the temperature sensing elements 142 are processed by the controller 130. Based upon temperature input, the controller 130 adjusts the time and power level of RF energy transmissions by the conductive shell 120, in order to achieve desired lesion patterns and other ablation objectives.

By way of example, the temperature sensing elements 142 can take the form of thermistors or thermocouples. The connection of the temperature sensing elements 142 to the conductive shell 120 or electrode body 108 can be achieved in various ways, such as by attaching to the interior surface of the electrode body 108, or attaching to the exterior surface of the electrode body 108 beneath the electrically conductive shell 120. Temperature sensing elements 142 are preferably placed along the edges of the shell 120, where it adjoins the electrically non-conductive region of the electrode body 108, where high current densities can occur that lead to higher temperatures at the edges than elsewhere on the shell 120. Placing temperature sensing elements 142 along the edges assures that the hottest temperature conditions are sensed.

Further details concerning the preferred use of temperature sensing elements 142 and the placement thereof on the electrode element 106 are disclosed and described in the above-incorporated U.S. application Ser. No. 08/630,719. Further details concerning the use of multiple temperature sensing elements, including edge temperature sensing elements, and the use of temperature prediction methodologies, are disclosed and described in co-pending U.S. patent application Ser. No. 08/439,824, filed May 12, 1995, and entitled "Systems and Methods for Controlling Tissue Ablation Using Multiple Temperature Sensing Elements," which is fully incorporated herein by reference for all it discloses and teaches.

Figure 13:
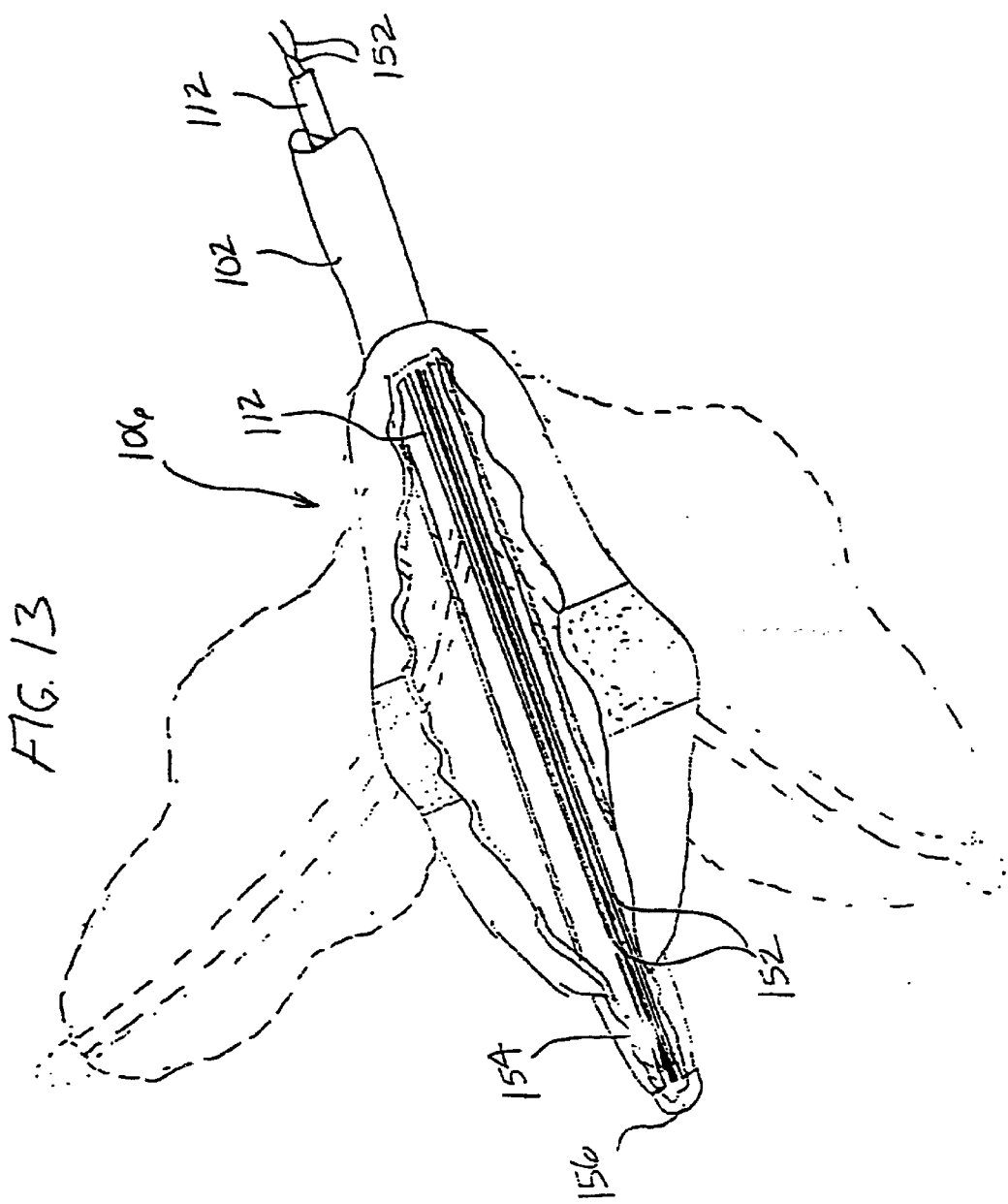
FIG. 13 is a partially cut-away perspective view of the electrode carrying structure of FIG. 2, particularly illustrating a preferred steering mechanism.

Referring again to FIG. 1, manipulation of the electrode carrying structure 106 through the vasculature and heart can be accomplished by use of a steering mechanism 146 incorporated into the handle 104 of the catheter assembly 100. The steering mechanism 146 can also be used to create contact between the electrode carrying structure 106 and the desired ablation tissue. The steering mechanism 146 includes a rotating cam wheel 148 coupled to an external steering lever 150 carried by the handle 104. The cam wheel 148 is attached to proximal ends of right and left steering wires 152. As seen in FIG. 13, the steering wires 152 pass with the ablation signal wires 124 through the main lumen 112 of the catheter tube 102 and connect at their distal ends to respective sides of a resilient bendable wire or center support 154 secured to the distal tip 156 of the catheter tube 102.

In operation, forward movement of the steering lever 150 bends or curves the center support 154, and with it the distal tip 156, in one direction, while rearward movement of the steering lever 150 bends or curves the center support 154, and with it the distal end 156, in the opposite direction. Such an arrangement allows the electrode carrying structure 106 to alternately deflect in opposite directions. As seen in FIGS. 2 and 3, opaque markers 162 are preferably deposited on the exterior surface of the catheter tube 102 proximal and distal to the electrode body 108, so that the physician can guide the device under fluoroscopy to the targeted site. Further details of this and other types of steering mechanisms are described in U.S. Pat. No. 5,254,088, issued to Lundquist et al., which is fully incorporated herein by reference for all it discloses and teaches.

Alternatively, the catheter assembly 100 and electrode carrying structure 106 can be delivered to the desired location within a pulmonary vein by employment of a guide wire, or a guide sheath, such as that disclosed in U.S. Pat. No. 5,636,634, issued to Kordis et al., which is fully incorporated herein by reference for all it discloses and teaches.

The electrode carrying structure 106 has been summarily described to provide a concise overview of the structural aspects of the invention. Further details and variations concerning the structure and manufacture of the electrode carrying structure 106 are disclosed in the above-incorporated U.S. application Ser. No. 08/630,719.

As will now be described, in accordance with a general aspect of the present invention, the catheter assembly 100 can be employed to isolate focal arrhythmia substrates in a pulmonary vein by creating a circumferential lesion inside of the pulmonary vein.

Figure 14:
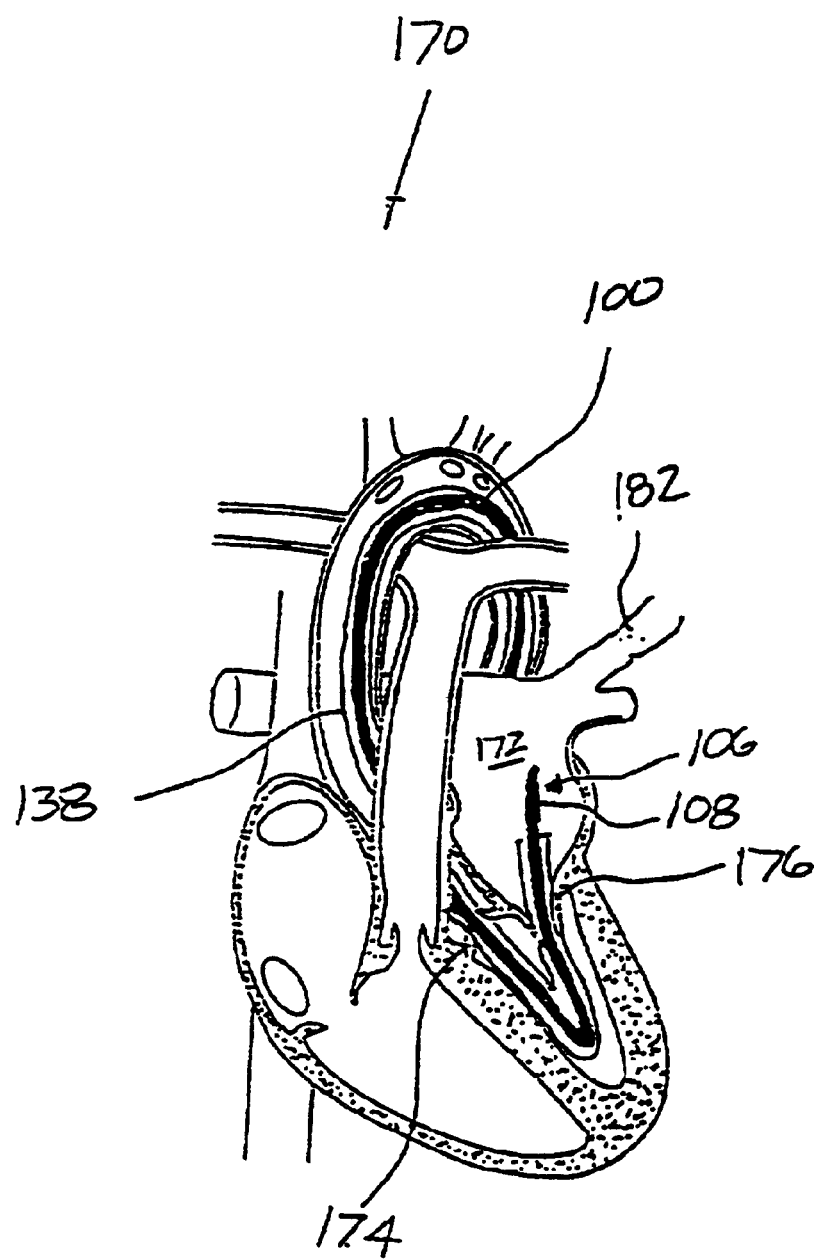
FIGS. 14 and 15 are simplified and somewhat diagrammatic perspective views of the internal human heart chambers and periphery.
Figure 15:
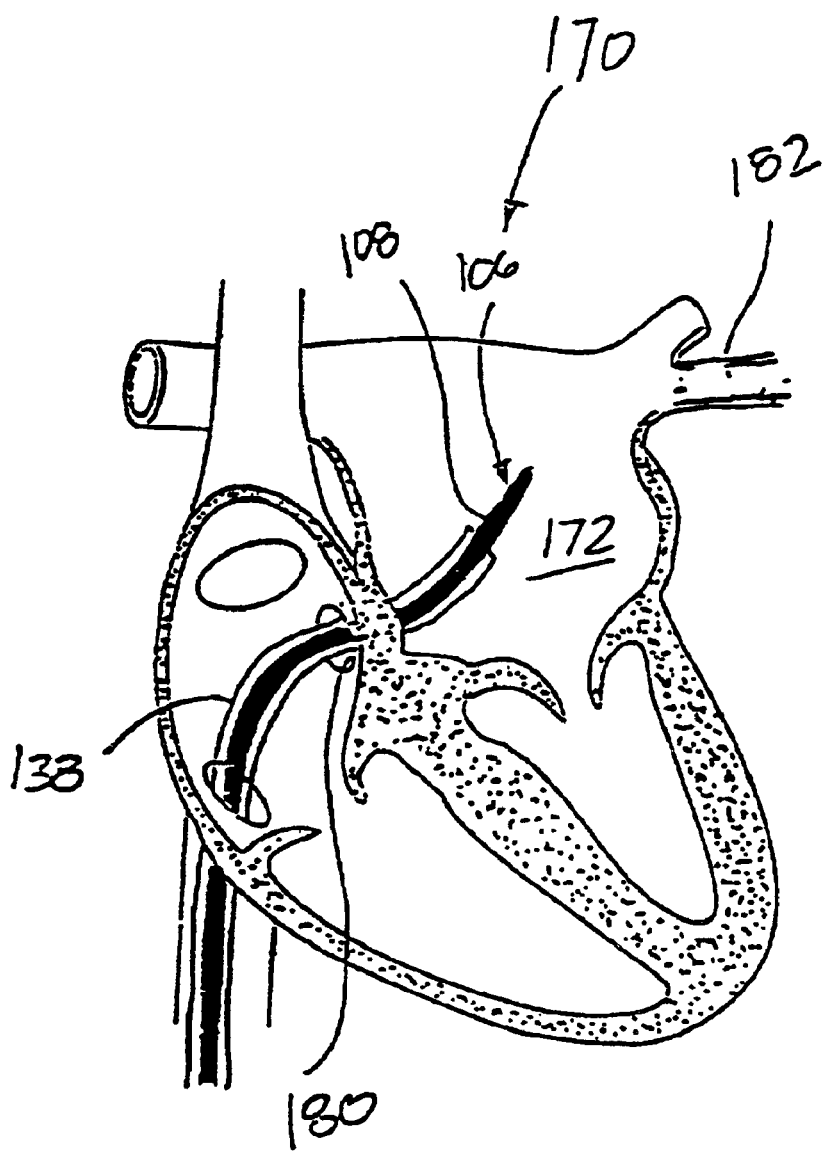

Referring to FIGS. 14 and 15, using the conventional introducer guide sheath 138 (or a guide wire), a physician can direct the electrode carrying structure 106 of the catheter assembly 100 into the left atrium 172, while the electrode body 108 is in its low profile (i.e., deflated) geometry. This can be accomplished via a conventional retrograde approach through the respective aortic and mitral valves 174 and 176 of the heart 170 (shown in FIG. 14). Alternatively, a transeptal approach can be employed to direct the electrode carrying structure 106 into the right atrium 178 through the atrial septum 180 and into the left atrium 172 (shown in FIG. 15). A detailed description of methods for introducing a catheter into the left atrium via a transeptal approach is disclosed in U.S. Pat. No. 5,575,810, issued to Swanson et al., which is fully incorporated herein by reference.

Once inside the left atrium 172, the physician can deliver the electrode carrying structure 106 into a desired pulmonary vein 182 by employing the steering mechanism 146 on the handle 104 of the catheter assembly 100. Alternatively, the guide sheath 138 or guide wire used to deliver the electrode carrying structure 106 into the left atrium 172 can be situated in the desired pulmonary vein 182 for delivery of the electrode carrying structure 106 therein.

Figure 16:
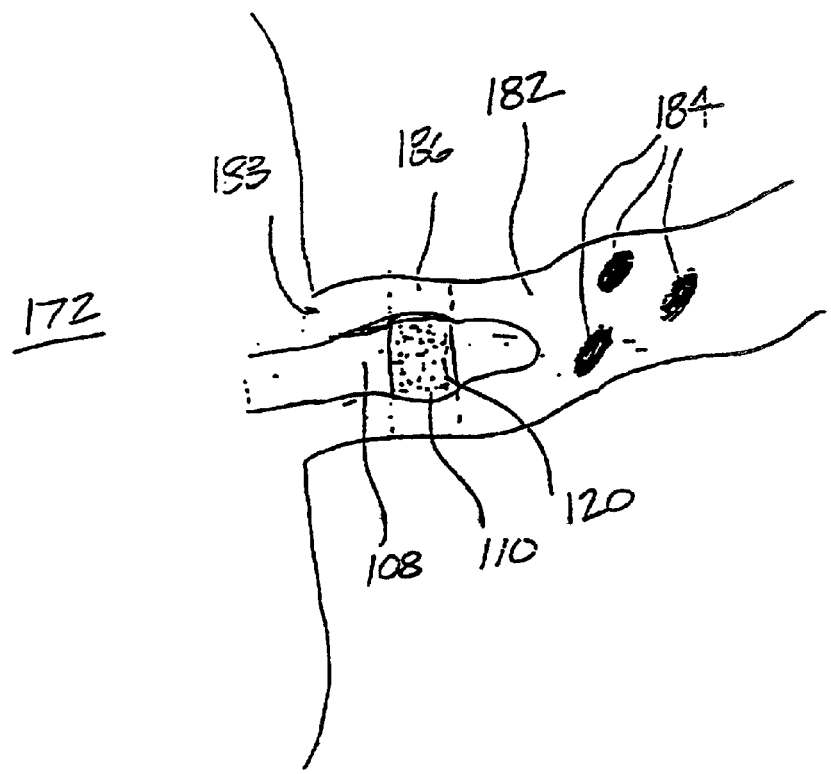
FIG. 16 is a side view of the electrode carrying structure of FIG. 2 disposed in a pulmonary vein in which focal arrhythmia substrates lie, wherein the electrode is depicted in a deflated geometry.
Figure 17:
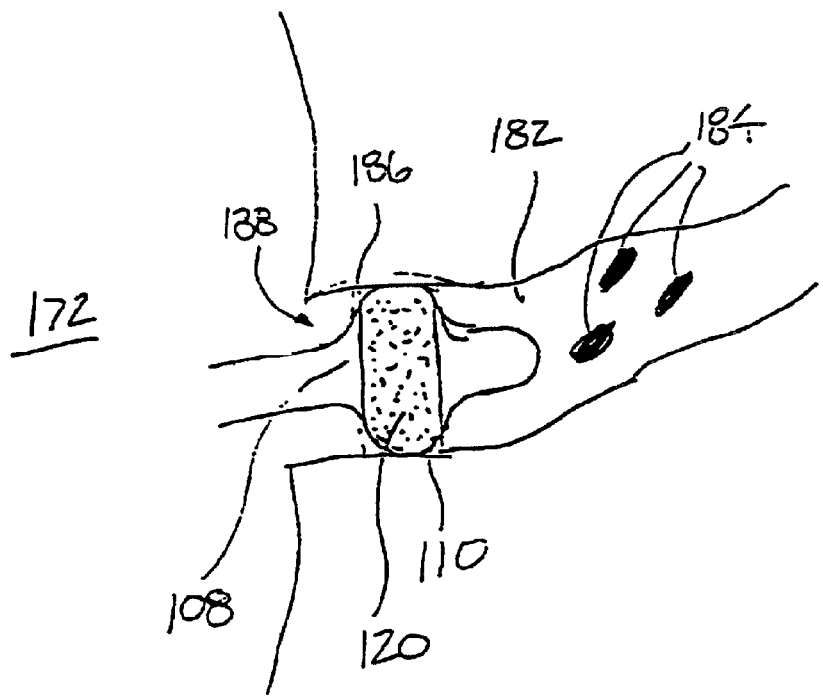
FIG. 17 depicts the electrode carrying structure of FIG. 16, wherein the electrode carrying structure is depicted in an expanded geometry.

Referring to FIG. 16, in order to isolate focal arrhythmia substrates 184 located in a pulmonary vein 182, the physician situates the electrode body 108 into the pulmonary vein 182, such that the enlarged circumferential region 110 is disposed in a selected tissue region 186 in the interior of the pulmonary vein 182, adjacent to the opening 188 into the left atrium 172. As depicted in FIG. 17, once the electrode carrying structure 106 is properly situated within the pulmonary vein 182, the physician causes the electrode body 108 to take its expanded geometry—i.e., via the injection of pressurized liquid through the inflation lumen 116, or by the retraction of a guide sheath (not shown in FIG. 16 or 17) to allow an internal support structure to expand (also not shown in FIG. 16 or 17), or both—thereby placing the conductive shell 120 on the electrode body 108 into firm contact with the selected tissue region 186 of the pulmonary vein 182.

The physician then causes RF energy to be conveyed from the generator 128 to the conductive shell 120 in a manner described above, as governed by the controller 130. The conductive shell 120 causes the RF energy to be transmitted into the tissue of the selected region 186 of the pulmonary vein 182 to a return electrode (not shown), which is preferably an external patch electrode, thereby forming a unipolar arrangement. Alternatively, in the case of the segmented conductive shell arrangement depicted in FIG. 4, the transmitted energy can pass through tissue between adjacent conductive segments 117 to form a bipolar arrangement.

Figure 18:
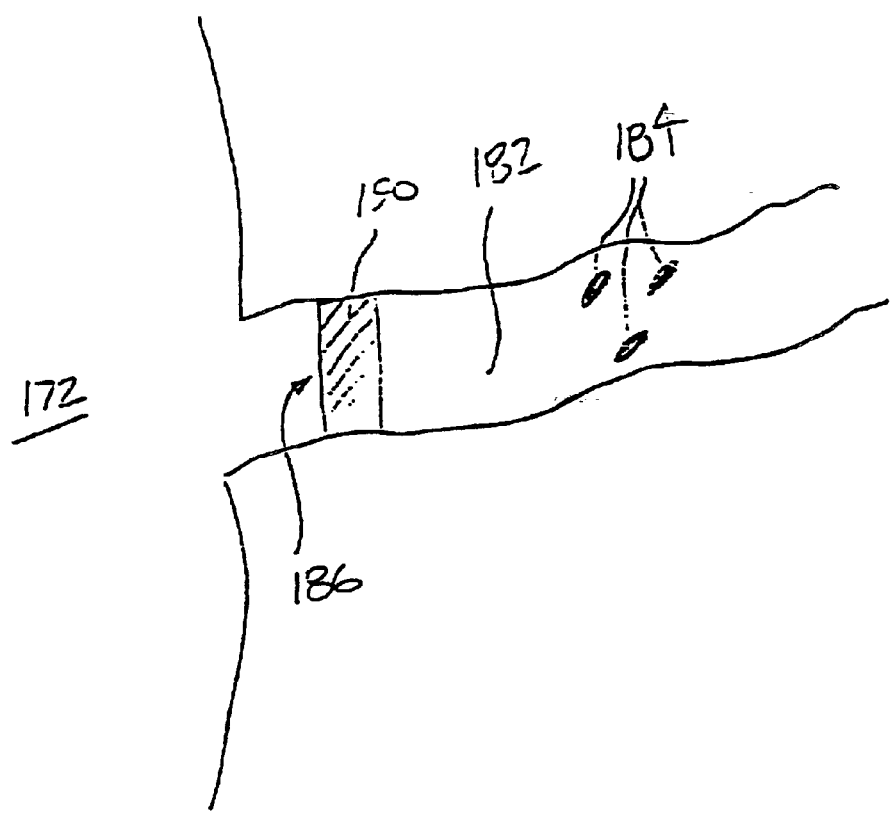
FIG. 18 depicts a lesion formed in the pulmonary vein of FIG. 16 following a preferred ablation procedure.

Referring to FIG. 18, the transmitted RF energy creates a lesion 190 covering the circumferential region 186 of the pulmonary vein 182 proximate the conductive shell 120, whereby the lesion 190 isolates the focal arrhythmia substrates 184 from the left atrium 172, restoring normal myocardial contraction.

Following the ablation process, the physician causes the electrode body 108 to return to its collapsed geometry—i.e., by removing the liquid inflation medium from the electrode body 108 through the port 118 and/or retracting the electrode body 108 into the guide sheath 138 if the electrode body 108 is further supported by an interior support structure 132. The physician can then extract the electrode carrying structure 106 from the pulmonary vein 182, after which it can be repositioned inside another pulmonary vein for continued ablation therapy or extracted altogether from the patient.

Figure 19:
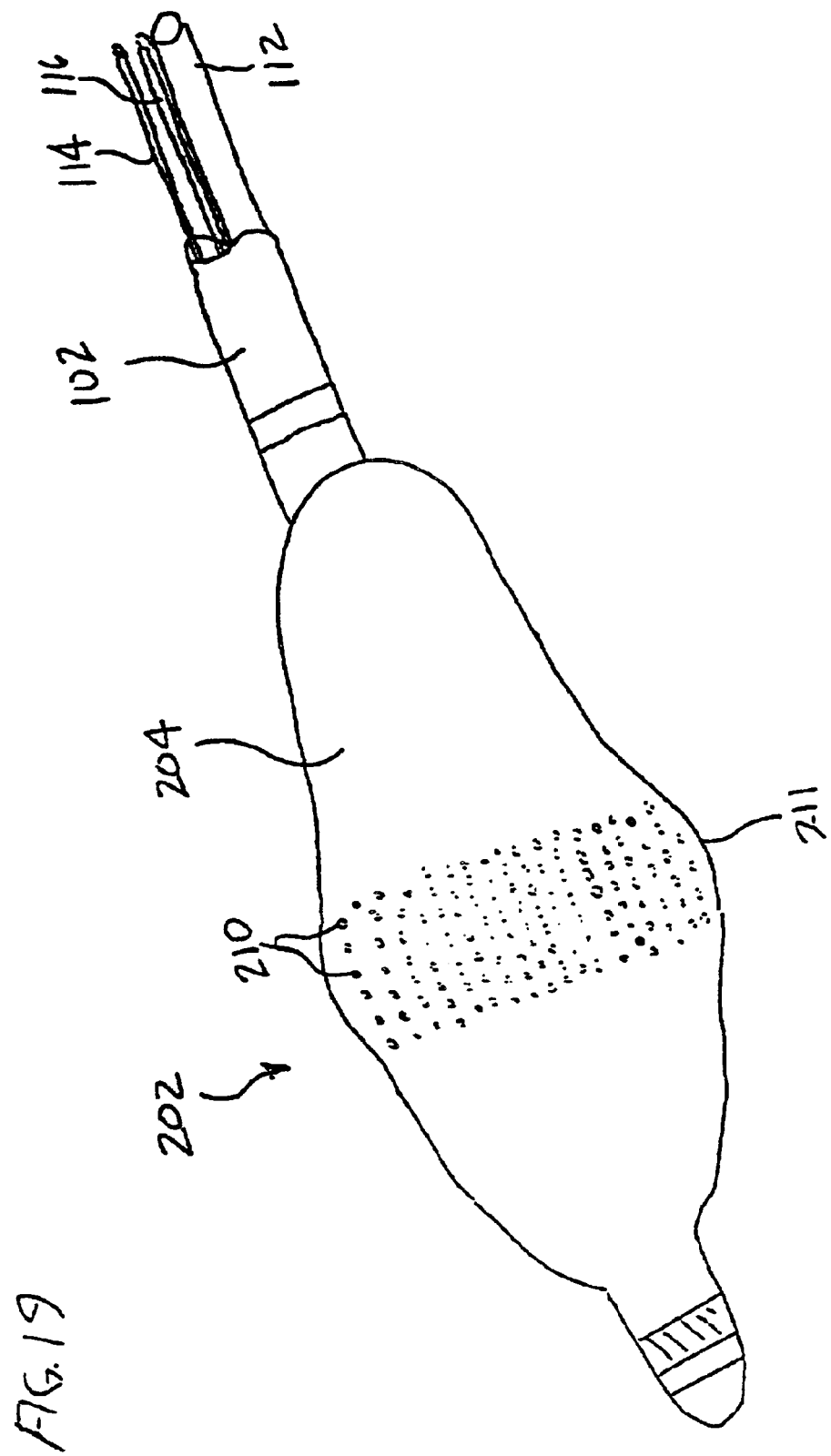
FIG. 19 is a partially cut-away perspective view of a further preferred electrode carrying structure for use in the catheter assembly of FIG. 1, employing a microporous-electrode carrying structure.
Figure 20:
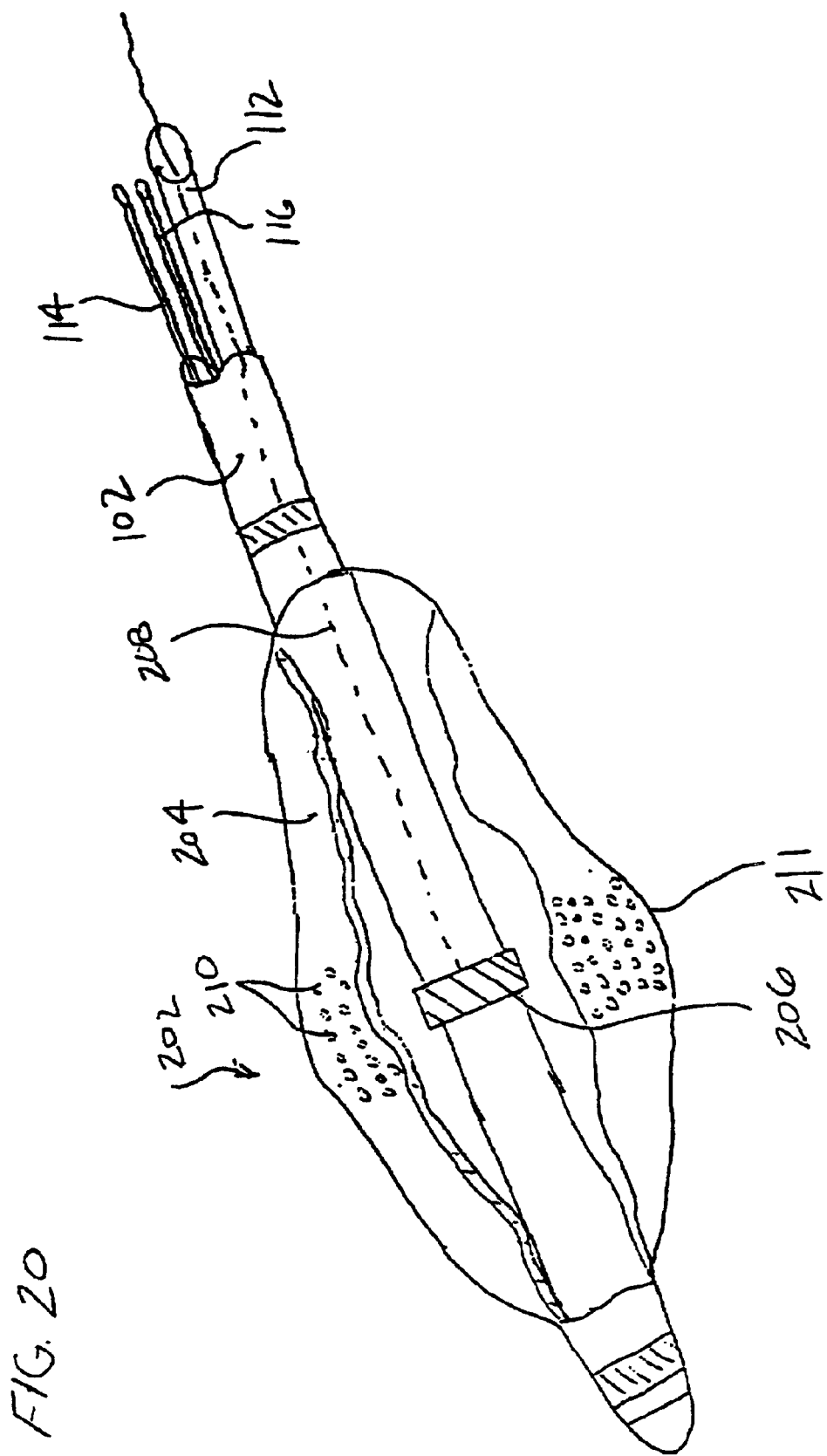
FIG. 20 is a partially cut-away perspective view of the electrode carrying structure of FIG. 19, particularly illustrating an interior electrode.

Referring to FIGS. 19 and 20, a second preferred electrode carrying structure 202 for use with the catheter assembly 100 comprises an electrode 206 that is positioned within the interior of a microporous expandable-collapsible body 204. In particular, the expandable-collapsible electrode body 204 is suitably bonded to, and disposed about, the catheter tube 102. The interior electrode 206 may comprise, by way of non-limiting example, a coil that wraps around the outer surface of the distal end of the catheter tube 102. Preferably, the interior electrode 206 is constructed of a material having both a relatively high electrical conductivity and a relatively high thermal conductivity. Materials possessing these characteristics include, among others, gold, platinum, platinum/iridium, conductive ink epoxy, or a combination thereof. In particular, noble metals are preferred.

With additional reference back to FIG. 1, an insulated ablation signal wire 208 (shown in phantom) is coupled to the interior electrode 206, and extends from the interior electrode 206, through the main lumen 112 of the catheter tube 102, to the external connector 126 on the handle 104. The connector 126 electrically couples the interior electrode 206 to the RF generator 128.

As with the previously described preferred electrode carrying structure 106, a liquid medium is conveyed with positive pressure to the interior of the body 204 through the inflation lumen 114, thereby allowing the body 204 to assume an expanded geometry. The liquid medium used to fill the body 204, however, includes an electrically conductive liquid. The liquid medium establishes an electrically conductive path, which conveys RF energy from the interior electrode 206.

In association with the interior electrode 206, the body 204 is formed by an electrically non-conductive thermoplastic or elastomeric material that contains a multiplicity of micropores 210 formed in a ring-like arrangement around an expanded circumferential area 211. The regions of the electrode body 204 that are immediately proximal and distal to the ring of micropores 210 are non-porous, i.e., do not include the micropores or are masked with a non-porous material. In accordance with this aspect of the invention, the micropores 210 (shown diagrammatically in enlarged form in FIGS. 19 and 20 for purposes of illustration) provide for ionic transport of ablation energy from the interior electrode 206, via the electrically conductive liquid medium, to tissue outside the electrode body.

The composition of the electrically conductive liquid medium can vary. Preferably, the selected liquid medium possesses a low resistivity to decrease ohmic losses, and thus ohmic heating effects, within the electrode body 204. By way of one preferred example, the liquid medium may comprise a hypertonic saline solution, having a sodium chloride concentration at or near saturation, which is about 9% weight by volume. Hypertonic saline solution has a low resistivity of only about 5 ohm-cm, compared to blood resistivity of about 150 ohm-cm and myocardial tissue resistivity of about 500 ohm-cm. The electrical resistivity of the electrode body 204 can be controlled by specifying the pore size of the material, the porosity of the material, and the water absorption characteristics (hydrophilic versus hydrophobic) of the material.

As will be appreciated by those skilled in the art, additional features may be incorporated into the electrode carrying structure 202. By way of non-limiting examples, the above-described "folding regions" can be pre-formed into the body 304, and temperature sensing elements can be formed into or at the edges of the microporous region of the body 304.

Operation and use of the electrode carrying structure 202 is similar to that of conductive-surface based electrode carrying structure 106, except that the RF energy is delivered to the tissue of the pulmonary vein in a different way. In particular, the electrode body 204 is maneuvered to a desired ablation site within a pulmonary vein in an identical fashion as discussed above in conjunction with FIGS. 16–17. Once in place, the attending physician inflates the electrode body 204 with the selected liquid medium, causing the circumferential porous ring area 211 to contact the tissue around the inner diameter of the pulmonary vein.

The physician then conveys RF energy from the generator 128 to the interior electrode 206, as governed by the controller 130, whereby RF currents are carried by the ions through the pores 210. The RF currents provided by the ions result in no net diffusion of ions, as would occur if a DC voltage were applied, although the ions do move slightly back and forth during the RF frequency application. Notably, this ionic movement (and current flow) in response to the applied RF energy does not require perfusion of the liquid medium through the pores 210. In particular, due largely to mass concentration differentials across the pores 210, ions in the liquid medium will pass therethrough—i.e., due to concentration differential-driven diffusion. Ion diffusion through the pores 210 will continue so long as a concentration gradient is maintained across the electrode body wall 204, wherein the ions provide the means for conducting current across the electrode body 204.

The ions convey RF energy through the pores 210 and into the surrounding body tissue to a return electrode, which is typically an external patch electrode, thereby forming a unipolar arrangement. This results in a circumferential lesion within the pulmonary vein as depicted in FIG. 18. A more detailed description of a preferred microporous electrode body and manufacture thereof is provided in the above-incorporated U.S. application Ser. No. 08/631,356.

Figure 21:
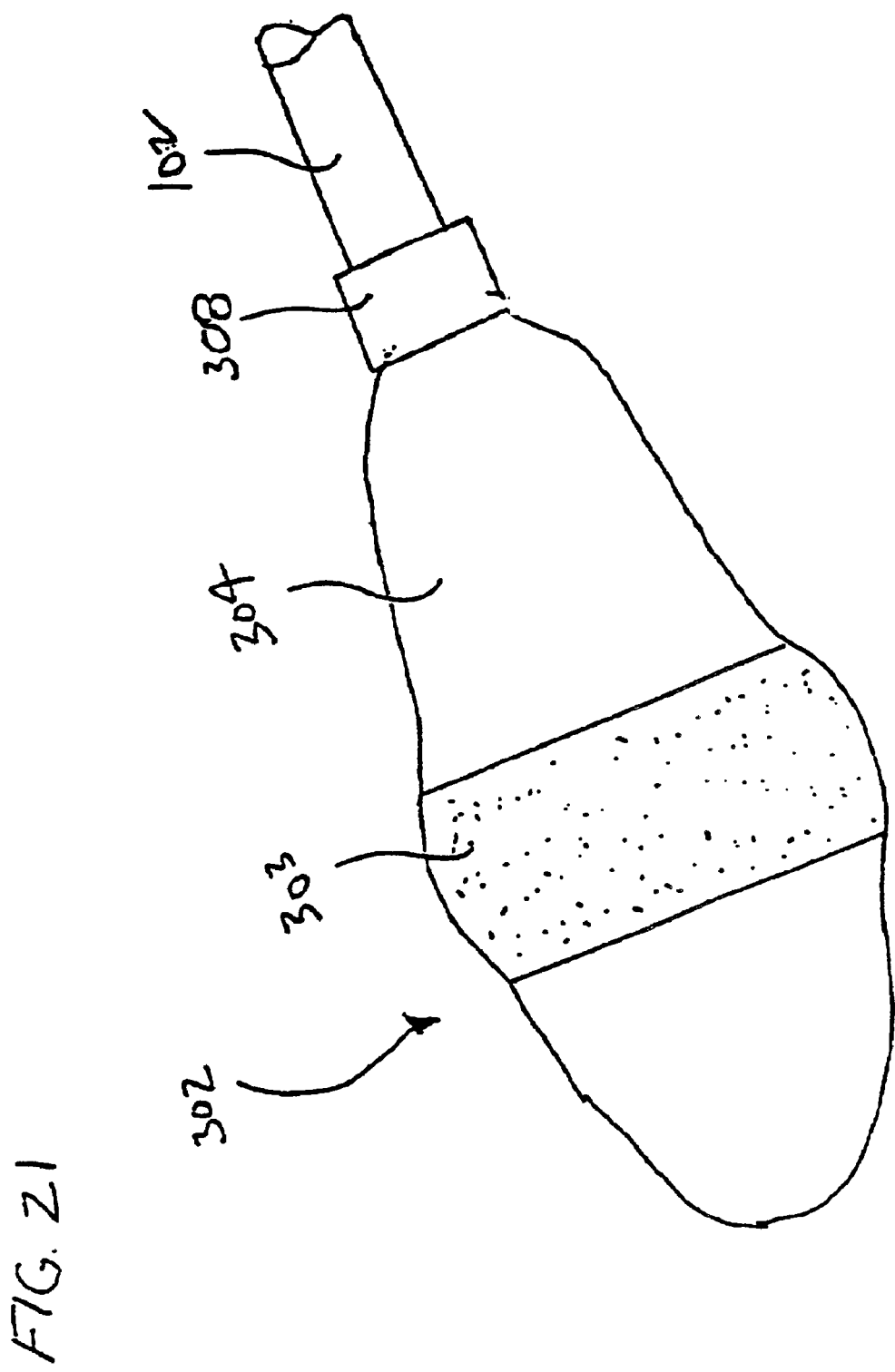
FIG. 21 is partially cut-away perspective view of a still further preferred electrode carrying structure for use in the catheter assembly of FIG. 1, wherein the electrode carrying structure is bonded to the open distal tip of the catheter tube.

Referring to FIG. 21, a third preferred electrode carrying structure 302 for use with the catheter assembly 100 includes an expandable-collapsible electrode body 304 that is suitably mounted to an open distal end of the catheter tube 102, rather than bonded to and disposed about a closed distal end, as with the afore-described preferred electrode carrying structures 106 and 202, respectively.

Figure 22:
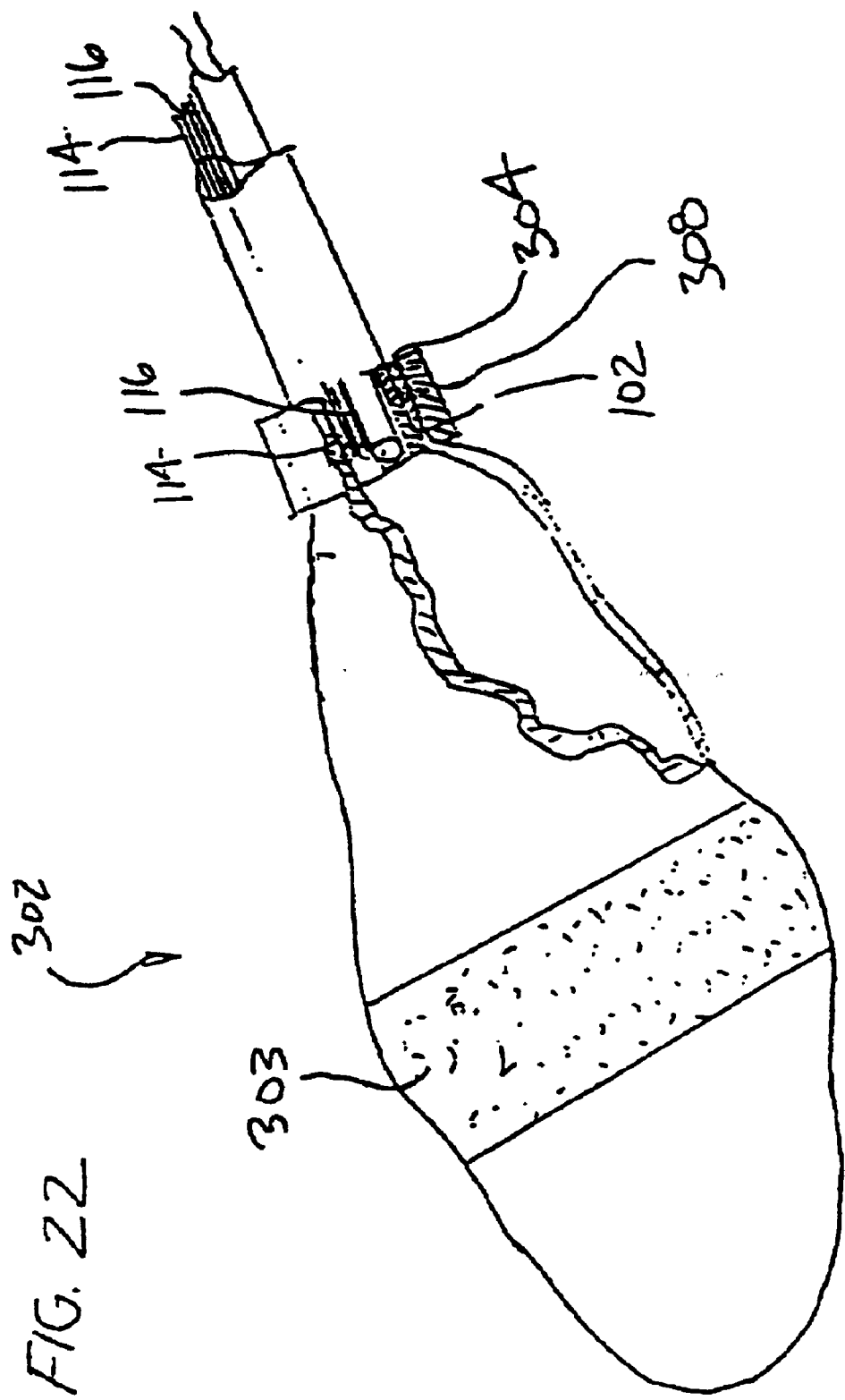
FIG. 22 is a partially cut-away perspective view of the electrode carrying structure of FIG. 21, particularly illustrating the connection between a catheter tube and an expandable-collapsible electrode body.

In particular, as best seen in FIG. 22, a sleeve 308 couples the proximal end of the body 304 to the open distal end of the catheter tube 102. Inflation and venting of the electrode body 304 is performed in the same manner as described above with respect to electrode carrying structures 106 and 202, with the notable exception that the distal ends of the inflation tube 114 and venting tube 116 open into the interior of the body 304 at the proximal end thereof. The sleeve 308 functions to withstand forces exerted to expand the electrode body 304, thereby preventing separation of the electrode body 304 from the catheter tube 102. Where an inflation medium is used, the sleeve 308 also forms a fluid seal that resists leakage of the liquid medium at inflation pressures. The sleeve 308 can be secured about the catheter tube 102 in various ways, including adhesive bonding, thermal bonding, mechanical bonding, screws, winding, or a combination of any of these.

The electrode carrying structure 302 includes an active radio frequency emitting mechanism 303 that may be either a conductive surface or microporous arrangement. As with the electrode carrying structure 202, additional features may be incorporated into structure 302, such as the above-described, pre-formed folding regions and temperature sensing elements.

Figure 23:
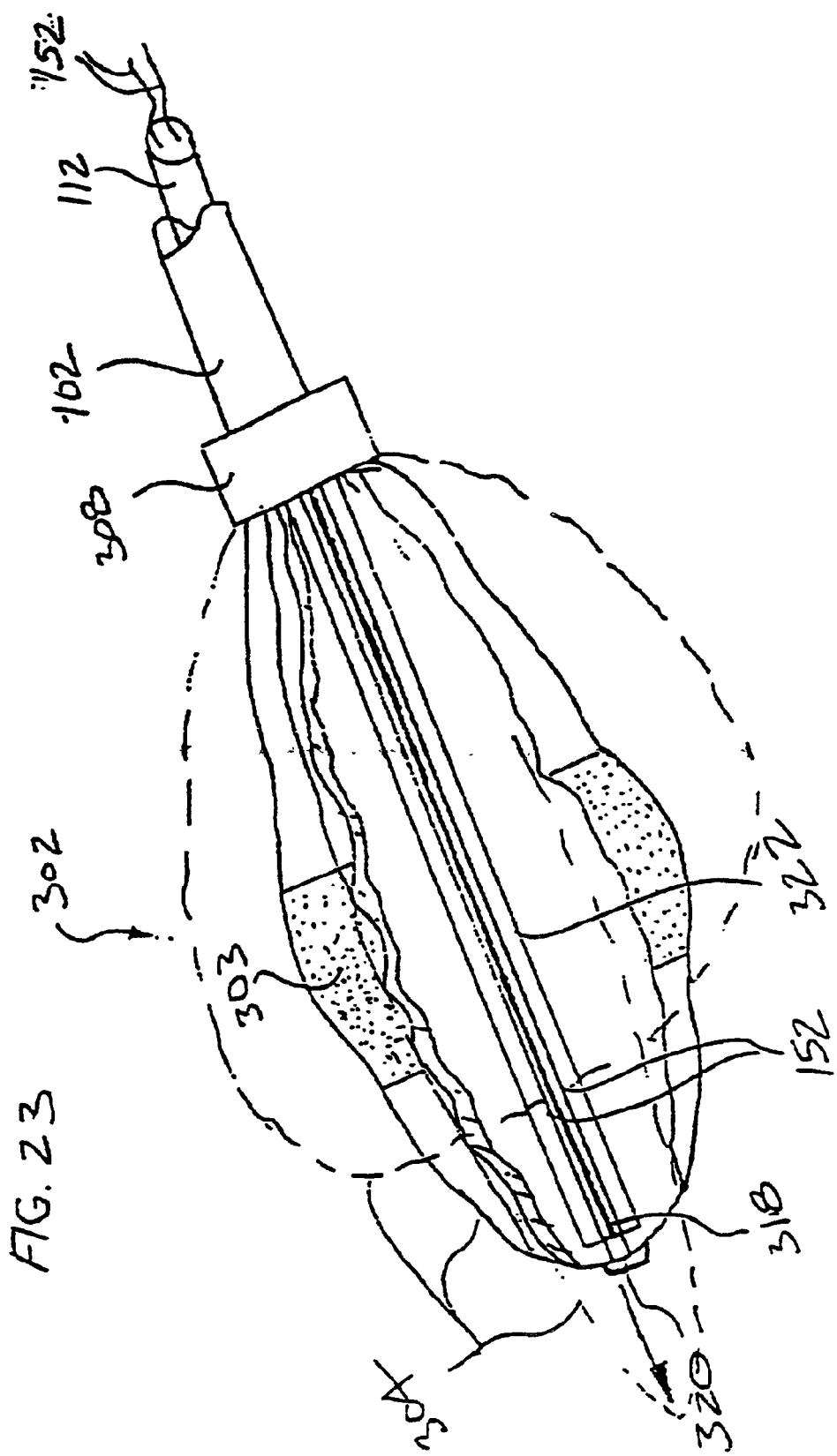
FIG. 23 is a partially cut-away perspective view of the electrode carrying structure of FIG. 21, particularly illustrating a preferred steering mechanism.

Manipulation of the electrode carrying structure 302 through the vasculature and heart can be accomplished through the steering mechanism 146 on the handle 104, as depicted in FIG. 1, or by the other aforedescribed steering means. In particular, referring to FIG. 23, the steering wires 152 pass through the main lumen 112 of the catheter tube 102 and connect to the left and right sides of a resilient bendable wire or center support 318 that extends beyond the distal end of the catheter tube 102 within a tube 322 inside the body 304. The distal end of the center support 318 is secured to a distal fixture 320 suitably bonded to the distal end of the body 304. Further details on the structure and attachment of the distal fixture 320 to the distal end of a catheter are disclosed and described in the above-incorporated U.S. application Ser. No. 08/630,719.

With reference again to FIG. 1, forward movement of the steering lever 150 of the steering mechanism 146 bends or curves the center support 318, and with it the distal fixture 320, in one direction. Rearward movement of the steering lever 150 bends or curves the center support 318, and with it the distal fixture 320, in the opposite direction. Such an arrangement allows the electrode carrying structure 302 to alternately deflect in opposite directions.

Figure 24:
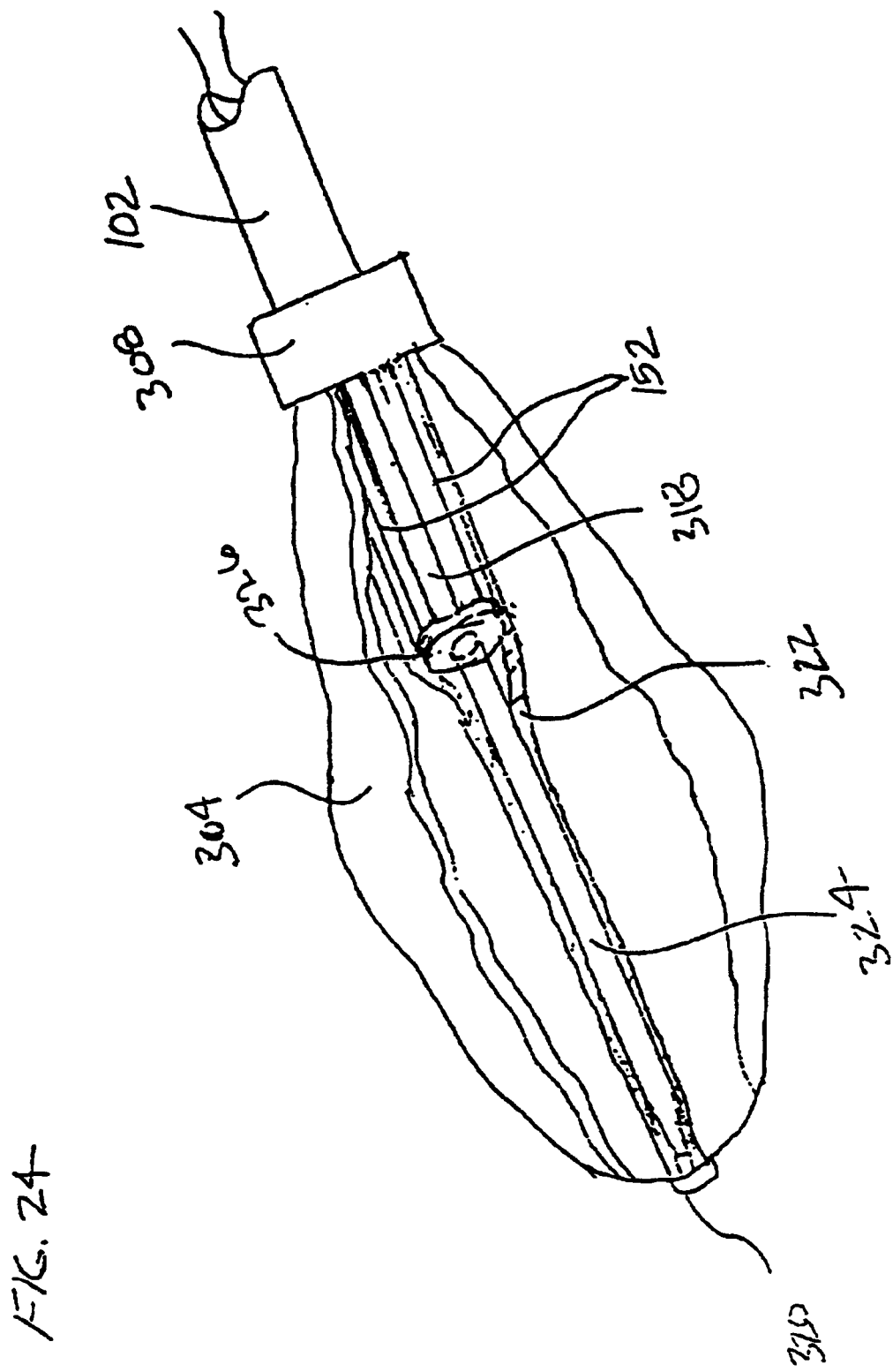
FIG. 24 is a partially cut-away perspective view of the electrode carrying structure of FIG. 21, particularly illustrating a preferred stilette and steering mechanism.

Referring to FIG. 24, a stilette 324 can be secured to the distal fixture 320, extending from the distal fixture 320 inside the tube 322 to a suitable push-pull controller 160 on the handle 104 of the distal mechanism (see FIG. 1). The stilette 324 is movable along the axis of the catheter tube 102. Moving the stilette 324 forward pushes axially upon the distal fixture 320, thus elongating the body 304. Moving the stilette 324 rearward pulls axially upon the distal fixture 320, thus expanding the body 304.

While the stilette 324 can be used by itself, in the illustrated and preferred embodiment, the stilette 324 is combined with the steering mechanism 146. The distal end of the stilette 324 near the distal fixture 320 comprises the bendable center support 318. A collar 326, through which the center support 318 at the end of the stilette 324 passes for movement along the axis of the catheter tube 102, is heat-shrunk fit within the tube 322. Steering wires 152 are attached to the collar 326. Pulling on the steering wires 152 radially deflects the collar 326, thereby bending the center support 318 at the end of the stilette 318 in the direction of the pulled steering wire 152. Thus, a radial steering function is provided in tandem with the axial push-pull action of the stilette 318.

Alternately, when used in association with a body that is internally supported by an interior support structure, such as shown in FIGS. 5, 6, and 7, the stilette 324 can be used instead of the guide sheath 138 to expand and collapse the body.

Operation and use of the electrode carrying structure 302 to create lesions within the desired pulmonary veins is similar to that described above with respect to the electrode carrying structures 106 and 202.

Figure 25:
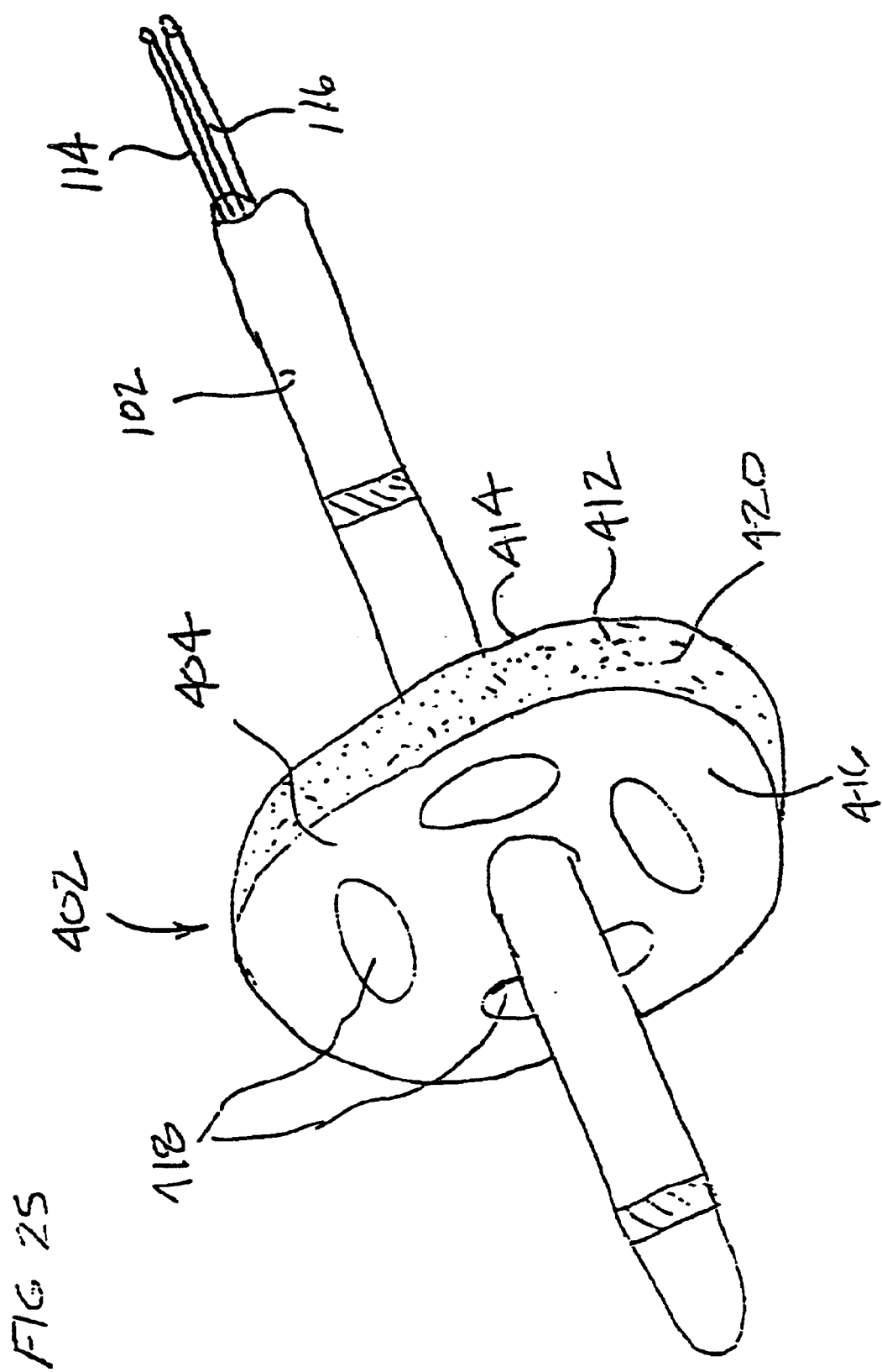
FIG. 25 is a partially cut-away perspective view of a yet further preferred electrode carrying structure for use in the catheter assembly of FIG. 1, wherein the electrode carrying structure employs a disk-shaped balloon-like body with blood infusion lumens.

Referring to FIG. 25, yet another preferred electrode carrying structure 402 for use with the catheter assembly 100 includes a disk-shaped expandable-collapsible electrode body 404 with blood infusion lumens 418. In particular, the body 404 is suitably bonded to, and disposed around, the distal portion of the catheter tube 102. The body 404 is made of a polymeric, electrically nonconductive material, like polyethylene, polyurethane, or PEBAX®. Inflation and venting of the body 404 is performed in the same manner as described above with respect to electrode carrying structures 106, 202, and 302. The geometry of the body 404 can be altered between a collapsed geometry (not shown) and an enlarged, or expanded, geometry (shown in FIG. 25), which takes the form of a disk with a circumferential region 412 and respective flat proximal and distal surfaces 414 and 416 that are orthogonal to the circumferential region 412. The body 404 has at least one, and preferably at least four blood infusion lumens 418, extending through the body 404 between the respective flat proximal and distal regions 414 and 416.

The active electromagnetic emitting mechanism of the electrode carrying structure 402 comprises a conductive shell 420 suitably formed on the circumferential region 412 of the body 404, in a manner substantially the same as the above-described conductive shell 120. For purposes of power efficiency, the flat proximal and distal regions 414 and 416 of the body 404 are preferably masked while the conductive shell 420 is deposited on the circumferential region 412.

Manipulation of the electrode carrying structure 402 through the vasculature and heart can be accomplished through the steering mechanism 146 on the handle 104 (shown in FIG. 1), or by other steering means. As with the previously describe electrode carrying structures 202 and 302, additional features may be incorporated into structure 402, such as pre-formed folding regions and temperature sensing elements. By way of further examples, the active radio frequency emitting mechanism of the electrode carrying structure 402 can be a microporous arrangement, rather than a deposited conductive shell. Also, the conductive shell 420 may be segmented rather than contiguous. Operation and use of the electrode carrying structure 402 is similar to that hereinbefore described with the exception that the blood infusion lumens extending through the body 418 allow passage of blood therethrough, while the body 404 is in its expanded geometry within a pulmonary vein.

Figure 26:
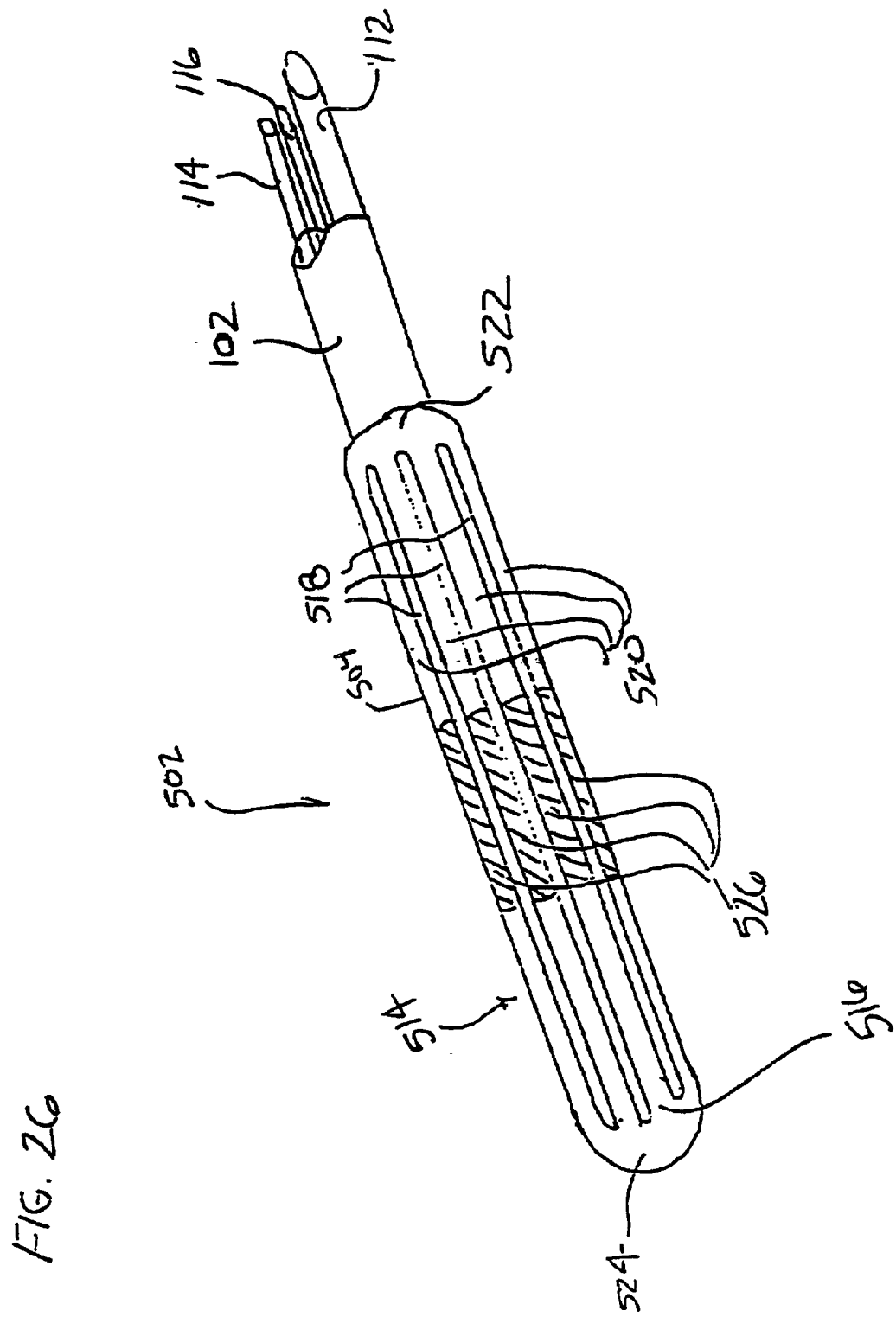
FIG. 26 is a partially cut-away perspective view of yet another preferred electrode carrying structure for use in the catheter assembly of FIG. 1, wherein the electrode carrying structure employs a balloon actuated splined tubular assembly mounted to the proximal end of a balloon-like body depicted in a expanded geometry.
Figure 27:
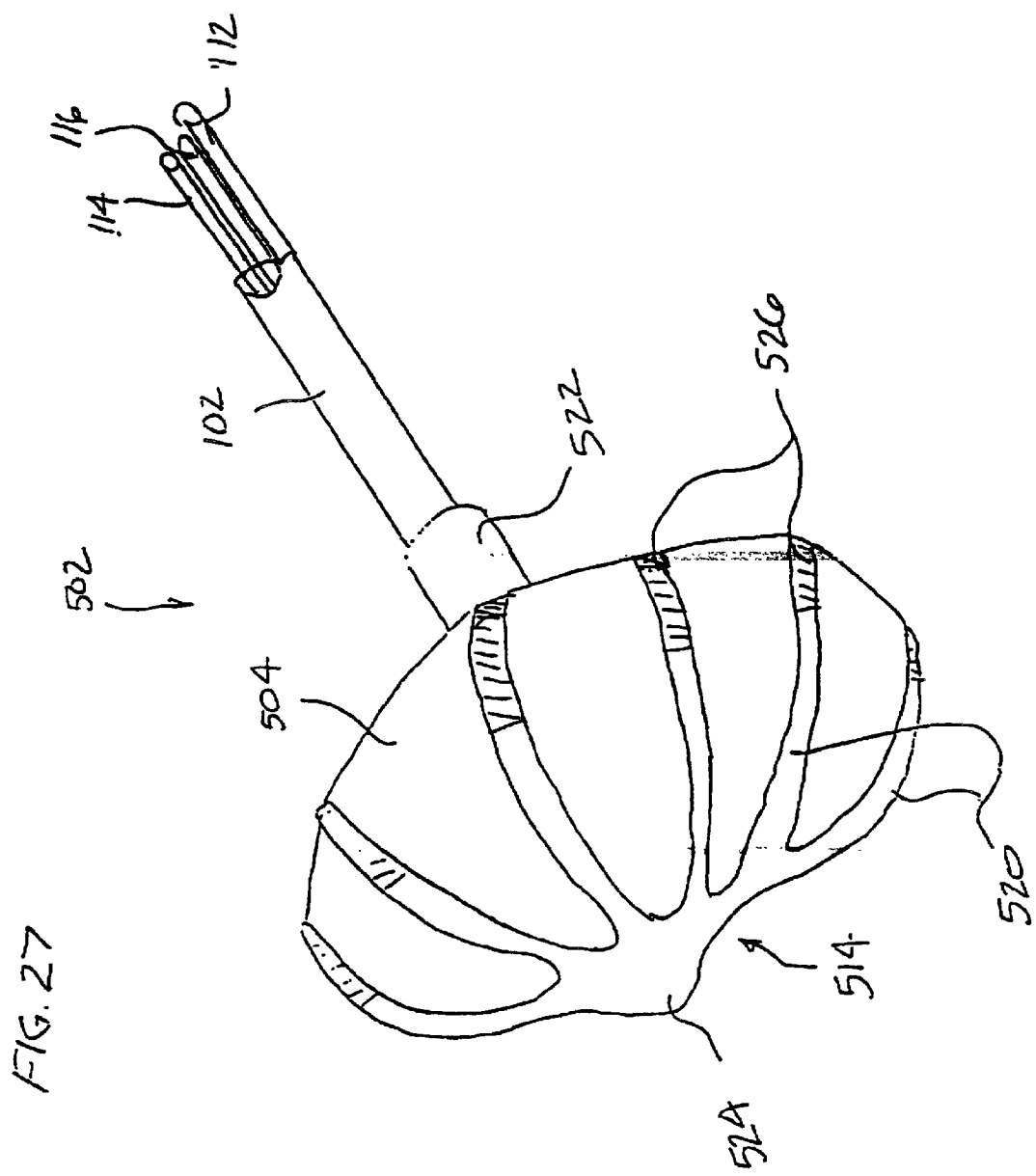
FIG. 27 is a partially cut-away perspective view of the electrode carrying structure of FIG. 26, wherein the electrode carrying structure is shown in a collapsed geometry.
Figure 28:
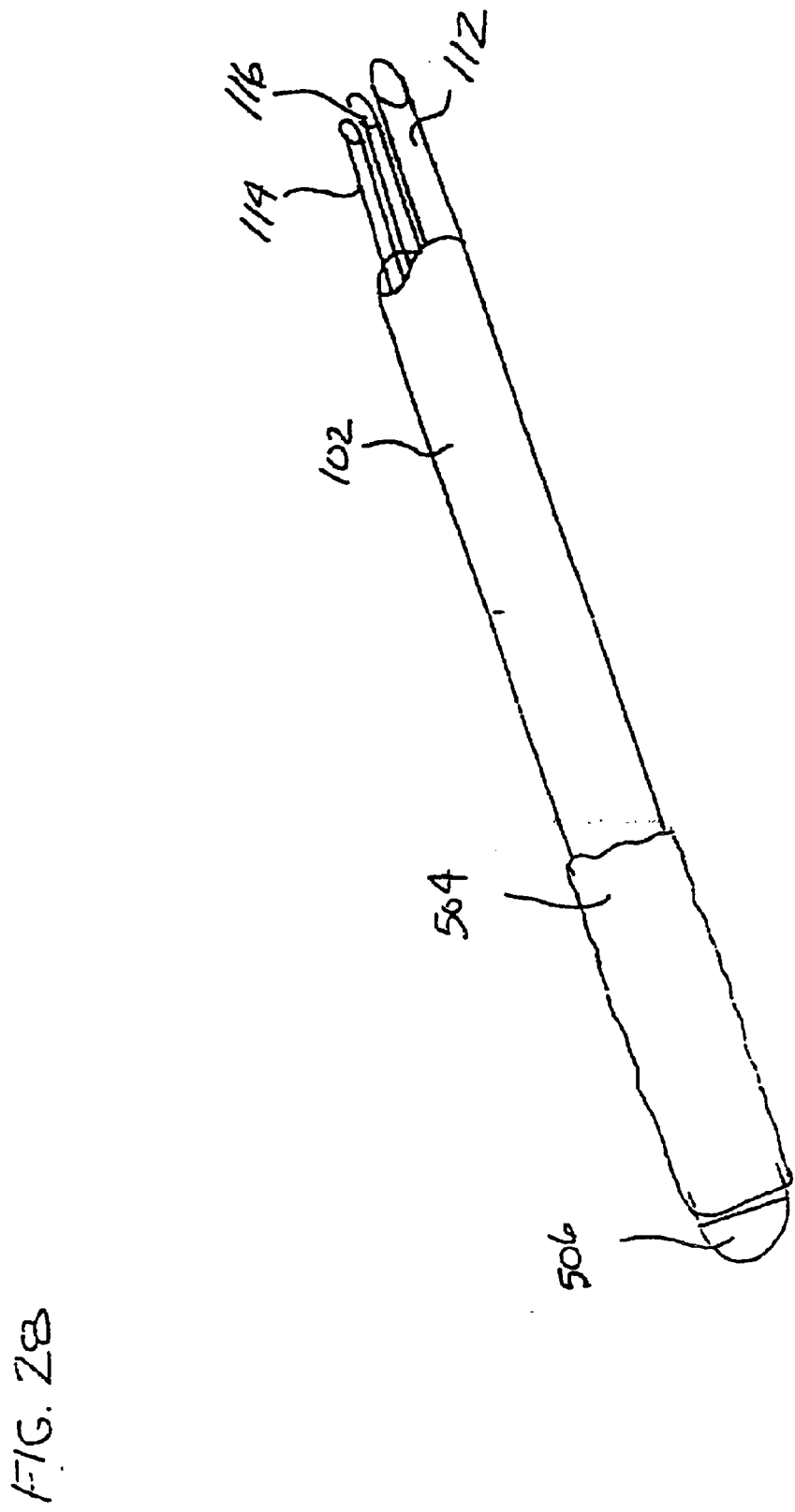
FIG. 28 is a partially cut-away perspective view of the balloon-like body of the electrode carrying structure of FIG. 26.

Referring to FIGS. 26–28, a still further preferred electrode carrying structure 502 for use with the catheter assembly 100 includes a balloon activated, splined tubular assembly 514.

In particular, the electrode carrying structure 502 includes an expandable-collapsible body 504 bonded to and disposed about the distal end of the catheter tube 102. Inflation and venting of the body 504 using the inflation lumen 114 and venting lumen 116 is performed in the same manner as described above with respect to electrode carrying structures 106 and 202.

The splined tubular assembly 514 comprises a slit plastic tube or a thin wall metal (foil) tubing or combination thereof. Several cuts are made along the longitudinal axis of the tubular assembly 516 to form alternating slits 518 and splines 520. Preferably, the slits 518 extend proximally and distally to about 1 mm from the respective proximal and distal ends of the tubular spline assembly 516 to form a proximal collar 522 and a distal cap 524 thereon.

If the splined tubular assembly 514 is made entirely out of plastic, flat metal electrodes 526 are suitably bonded to the geometric center of the splines 520 (best shown in FIG. 26) to serve as the transmitter of the RF ablation energy. Alternatively, a highly conductive material can be deposited on the splines 520 in the manner described above with respect to the electrode carrying structure 106. If the tubular assembly 516 is made from a combination of plastic and thin wall metal tubing, the metal is formed in the geometric center of the splines 520 to form electrodes 526 thereon.

The splined tubular assembly 514 is disposed about the body 504 with the distal cap 524 of the tubular assembly 514 suitably bonded to the distal tip (not shown) of the catheter tube 102. The splines 520 and proximal collar 522 are not affixed to the body 504 or the catheter tube 102. In this manner, the splines 520 are free to move in relation to the body 504, and the proximal collar 522 is free to move axially in the distal direction relative to the catheter tube 102. In this manner, the body 504 acts as an actuator member for the tubular assembly 514. That is, the tubular assembly 514 expands and contracts as the body 504 respectively expands and contracts. The body 504, however, must not be too large or elastic that portions of the body 504 do not extend outside the profile of the tube 514.

In a presently preferred embodiment, the respective length and diameter of the tubular assembly is configured to allow advancement of the electrode carrying structure 502 through the human vasculature. The expanded body 504 takes on a generally spherical shape, but ultimately, however, the structure of the tubing assembly 516 will dictate the dimensions of the body 504. That is, the size of the expanded body 504 must correspond with the size of the tubular assembly 514, thereby creating a firm fit therebetween upon expansion of the body 504. Preferably, the longitudinal centers of the body 504 and the tubular assembly 514 are in a positional relationship with each other, such that when the body 504 is fully expanded, the electrodes 526 will be located at the outermost circumference of the expanded tube 514 (best seen in FIG. 27), thereby ensuring intimate contact between the electrodes 526 and the tissue to be ablated.

Each electrode 526 is electrically coupled in parallel to a pair of ablation signal wires (not shown) that extend through the main lumen 112 of the catheter tube 102 to the RF generator, wherein the controller 130 governs the deliver of RF ablation energy to the electrodes 526 according to preestablished criteria. The number of splines 520 determines the spacing of the electrodes 526, which must be optimized to create contiguous lesions. Further details concerning the preferred spacing of segmented electrodes are disclosed in Swanson et al., U.S. Pat. No. 5,582,609.

The electrode carrying structure 502 can include various other features that were described with respect to the previous electrode carrying structures 106, 202, 302 and 402. For example, an interior support structure can be incorporated into the body 504 to augment or replace the force of the liquid medium pressure inside the body 504. The electrodes 526 can be segmented to optimize current density. The body 504 can be molded with crease regions to aid in the folding thereof. Temperature sensing elements can be placed underneath the electrodes 526 at locations dictated by consideration of the aforementioned criteria.

Operation and use of the electrode carrying structure 502 is similar to that described with respect to the electrode carrying structure 106. By employing the afore-described methods, the electrode carrying structure 502 is located within the desired pulmonary vein, while the body 504 is in its collapsed geometry. When the electrode carrying structure 502 is situated in the desired location, the physician enlarges the body 504 of the electrode carrying structure 502 into its expanded geometry. Expansion of the body 504 causes the splines 520 of the tubular assembly 514 to correspondingly expand. As the splines 520 expand, the proximal collar 522 of the tubular assembly 514 moves axially in the distal direction until it abuts the proximal end of the body 504. At this point, the body 504 is fully expanded, thereby placing the electrodes 526 on the splines 520 into firm contact with the tissue within the pulmonary vein.

The physician then conveys RF energy from the generator 128 to the electrodes 526, as governed by the controller 130.

The electrodes 526 transmit RF energy into a circumferential region of the pulmonary vein the tissue in the pulmonary vein to a return electrode (unipolar arrangement) or an adjacent electrode (bipolar arrangement). As with the electrode carrying structure 106, a circumferential lesion is created in the pulmonary vein, thereby isolating any focal arrhythmia substrates within the pulmonary vein from the left atrium of the heart.

Deflation of the body 504 will cause the splines 520 to correspondingly collapse. As the splines 520 collapse, the proximal collar 522 of the tubular assembly 514 moves axially in the proximal direction until the splines 520 fully collapse, at which point the electrode carrying structure 502 can be extracted from the pulmonary vein and either repositioned within another pulmonary vein for continued ablation therapy or can be extracted all together from the patient.

Figure 29:
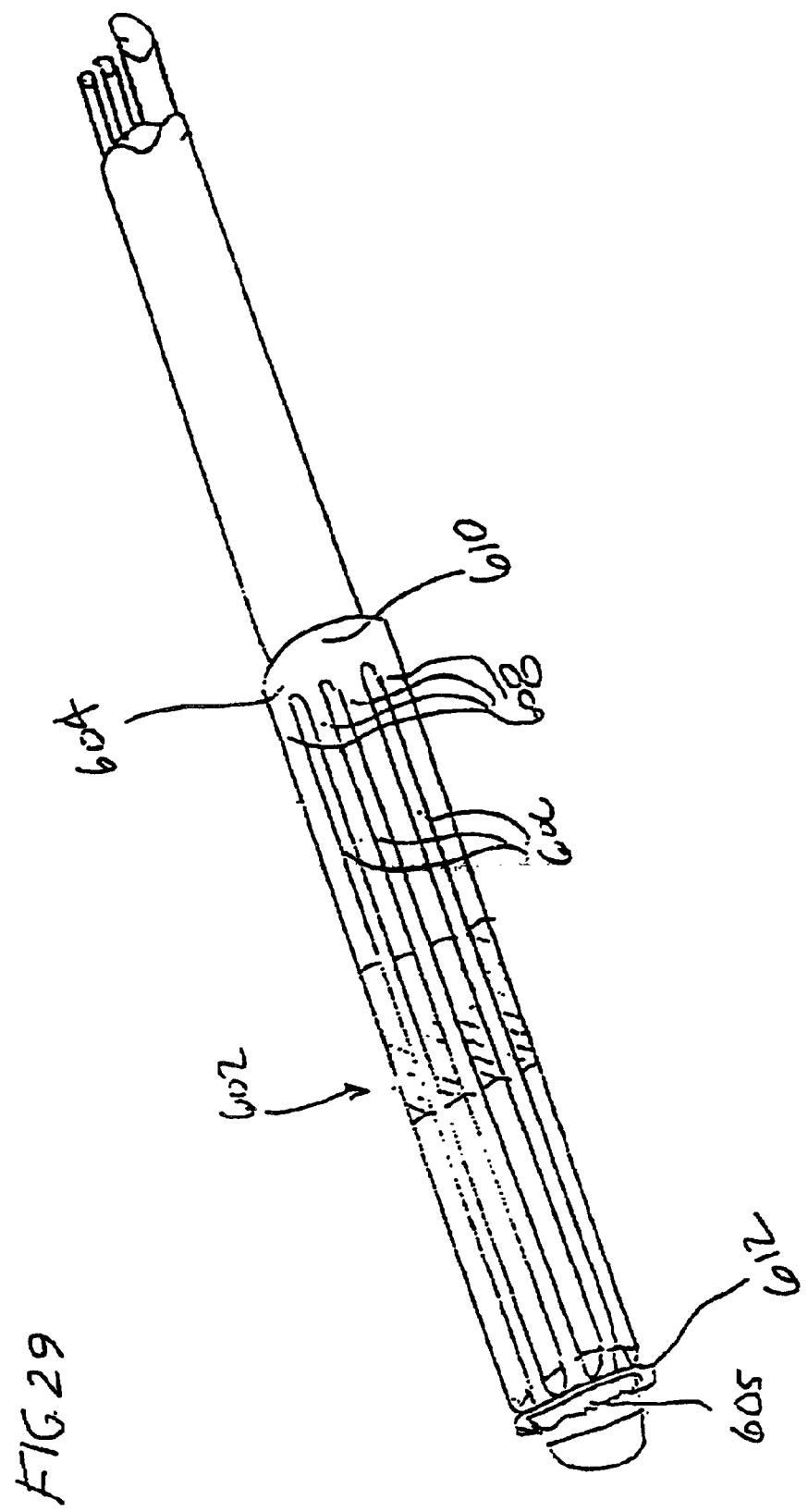
FIG. 29 is a partially cut-away perspective view of yet another preferred electrode carrying structure for use in the catheter assembly of FIG. 1, wherein the electrode carrying structure employs a balloon actuated splined tubular assembly mounted to the distal end of a balloon-like body via a ring and hinge assembly depicted in a expanded geometry.

Referring to FIG. 29, an alternate preferred electrode carrying structure 602 includes a balloon activated splined tubular assembly 604 that is open at both the proximal and distal ends thereof, rather than solely at the proximal end, as with the afore-described preferred electrode carrying structure 502.

In particular, the tubular assembly 604 is formed from a slitted tube that is open at both the proximal and distal ends thereof. Longitudinal cuts are made in the tubular assembly 604 to form alternating slits 606 and splines 608 thereon. The slits 606 extend distally from about 1 mm from the proximal end of the tubular assembly 604, leaving a proximal collar portion 610, through the distal end of the tubular assembly 604, such that the splines 608 are not distally connected. Instead, the distal ends of the splines 608 are affixed to the distal end of the catheter tube 102 through a ring and hinge assembly 612.

The tubular assembly 604 is disposed about an expandable-collapsible body 605. Inflation and venting of the body 605 using the respective inflation and venting lumens 114 and 116 is performed in the same manner as described above with respect to the expandable-collapsible body 504 in the electrode carrying structure 502.

Figure 30:
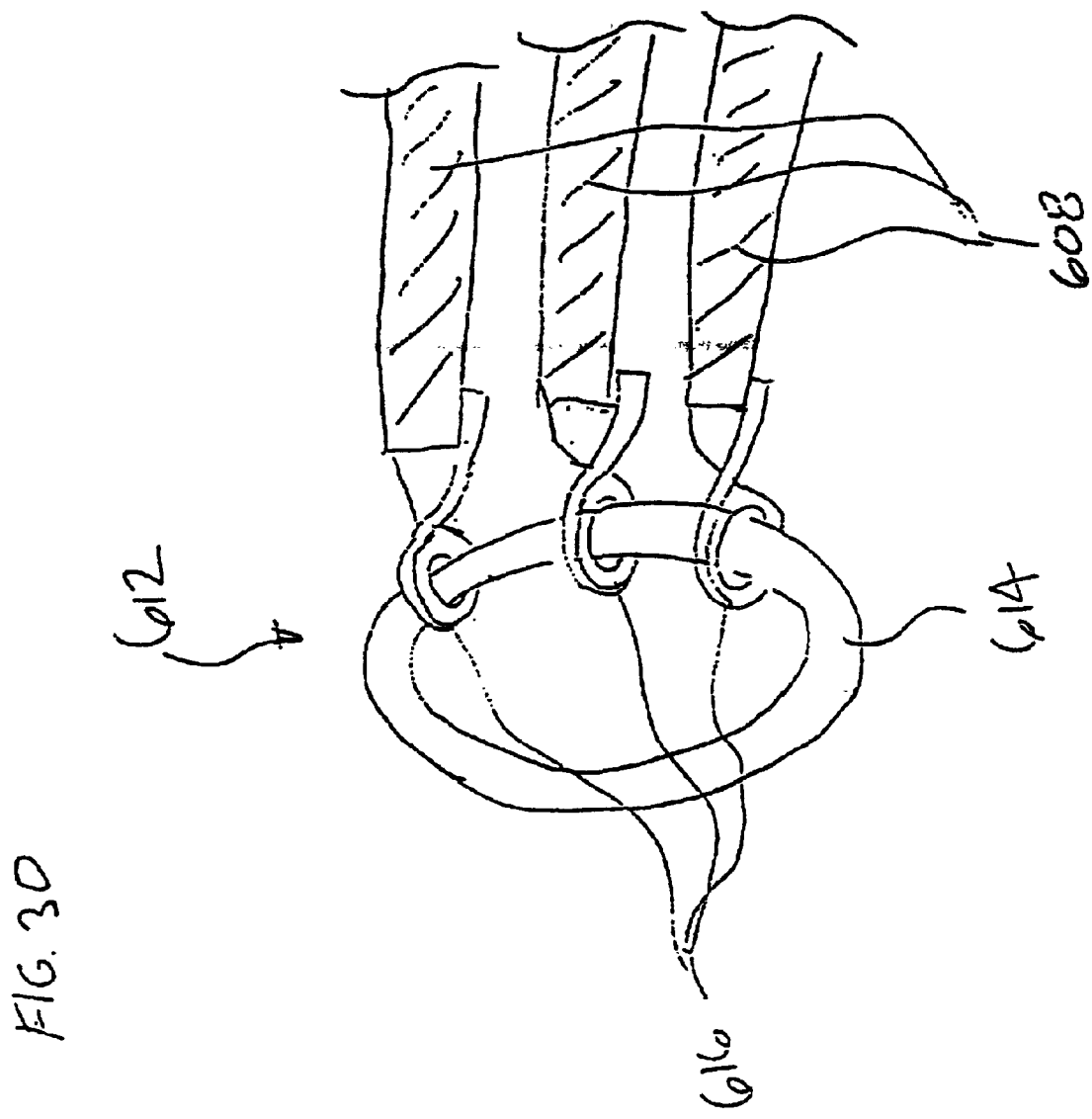
FIG. 30 is a partially cut-away perspective view of the ring and hinge assembly of the electrode carrying structure of FIG. 29.

Referring to FIG. 30, the ring and hinge assembly 612 comprises a plastic ring 614 with hinges 616. Each hinge 616 is made of generally rectangular piece of plastic with a rounded end having a hole therethrough. The hinges 616 are rotatably mounted to the ring 614 by disposed the ring 614 through the holes of the hinges 616. The number of hinges 616 installed on the ring 614 is preferably equal to the number of splines 608 on the tubular assembly 604. The ring and hinge assembly 612 is suitably bonded to the distal end of the body 605, and the distal ends of the splines 608 are then suitably bonded to the proximal ends of the hinges 616. In this manner, the distal ends of the splines 608 can move tangentially relative to the catheter tube 102, thereby facilitating the expansion of the tubular assembly 604 in response to the expansion of the body 605. Notably, the hinges 616 have a 90° twist to further facilitate expansion of the tubular assembly 604.

Operation and use of the electrode carrying structure 602 is similar to that of the electrode carrying structure 502, with the exception that expansion of the tubular assembly 604 is facilitated by the ring and hinge assembly 612.

Figure 31:
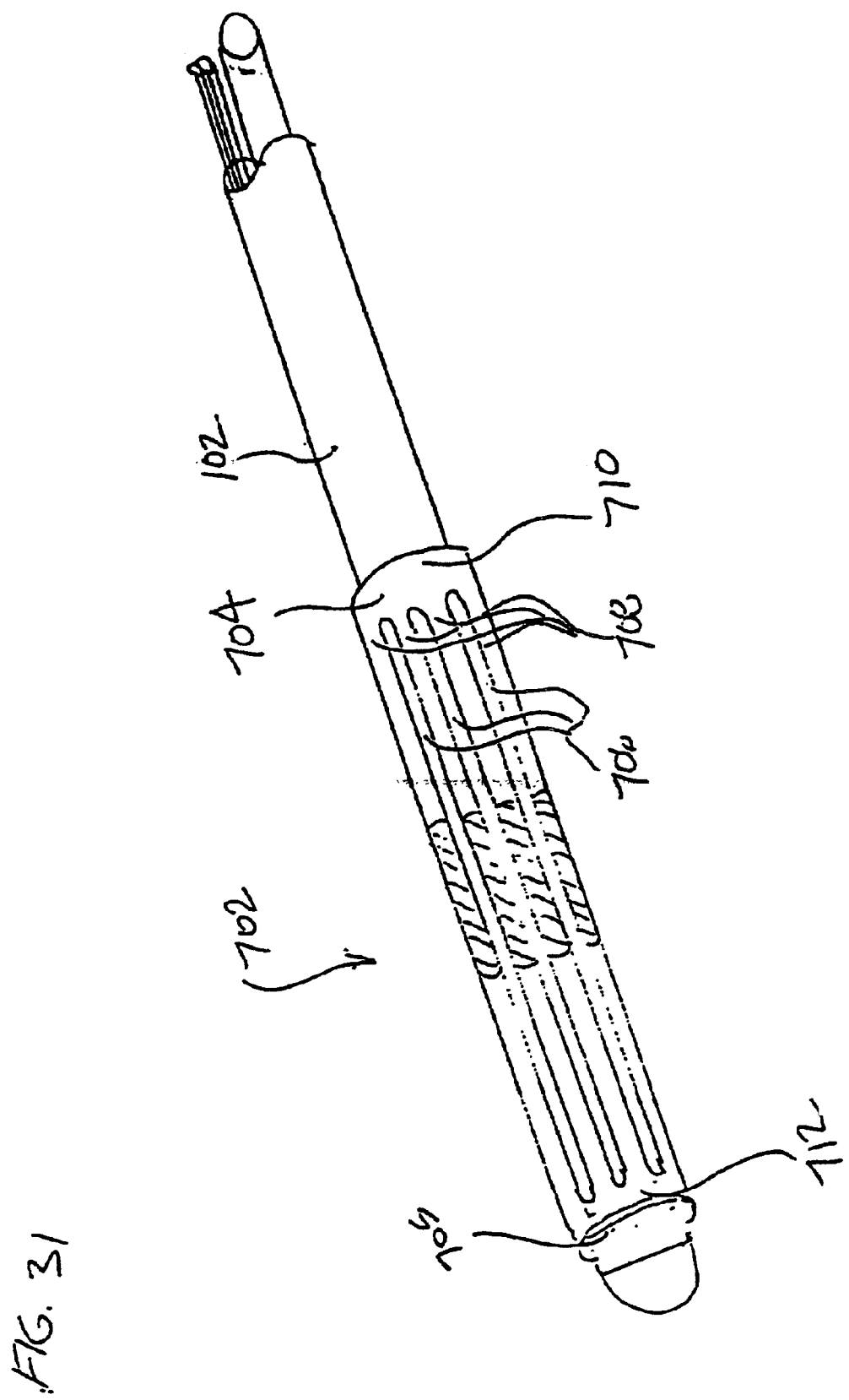
FIG. 31 is a partially cut-away perspective view of a still further preferred electrode carrying structure for use in the catheter assembly of FIG. 1, wherein the electrode carrying structure employs a balloon actuated splined tubular assembly mounted to the proximal end of the balloon-like body depicted in a deflated geometry.
Figure 32:
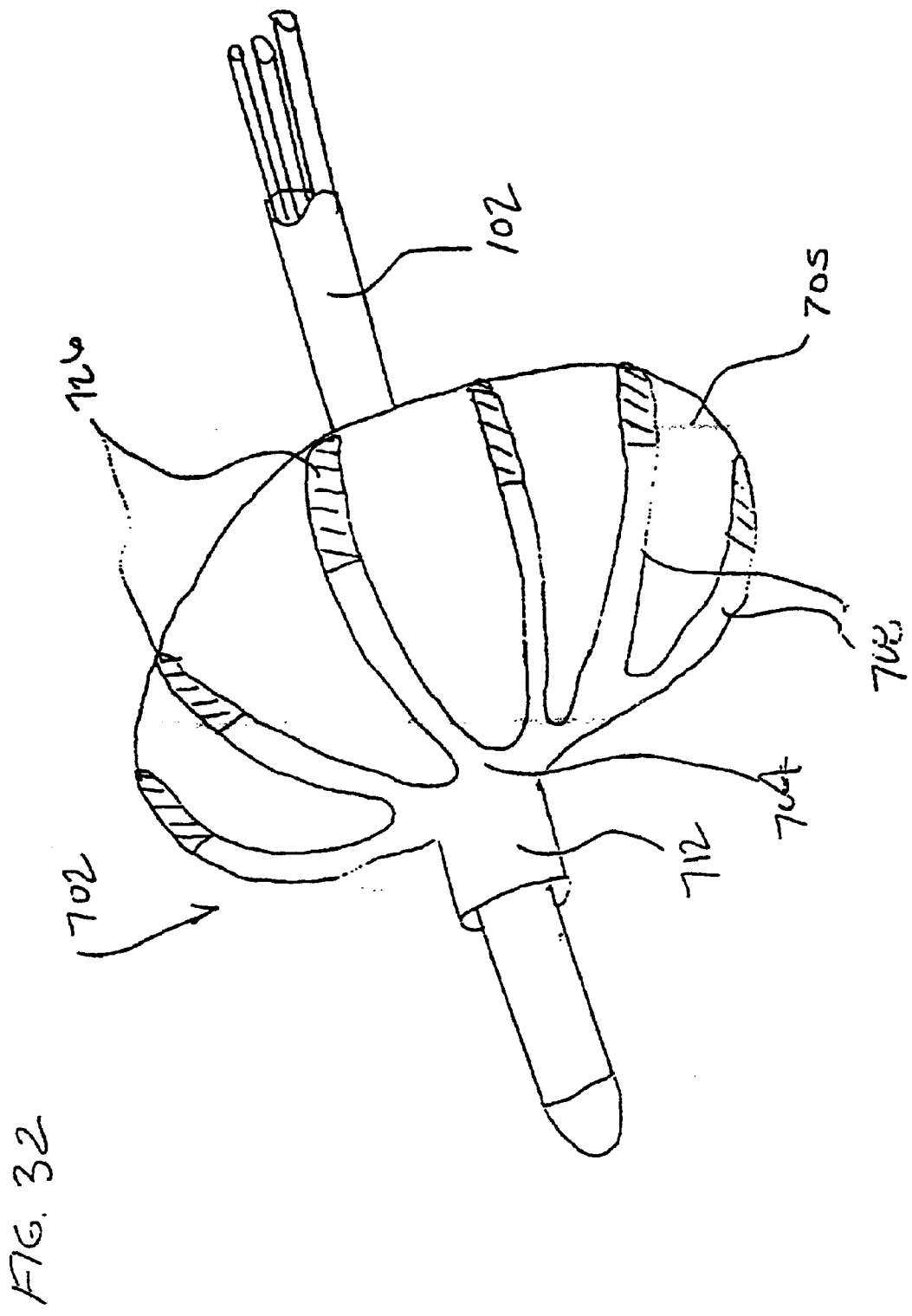
FIG. 32 is a partially cut-away perspective view of the electrode carrying structure of FIG. 31, wherein the balloon-like body is shown in an inflated geometry.

Referring to FIGS. 31 and 32, yet another alternate electrode carrying structure 702 includes a balloon activated splined tubular assembly 704 that is affixed to an expandable collapsible body 705 at the proximal end of the tubular assembly 704. In particular, the tubular assembly 704 is made of a slitted tube that is open at both the proximal and distal ends thereof. Longitudinal cuts are made in the tubular assembly 704 to form alternating slits 706 and splines 708 thereon. Preferably, the slits 706 extend proximally and distally to about 1 mm from the respective proximal and distal ends of the tubular assembly 704 to form a proximal collar 710 and a distal collar 712 thereon.

The tubular assembly 704 is disposed about the body 504 with the proximal collar 710 of the tubular assembly 704 suitably bonded to the proximal end of the body 705. The splines 708 and distal collar 712 are not affixed to the body 705 or the catheter tube 102. In this manner, the splines 708 are free to move in relation to the body 705, and the distal collar 712 is free to move axially in the proximal direction relative to the catheter tube 102.

Operation and use of the electrode carrying structure 702 is similar to that described above with respect to the catheter 502, except for a notable functional modification. In particular, as seen in FIG. 32, as the expansion of the body 705 causes the splines 708 to correspondingly expand, the distal collar 712 of the tubular assembly 704 moves axially in the proximal direction until it abuts the distal end of the body 705, at which point the body 705 is fully expanded, thereby placing electrodes 726 on the splines 708 into firm contact with the tissue within the pulmonary vein.

Figure 33:
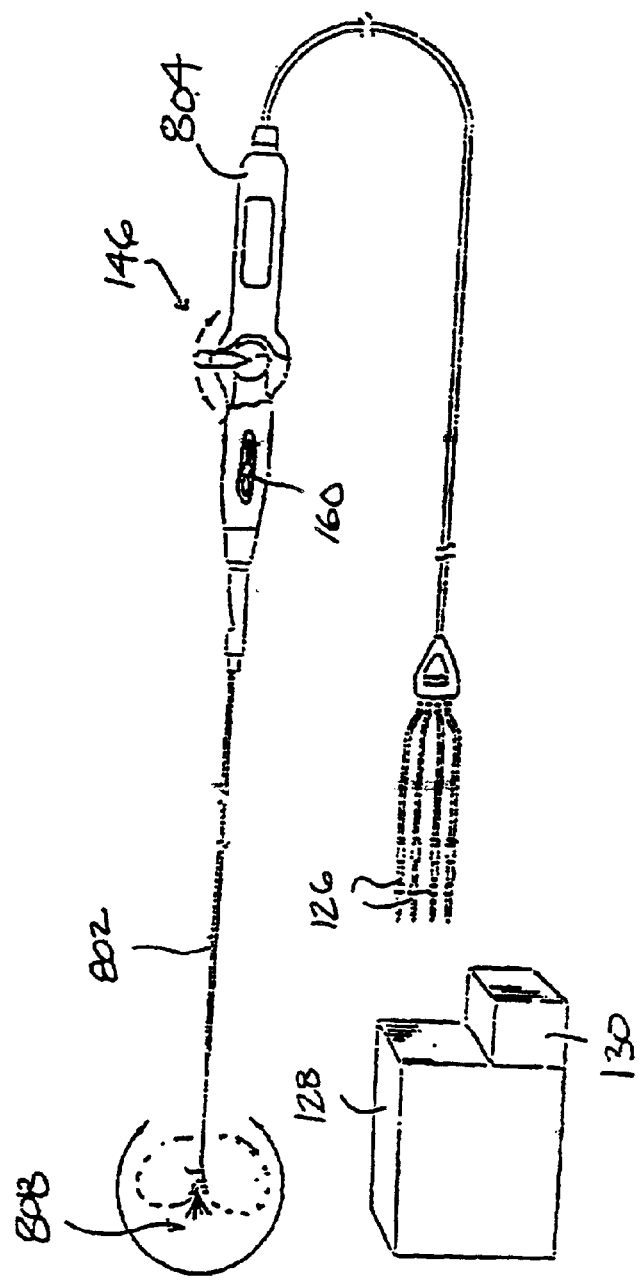
FIG. 33 is a perspective elevation view of an alternate preferred tissue ablation catheter assembly.
Figure 34:
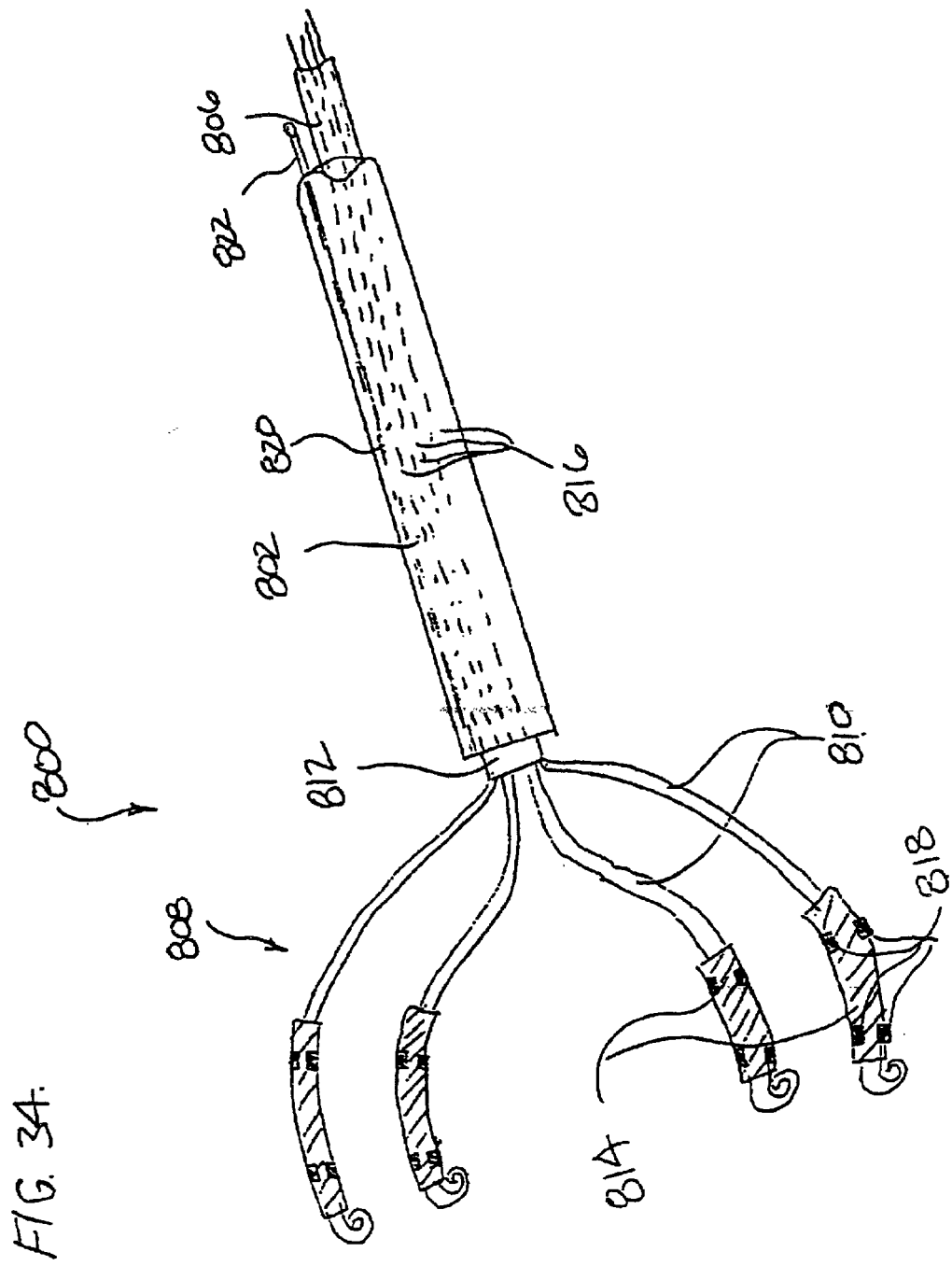
FIG. 34 is a partially cut-away perspective view of a preferred electrode carrying structure for use in the catheter assembly of FIG. 33, wherein the electrode carrying structure includes an array of resilient splines depicted in an expanded geometry.
Figure 35:
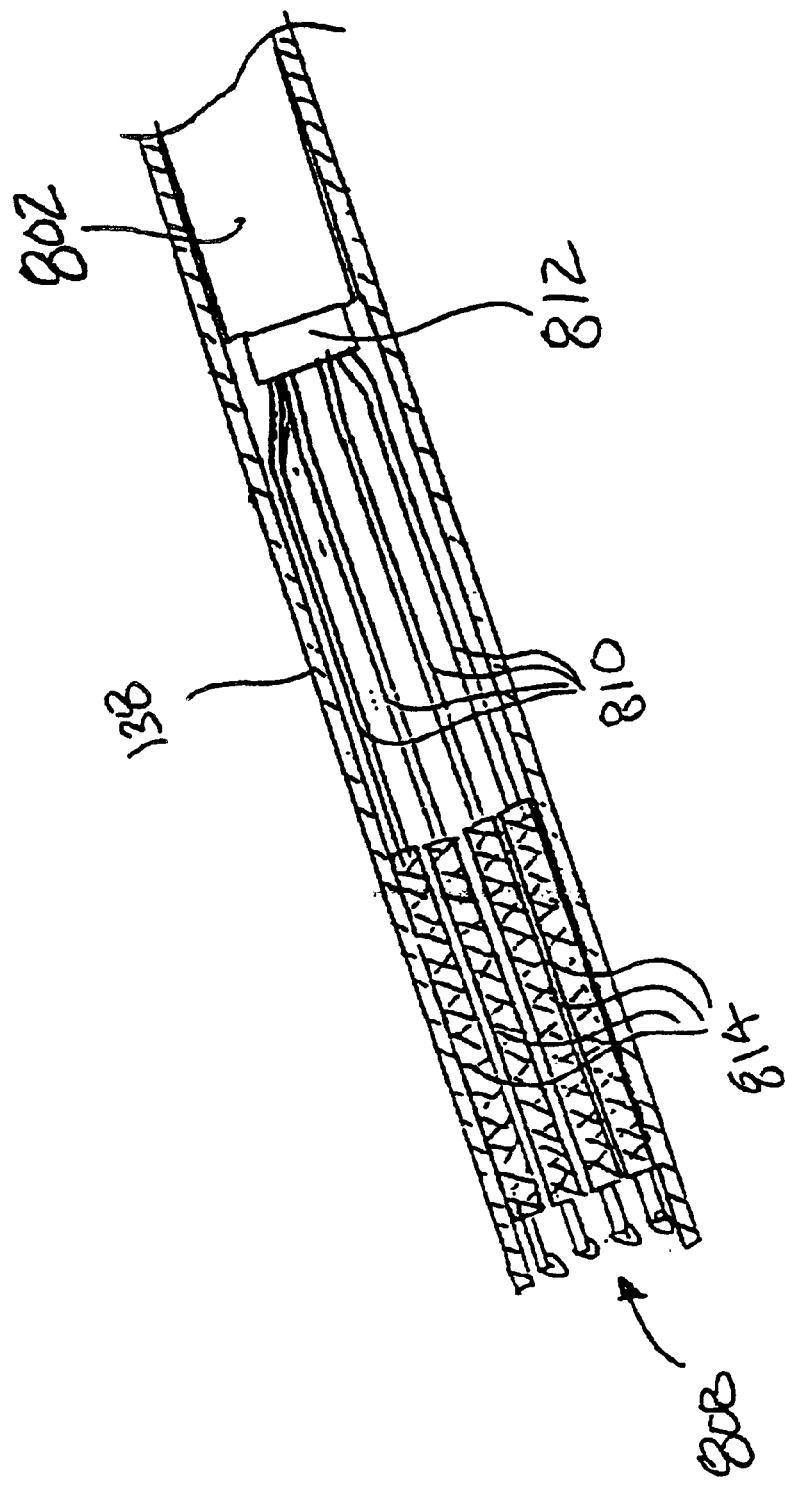
FIG. 35 is a second partially cut-away perspective view of the distal end of the catheter assembly of FIG. 34, wherein the array of resilient splines are depicted in a collapsed geometry.
Figure 36:
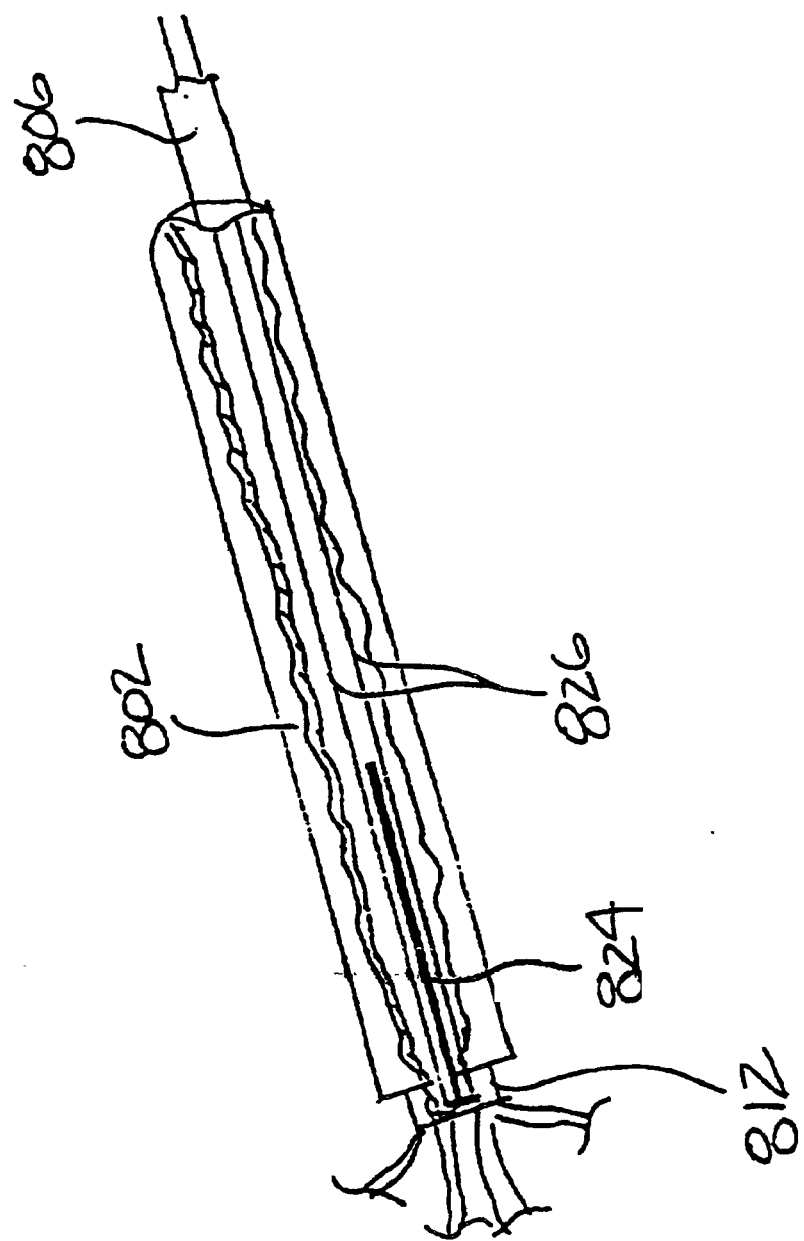
FIG. 36 is a partially cut-away perspective view the electrode carrying structure of FIG. 34, particularly illustrating a preferred steering mechanism.

Referring to FIGS. 33–35, an alternate preferred catheter assembly 800 is configured to create a circumferential lesion within a pulmonary vein by employing an electrode carrying structure 808 having an array of resilient longitudinal splines 810.

In particular, the catheter assembly 800 includes a flexible catheter tube 802 made of a polymeric, electrically nonconductive material, like polyethylene, polyurethane, or PEBAX®. The catheter tube 802 has an open proximal end that is connected to a handle 804, as shown in FIG. 33. The handle 804 is similar to handle 804, with the exception that handle 804 does not include inflation and venting ports, since the catheter assembly 800 does not employ an expandable-collapsible electrode body. The handle 804 includes the aforedescribed steering mechanism 146, as well as the external connectors 126, which are electrically coupled to the RF generator 128 and controller 130. The catheter tube 802 has a main interior lumen 806, which can house ablation signal wires or steering wires.

As best seen in FIG. 34, the electrode carrying structure 808 is mounted on the open distal end of the catheter tube 802. Specifically, the longitudinal splines 810 are circumferentially spaced and extend from a base member 812 on the distal end of the catheter tube 802. Each spline 810 is substantially rectangular in cross section and is made of a resilient, inert wire, such as nickel titanium (commercially available as Nitinol material), stainless steel 17-7, or thermoplastic material.

The splines 810 collapse into a closed, compact bundle in response to an external compression force, which occurs, for instance, when the electrode carrying structure 808 is disposed in the guide sheath 138, as depicted in FIG. 35. Contrariwise, the splines resiliently spring open to assume a three-dimensional shape, as depicted in FIG. 34. In this condition, the resilient splines 810 bend and conform to the tissue surface they contact. To prevent tissue trauma, the distal ends of the splines 810 are blunted by curling (as shown in FIG. 34) or, alternately, by suitably attaching a ball of adhesive thereto.

To facilitate collapsing of the splines 810 into the guide sheath 138, the splines 810 may alternately be given a generally elliptical cross-section, with a sufficient width for supporting the ablation process, but with a decreased thickness at the edges (widthwise).

Each spline 810 carries at least one electrode 814 located at its distal end, which can be created as part of the respective spline itself, depending upon the material used. For example, if the splines 810 are made of an electrically conductive material, the electrodes 814 can be formed by exposing a portion of the spline material. To improve the conductive properties and bio-compatibility of the electrodes 814, flexible coil electrodes can be suitably bonded to the splines 810, or the exterior surfaces of the splines 810 can be coated with an electrically conducting material—, e.g., using ion beam deposition or equivalent techniques. Materials possessing these characteristics include, among others, gold, platinum, platinum/iridium, conductive ink epoxy, or a combination thereof. In particular, noble metals are preferred.

An alternate way to make the electrodes is to use conductive, flexible ink, covered by a layer of protective regenerated cellulose. A preferred methodology for forming electrodes by applying a conductive ink coating to the surface of a (nonconductive) spline 810 is disclosed and described in U.S. patent application Ser. No. 08/879,343, filed Jun. 20, 1997, entitled "Surface Coating For Catheters And Similar Devices," which is fully incorporated herein by reference for all it discloses and teaches. In this instance, insulating material may be applied to the portion of the splines 810 proximal to the electrodes 814 to form a nonconductive region thereon.

If the splines 810 are made of an electrically non-conducting material, such as a plastic with elastic memory, the electrodes 814 may be formed on the distal ends of the splines 810 by suitably bonding flexible coil electrodes on the splines 810, or coating the exterior surfaces with an electrically conducting material as described above.

The size and spacing of the electrodes 814 are preferably optimized, such that the electrode carrying structure 808 will be able to produce a contiguous circumferential lesion, e.g., when located within a pulmonary vein. Notably, the spacing of the electrodes 814 is dictated by the number of splines 810. For example, the electrode carrying structure 808 comprises four splines 810. More or fewer splines 810 can be used depending on the size of the electrodes 814. FIG. 34 and the following figures exaggerate the difference in diameter the electrodes 814 and the nonconducting regions on the respective splines 810 for purposes of illustration. The actual difference in diameter between the electrodes 814 and the nonconducting regions on the splines 810 in presently preferred embodiments is minimal, i.e., difficult to detect with the naked eye. Further details concerning the preferred size and spacing of the electrodes 814 are disclosed in Swanson et al., U.S. Pat. No. 5,582,609.

The electrode 814 of each spline 810 is electrically coupled to an ablation signal wire 816 (shown in phantom) that extends through the base member 812 and main lumen 806 of the catheter tube 802 (see FIG. 34) into the handle 804. In turn, the handle 804 is electrically coupled to the RF generator 128 through connectors 126 (see FIG. 33).

Temperature sensing elements 818, such as thermistors or thermocouples, can be suitably mounted to the electrodes 814 for more controlled lesion creation. The temperature sensing elements 818 are coupled to the controller 130 through temperature sensing element wires 820 (shown in phantom) extending through a temperature sensing element wire lumen 822 carried within the catheter tube 102. The temperature sensing element wires 144 are shielded to block RF interference emitted by the ablation signal wires 816. Preferably, the temperature sensors 818 are located at the edges of the electrodes 814 where the highest current density is found.

Steering of the electrode carrying structure 808 into the desired pulmonary vein by the steering mechanism 146 is accomplished through a center support 824 carried within the distal end of the catheter tube 802. Steering wires 826 carried within the main lumen 806 of the catheter tube 802 are attached at their distal ends to the respective left and right sides of the center support 824 mounted to the base member 812, and at their proximal ends to the steering mechanism 146 as hereinbefore described.

In alternate preferred embodiments, the catheter assembly 800 need not comprise the center support 824 and steering wires 826, but can be introduced into the desired pulmonary vein through other means. For instance, the guide sheath 138 used to introduce the electrode carrying structure 808 into the left atrium of the heart can be inserted into the pulmonary vein for guidance of the electrode carrying structure 808 therein. Alternatively, the catheter tube 802 can carry a guide wire that is inserted into the pulmonary vein for guidance of the electrode carrying structure 808 therein (see FIG. 42).

Figure 37:
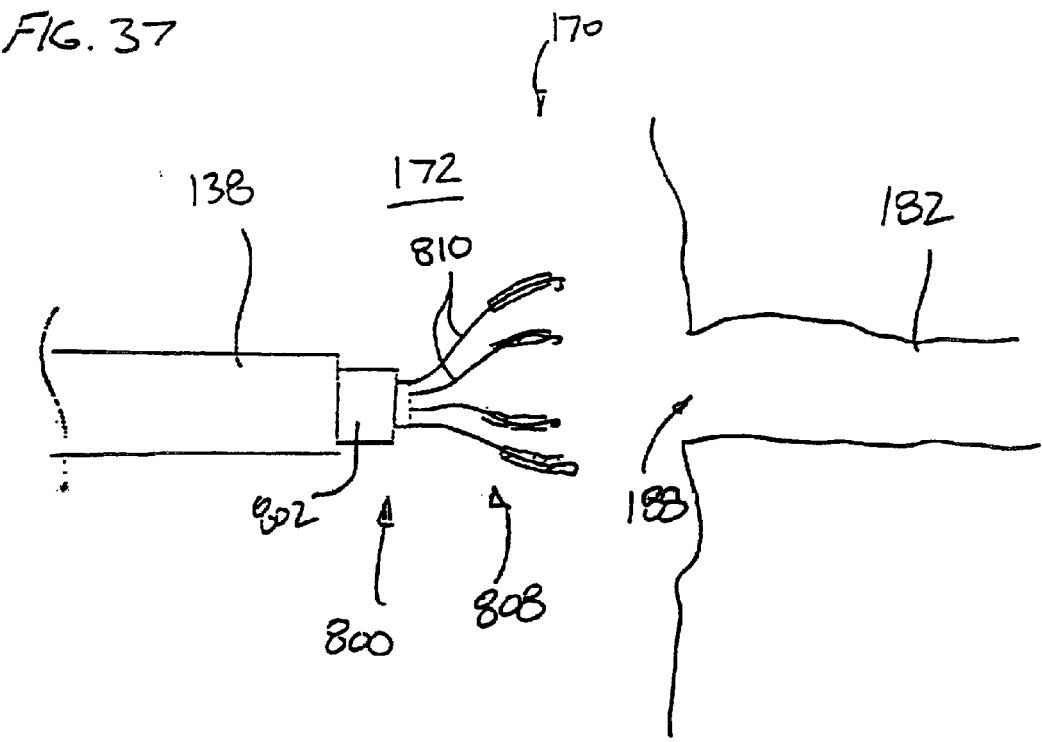
FIG. 37 is a side view of the electrode carrying structure of FIG. 34 disposed in the left atrium of the heart via a guide sheath, wherein the array of resilient splines are expanded.

In accordance with the present invention, the catheter assembly 800 is used to isolate focal arrhythmia substrates in a pulmonary vein by creating a circumferential lesion inside of the pulmonary vein. As depicted in FIG. 37, the physician can introduce the electrode carrying structure 808 into the left atrium 172 via the guide sheath 138 through the aforedescribed retrograde or transeptal approaches. The physician can introduce the electrode carrying structure 808 into the desire pulmonary vein 182 in various ways.

Figure 38:
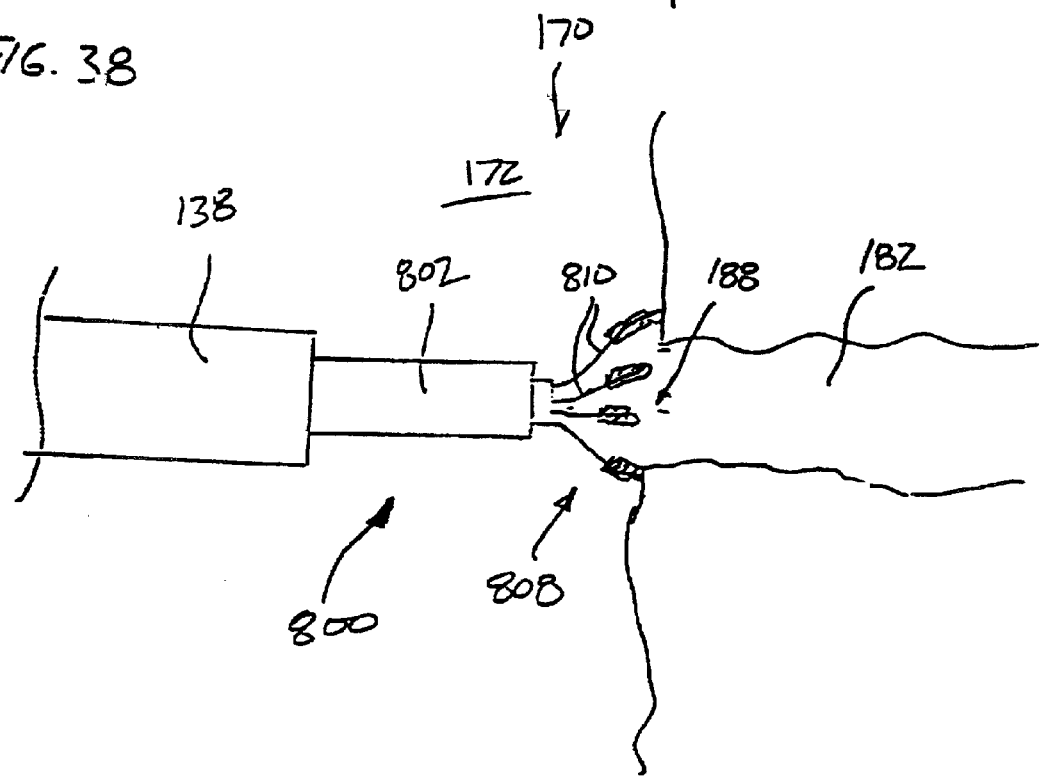
FIG. 38 depicts the electrode carrying structure of FIG. 37, wherein the distal end of the array of resilient splines are butted up against the opening of the pulmonary vein.

For example, the guide sheath 138 can be retracted from the electrode carrying structure 808, thereby allowing the splines 810 to open to their expanded position. The electrode carrying structure 808 is then be steered towards the opening 188 of the pulmonary vein 182 via the steering mechanism 146, until it butts up against the opening 188 of the pulmonary vein 182, with the distal ends of the respective splines 810 in contact with the tissue surrounding and outside of the opening 188 (see FIG. 38).

Figure 39:
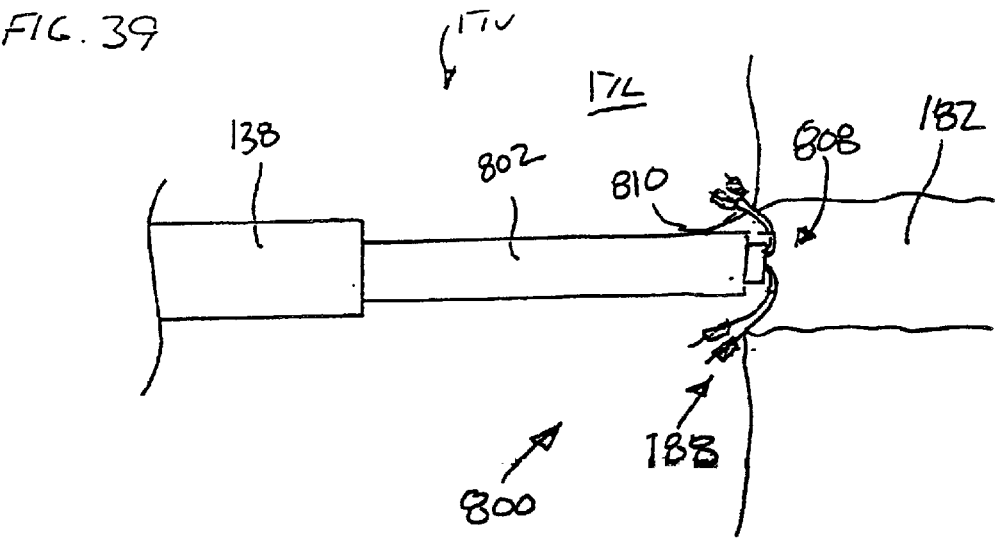
FIG. 39 depicts the electrode carrying structure of FIG. 37, wherein the array of resilient splines are bent in the distal direction as the electrode carrying structure enters the pulmonary vein.
Figure 40:
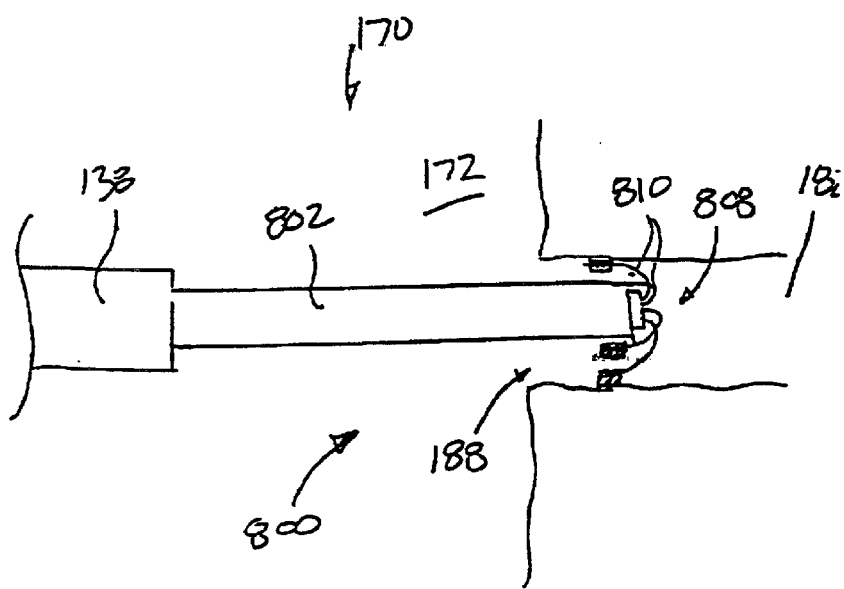
FIG. 40 depicts the electrode carrying structure of FIG. 37, wherein the array of resilient splines are fully disposed in the pulmonary vein.
Figure 41:
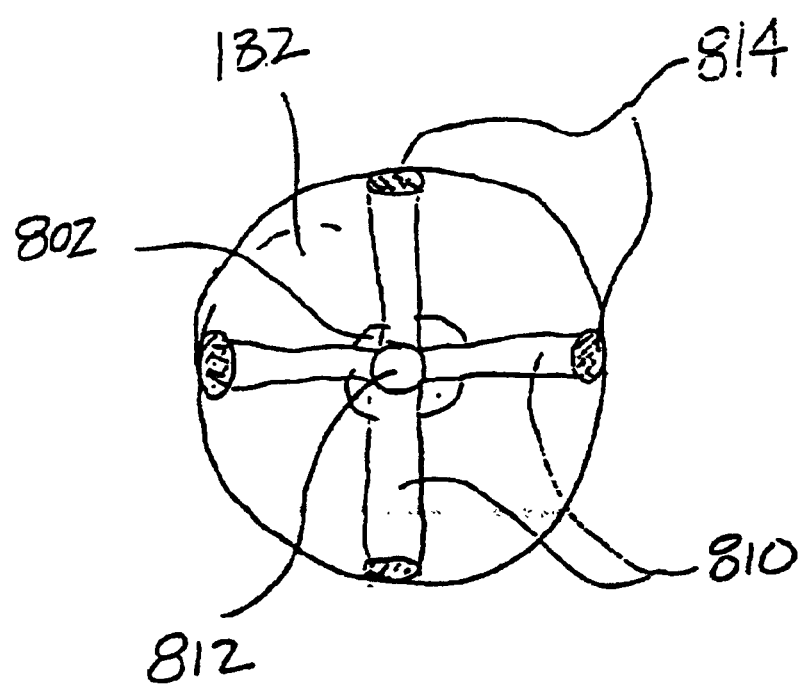
FIG. 41 is an axial view of the array of splines of the electrode carrying structure of FIG. 37, as they are depicted in FIG. 40.

The electrode carrying structure 808 may then be further pushed, folding the splines 810 proximally upon themselves (shown in FIG. 39), until the distal ends of the splines 810 are disposed within the pulmonary vein 182 (shown in FIG. 40). The resiliency of the splines 810 creates firm contact between the electrodes 814 and the tissue within the pulmonary vein 182 (see FIG. 41).

Each of the electrodes 814 are preferably sized to create an tissue lesion covering (at least) a 45° arc of the inner circumference of a pulmonary vein. In this manner, in order to form a contiguous lesion around the entire inner circumference of the vein, the physician first locates the electrodes 814 at the desired location within the vein, and then applies RF energy to form a first set of four lesions about a circumference within the vein (i.e., one lesion per electrode 1014). The physician then rotates the catheter 802 by 45° degrees (i.e., one-eighth of the circumference of the vein), which, in turn, rotates the respective splines 810 and electrodes 814 by 45°. This rotation is most easily accomplished by first moving the guide sheath 138 back over the proximal ends of, thereby slightly compressing, the splines 810, so that the electrodes 814 are no longer in contact with the inner wall tissue of the vein.

Once the electrodes 814 have been rotated 45°, the guide sheath 138 is again retracted, allowing the splines 810 to expand and the respective electrodes 814 to make firm contact with the tissue of the inner vein wall. The physician then applies RF energy to form a second set of lesions, whereby the first and second set of lesions collectively form a contiguous lesion around the entire inner circumference of the vein.

Figure 42:
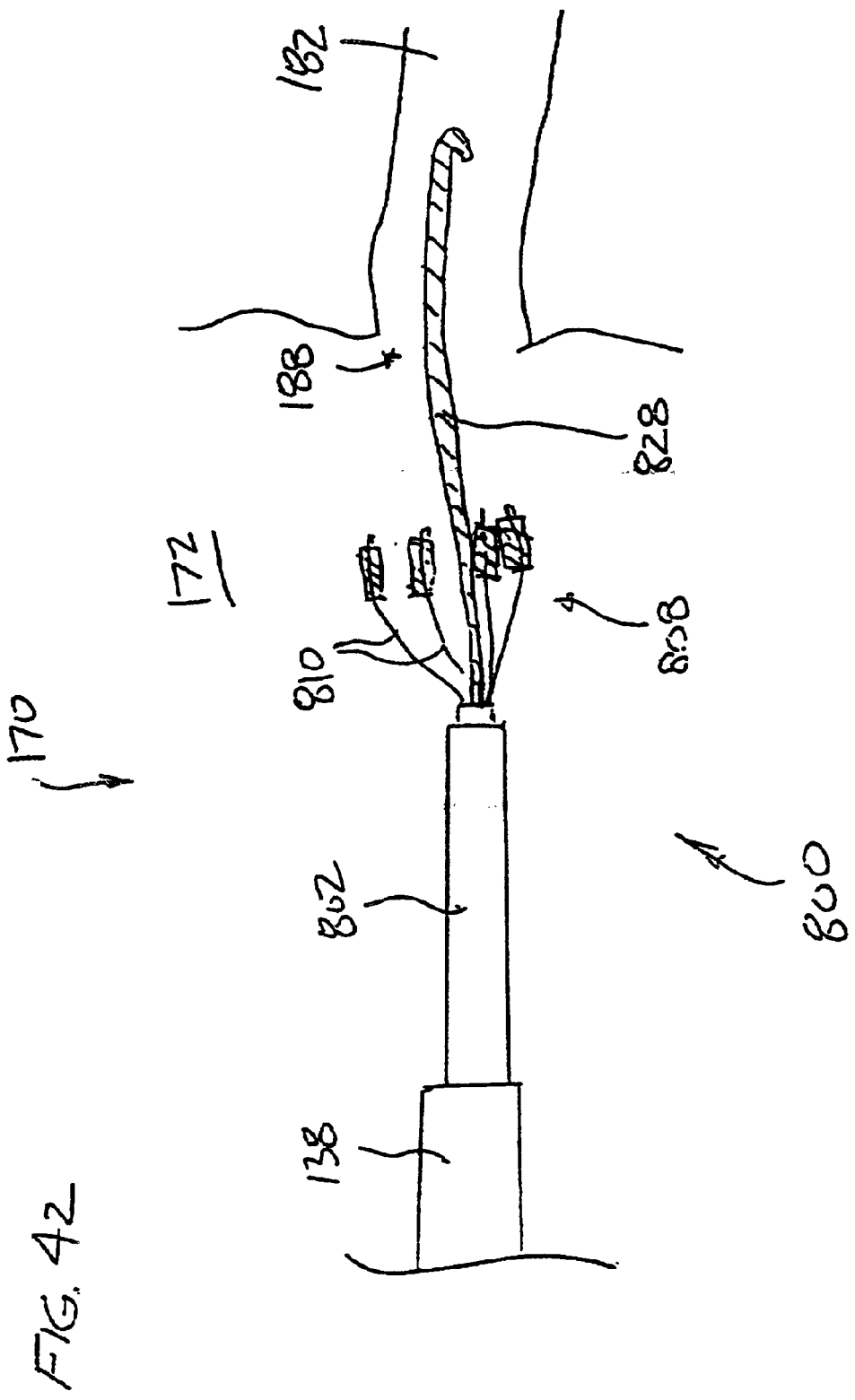
FIG. 42 is a side view of the electrode carrying structure of FIG. 37, wherein the catheter assembly employs a guide wire to guide the electrode carrying structure into the pulmonary vein.

Alternatively, in lieu of the steering mechanism 146, the catheter tube 802 can carry a guide wire 828, which is inserted into the pulmonary vein 182 for guidance of the electrode carrying structure 808. In this manner, the splines 810 of the electrode carrying structure 808 will be disposed proximally as depicted in FIG. 42.

In yet another alternative, the guide sheath 138 can be inserted into the pulmonary vein 182 for guidance of the electrode carrying structure 808. In this manner, the splines 810 of the electrode carrying structure 808 will be disposed distally as depicted in FIG. 43A.

Figure 43B:
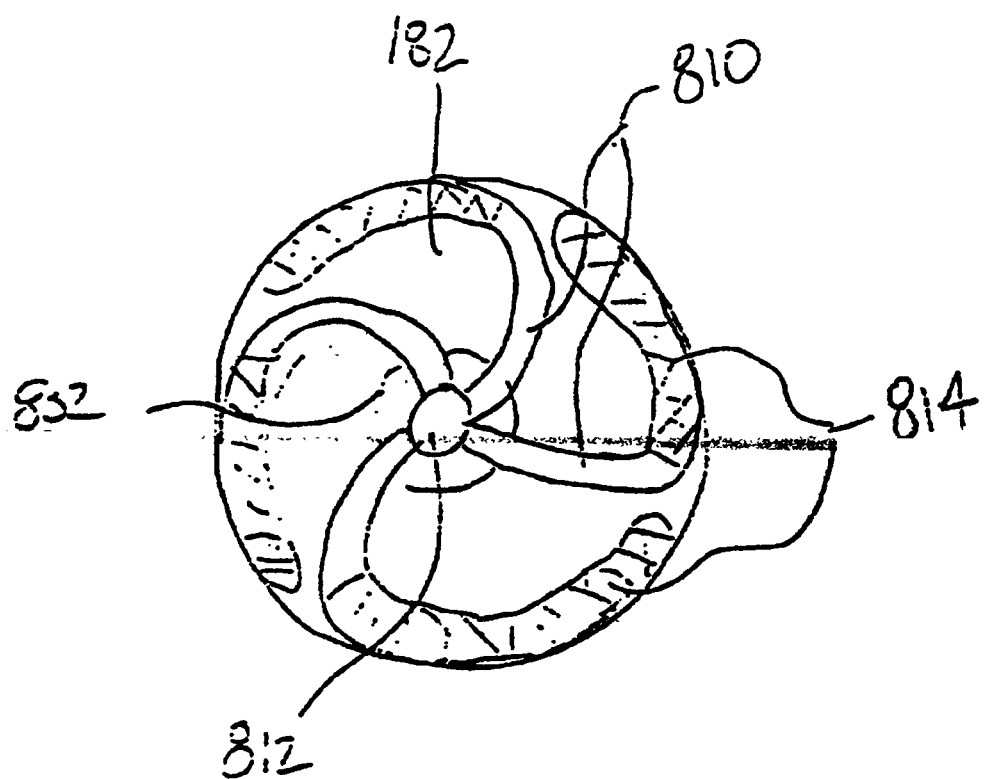
FIG. 43B is an axial view of the array of splines of the electrode carrying structure of FIG. 37, as they are depicted in FIG. 40, wherein the electrode carrying structure is torqued to tangentially align the splines.

Subsequent to inserting the electrode carrying structure 808 into the pulmonary vein 182, at the physician's option, the electrode carrying structure 808 can be torqued until the splines 810 of the electrode carrying structure 808 are disposed tangentially within the pulmonary vein 182, as depicted in FIG. 43B. In this manner, the tangential disposition of the electrodes 814 lessens the distance therebetween, so that a contiguous circumferential lesion can be more easily created. The physician can then deliver RF ablation energy from the RF generator 128 to the electrodes 814 on the splines 810 to produce a circumferential lesion within the pulmonary vein 182, thereby isolating the focal substrates from the left atrium 172 of the heart 10.

Figure 44:
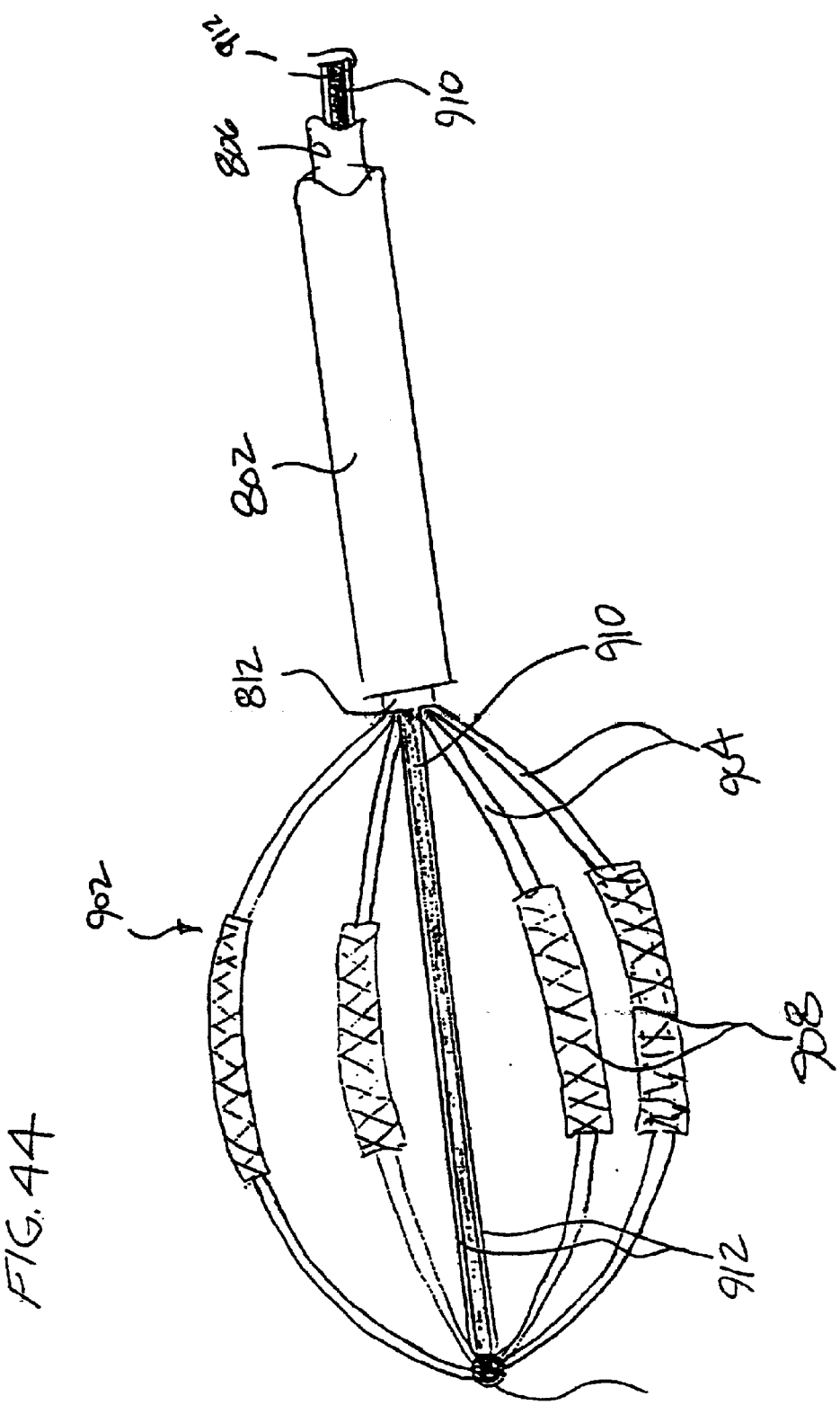
FIG. 44 is a partially cut-away perspective view of a further preferred electrode carrying structure for use in the catheter assembly of FIG. 33, wherein the array of resilient splines includes a stilette and is depicted in an expanded geometry.
Figure 45:
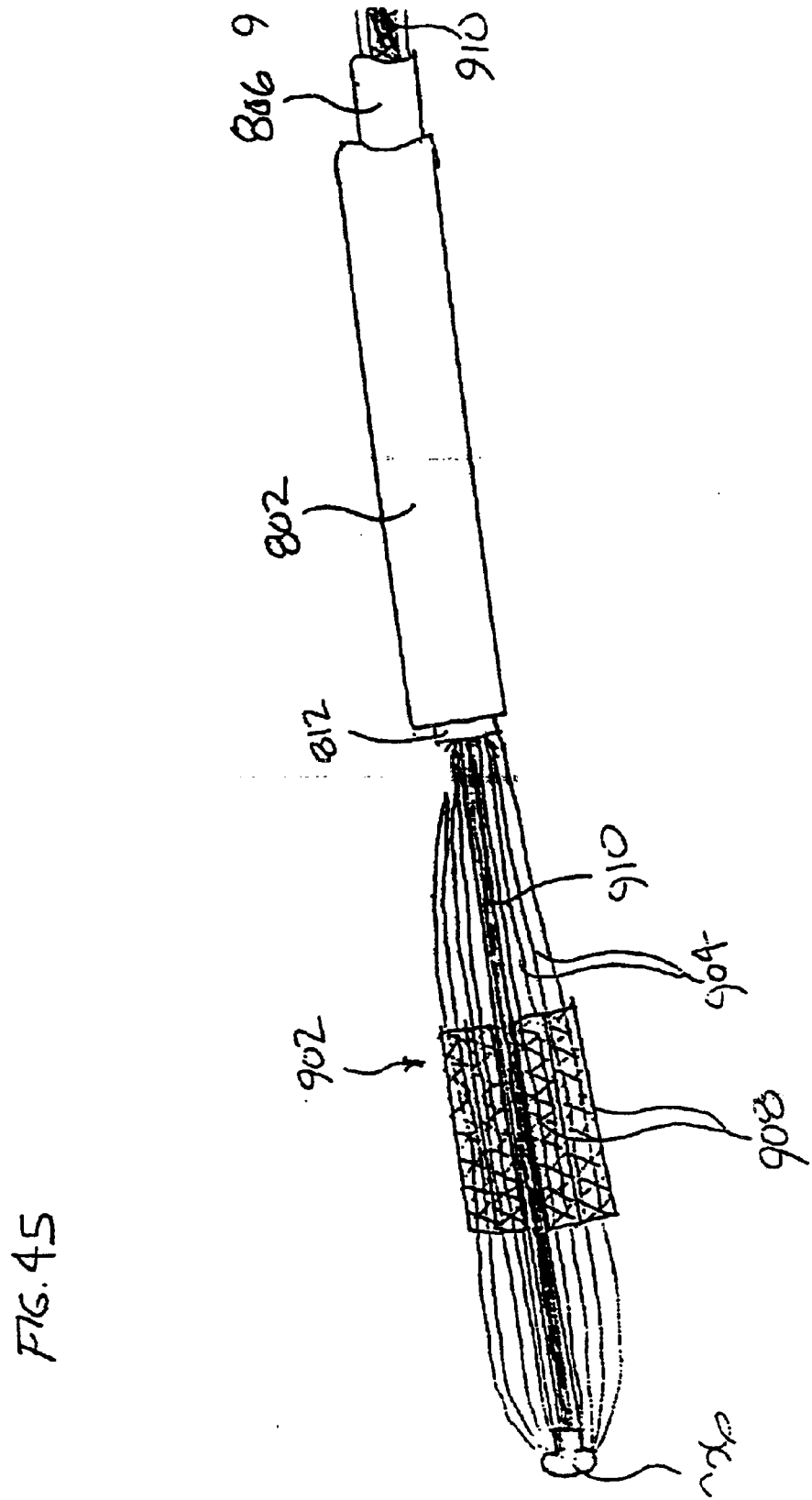
FIG. 45 is a partially cut-away perspective view of the electrode carrying structure of FIG. 44, wherein the array of splines are depicted in a collapsed geometry.
Figure 46:
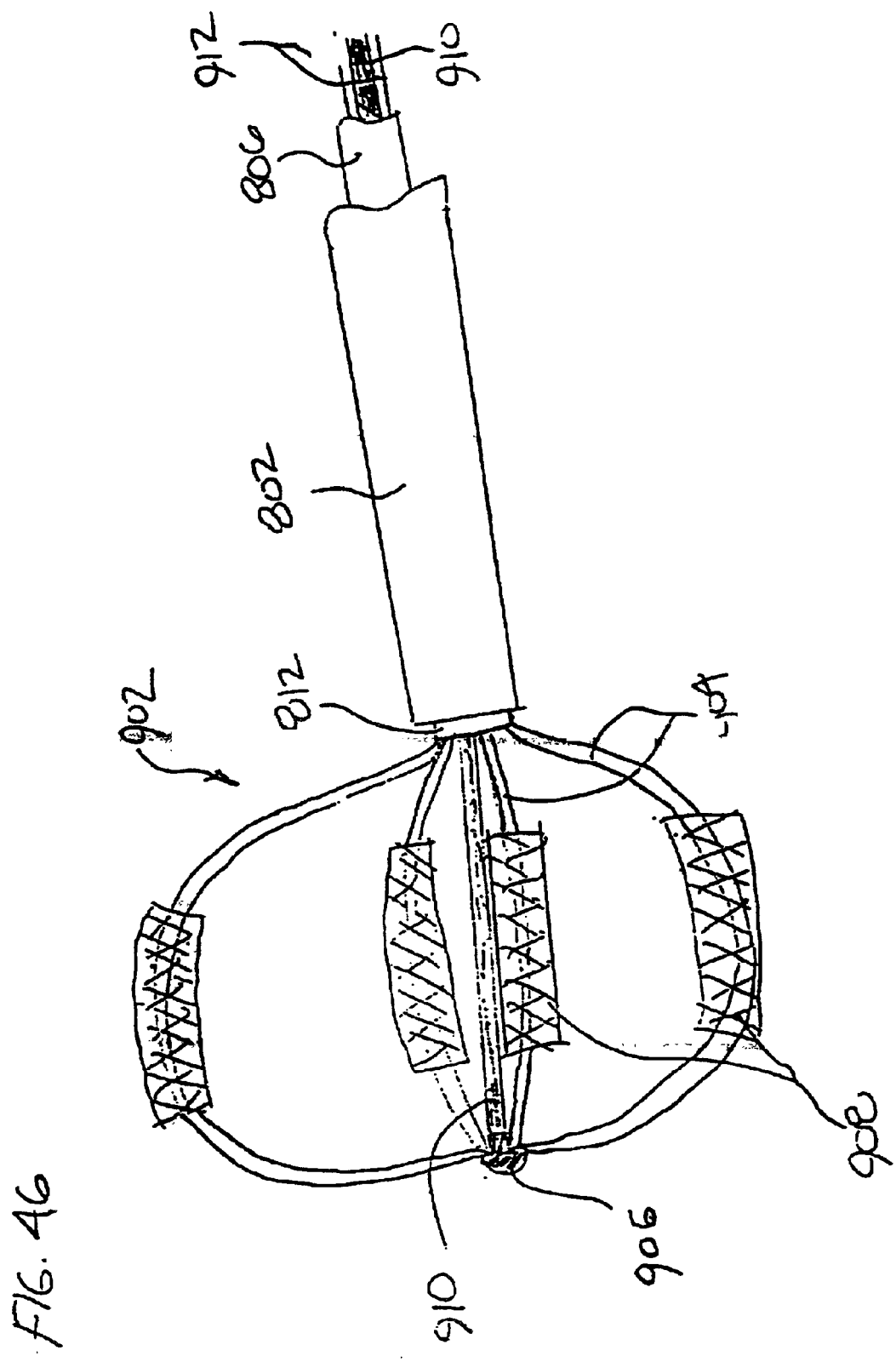
FIG. 46 is a partially cut-away perspective view of the electrode carrying structure of FIG. 44, wherein the array of splines are depicted in a longitudinally compressed geometry.

Referring to FIGS. 44–46, an alternate preferred electrode carrying structure 902 for use with the catheter assembly 800 comprises longitudinal splines 904 that are connected to a stilette 910. The splines 904 are connected at their proximal ends to the base member 812 of the catheter tube 802 and at their distal ends to an end cap 906. As with the splines 810 of the afore-described electrode carrying structure 808, the splines 904 are made of a resilient, inert wire, such as nickel titanium (commercially available as Nitinol material), stainless steel 17-7, or thermoplastic material. The splines 904 have electrodes 908 disposed thereon in the same manner as described above with respect to the electrodes 814, except that the electrodes 908 are located in the approximate longitudinal center of the respective splines 904.

The stilette 910 extends from the end cap 906 through the base member 812 and main lumen 806, respectively, of the catheter tube 802, and to the push-pull controller 160 on the handle 804 of the catheter assembly 800 (see FIG. 33). Left and right steering wires 912 are suitably bonded to the distal end of the stilette 910 and extend therefrom through the base member 812 and main lumen 806 to the steering mechanism 146 on the handle 804. In this manner, the electrode carrying structure 902 can be elongated (as shown in FIG. 45) or longitudinally compressed (shown in FIG. 46) by manipulation of the push-pull controller 160, as well as steered by manipulation of the steering mechanism 146.

Operation and use of the electrode carrying structure 902 is similar to that of the electrode carrying structure 808. Any of the aforedescribed methods used to locate the electrode carrying structure 808 can also be used to insert the electrode carrying structure 902 into a desired pulmonary vein. The electrode carrying structure 902 can be elongated to ease insertion into the pulmonary vein, by pushing the push-pull controller 160 on the handle 804. Once the electrode carrying structure 902 is properly disposed within a pulmonary vein, the push-pull controller 160 can be pulled to longitudinally compress the electrode carrying structure 902, thereby urging the electrodes 908 against the wall of the vein to facilitate the ablation of tissue located on the interior surface thereof.

Notably, because the splines 904 of the electrode carrying structure 902 are connected distally as well as proximally, the disposition of the electrodes 908 in the pulmonary vein does not vary with the method of insertion used,—i.e., the splines 904 will not fold back upon themselves as depicted in FIGS. 39 and 40.

Referring to FIGS. 47A–C and 48A–B, a still further alternate preferred catheter assembly 1000, comprises a flexible catheter tube 1002 made of a polymeric, electrically nonconductive material, like polyethylene, polyurethane, or PEBAX®, which forms a main lumen 1014 used to carry ablation signal and steering wires 1009. At its distal and, the catheter tube 1002 forms a preshaped circular electrode carrying structure 1004, in which is disposed a center support 1010 (shown in FIG. 48) made of a resilient, inert wire, such as nickel titanium (commercially available as Nitinol material), stainless steel 17-7, or thermoplastic material, for maintaining the circular shape.

The distal end of the center support 1010 is mounted to a distal tip 1008, which is suitably bonded to the distal end of the electrode carrying structure 1004. If required, a resilient wire (not shown) can additionally be disposed within the circular electrode carrying structure 1004 to further maintain the electrode carrying structure 1004 in a circular pattern.

As shown in FIG. 47, the electrode carrying structure 1004 is positioned co-planar with the distal portion of the catheter tube 1002 proximal thereto. The electrode carrying structure 1004, however, can also be positioned orthogonal to the catheter tube 1002, as shown in FIG. 50. This flexible arrangement allows the electrode carrying structure 1004 to be more easily located in a pulmonary vein, or around the opening outside of the pulmonary vein.

The diameter of the circular electrode carrying structure 1004 will depend on whether it is desired to ablate within the pulmonary vein or outside and around the opening of the pulmonary vein. That is, an electrode carrying structure 1004 designed to ablate around the opening of a pulmonary vein will have a larger diameter than an electrode carrying structure 1004 that is designed to ablate within a pulmonary vein.

More particularly, the electrode carrying structure 1004 includes multiple, generally rigid segmented electrodes 1006 arranged in a spaced apart, segmented relationship thereupon. The segmented electrodes 1006 may comprise, e.g., solid rings of a conductive material, like platinum, that are interference fitted about the catheter tube 1002. The flexible portions of the catheter tube 1002 between the segmented electrodes 1006 comprise electrically nonconductive regions.

Alternately, the segmented electrodes 1006 may be formed by using conductive, flexible ink, covered by a layer of protective regenerated cellulose, as is disclosed and described in the above-incorporated U.S. application Ser. No. 08/879,343.

The segmented electrodes 1006 are electrically coupled to ablation signal wires 1009, one serving each segmented electrode 1006, to conduct ablating energy to them. Preferably, there are two spaced apart ablation signal wires 1009 electrically coupled to each segmented electrode 1006. By this arrangement, power is delivered in parallel to each segmented electrode 1006. This decreases the effect of voltage gradients within each segmented electrode 1006, which, in turn, improves the uniformity of the delivered current density. The selected spacing within the electrode carrying structure 1004 of the multiple ablation signal wires 1009 serving the respective segmented electrodes 1006 is preferably selected to achieve the uniformity of current density desired.

The ablation signal wires 1009 extend through the main lumen 1014 of the catheter tube 1002 and are suitably electrically coupled to the RF generator 128 and the amount of the RF ablation energy emitted by the segmented electrodes 1006 is controlled by a controller 130 (see FIG. 34). The simultaneous emission of energy by the segmented electrodes 1006 forms a continuous circular curvilinear lesion. Further details regarding the creation of circular curvilinear lesions using segmented electrodes are disclosed in Swanson et al., U.S. Pat. No. 5,582,609, which has been previously incorporated herein by reference. The catheter assembly 1000 can be either operated, at the physician's option, in a bipolar ablation mode or a unipolar ablation mode as previously described.

Figure 48B:
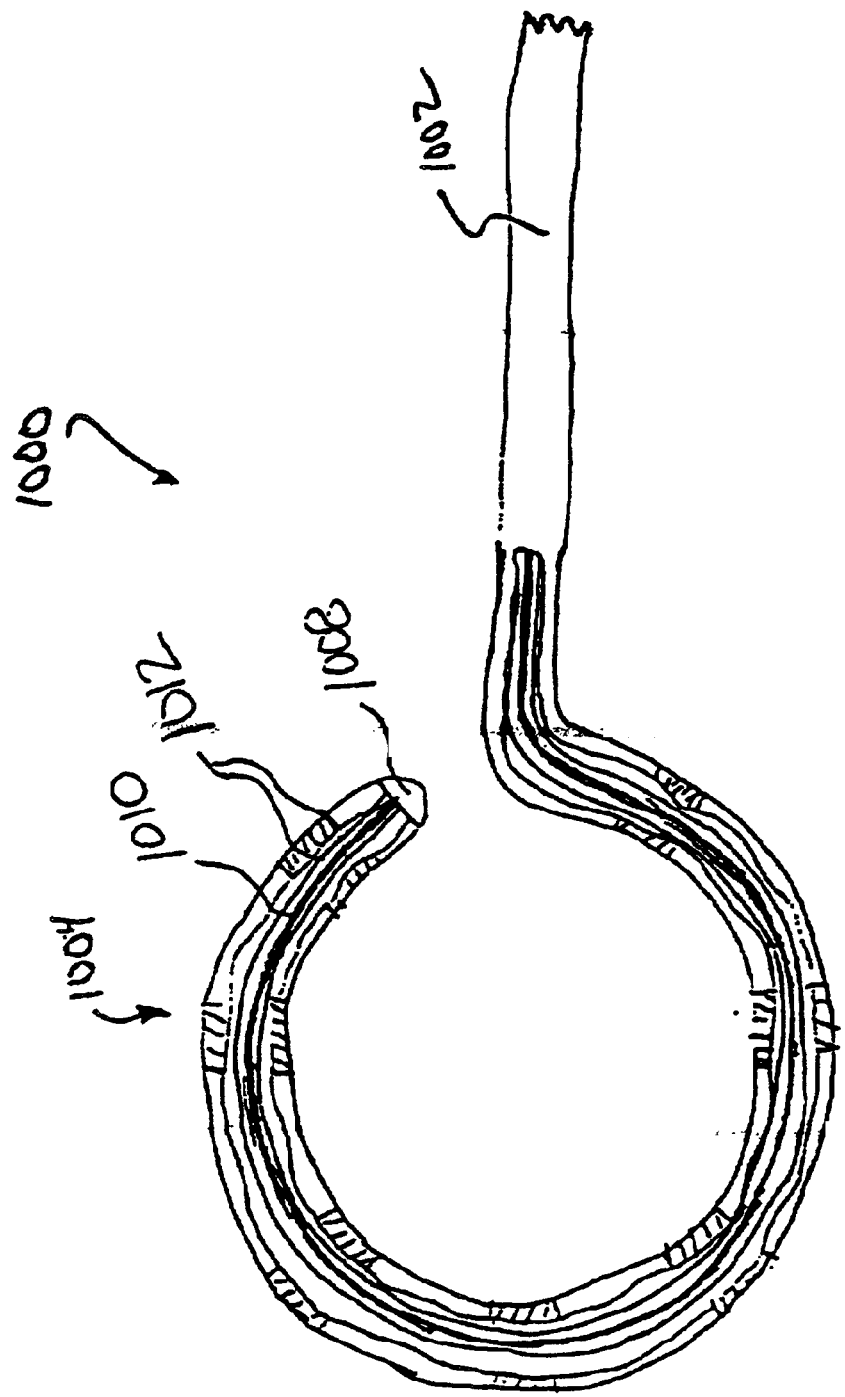
FIG. 48B is a partially cut-away perspective view of the electrode carrying structure of FIG. 47A, particularly illustrating an alternative preferred steering mechanism.

As shown in FIG. 48A, steering of the electrode carrying structure 1006 may be accomplished by suitably bonding the distal ends of left and right steering wires 1012 to the center support 1010 just proximal to the circular electrode carrying structure 1004. The steering wires 1012 extend through the main lumen 1014 of the catheter tube 1002, with their proximal ends connected to the steering mechanism 146 on the handle 804. Alternatively, as depicted in FIG. 48B, the distal ends of the steering wires 1012 can be suitably bonded to the center support 1010 at the distal tip 1008 to allow the radius of the circular electrode carrying structure 1004 to be manually increased or decreased.

Figure 47B:
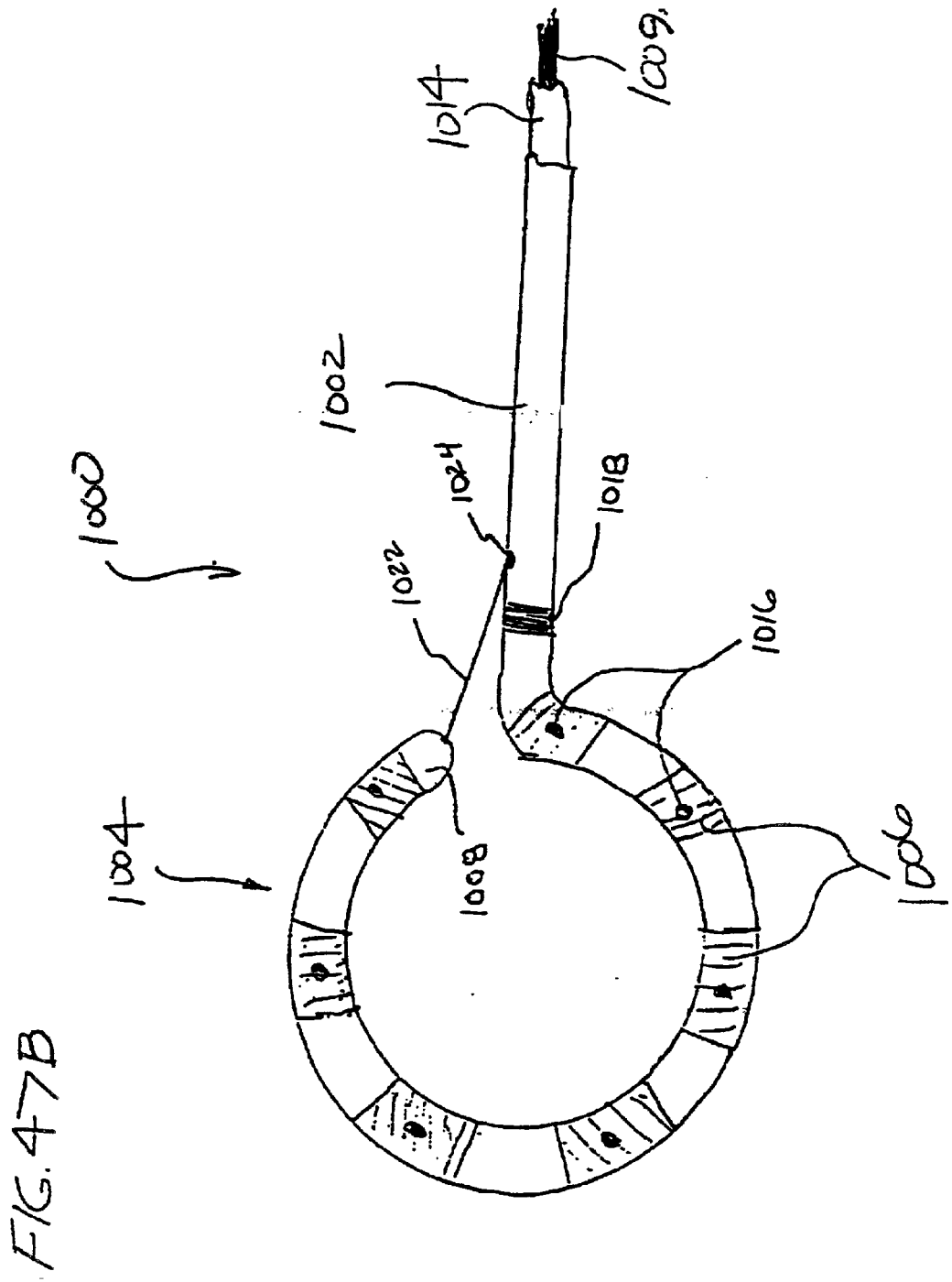
FIG. 47B is a partially cut-away perspective view of the electrode carrying structure of FIG. 47A, particularly illustrating a first preferred pullwire mechanism.
Figure 47C:
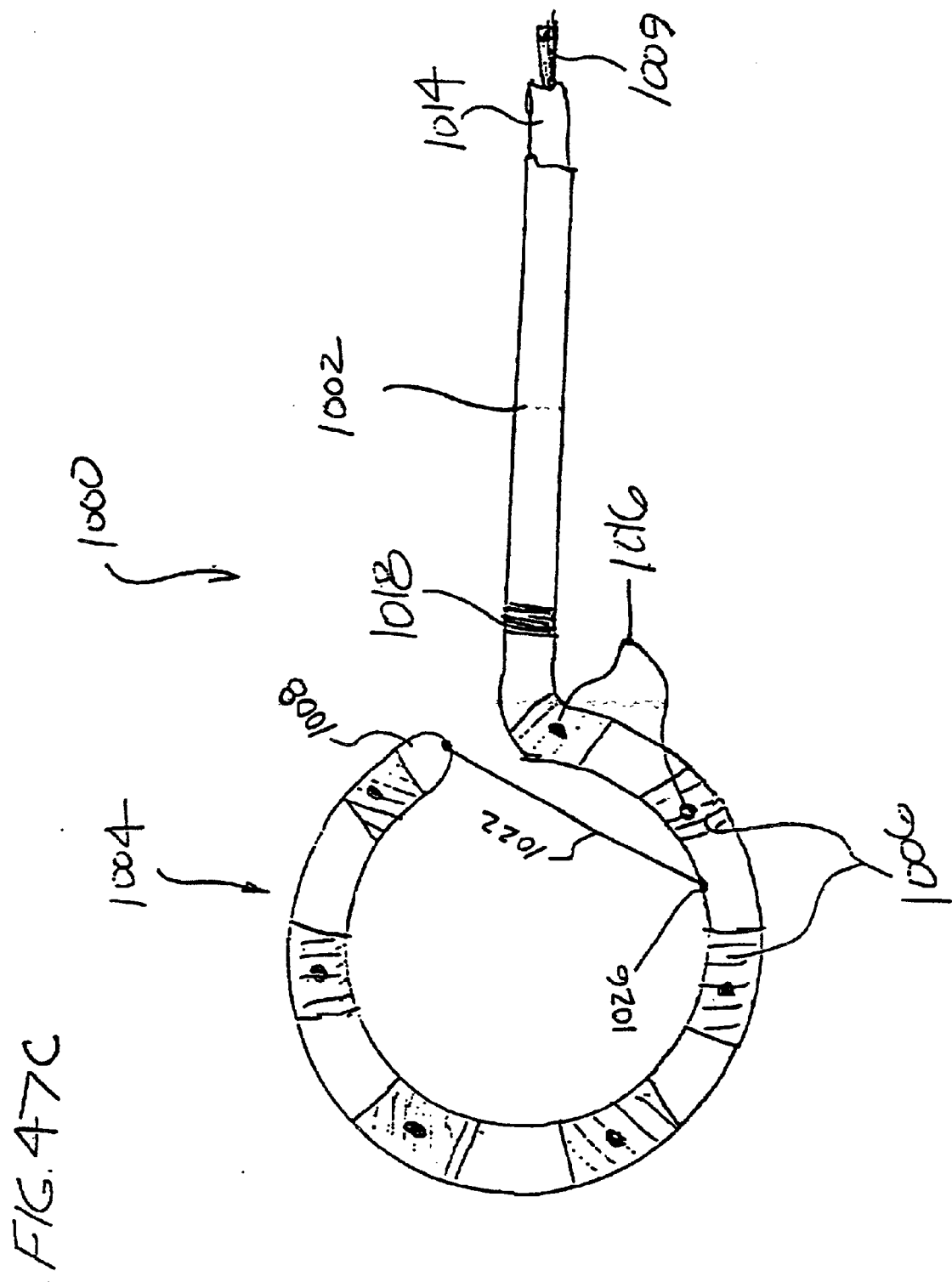
FIG. 47C is a partially cut-away perspective view of the electrode carrying structure of FIG. 47A, particularly illustrating an alternative preferred pullwire mechanism.

As shown in FIGS. 47B and 47C, the electrode carrying structure 1004 can be further manipulated through the employment of a pullwire 1022.

In FIG. 47A, the pullwire 1022 extends through the main lumen 1014, along with the ablation signal wires 1009 and steering wires 1012, and out through an opening 1024 in the catheter tube 1002 located proximal to the circular electrode carrying structure 1004. The distal end of the pullwire is suitably bonded to the distal tip 1008 of the electrode carrying structure 1004. Accordingly, pulling the pullwire 1022 from the proximal end of the catheter tube 1002 causes the distal tip 1008 to be pulled back toward the opening 1024, while relaxation of the pullwire 1022 allows the circular electrode carrying structure 1004 to return to its preformed geometry.

As shown in FIG. 47B, the pullwire can alternatively extend out an opening 1026 in the wall of the circular electrode carrying structure 1004. In this case, pulling the pullwire 1022 from the proximal end of the catheter tube 1002 causes the radius of the circular electrode carrying structure 1004 to decrease, or tighten. Again, relaxation of the pullwire 1022 causes the circular electrode carrying structure 1004 to return to its preformed geometry.

In the illustrated preferred embodiments, each segmented electrode 1006 carries at least one temperature sensing element 1016, such as a thermistor or thermocouple. The respective sensing elements 1016 are preferably located in an aligned relationship along that side of the segmented electrodes 1006 that will face the tissue to be ablated. By way of examples, the location of the temperature sensing elements 1016 on the segmented electrodes 1006 shown in FIGS. 47A–C contemplates usage of the catheter 1000 to create lesions around the opening outside of a pulmonary vein, whereas the location of the temperature sensing elements 1016 on the segmented electrodes 1006 depicted in FIG. 49 contemplates usage of the catheter 1000 to create lesions within a pulmonary vein.

The catheter tube 1002 carries a fluoroscopic marker like the stripe 1018 proximal to the electrode carrying structure 1004 for orientation purposes. The temperature sensing elements 1016 can be on the same side as the fluoroscopic marker 1018, or on the opposite side, as long as the physician is aware of the relative position of them. Further details regarding the structure and use of temperature sensing elements 1016 and fluoroscopic markers 1018 are disclosed in Swanson et al., U.S. Pat. No. 5,582,609, which has been previously incorporated herein by reference.

Referring to FIG. 49, in an alternate preferred embodiment, one side of one or more of the segmented electrodes 1006 is covered with a coating 1020 of an electrically and thermally insulating material. The coating 1020 is preferably applied to the side of the respective electrodes 1006 opposite of the temperature sensing elements 1016. This coating 1020 can be applied, for example, by brushing on a UV-type adhesive or by dipping in polytetrafluoroethylene (PTFE) material. The focused application of ablating energy that the coating 1020 provides helps .to control the characteristics of the lesion. The coating 1020 also minimizes the convective cooling effects of the blood pool upon the segmented electrodes 1006 while ablating energy is being applied, thereby further enhancing the efficiency of the lesion formation process.

In a still further alternative embodiment, the electrode carrying structure 1004 can comprise flexible electrodes, or ribbon electrodes, which enable it to be bent back upon itself to assume a circular periphery as described above. Further details concerning these alternative structures, as well as further details on the general structure of segmented electrode catheters are disclosed in Swanson et al., U.S. Pat. No. 5,582,609, which has previously been incorporated herein by reference.

Referring generally to FIGS. 51–58, the catheter assembly 1000 can be employed to isolate focal arrhythmia substrates in a pulmonary vein by creating a circumferential lesion at the base of the pulmonary vein or inside of the pulmonary vein depending on the size of the electrode carrying structure 1004.

Figure 51:
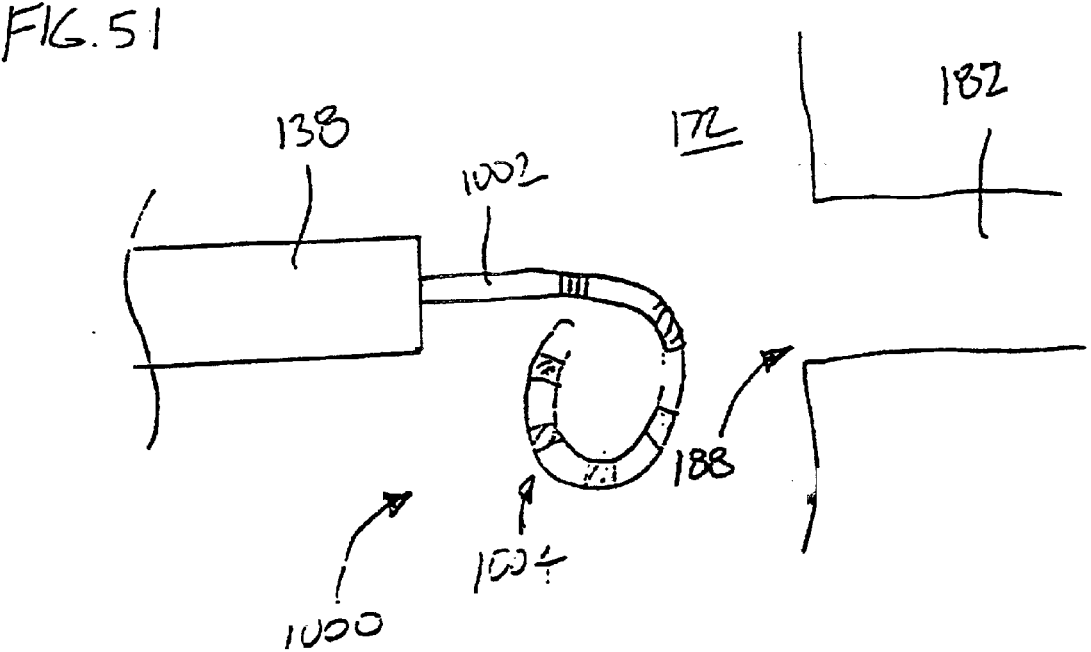
FIG. 51 is a side view of the electrode carrying structure of FIG. 47A disposed in the left atrium of the heart via a guide sheath.

Specifically, a physician locates the electrode carrying structure 1004 in the left atrium 172 of the heart via the guide sheath 138 through either of the aforementioned retrograde or transeptal methods, as shown in FIG. 51. If the electrode carrying structure 1004 is sized for creating circumferential lesions within a pulmonary vein 182, the physician can, using the steering mechanism (146) or other suitable means, insert the electrode carrying structure 1004 into the pulmonary vein 182 as depicted in FIGS. 52, 53, and 54.

Figure 52:
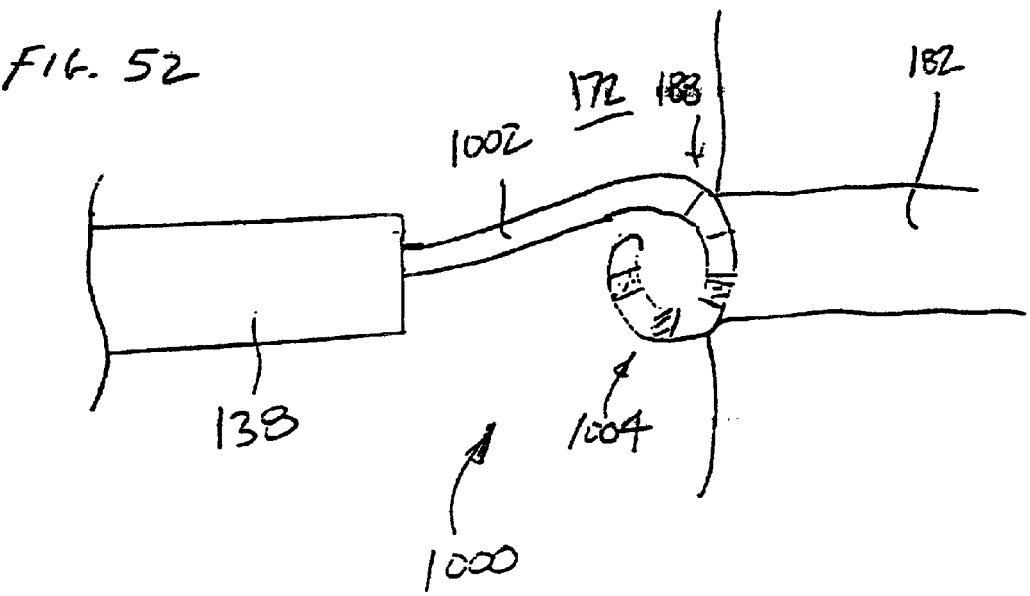
FIG. 52 depicts the electrode carrying structure of FIG. 51, wherein the preformed circular electrode carrying structure is butted up against the opening of the pulmonary vein.
Figure 53:
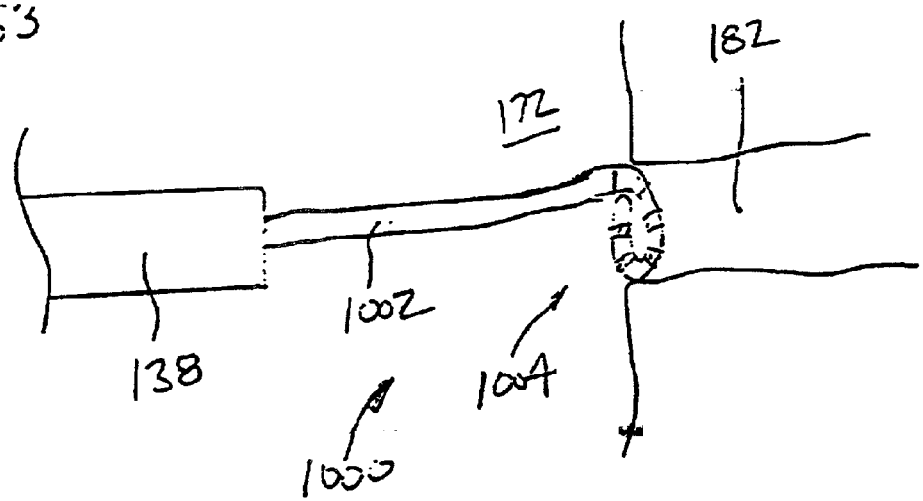
FIG. 53 depicts the electrode carrying structure of FIG. 51, wherein the preformed circular electrode carrying structure is bent orthogonal to the portion of the catheter tube proximal thereto while the preformed portion is being inserted into the pulmonary vein.

This is accomplished by steering the electrode carrying structure 1004 until it butts up against the opening 188 of the pulmonary vein 182 (shwon in FIG. 52). The electrode carrying structure 1004 is then further pushed forward, causing the electrode carrying structure 1004 to become orthogonal with respect to the portion of the catheter tube 1002 proximal thereto (shown in FIG. 53). If the electrode carrying structure 1004 is pre-shaped orthogonal to the portion of the catheter tube 1002 proximal thereto, as shown in FIG. 50, this step need not be performed.

Figure 54:
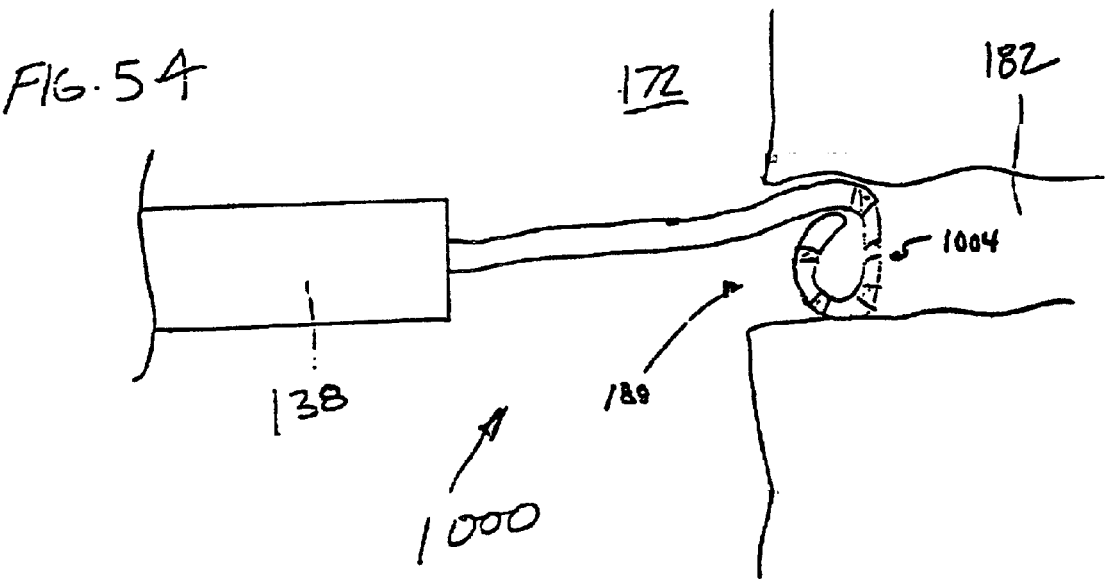
FIG. 54 depicts the electrode carrying structure of FIG. 51, wherein the preformed circular electrode carrying structure is fully disposed in the pulmonary vein.
Figure 55:
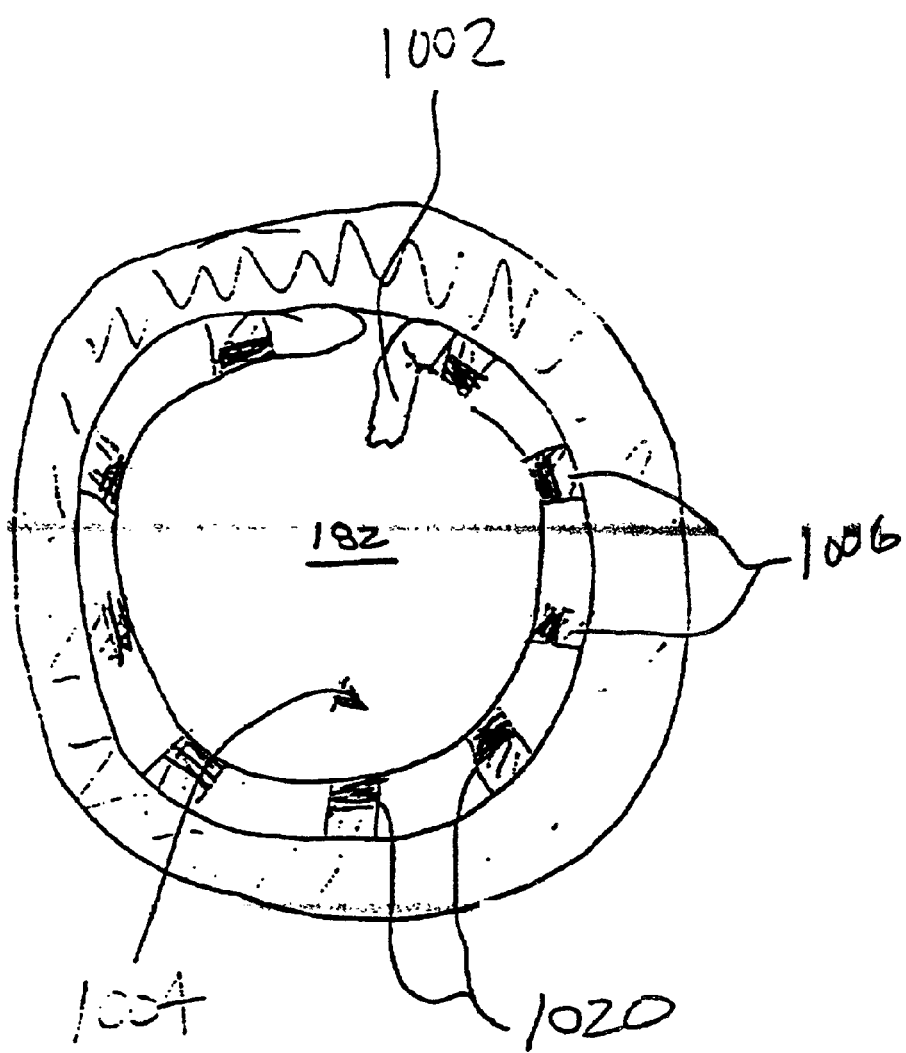
FIG. 55 is an axial view of the preformed circular electrode carrying structure as depicted in FIG. 54.

The electrode carrying structure 1004 is then pushed into the pulmonary vein 182, until all of the segmented electrodes 1006 are in contact with the tissue of the pulmonary vein 182, as shown in FIGS. 54 and 55. If a pullwire (1022) is employed, the circular electrode carrying structure 1004 can more easily be manipulated into the pulmonary vein 182. If the segmented electrodes 1006 comprises a masking coating 1020, the coating 1020 should be facing away from the tissue as shown in FIG. 55.

The physician then conveys RF energy from the generator 128 to the segmented electrodes 1006, as governed by the controller 130. The segmented electrodes 1006 transmit RF energy into a circumferential tissue region of the pulmonary vein to a return electrode (unipolar arrangement) or an adjacent segmented electrode 1006 (bipolar arrangement). As with the catheter assembly 100, a circumferential lesion is thereby created in the pulmonary vein, isolating any focal arrhythmia substrates within the pulmonary vein 182 from the left atrium 172.

If the electrode carrying structure 1004 is sized for creating a circumferential lesion around the opening 188 and outside of the pulmonary vein 182, the physician can butt the electrode carrying structure 1004 up against the opening 188 of the pulmonary vein 182 (see FIG. 56) until the electrode carrying structure 1004 is orthogonal to the portion of the catheter tube 1002 proximal thereto (see FIG. 57). If the electrode carrying structure 1004 is pre-shaped orthogonal to the portion of the catheter tube 1002 proximal thereto, as shown in FIG. 50, this step need not be performed.

At this point, if a masked coating 1020 is disposed on a portion of the segmented electrodes 1006, the physician must verify that the coating 1020 is facing away from the tissue to be ablated. The physician, however, will not need to verify this if the electrode carrying structure 1004 is pre-shaped orthogonal to the portion of the catheter tube 1002 proximal thereto, since this arrangement will ensure that the masked coating 1020 is always facing away from the tissue. The electrode carrying structure 1004 is then slid along the opening 188 of the pulmonary vein 182 until the segmented electrodes 1006 circumscribe the opening 188 (see FIG. 58).

RF energy is then delivered to the segmented electrodes 1006, thereby creating a circumferential lesion around the opening 188 of and outside the pulmonary vein 182 and isolating any focal arrhythmia substrates within the pulmonary vein 182 from the left atrium 172.

Referring to FIG. 59, a still further preferred embodiment of a catheter assembly 1100 is configured to create a circumferential lesion within a pulmonary vein, or alternatively around the opening of the pulmonary vein, by employing a still further preferred sheath-activated electrode carrying structure 1104. The catheter assembly 1100 preferably includes a handle with a steering mehanism, such as the above-described handle 804 and steering mechanism 146 used with catheter assembly 800 (shown in FIG. 33.

More particularly, the catheter assembly 1100 comprises a flexible catheter tube 1102 having a proximal end that is attached to a handle (not shown), and a distal end attached to the electrode carrying structure 1104. The catheter tube 1102 Forms a main lumen 1106 used to house signal wires (not shown) and steering wires 1126. The electrode carrying structure 1104 comprises a sleeve 1106, on which multiple electrodes 1110 are disposed. The sleeve 1108 is made of, for example, a polymeric, electrically nonconductive material, like polyethylene, polyurethane, or PEBAX®.

The proximal end of the sleeve 1108 is suitably bonded to the distal end of the catheter tube 1102. Disposed within the sleeve 1108 is a center support member 1112 (shown in phantom) made from resilient, inert wire, such as nickel titanium (commercially available as Nitinol material), stainless steel 17-7, or thermoplastic material. The center support member 1112 is preferably rectilinear in cross section for stability.

Figure 60:
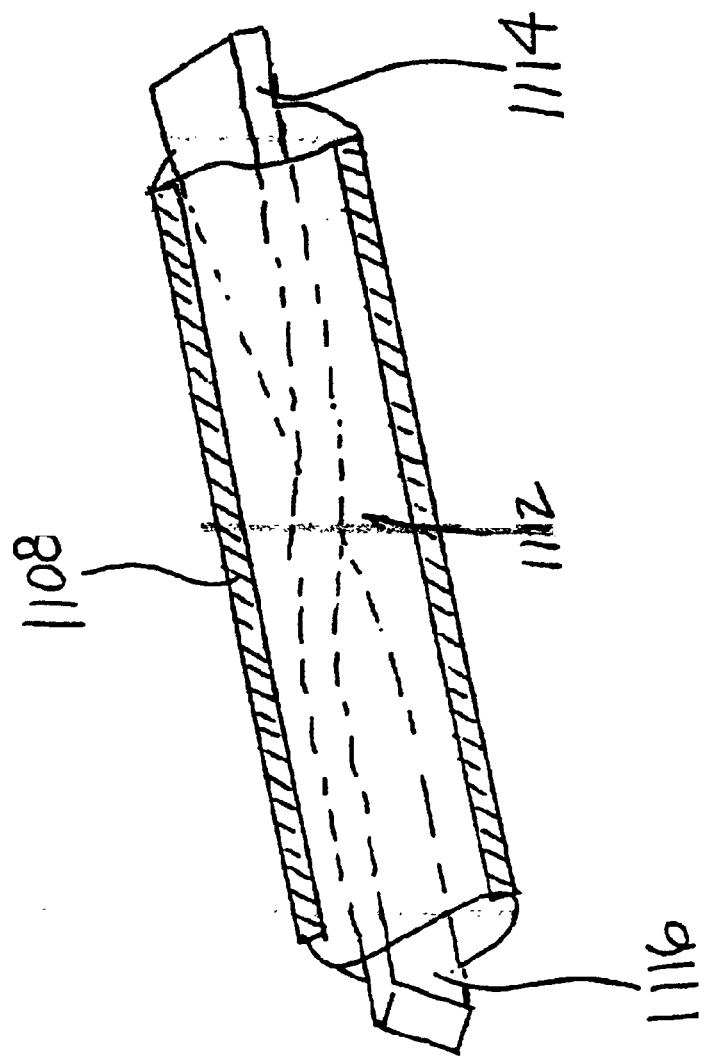
FIG. 60 is a partially cut-away perspective view of a center support employed by the electrode carrying structure of FIG. 59.

As seen in FIG. 60, the center support member 1112 is preformed in a normally twisted condition, having two sections 1114 and 1116, with section 1114 distal to section 1116. The sections 1114 and 1116 are arranged essentially orthogonally relative to each other, being offset by about 90°.

If desired, the center support 1112 can be decreased in cross sectional area in a distal direction, by varying, e.g., thickness or width or diameter (if round), to provide variable stiffness along its length. Variable stiffness can also be imparted by composition changes in materials or by different material processing techniques.

The electrodes 1110 can be assembled onto the sleeve 1108 in various ways. They can, by way of example, comprise multiple, generally rigid electrode elements, such as solid rings of conductive material interference fit about the sleeve 1108, arranged in a spaced apart, segmented relationship. Alternatively, the electrodes 1110 can comprise a conductive material coated upon the sleeve 1108 using ion beam deposition or equivalent techniques. Materials possessing these characteristics include, among others, gold, platinum, platinum/iridium, conductive ink epoxy, or a combination thereof. In particular, noble metals are preferred.

Still further alternatively, the electrodes 1110 can comprise spaced apart lengths of closely wound, spiral coils wrapped about the sleeve 1108 to form an array of generally flexible electrodes 1110. The coils are made of electrically conducting material, like copper alloy, platinum, or stainless steel, or compositions such as drawn-filled tubing. The coils can be further coated with electrically conductive material using ion beam deposition or equivalent techniques to improve its conduction properties and biocompatibility. Materials possessing these characteristics include, among others, gold, platinum, platinum/iridium, conductive ink epoxy, or a combination thereof. In particular, noble metals are preferred.

As in previously described preferred embodiments, the electrodes 1110 may also be formed by using conductive, flexible ink, covered by a layer of protective regenerated cellulose, as is disclosed and described in the above-incorporated U.S. application Ser. No. 08/879,343.

The electrodes 1110 are electrically coupled to the RF generator 128 by the ablation signal wires that pass through the main lumen 1106 in the catheter tube 1102 and into the handle, where they are electrically coupled to the connector 126. The electrodes 1110 can be operated in either a unipolar or a bipolar mode as hereinbefore described.

The size and spacing of the electrodes 1110 must be optimized to provide contiguous lesions within the ablation area. Further details on the use of segmented electrodes to form contiguous lesions are disclosed in Swanson, et al., U.S. Pat. No. 5,582,609, which has been previously incorporate herein by reference.

The length of the electrode carrying structure 1104 depends on the particular application thereof. For instance, a lesion created around the opening of the pulmonary vein will be circumferentially longer than a lesion that is made in the pulmonary vein. Therefore, the length of an electrode carrying structure 1104 employed to create a lesion around the opening of the pulmonary vein will be greater than one that is employed to create a lesion within the pulmonary vein. Thus, the length of the electrode carrying structure 1104 is dictated by the circumferential length of the lesion to be created.

The catheter 1000 includes a sheath 1118 disposed about the catheter tube 1102. The proximal section of the sheath 1118 preferably includes a raised gripping surface (not shown) that terminates in the handle (also not shown).

Figure 61:
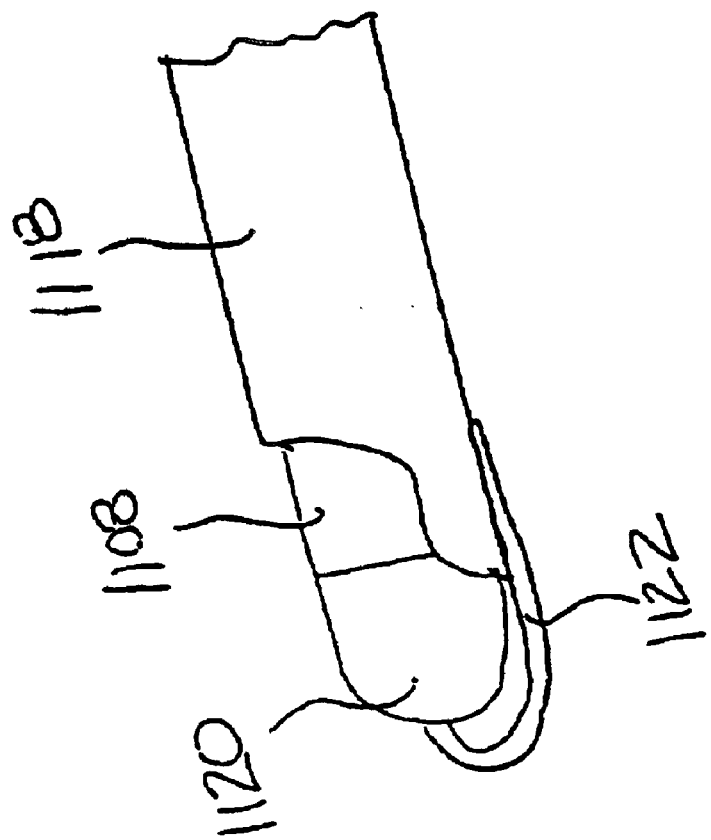
FIG. 61 is a partially cut-away perspective view of the electrode carrying structure of FIG. 59, wherein the wire is alternatively bonded to the exterior of the sheath.

The sheath 1118 extends about the electrode carrying structure 1104 and is joined at its distal end to a distal cap 1120 suitably bonded to the distal end of the electrode carrying structure 1104 by a flexible wire joint 1122. The wire joint 1122 is joined to the distal cap 1120 and the distal end of the sheath 1118, for example, by adhesive or thermal bonding. As FIG. 59 shows in phantom, the wire joint 1122 is depicted as being attached to the interior surface of the sheath 1118. Alternatively, as FIG. 61 shows, the wire joint 1122 can be bonded to the exterior of the sheath 1118.

More particularly, the wire joint 1122 comprises a flexible, inert cable constructed from strands of metal wire material, such as nickel titanium (commercially available as Nitinol material), stainless steel 17-7, or thermoplastic material. Alternatively, the wire joint 1122 can comprise a flexible, inert stranded or molded plastic material.

As shown in FIG. 59, the wire joint 1122 is round in cross section, although other cross sectional configurations can be used. The wire joint 1122 may be attached to the sheath 1118 by thermal or chemical bonding, or can be a continuation of the center support 1112 that forms the core of the electrode carrying structure 1104. The wire joint 1122 can also extend through the wall of the sheath 1118. The need to provide an additional distal hub component to secure the wire joint 1122 to the remainder of the electrode carrying structure 1104, is thereby eliminated.

The sheath 1118 is made from a material having a greater inherent stiffness than the electrode carrying structure 1104 itself, e.g., composite materials made from PTFE, braid, and polyamide. The selected material for the sheath 1118 is preferably also lubricious. For example, materials made from polytetrafluroroethylene (PTFE) can be used for the sheath 1118. Further details concerning the manufacture of a sheath with increased stiffness are disclosed in co-pending U.S. application Ser. No. 08/769,856, filed Dec. 19, 1196, entitled "Loop Structures for Supporting Multiple Electrode Elements," which is fully incorporated herein by reference for all that it discloses and teaches.

Figure 62:
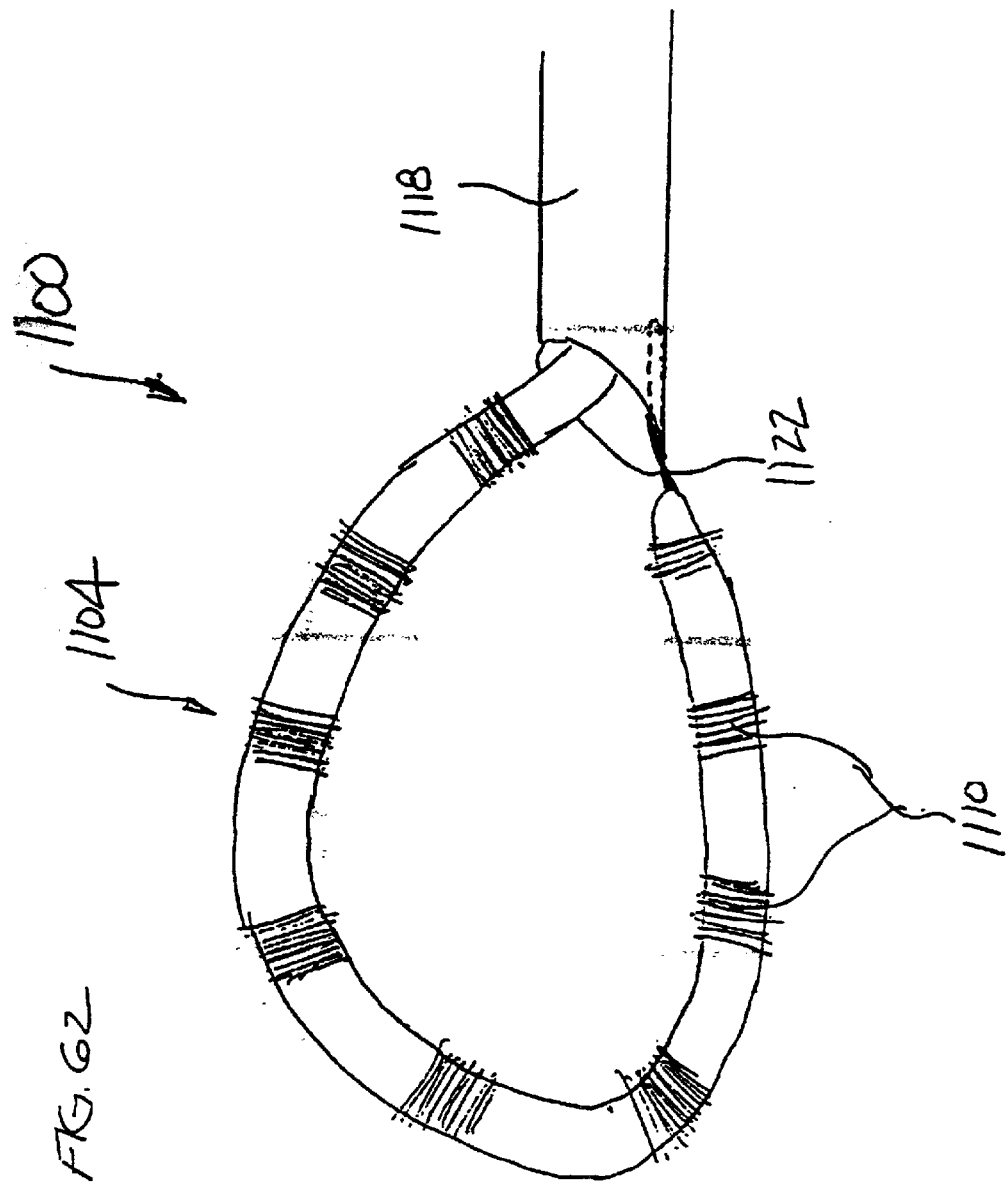
FIG. 62 is a partially cut-away perspective view of the electrode carrying structure of FIG. 59, wherein the electrode carrying structure is partially retracted from the sheath.
Figure 63:
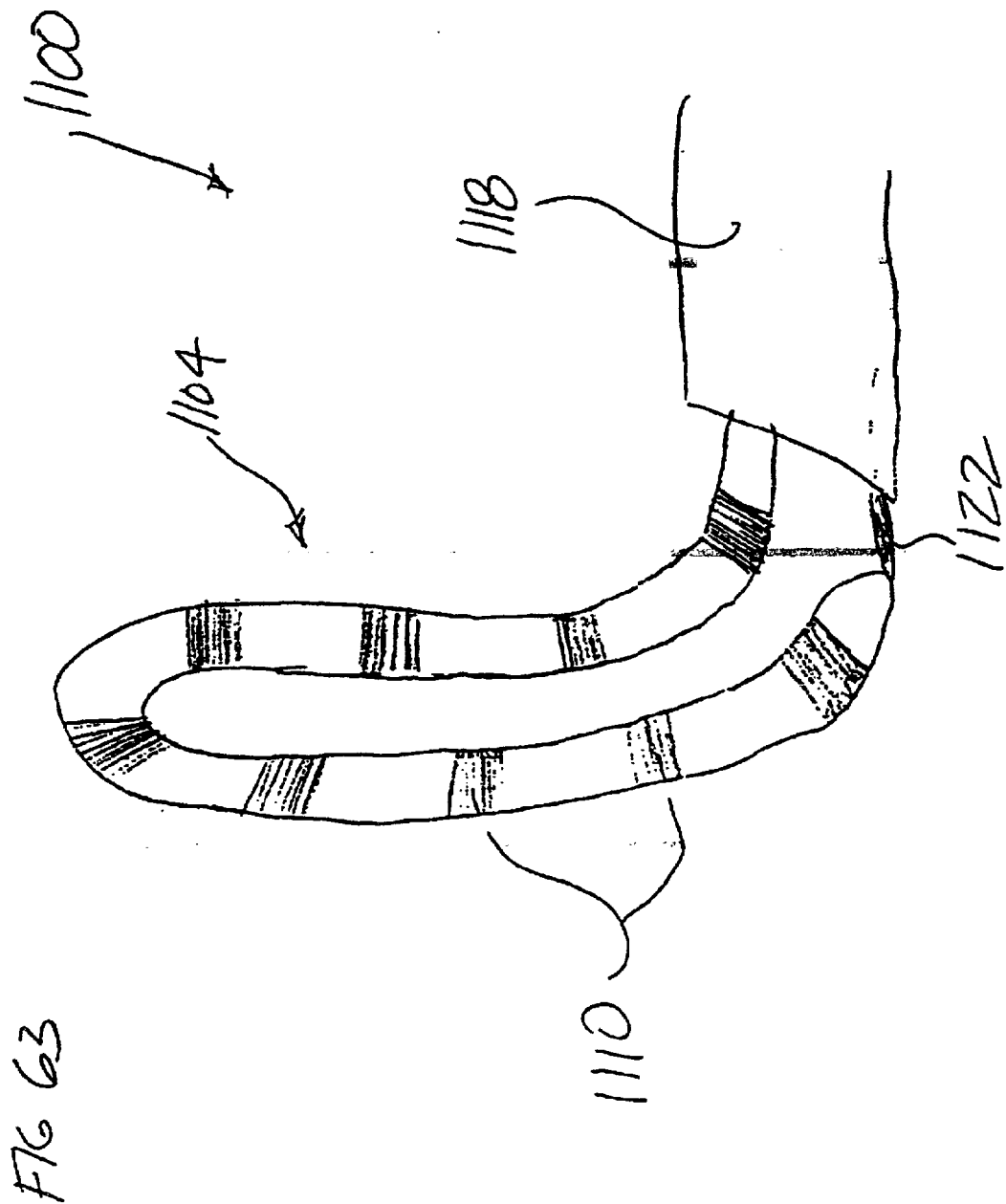
FIG. 63 is a partially cut-away perspective view of the electrode carrying structure of FIG. 59, wherein the electrode carrying structure is fully retracted from the sheath so that the electrode carrying structure forms a loop that is orthogonal to the catheter tube.

The catheter tube 1102 is slidable within the sheath 1118 to deploy the electrode carrying structure 1104. Grasping the raised gripping surface at the proximal end of the sheath 1118, while pushing the catheter tube 1102 in the distal direction through the sheath 1118, moves the electrode carrying structure 1104 toward the distal end of the sheath 1118. The electrode carrying structure 1104 thereby is bent into a loop, as FIG. 62 shows. The twisted bias of the rectilinear center support 1112 causes the formed loop to bend orthogonally to its main axis when the electrode carrying structure is fully extended, as FIG. 63 shows. Such an arrangement facilitates the creation of circular curvilinear lesions.

The wire joint 1122 possesses the flexibility and strength to maintain loop stress within the electrode carrying structure 1104 during manipulation, to thereby establish and maintain intimate contact between the electrodes 1110 and tissue. The wire joint 1122 presents a relatively short length, thereby minimizing tissue trauma.

Moving the electrode carrying structure 1104 fully in the proximal direction returns the electrode carrying structure 1104 into a low profile, generally straightened configuration within the sheath 1118 (shown in FIG. 59), which is well suited for introduction into the intended body region.

In the illustrated embodiments shown in FIGS. 59 and 62, the distal end of the sheath 1118 is cut at an angle and tapered in a transverse direction relative to the axis of the sheath 1118. The angled linear cut on the distal end of the sheath 1118 may also be a contoured elongated opening (see FIG. 61) to make the initiation of the loop formation easier. The angle cut on the sheath 1118 helps deploy and minimizes the length of the wire joint 1122. The distal end of the sheath 1118 thereby also serves to shield the wire joint 1122 as much as possible from direct surface contact with tissue. The possibility of cutting tissue due to contact with the wire joint 1122 is thereby minimized.

Steering of the electrode carrying structure 1104 is accomplished by mounting a center support 1124 in the distal end of the catheter tube 1102. The center support 1124 is made from resilient, inert wire, such as nickel titanium (commercially available as Nitinol material), stainless steel 17-7, or thermoplastic material. Steering wires 1126 are suitably bonded to the left and right sides of the center support 1124 just proximal to the electrode carrying structure 1104.

The steering wires 1126 extend through the main lumen 1106 of the catheter tube 1102. The proximal ends of the steering wires 1126 are connected to a steering mechanism (not shown) on the handle, which pulls on the steering wires 1126 to apply bending forces to the center support 1124. Bending of the center support 1124 bends the distal end of the catheter tube 1102. Further details concerning alternative embodiments of the catheter 1100 are disclosed and described in the above-incorporated U.S. application Ser. No. 08/769,856.

Figure 64:
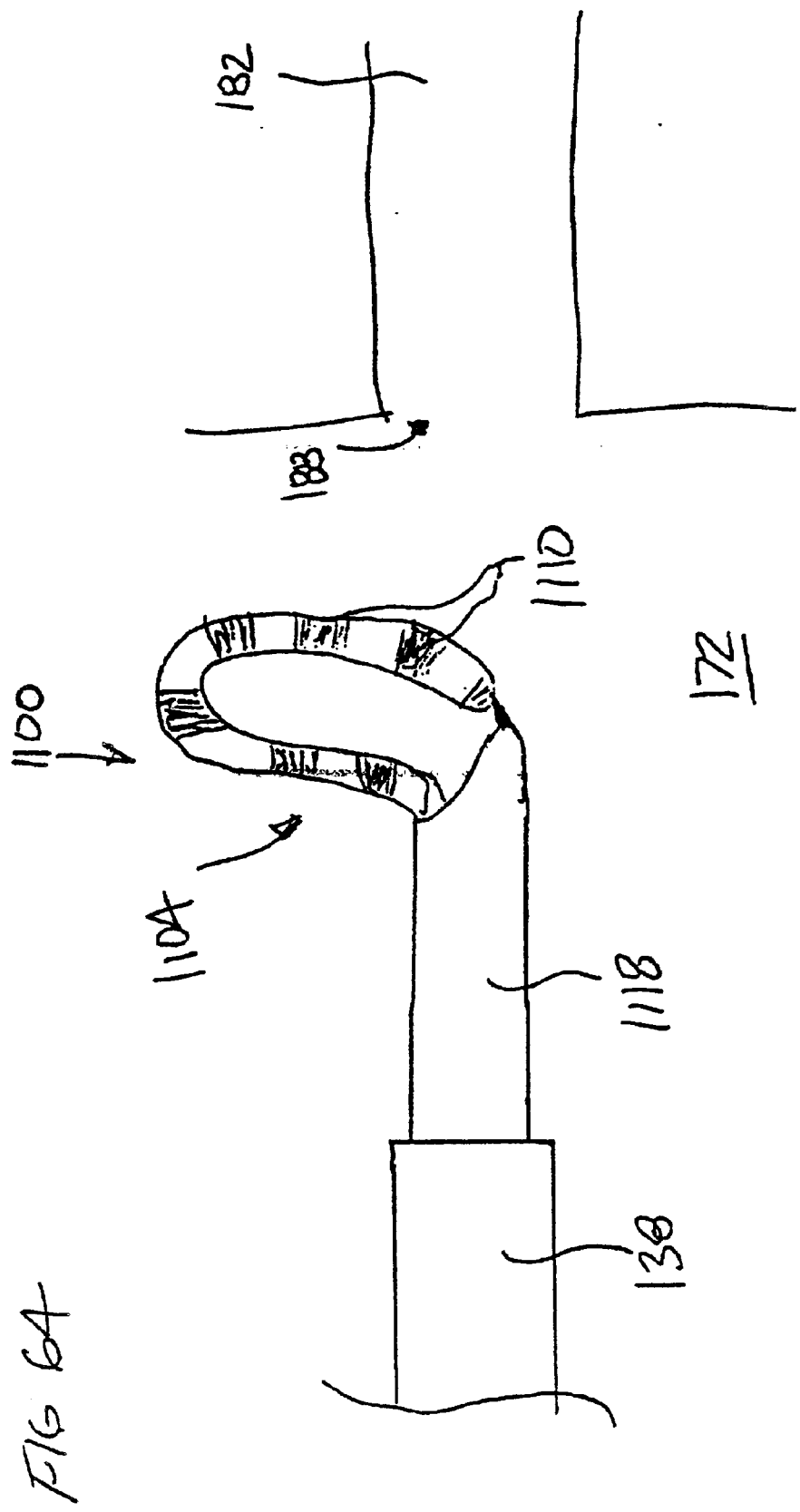
FIG. 64 is a side view of the electrode carrying structure of FIG. 59 disposed in the left atrium of the heart via a guide sheath, wherein the electrode carrying structure is fully retracted from the sheath.

The catheter 1100 can be employed to isolate focal arrhythmia substrates in a pulmonary vein by creating a circumferential lesion inside the pulmonary vein or around the opening and outside of the pulmonary vein depending on the size of the electrode carrying structure 1104. Operation and use of the catheter 1100 is similar to that of the catheter 1000. The electrode carrying structure 1104 and the sheath 1118 in which it is enclosed, is located in the left atrium 172 of the heart via a guide sheath (such as guide sheath 138) through either of the aforementioned retrograde or transeptal methods, as shown in FIG. 64.

The electrode carrying structure 1104 is then deployed from the sheath 1118 by holding the raised gripping surface at the proximal end of the sheath 1118 and then fully pushing the catheter 1102 in the distal direction to form an orthogonal loop as described above. If the electrode carrying structure 1104 is sized for creating circumferential lesions within the pulmonary vein 182, the physician can, using the steering mechanism 146 or other suitable means, insert the electrode carrying structure 1104 as described with respect to the catheter 1000 (see FIGS. 52–55), with the exception that manual orthogonal bending need not be performed, since the electrode carrying structure 1104 automatically becomes orthogonal to the catheter tube 1102 upon full deployment thereof. The physician then conveys RF energy to the electrodes 1110, thereby creating a circumferential lesion in the pulmonary vein 172.

If the electrode carrying structure 1104 is sized for creating a circumferential lesion around the. opening 188 and outside of the pulmonary vein 182, the physician can locate the electrode carrying structure 1104 around the opening 188 and outside of the pulmonary vein 172 in the same manner as described with respect to the catheter 1000 (see FIGS. 56–58), with the exception that manual orthogonal bending need not be performed. The physician then conveys RF energy to the electrodes 1110, thereby creating a circumferential lesion around the opening 188 of and outside of the pulmonary vein 172.

Figure 65:
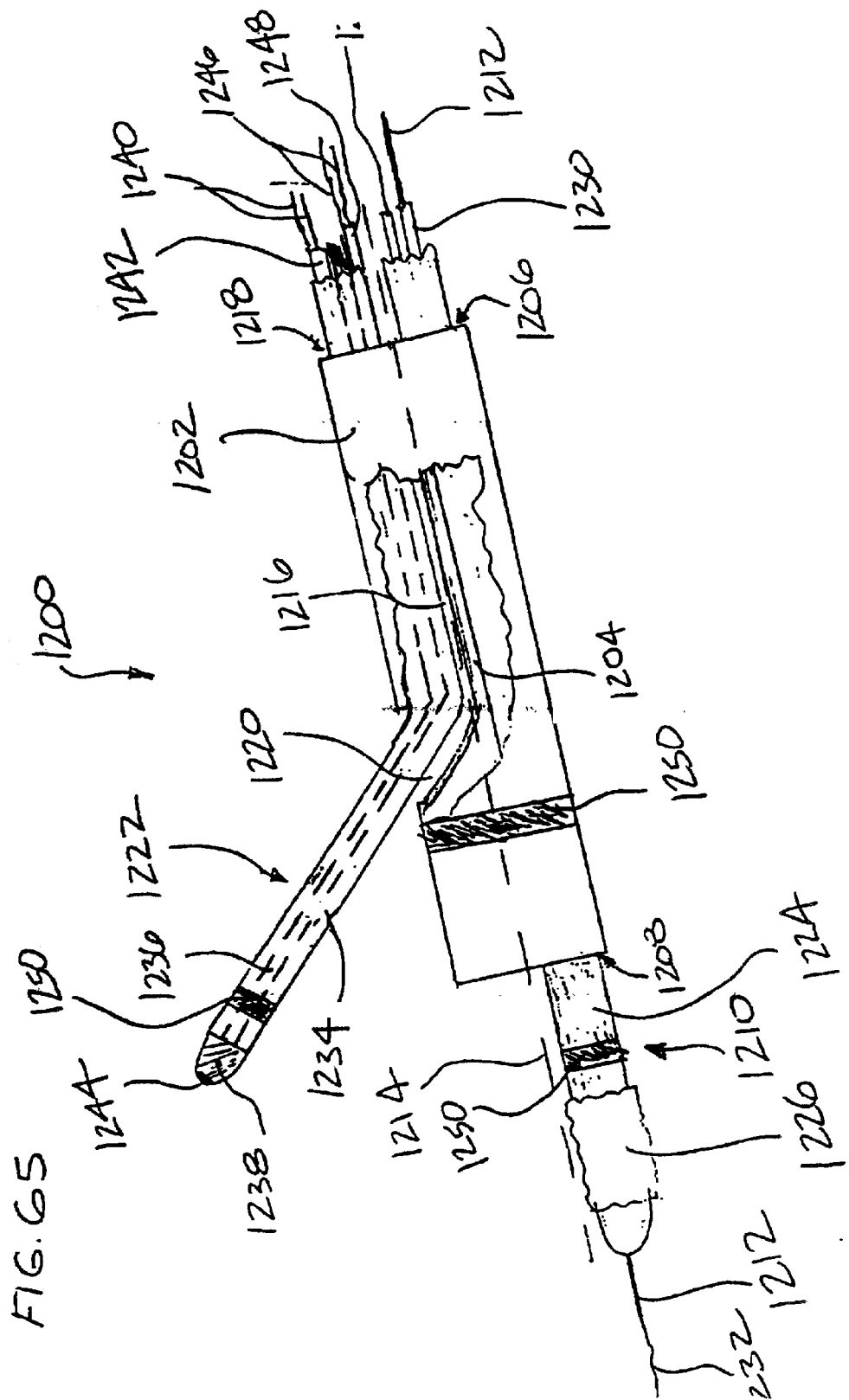
FIG. 65 is a partially cut-away perspective view of the distal end of a still further preferred catheter assembly, including an ablation catheter and a balloon catheter, both of which are disposed in a dual lumen tubular body.
Figure 66:
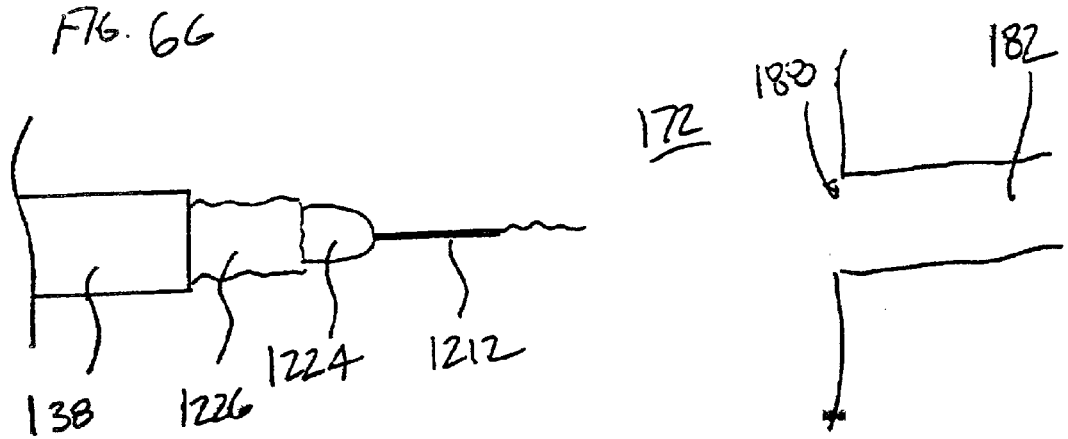
FIG. 66 is a side view of the balloon catheter of the catheter assembly of FIG. 65 disposed in the left atrium the heart via a guide sheath, wherein the balloon catheter includes a guide wire.

Referring to FIG. 65, yet another preferred embodiment of a catheter assembly 1200 is configured to create a circumferential lesion around the opening of a pulmonary vein by employing a dual lumen tubular body 1202 in conjunction with a balloon catheter 1210 to provide an anchoring point for an ablation catheter 1222.

In particular, the dual lumen tubular body 1202 is made of a polymeric, electrically nonconductive material, like polyethylene, polyurethane, or PEBAX®. The tubular body 1202 includes an anchoring lumen 1204 having an accessible inlet 1206 at the proximal end of the tubular body 1202 and an outlet 1208 at the distal end of the tubular body 1202. The anchoring lumen 1204 allows passage of an anchoring mechanism, such as the balloon catheter 1210 on a guide wire 1212, therethrough. The distal end of the balloon catheter 1210 and guide wire 1212 extend outward beyond the outlet 1208 of the anchoring lumen 1204, generally along the same axis 1214 as the tubular body 1202.

The tubular body 1202 further includes an operative lumen 1216 having an accessible inlet 1218 at the proximal end of the catheter tube 1202 and a slotted outlet 1220 proximal to the distal end of the catheter tube 1202. The ablation catheter 1222 is removably disposed within the operative lumen 1216 and can longitudinally slide within the operative lumen 1216. Preferably, the ablation catheter 1222 and the operative lumen 1216 have matching asymmetric cross sections, so that the ablation catheter 1222 does not rotate about itself, and movement thereof is restricted to longitudinal sliding along the operative lumen 1216.

The slotted outlet 1220 is angled at approximately 45 degrees to the longitudinal axis 1214 of the tubular body 1202. In this manner, the ablation catheter 1222 extends from the slotted outlet 1220 at approximately a 45 degree angle to the longitudinal axis 1214 of the tubular body 1202.

The balloon catheter 1210 includes a catheter tube 1224 made of a polymeric, electrically nonconductive material, like polyethylene, polyurethane, or PEBAX®. An expandable-collapsible body 1226 is mounted to and disposed about the distal end of the catheter tube 1224 in the same manner hereinbefore described. The catheter tube 1224 carries an inflation lumen 1228 that opens at its distal end into the body 1226 and at its proximal end into a port (not shown) for conveyance of a liquid inflation medium. As hereinbefore described, conveyance of the liquid inflation medium under positive pressure through the inflation lumen 1228 will expand the body 1226, and conveyance of the liquid inflation medium under negative pressure from the body 1226 and through the inflation lumen 1228 will collapse the body 1226.

The catheter tube 1224 carries a guide lumen 1230 for disposal of a suitable guide wire 1212 therethrough. The guide wire 1212 includes a tip, which prevents or minimizes traumatic contact with tissue. The distal end of the guide wire 1212 includes a floppy tip 1232 for this purpose. The distal end of the guide wire 1212, however, can include a J-tip with similar results.

The guide wire 1212 provides the guidance of the balloon catheter 1210 into the desired location. In lieu of a guide wire 1212, however, a steering platform, such as the type hereinbefore described, can be incorporated into the balloon catheter 1210 to locate the expandable-collapsible body in the desired location.

The ablation catheter 1222 includes a catheter tube 1234 made of a polymeric, electrically nonconductive material, like polyethylene, polyurethane, or PEBAX®. Disposed within the catheter tube 1234 is a center support 1236 (shown in phantom) formed from a resilient, inert wire, such as nickel titanium (commercially available as Nitinol material), stainless steel 17-7, or thermoplastic material. The catheter tube 1234 includes at an ablation electrode 1238 that is disposed about the entire distal tip thereof. In the preferred and illustrated embodiment, the electrode 1238 uses RF energy to ablate tissue with which it makes contact. Preferably, the electrode 1238 is formed by coating the outer surface on the distal end of the catheter tube 1234 with an electrically conducting material At least one, and preferably, at least two insulated ablation signal wires 1240 electrically couple the electrode 1238 to an RF source, such as the aforedescribed RF generator 128. The ablation signal wires 1240 are disposed in first lumen 1242 formed within the catheter tube 1234.

Preferably, at least one temperature sensing element 1244, such as a thermistor or thermocouple, is suitably mounted to the electrode 1238, and preferably at the tip thereof. Temperature sensing element signal wires 1246 electrically couple the temperature sensing elements 1244 to a controller, such as the aforedescribed controller 130. The temperature sensing element signal wires 1246 are disposed in a second lumen 1248 formed within the catheter tube 1234.

To aid in guiding the tubular body 1202, the balloon catheter 1210, and the ablation catheter 1222, radiopaque markers 1250 can be placed near the slotted opening 1250 of the tubular body 1202, at the distal ends of the balloon catheter 1210 and the ablation catheter 1222, for visualization under fluoroscopy. The markers 1250 can be located at other parts of the catheter assembly 1200, as well, to aid in the manipulation thereof.

The dual lumen tubular body 1202 is not limited to usage with the ablation catheter 1222 depicted in FIG. 65, but may also be used with the previously described electrode carrying structures.

Figure 69:
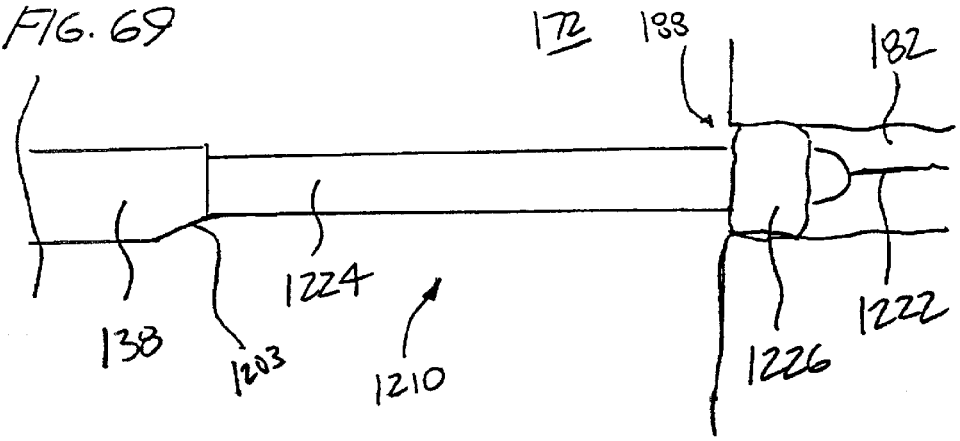
FIG. 69 depicts the balloon catheter of FIG. 68, wherein the balloon catheter is inflated.
Figure 70:
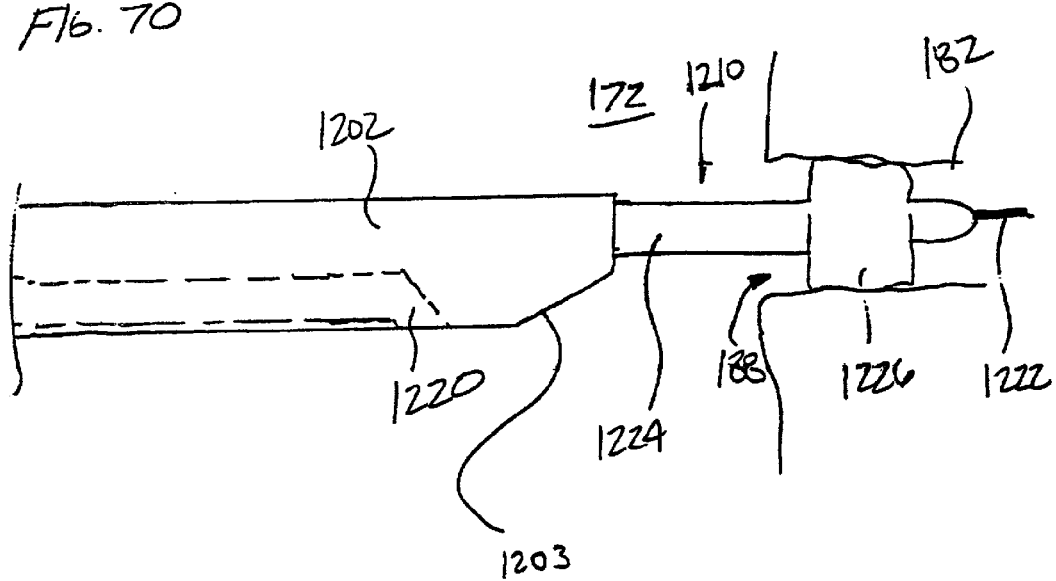
FIG. 70 depicts the dual lumen tubular body of FIG. 65, wherein the tubular body is disposed in the left atrium of the heart about the balloon catheter.

Referring generally to FIGS. 66–73, the catheter assembly 1200 can be employed to create a lesion that circumscribes the opening of the desired pulmonary vein. The physician can introduce the guide wire 1212 into the left atrium 172 via the guide sheath 138 through the aforedescribed retrograde or transeptal approaches (see FIG. 66). At the physician's option, the balloon catheter 1210 can be introduced into the left atrium 172, either concurrently with or subsequent to the location of the guide wire 1212 within the left atrium 172. As shown in FIGS. 69 and 70, the tubular body 1202 may be formed with a tapered distal end 1203, to facilitate introduction of the body 1202 from the right atrium to the left atrium.

Figure 67:
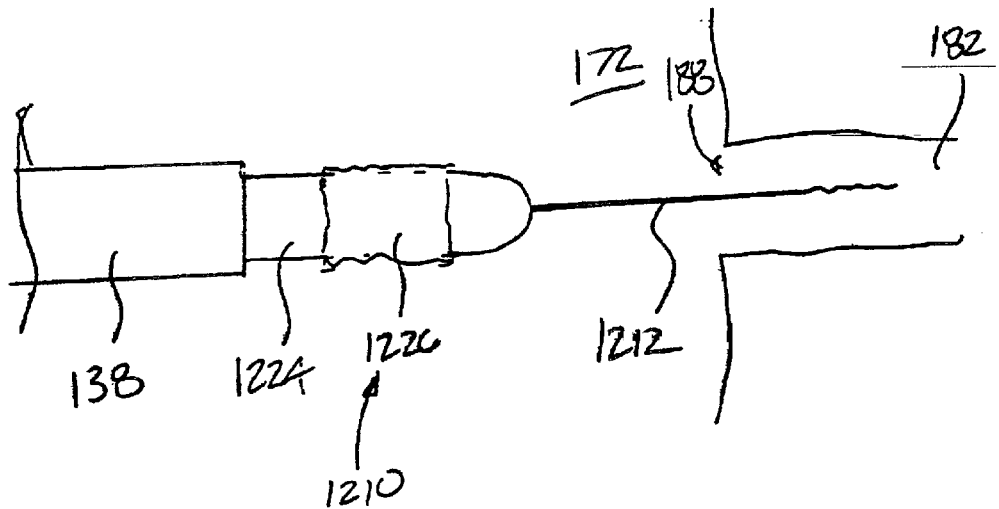
FIG. 67 depicts the balloon catheter of FIG. 66, wherein the distal end of the guide wire is disposed in the pulmonary vein.
Figure 68:
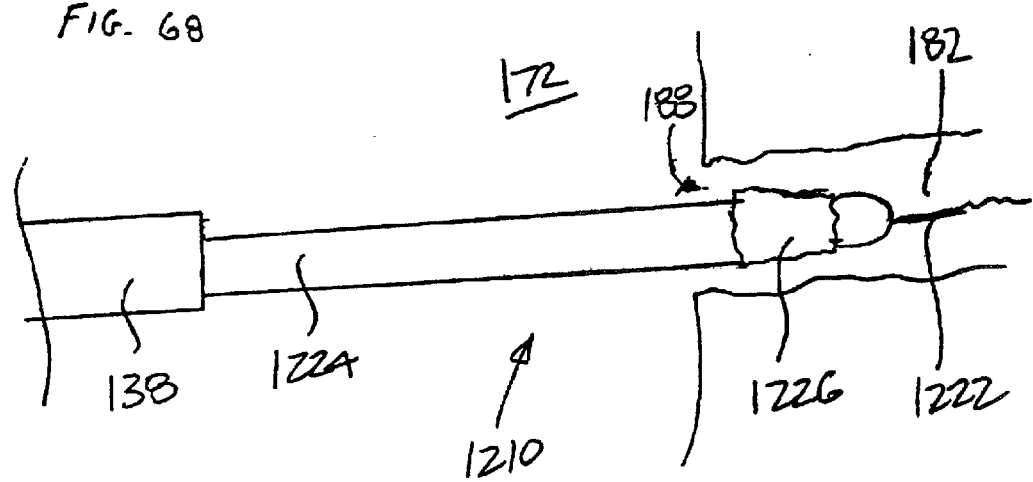
FIG. 68 depicts the balloon catheter of FIG. 66, wherein the guide wire and balloon catheter are disposed in the pulmonary vein.

The guide wire is manipulated through the opening 188 and into the pulmonary vein 182 (see FIG. 67). The body 1226 of the balloon catheter 1210 is then guiding via the guide wire 1212 into the pulmonary vein 182 (see FIG. 68). Alternatively, if a steering platform is incorporated into the balloon catheter 1210, the balloon catheter 1210 can solely be introduced through the guide sheath 138 into the left atrium 172, and then steered into the pulmonary vein 182. The physician then conveys the liquid inflation medium under pressure through the inflation port until the body 1226 expands to a tight fit within the pulmonary vein 182 (see FIG. 69).

The guide sheath 138 is extracted from the patient's body, and the physician introduces anchor lumen 1204 of the dual lumen tubular body 1202 over the balloon catheter 1210. The tubular body 1202 is advanced up the balloon catheter 1210 until the slotted opening 1220 in the tubular body 1202 is located within the left atrium 172 (see FIG. 70).

Figure 71:
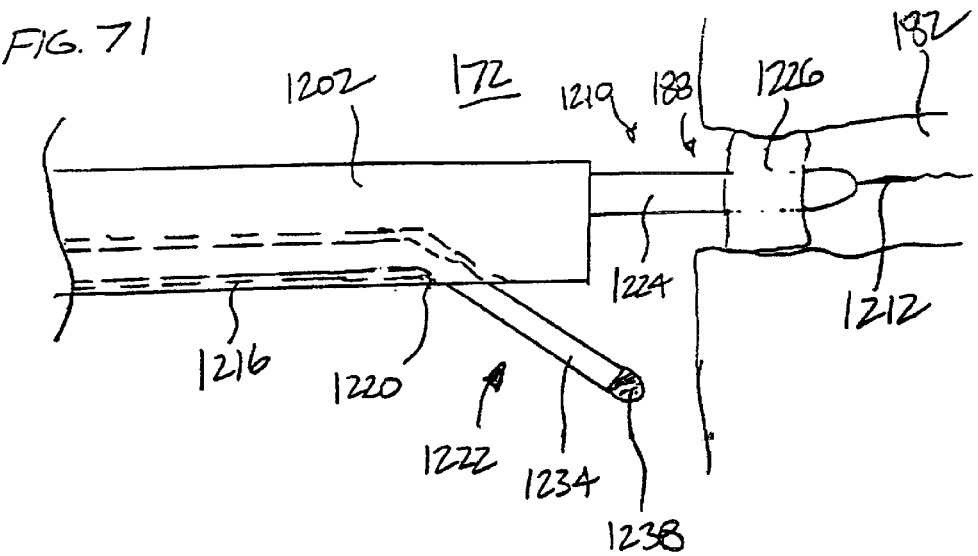
FIG. 71 depicts the dual lumen tubular body of FIG. 70, wherein the ablation catheter is disposed in the left atrium of the heart.
Figure 72:
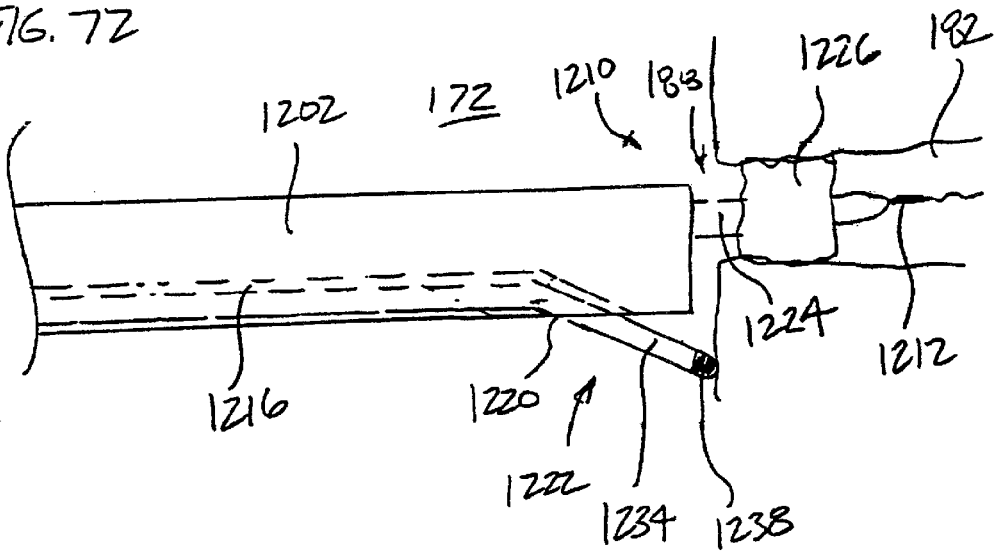
FIG. 72 depicts the dual lumen tubular body of FIG. 71, wherein the tubular body is advanced distally to make contact between the tip of the ablation catheter and the tissue surrounding the opening of the pulmonary vein.
Figure 73:
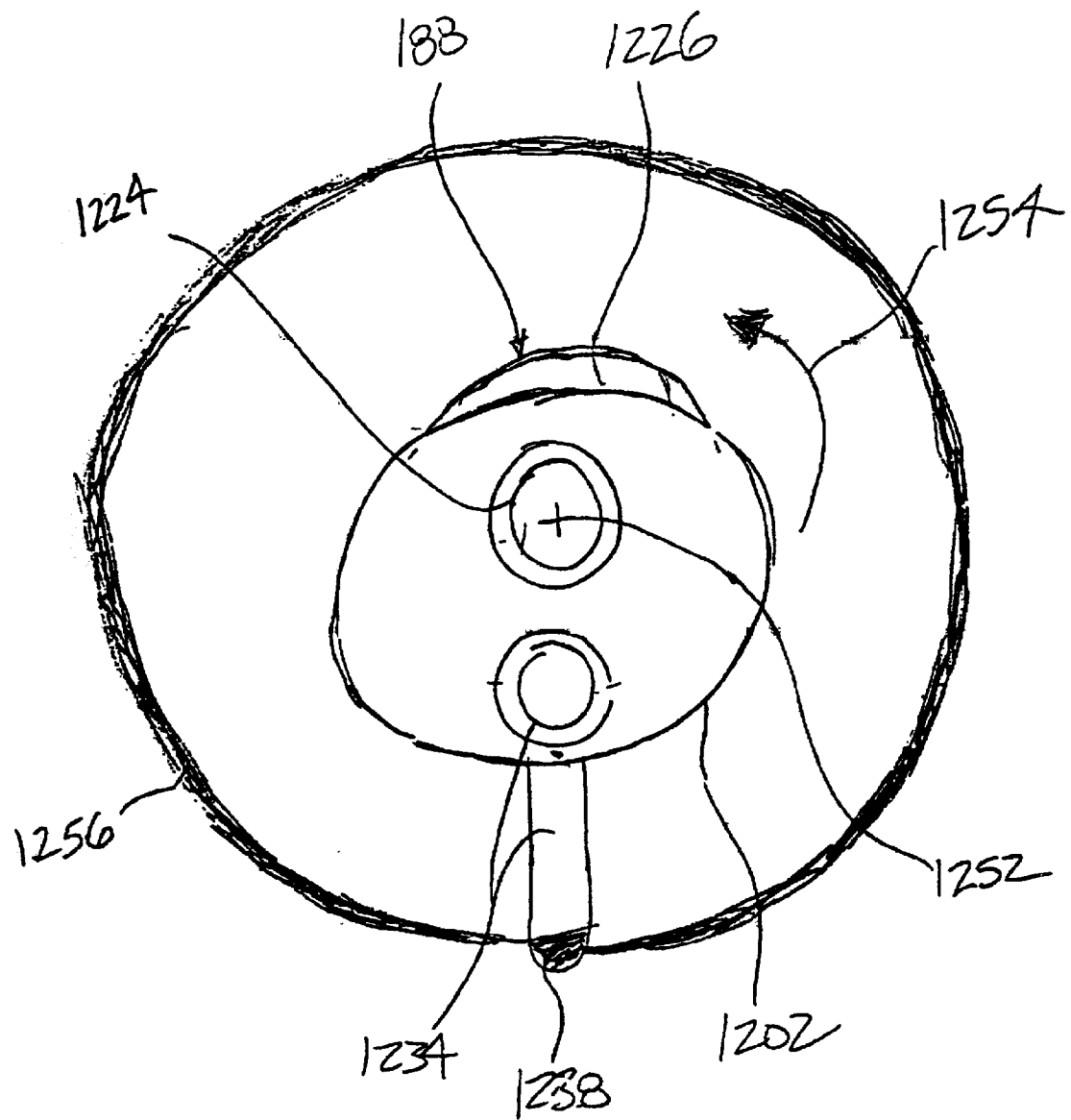
FIG. 73 depicts a lesion formed around the opening of the pulmonary vein of FIG. 66 following a preferred ablation procedure.
Figure 77:
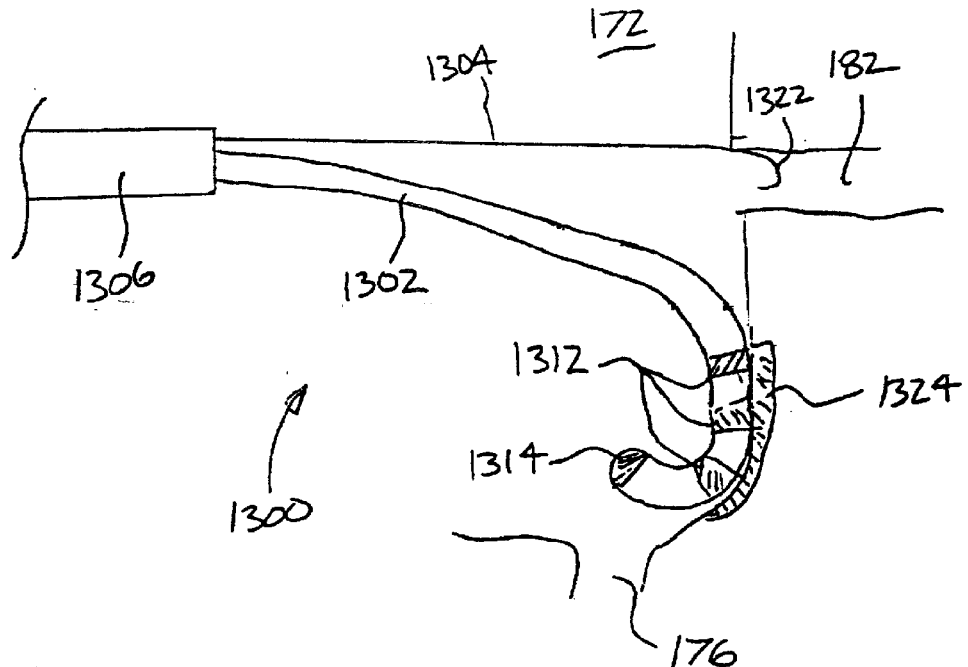
FIG. 77 depicts the ablation catheter of the catheter assembly of FIG. 75 creating a lesion on the wall of the left atrium between the pulmonary vein and the mitral valve.

The physician next introduces the ablation catheter 1222 into the operative lumen 1216 of the tubular body 1202 until the electrode 1238 on the distal tip of the catheter tube 1234 is located distal of the tubular body 1202 (see FIG. 71). Contact between the electrode 1238 and the tissue surrounding the opening 188 of the pulmonary vein 182 is made by advancing the dual lumen tubular body 1202 distally until the electrode 1238 contacts the tissue (see FIG. 72). Alternatively, the ablation catheter 1222 can be advanced distally through the operative lumen 1216 of the tubular body 1202 until the electrode 1238 contacts the tissue.

The physician then conveys RF energy from the generator 128 to the electrode 1238, as governed by the controller 130. The electrode 1238 transmits RF energy to an external patch electrode through the tissue region adjacent to the electrode 1238, thereby forming a lesion in the tissue contacted by the electrode 1238. The physician, simultaneous with the emission of RF energy by the electrode 1238, drags the electrode 1238 around the opening 188 by rotating the dual lumen tubular body 1202 about the longitudinal axis 1252 of the balloon catheter 1210 (indicated by arrow 1254) (see FIG. 73).

In this manner, a circular lesion 1256 is formed around the opening 188 of the pulmonary vein 182, and any focal arrhythmia substrates within the pulmonary vein 182 are thereby isolated from the left atrium 172.

The catheter assembly 1200 can be used for other applications besides ablating around the opening 188 of the pulmonary vein 182 by dragging an electrode. For instance, the catheters 1000 and 1100 can be advanced through the operative lumen 1216 of the tubular body 1202 to form lesions around the opening 188 of the pulmonary vein 182.

Referring to FIG. 74, yet another preferred embodiment of a catheter assembly 1300 is configured to create a series of lesions around anatomical structures, and particularly around pulmonary veins of the heart, by employing a steerable ablation catheter 1302, a guide wire 1304, and a guide sheath 1306. The catheter assembly 1300 preferably employs a handle with a steering mechanism, such as the afore-described handle 804 with the steering mechanism 146 used in conjunction with assembly 800 (Shown in FIG. 33).

In particular, the steerable ablation catheter 1302 and the guide wire 1304 are separately disposed in the guide sheath 1306. The guide sheath 1306 is a typical guide sheath used to locate catheters and guide wires within the cavities of the body, such as guide sheath 138, and more particularly within the left atrium of the heart. The guide sheath 1306 comprises a soft distal tip 1308 to minimize tissue trauma. The soft distal tip 1308 comprises any soft biocompatible material known in the art. To aid the physician in locating the guide sheath 1306, the guide sheath 1306 also comprises a radiopacue marker 1310 at its distal end for visualization under fluoroscopy.

The steerable ablation catheter 1302 has a proximal end that is connects to a handle (not shown) and a distal end that includes at least one electrode. In the illustrated embodiment, the ablation catheter 1302 includes a series of segmented electrodes 1312 and a distal ablation electrode 1314 on the distal end of the ablation catheter 1302. The segmented electrodes 1312 and the distal electrode 1314 can be made of rigid conductive electrodes, flexible electrodes, or ribbon electrodes, such as those disclosed in Swanson et al., U.S. Pat. No. 5,582,609.

Alternately, the segmented electrodes 1312 and the distal electrode 1314 can be made of deposited conductive material or coiled electrodes, such as those disclosed and described in the above-incorporated U.S. application Ser. No. 08/769,856, or of a conductive, flexible ink covered by a regenerated cellulose coating, such as disclosed and described in the above-incorporated U.S. application Ser. No. 08/879,343.

The size and the spacing of the segmented electrodes 1312 are optimized to create contiguous lesions. Further details concerning the spacing of segmented electrodes are disclosed in Swanson et al., U.S. Pat. No. 5,582,609, which has been previously incorporated herein by reference.

The segmented electrodes 1312 and the distal electrode 1314 are electrically coupled to the RF generator 128 through ablation signal wires (not shown), which extend through the ablation catheter 1302 to the handle. As depicted in FIG. 34, the handle (804) is preferably electrically coupled to an RF generator (128) through suitable connectors (126).

Preferably, temperature sensing elements 1316 can be incorporated into the segmented electrodes 1312 and the distal electrode 1316 to provide temperature feedback to the controller 128. In the illustrated embodiment, the temperature sensing elements 1316 are thermocouples. A $T_C$ cold junction element 1318 is provided between the segmented electrodes 1312 and the distal electrode 1314. Temperature sensing wires (not shown) are employed to electrically couple the temperature sensing elements 1316 and the $T_C$ cold junction element 1318 to the controller 128.

A sensing electrode 1320 is provided proximal to and in conjunction with the distal electrode 1314 for mapping in the heart, and in particular, in and around the pulmonary veins of the left atrium. The $T_C$ cold junction element 1318 can be coupled with the sensing electrode 1320. A detailed description of a method of mapping heart tissue using electrodes is disclosed in Swanson et al., U.S. Pat. No. 5,595,183.

The guide wire 1304 comprises a 0.018" resilient wire made of a resilient, inert wire, such as nickel titanium (commercially available as Nitinol material), stainless steel 17-7, or thermoplastic material. To minimize tissue trauma, the distal end of the guide wire 1304 comprises a J-tip coil 1322. The distal end of the guide wire 1304, however, can also comprise a floppy tip to achieve the same result. The ablation catheter 1302 is bi-directionally steered using a center support (not shown) and steering wires (not shown) in a manner hereinbefore described.

Referring to FIGS. 75–78, the catheter assembly 1300 can be employed to create linear lesions around an anatomical structure within the heart such as the pulmonary veins. As will be appreciated from the following discussion, anchoring of the guide wire 1304 within an anatomical structure in the heart, such as a pulmonary vein, serves to stabilize the guide sheath 1306, thereby enhancing the placement and control of the ablation catheter 1302 in the tissue area surrounding the anatomical structure.

Referring specifically to FIG. 75, the physician first introduces the guide sheath 1306 into the left atrium 172 via the aforedescribed retrograde or transeptal approaches. Preferably, the guide wire 1304 is first introduced into the guide sheath 1306 and advanced therethrough until the guide wire 1304 is located in the left atrium 172. The ablation catheter 1302 is then introduced into the guide sheath 1306 and advanced therethrough until the ablation catheter 1302 is located in the left atrium 172. Alternatively, the guide wire 1304 and the ablation catheter 1302 can be introduced into the left atrium 172 through the guide sheath 1306 simultaneously.

The J-tip 1322 of the guide wire 1304 is inserted into the pulmonary vein 182 to stabilize the guide sheath 1306, thereby creating a stable platform on which the ablation catheter 1302 can be manipulated (see FIG. 76).

The physician can move the ablation catheter 1302 independently of the guide wire 1304, since the guide wire 1304 is disposed in the guide sheath 1306, rather than in the ablation catheter 1302. By manipulation of the steering lever 150 on the steering mechanism 146 (see FIG. 33), and using the guide sheath 1306 as a stable platform, the physician can properly locate the ablation catheter 1302 adjacent to the desired ablation region. Further manipulation of the steering lever 150 (e.g., by "backsteering" the distal end of the catheter 1302) will allow the physician to place the segmented electrodes 1312 or the distal electrode 1314 in proper contact with tissue around the pulmonary veins 182, or the tissue from the pulmonary veins 182 to the mitral valve 176, for further mapping and/or ablation procedures (see FIG. 77).

Figure 78:
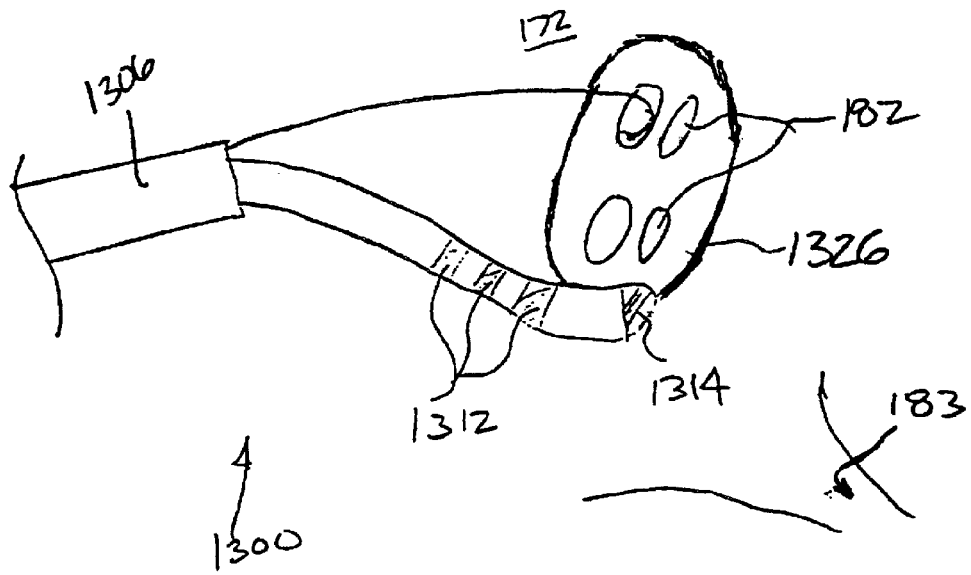
FIG. 78 depicts the ablation catheter of the catheter assembly of FIG. 75 creating a circular lesion around the four pulmonary veins.

After proper contact is established, the physician can create a lesion by operating the RF generator 128, which is governed by the controller 130, to convey RF energy to the either of the segmented electrodes 1312 or the distal electrode 1314 for delivery of RF energy into the adjacent tissue. Stabilized by the guide sheath 1306, the physician can create controlled contiguous lesions within the left atrium near the pulmonary vein 182. For instance, a linear lesion 1324 can be created between the pulmonary veins 182 and the mitral valve 176 by placing the segmented electrodes 1312 therebetween and operating the RF generator 128 for delivery of RF energy to the segmented electrodes 1312. Alternatively, as shown in FIG. 78, the four pulmonary veins 182 can be circumscribed with a contiguous lesion 1326 by dragging and ablating with the distal electrode 1314 or the segmented electrodes 1312.

Figure 79:
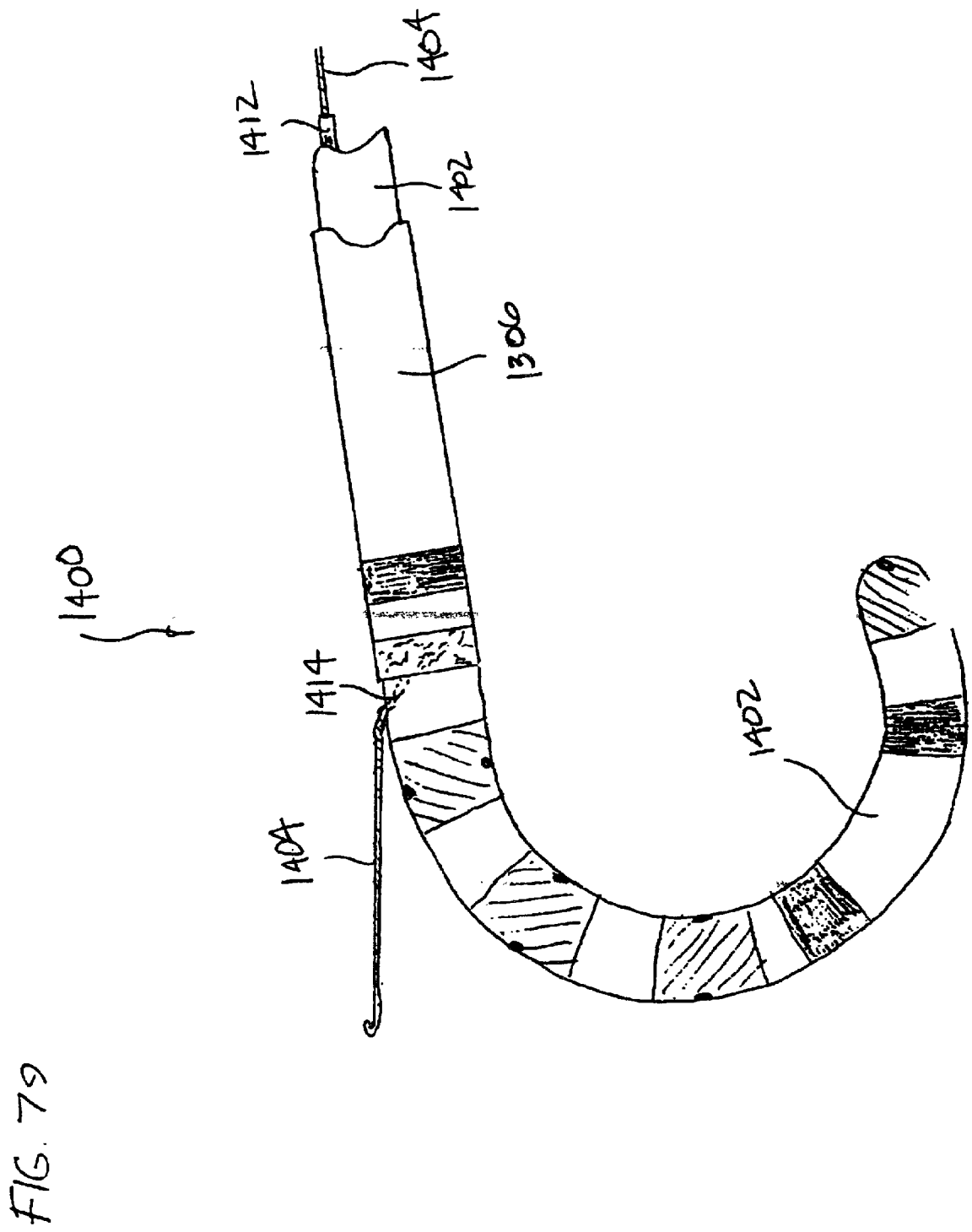
FIG. 79 is a partially cut-away perspective view of the distal end of yet another preferred tissue ablation catheter assembly, including an ablation catheter disposed in a guide sheath, wherein the ablation catheter and a guide wire are configured as an "over the wire" design.
Figure 80:
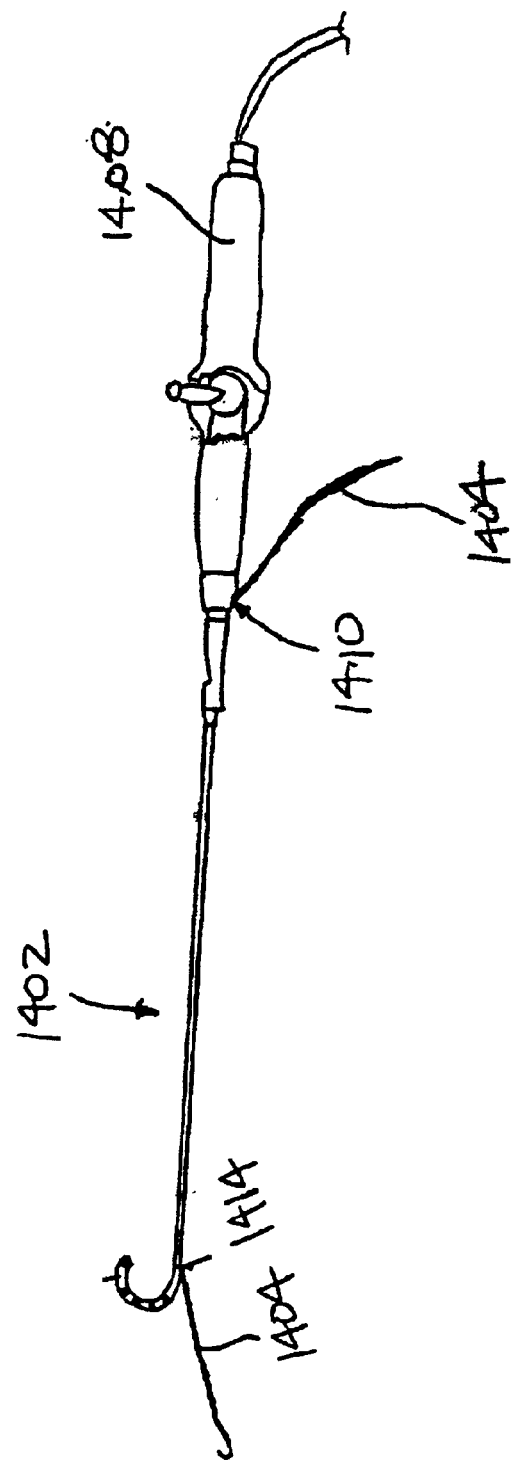
FIG. 80 is perspective elevation view of the tissue ablation catheter assembly of FIG. 79 without the guide sheath.

Referring to FIGS. 79 and 80, yet another preferred catheter assembly 1400 is configured to create a series of lesions around anatomical structures, and particularly around pulmonary veins of the heart, by employing the afore-described guide sheath 1306 with a steerable ablation catheter 1402 having a guide wire 1404. To the extent that the components of the catheter assembly 1300 are identical to those of the catheter assembly 1400, the same reference numerals have been used.

In particular, the guide wire 1404 is disposed in an interior guide lumen 1412 of the steerable ablation catheter 1402 ("over-the-wire" design). The ablation catheter 1402 and the guide wire 1404 are disposed in the guide sheath 1306.

Figure 81:
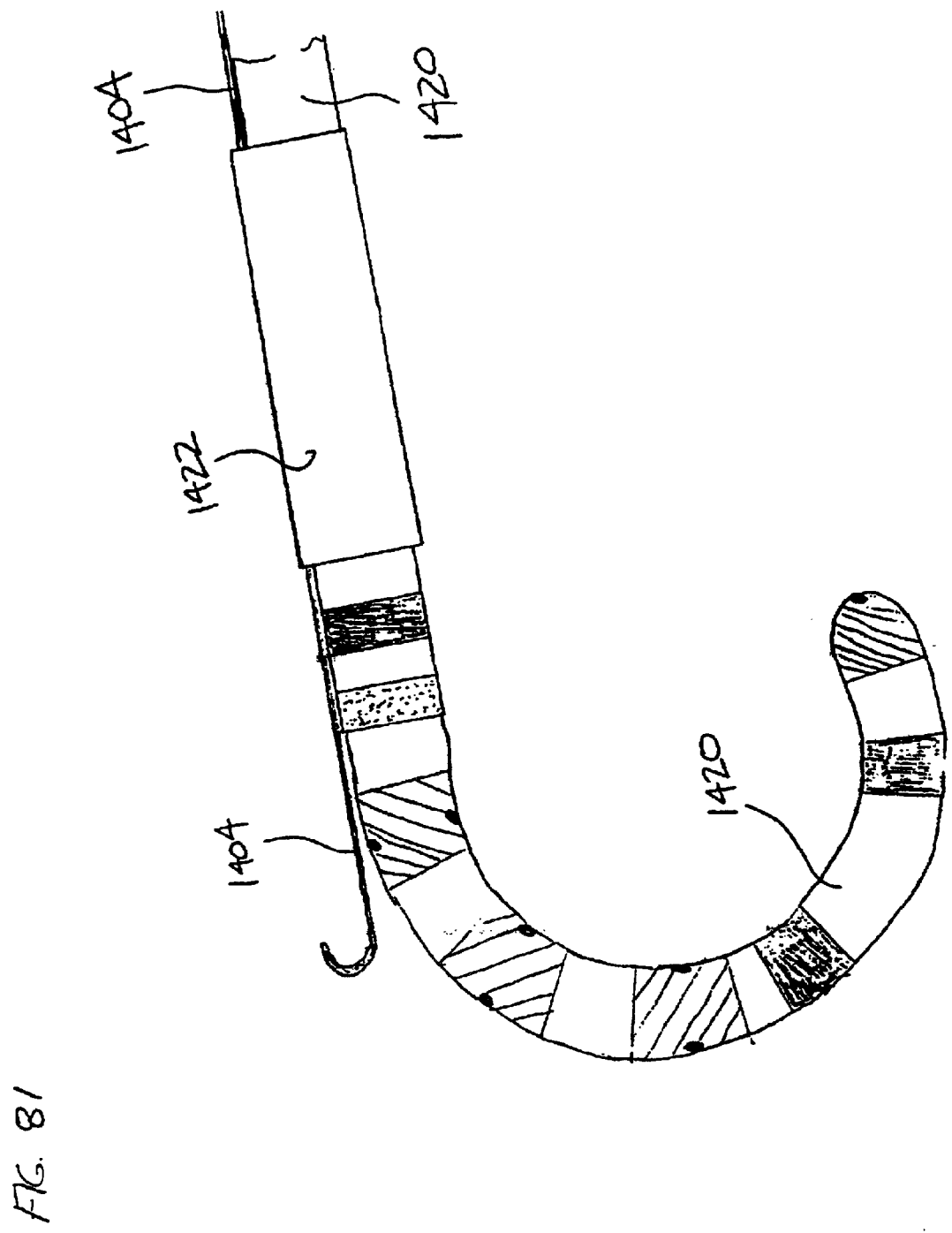
FIG. 81 is a partially cut-away perspective view of the catheter assembly of FIG. 79, wherein the ablation catheter and a guide wire are alternately configured in an "on the wire" design.

The ablation catheter 1402 is connected at its proximal end to a handle 1408, which is identical to the handle 804 (see FIG. 33) with the exception that the handle 1408 includes a guide wire port 1410 for insertion of the guide wire 1404 (see FIG. 81). The guide wire 1404 extends through the guide wire lumen 1412 of the ablation catheter 1402 and out through an external guide wire port 1414 that opens into the guide wire lumen 1412 of the ablation catheter 1402. The guide wire 1404 can thus slide through the guide wire lumen 1412.

Referring to FIG. 81, the catheter assembly 1400 can alternatively include an ablation catheter 1420 with an external guide wire lumen or rail 1422, rather than an internal lumen 1412, through which the guide wire 1404 slides ("on the wire" design). In the illustrated and preferred embodiment, the rail 1422 is formed by suitably bonding a sleeve to the distal end of the ablation catheter 1420. If the guide wire 1404 needs to be made more slidable with respect to the catheter 1420, the rail 1422 may extend as much as the full length of the catheter 1420.

Operation and use of the catheter assembly 1400 is similar to that of the catheter assembly 1300, with the exception that disposal of the guide wire 1404 in the ablation catheters 1402 or the ablation catheter 1420 allows the anchored guide wire 1404 to stabilize not only the guide sheath 1306, but the respective ablation catheters 1402 or 1420 as well. The ablation catheter 1402 or ablation catheter 1420 is not manipulated independently of the anchored guide wire 1404. Instead, the guide wire 1404 is employed to guide the ablation catheter 1402 or ablation catheter 1420 to the desired ablation region. The guide wire 1404 in conjunction with the guide sheath 1306 can provide a stable platform for manipulation of the respective ablation catheter 1402 or 1420.

Figure 82A:
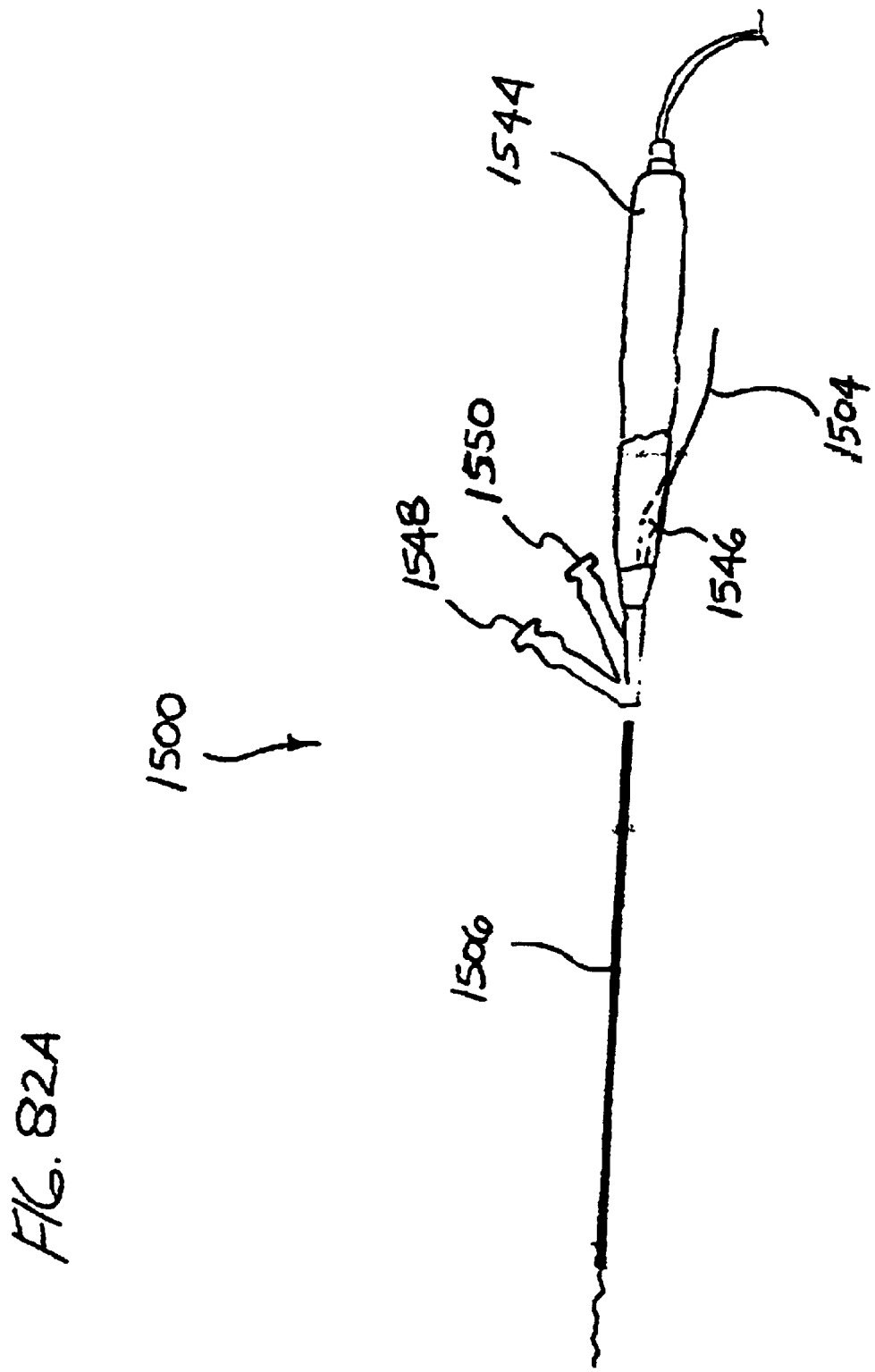
FIG. 82A is perspective elevation view of the tissue ablation catheter assembly of FIG. 82.

Referring to FIGS. 82 and 83, a still further preferred embodiment of a tissue ablation catheter assembly is configured to create lesions in and around the opening of the pulmonary veins of a patient by employing a flexible catheter tube 1506 having an open proximal end connected to a handle 1505 (see FIG. 82A) and a distal end that is connected to a preferred electrode carrying structure 1502. The handle 1544 is similar to the handle 104 (FIG. 1) used with catheter assembly 100, with the exception that the handle 1544 comprises a guide wire port 1546 (shown in phantom) for insertion of a guide wire 1504, instead of the steering mechanism 146.

The catheter tube 1506 is made of a polymeric, electrically nonconductive material, like polyethylene, polyurethane, or PEBAX®. The distal end of the catheter tube 1506 is suitably bonded to a preferred electrode carrying structure 1502, which includes an expandable-collapsible body 1508. The structure of the body 1508 and manner in which it is formed onto the catheter tube 1506 is substantially the same as described above with respect to similar features of the catheter assemblies 100 and 200.

Disposed within the catheter tube 1506 is an inflation lumen 1510 and a venting lumen 1512, which open at their distal ends into the opposite sides of the body 1508 and at the proximal ends to respective ports 1548 and 1550 of the handle 1544. As hereinbefore described, the inflation lumen 1510 and venting lumen 1512 can be employed to convey liquid inflation medium to and from the body 1508 to alternately place the body 1508 in its expanded geometry (see FIG. 83) and collapsed geometry (FIG. 82).

Referring to FIG. 83, the center portion of the body 1508 forms a pronounced ring 1514 having a distally facing surface 1516 and a proximally facing surface 1518. The ring 1510 divides the body 1508 into a distal region 1520 and proximal region 1522. The circumference of the ring 1514 is greater than the circumference of the opening of the vessel in which the electrode carrying structure 1502 is intended to ablate in and around. In this manner, the distally facing surface 1516 of the ring 1514 rests against the tissue outside the opening of the vessel as the distal region 1520 of the body 1508 is inserted into the vessel.

The body 1508 includes a conductive shell 1524 comprising a highly conductive material deposited on the surface thereon, as previously described with respect to catheter assembly 100. Alternatively, the body 1508 can be formed of a microporous material with an electrode disposed in the interior of the body 1508, as previously described with respect to catheter assembly 200. Preferably, the proximally facing surface 1518 of the ring 1514 and the proximal region 1522 of the body 1508 are masked when the conductive shell 1524 is formed on the surface of the body 1508, so that the distally facing surface 1516 of the ring 1514 and the distal region 1520 are conductive, and the proximally facing surface 1518 of the ring 1514 and the proximal region 1522 are non-conductive. If the electromagnetic energy emitting mechanism of the electrode carrying structure 1502 comprises the microporous arrangement, only the distally facing surface 1516 of the ring 1514 and the distal region 1520 are microporous.

The conductive shell 1524 is electrically coupled to the RF generator 128 through ablation signal wires (not shown). Preferably, as shown in FIG. 83, temperature sensing elements 1526 are suitably formed into the body 1508 around the ring 1514, as hereinbefore described, and are electrically coupled to the controller 130 through temperature sensing signal wires (not shown). A radiopaque marker 1526 (shown in phantom) is formed on the catheter tube 1506 underneath the ring 1514 of the body 1508 for fluoroscopic visualization.

Figure 84:
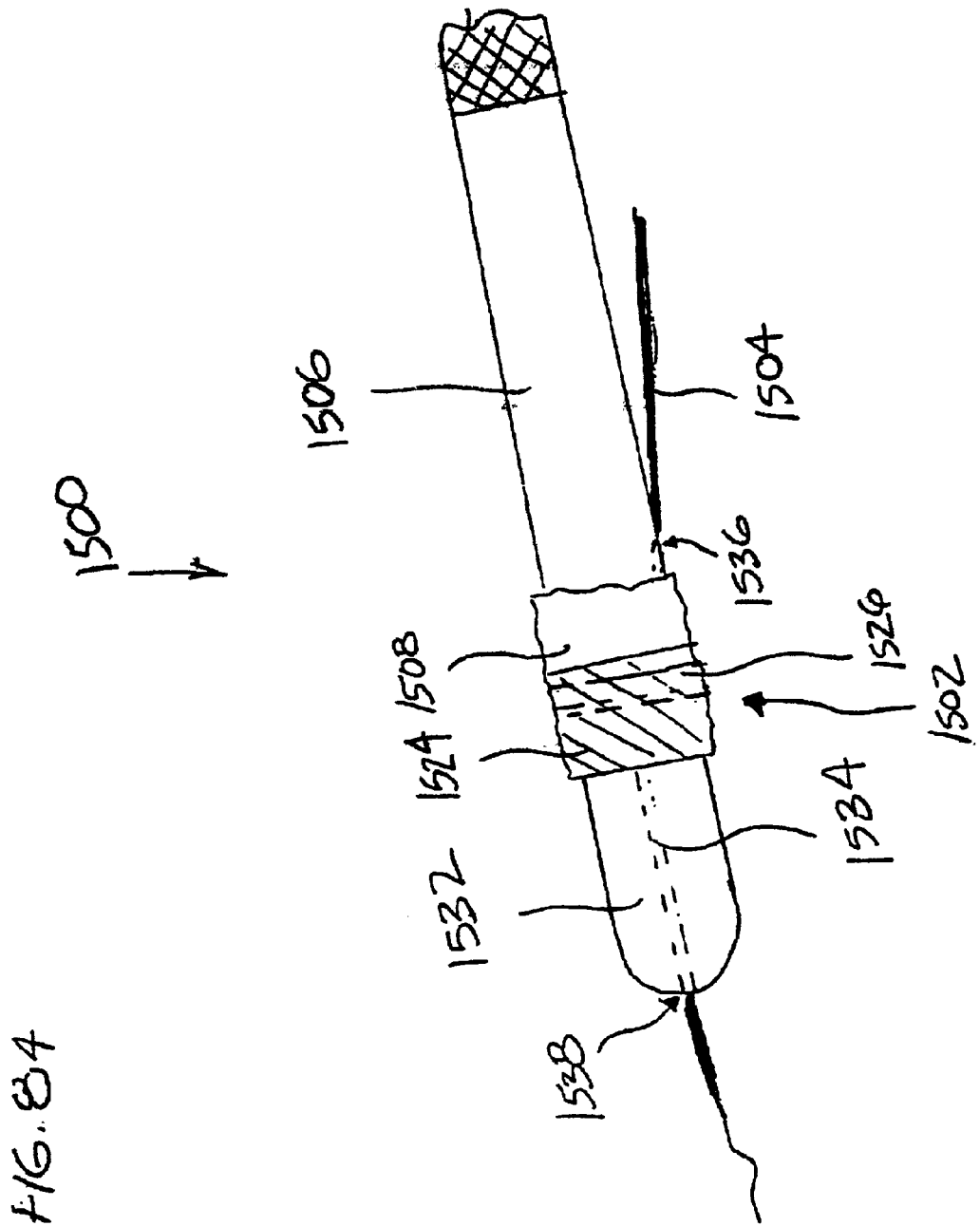
FIG. 84 is a partially cut-away perspective view of the distal end of the catheter assembly of FIG. 82, wherein the catheter includes a distal guide wire section.
Figure 85:
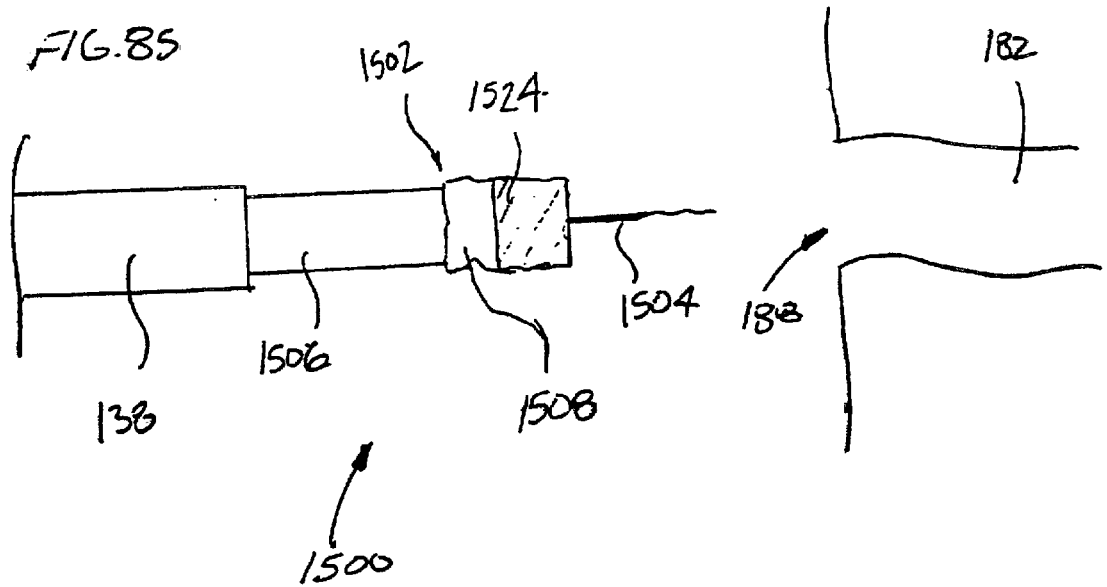
FIG. 85 is a side view of the catheter assembly of FIG. 82 disposed in the left atrium of the heart.
Figure 86:
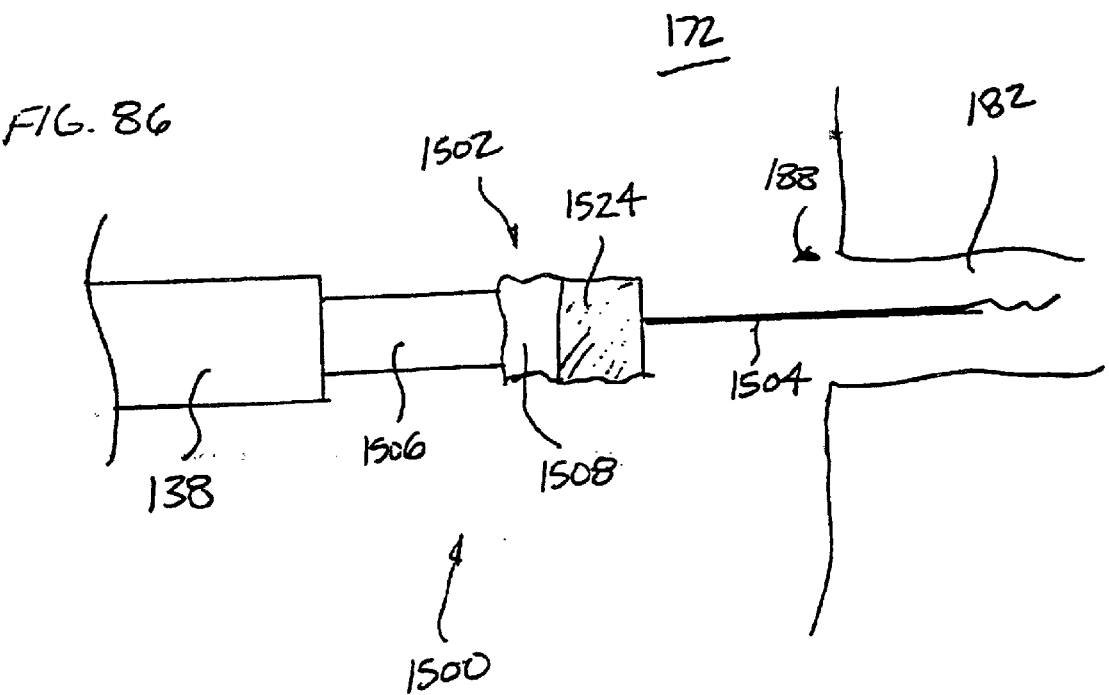
FIG. 86 depicts the guide wire of the catheter assembly of FIG. 85 disposed in the pulmonary vein.
Figure 87:
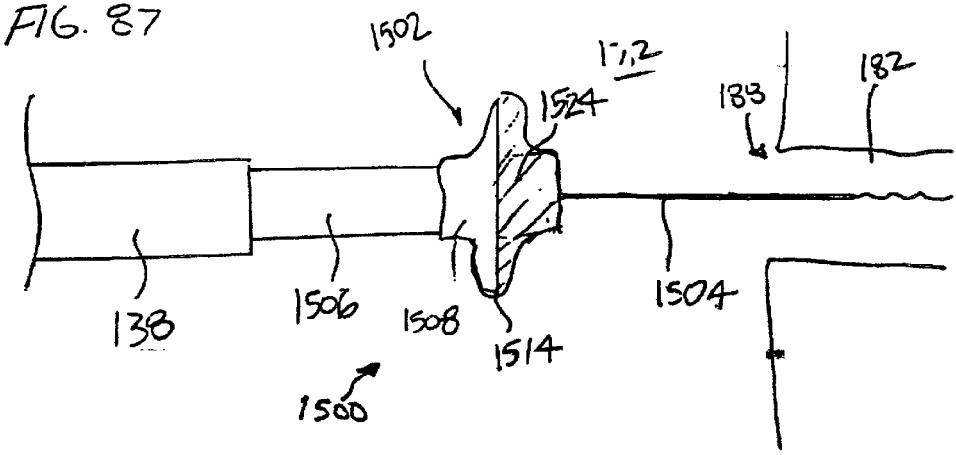
FIG. 87 depicts the balloon-like body of the catheter assembly of FIG. 86 in an expanded geometry.

The catheter tube 1506 forms a guide wire lumen 1528 therein for disposition of the guide wire 1504 ("over the wire" design). The guide wire 1504 includes a floppy tip 1530 on the end thereof for minimizing tissue trauma. The guide wire 1504, however, can include a J-tip on the end thereof with similar results. The guide wire lumen 1528 includes a guide wire exit port 1529. Alternatively, as shown in FIG. 84, the catheter tube 1506 can, instead of having the guide wire lumen 1528 extending through the catheter tube 1506, have a distal guide wire section 1532 with a guide wire lumen 1534 extending therethrough for disposition of the guide wire 1504 ("on the wire" design). The guide wire lumen 1534 includes a guide wire entrance port 1536 located proximal to the body 1508 and a guide wire exit port 1538 located at the tip of the distal guide wire section 1532.

The catheter tube 1506 includes a proximal portion 1540 that is suitably braided to provide the catheter tube 1506 with axial strength. The portion of the catheter tube 1506 distal to the braided portion is long enough, so that the portion of the catheter tube 1506 extending from the guide sheath 1505 used to introduce the body 1508 into the ablation area does not include the braided portion 1540, thereby minimizing any tissue trauma.

Referring to FIGS. 85–88, the catheter assembly 1500 can be employed to create lesions in and around the opening of a vessel, such as a pulmonary vein. The physician can, while the body 1508 is in its collapsed geometry, introduce the electrode carrying structure 1502 and the guide wire 1504 into the left atrium 172 (see FIG. 85). This is accomplished via a guide sheath, such as the aforedescribed guide sheath 138, using the aforedescribed retrograde or transeptal methods. The guide wire 1504 is then manipulated into the pulmonary vein 182 (see FIG. 86). The physician can fully inflate the body 1508 of the electrode carrying structure 1502 by conveying liquid inflation medium therein through the inflation lumen 1510 (see FIG. 87). The catheter tube 1506 is then advanced distally along the guide wire 1504 until the distal region 1520 of the body 1508 engages the tissue inside the opening of the pulmonary vein 182 and the distally facing surface 1516 of the ring 1514 engages the tissue surrounding the opening 188 of the pulmonary vein 182 (see FIG. 88).

Figure 88:
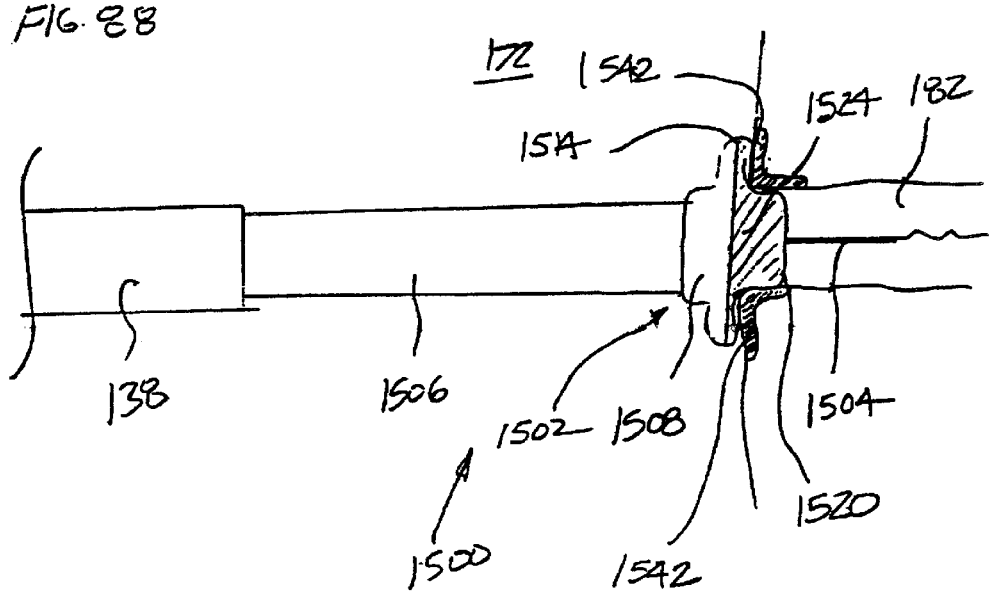
FIG. 88 depicts the catheter assembly of FIG. 82 creating a circumferential lesion in and around the opening of the pulmonary vein.

The physician then operates the RF generator to deliver RF energy to the conductive shell 1524. In turn, RF energy is emitted from the conductive shell 1524 into the tissue in contact therewith, which returns to an external electrode (unipolar mode), thereby ablating a circumferential lesion 1542 adjacent to the opening 188 inside and outside of the pulmonary vein 182, as depicted in FIG. 88.

Subsequent to the ablation procedure on the pulmonary vein 182, the physician may opt to repeat the ablation procedure on another pulmonary vein. If so, the physician can retract the catheter tube 1506 in the proximal direction along the guide wire 1504 so that the electrode carrying structure 1502 is removed from the pulmonary vein 182, removing the guide wire 1504 and manipulating it into the other pulmonary vein, advancing the catheter tube 1506 in the distal direction along the guide wire 1504 so that the electrode carrying structure 1502 engages the opening of the other pulmonary vein, and conveying RF energy to the conductive shell 1524 for ablation. When the ablation procedure is fully completed, the physician can convey the liquid inflation medium from the body 1508 through the venting lumen 1512 to place the body 1508 in its collapsed geometry. The catheter tube 1506 and guide wire 1504 can then be removed from the patient's body through the guide sheath 138.

Figure 89:
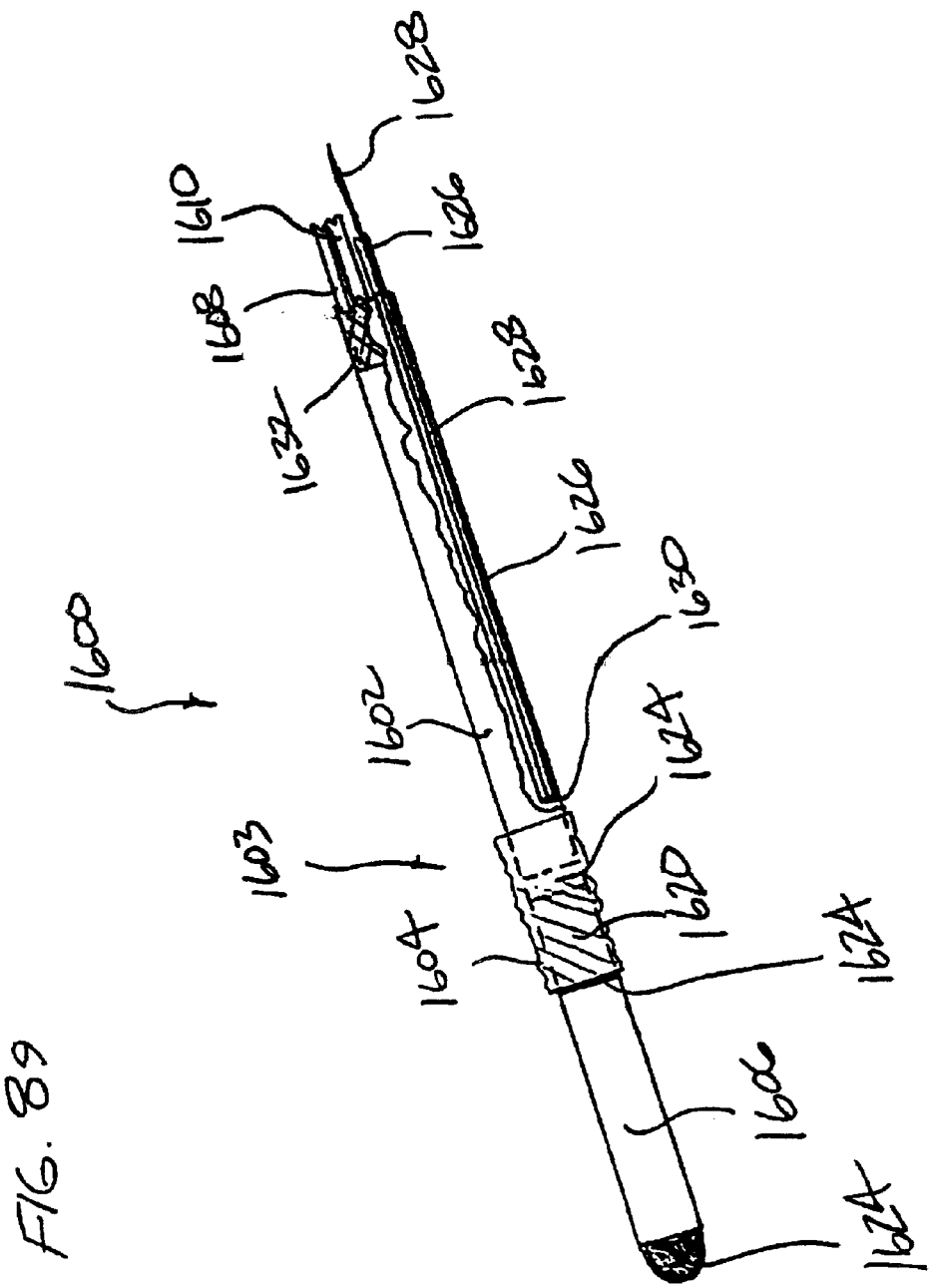
FIG. 89 is a partially cut-away perspective view of the distal end of a still further preferred tissue ablation catheter assembly, including a catheter having conductive shell disposed over a balloon-like body depicted in a deflated geometry.
Figure 90:
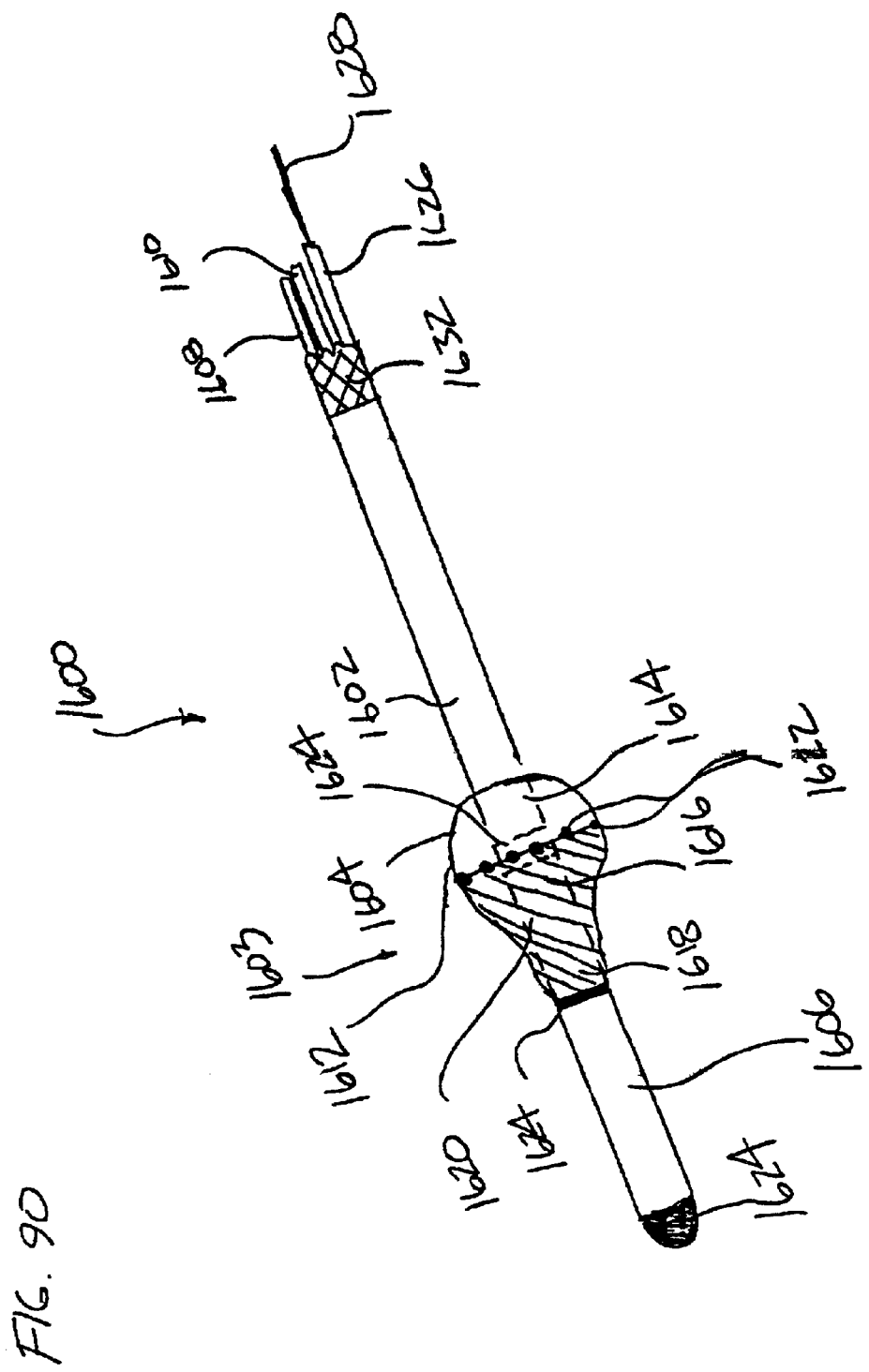
FIG. 90 is a partially cut-away perspective view of the distal end of the catheter assembly of FIG. 89, wherein the balloon-like body is expanded.
Figure 91:
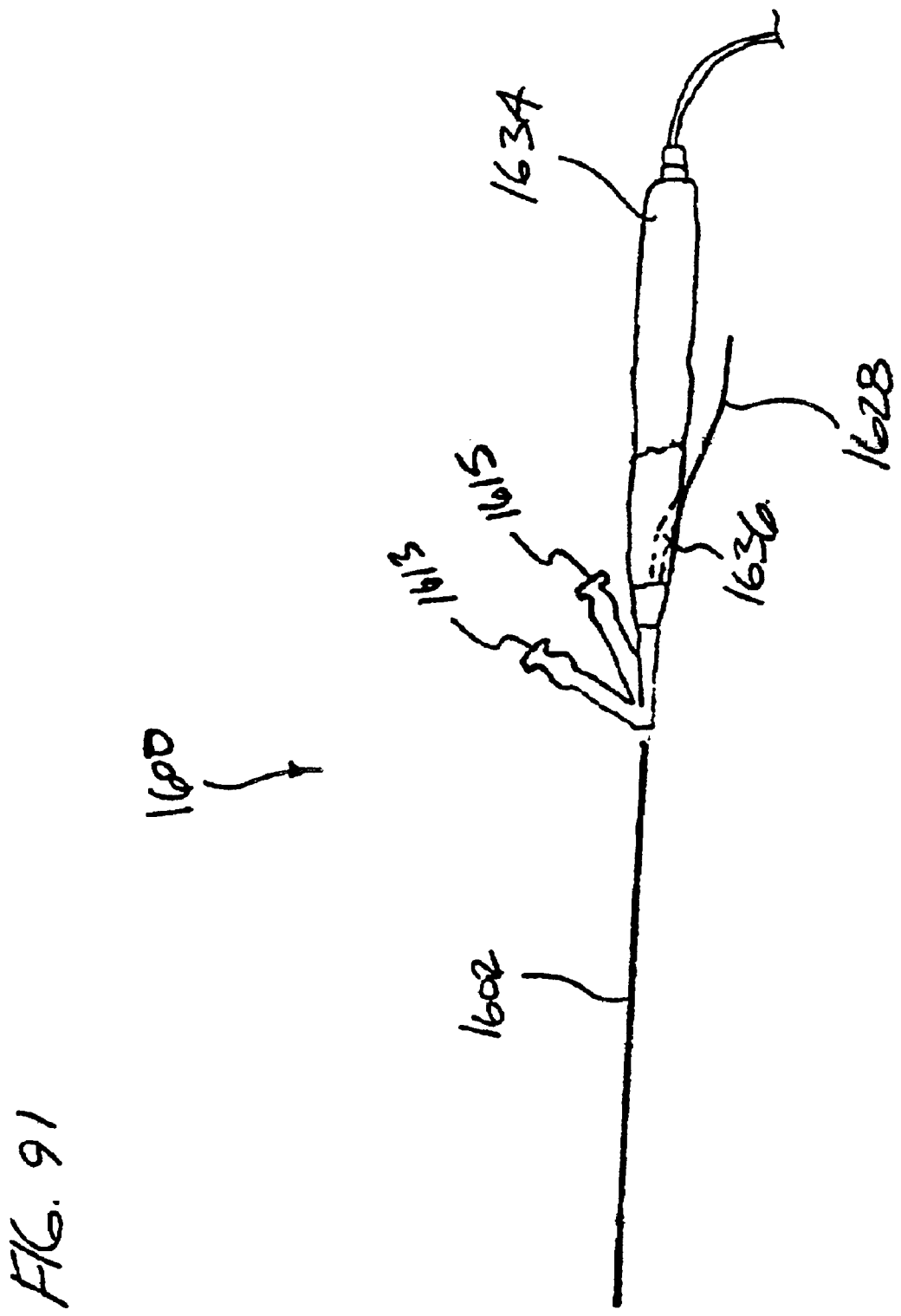
FIG. 91 is a perspective elevation view of the tissue ablation catheter assembly of FIG. 89.
Figure 92:
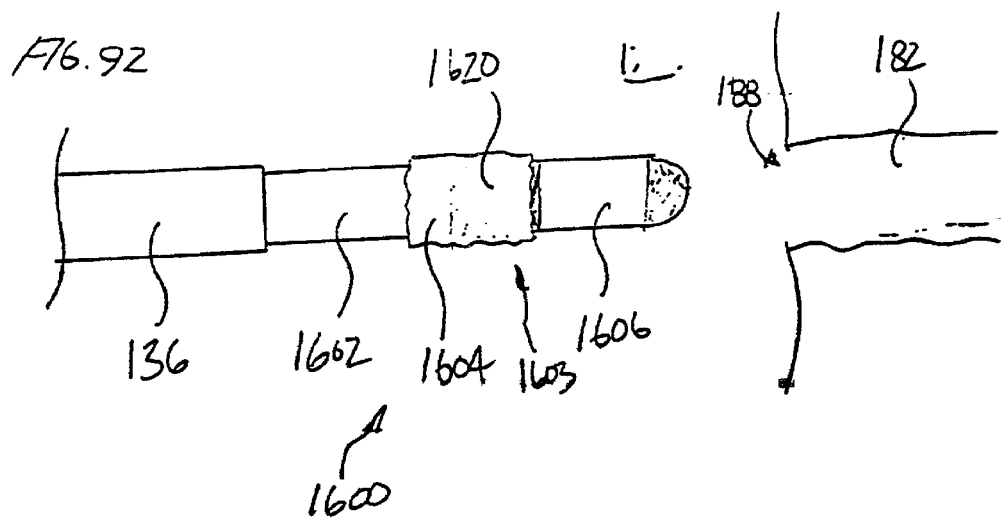
FIG. 92 is a side view of the catheter assembly of FIG. 89 disposed in the left atrium of the heart via a guide sheath, wherein the balloon-like body is in a deflated geometry.

Referring to FIGS. 89–91, a still further preferred embodiment of a tissue ablation catheter assembly 1600 is configured to create lesions in and around the opening of the pulmonary veins of a patient by employing a flexible catheter tube 1602 having an open proximal end connected to a handle 1634 (see FIG. 91) and a distal end that is connected to a preferred electrode carrying structure 1603. The handle 1634 is similar to the handle 104 (FIG. 1) used with catheter assembly 100, with the exception that the handle 1634 comprises a steering wire port 1636 (shown in phantom) for insertion of a steering wire 1628, instead of the steering mechanism 146.

In particular, the catheter tube 1602 is made of a polymeric, electrically nonconductive material, like polyethylene, polyurethane, or PEBAX®. The electrode carrying structure 1603 includes an expandable-collapsible body 1604 bonded to and disposed about the distal end of the catheter tube 1602. The body 1604 is disposed on the catheter tube 1602 proximal to the distal tip of the catheter tube 1602 to leave an exposed distal anchoring section 1606 distal to the body 1604. The structure of the body 1604 and manner in which it is formed onto the catheter tube 1602 is the substantially the same as described above with respect to similar features of catheter assemblies 100 and 200.

Disposed within the catheter tube 1602 is an inflation lumen 1608 and a venting lumen 1610, which open at their distal ends into the opposite sides of the body 1604 and at the proximal ends to respective ports 1613 and 1615 of the handle 1634. As hereinbefore described, the inflation lumen 1608 and venting lumen 1610 can be employed to convey liquid inflation medium to and from the body 1604 to alternately place the body 1604 in its expanded geometry (see FIG. 90) and collapsed geometry (FIG. 89).

Referring to FIG. 90, the body 1508 has a proximal spherical region 1612 having respective proximal and distal hemispheres 1614 and 1616, and an elongated distal region 1618 with a circumference less than the circumference of the proximal spherical region 1618. The circumference of the spherical region 1612 is greater than the circumference of the opening of the vessel in which the catheter 1600 is intended to ablate in and around. In this manner, the distal hemisphere 1616 of the body 1604 rests against the tissue outside the opening of the vessel as the elongated region 1618 is fully inserted into the vessel.

The body 1604 includes a conductive shell 1620 comprising a highly conductive material deposited on the surface thereon, as previously described with respect to the catheter 100. Alternatively, the body 1604 can be formed of a microporous material with an electrode disposed in the interior of the body 1604, as previously described with respect to the catheter 200. Preferably, the proximal hemisphere 1614 of the body 1604 is masked when the conductive shell 1620 is formed on the surface of the body 1604, so that the elongated region 1618 and distal hemisphere 1616 of the body 1604 are conductive, and the proximal hemisphere 1614 of the body 1604 is nonconductive. If the electromagnetic energy emitting mechanism of the electrode carrying structure 1602 comprises the microporous arrangement, only the distal region 1618 and distal hemisphere 1616 of the body 1604 comprise pores.

The conductive shell 1620 is electrically coupled to the RF generator 128 through ablation signal wires (not shown). Preferably, temperature sensing elements 1622 are suitably formed into the body 1604 around the spherical region 1612 and are electrically coupled to the controller 130 through temperature sensing signal wires (not shown). Radiopaque markers 1624 are formed on catheter tube 1602 underneath the spherical region 1612 (shown in phantom) of the body 1604, at the distal end of the body 1604, and at the distal tip of the catheter tube 1602 for fluoroscopic visualization.

The catheter tube 1602 comprises a steering wire lumen 1626 off center from the axis of the catheter tube 1602. The steering wire lumen extends from the proximal end of the catheter tube 1602 to the portion of the catheter tube 1602 just proximal to the body 1604. Disposed in the steering wire lumen 1626 is a steering wire 1628 having a proximal end that passes out of the proximal end of the steering wire lumen 1626 and through the port 1636 on the handle 1634, and a distal end that is suitably mounted to the distal end of the steering wire lumen 1626 to create a steering wire anchor point 1630.

The catheter tube 1602 includes a proximal portion 1632 that is suitably braided to provide the catheter tube 1602 with axial strength. The portion of the catheter tube 1602 distal to the braided portion is long enough, so that the portion of the catheter tube 1602 extending from a guide sheath (e.g., guide sheath 138) used to introduce the body 1604 into the ablation area does not include the braided portion 1632, thereby minimizing any tissue trauma.

Referring to FIGS. 92–95, the catheter assembly 1600 can be employed to create lesions in and around the opening of a vessel, such as a pulmonary vein. The physician can, while the body 1604 is in its collapsed geometry, introduce the electrode carrying structure 1603 into the left atrium 172 (see FIG. 92). This is accomplished via the guide sheath (138) using the aforedescribed retrograde or transeptal methods.

Figure 93:
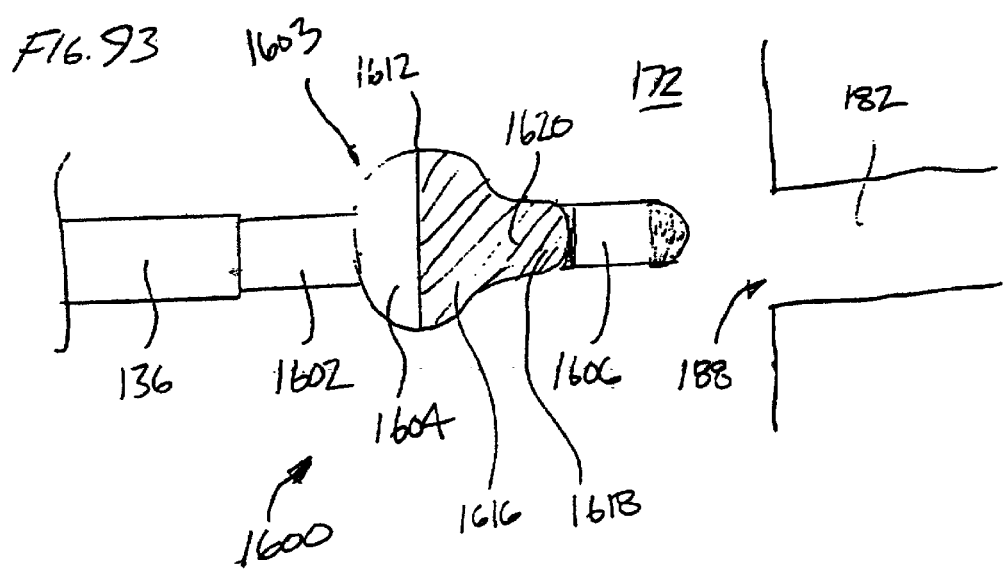
FIG. 93 depicts the catheter assembly of FIG. 92, wherein the balloon-like body is in an expanded geometry.

As shown in FIG. 93, The body 1604 of the catheter tube 1602 is then inflated by conveying liquid inflation medium therein through port 1613 and inflation lumen 1608, respectively. The distal anchoring section 1606 of the catheter tube 1602 is then manipulated into the pulmonary vein 182 until the distal hemisphere 1616 of the spherical region 1612 of the body 1604 engages the tissue surrounding the opening 188 of the pulmonary vein 182 (see FIG. 94).

Steering of the distal tip of the catheter tube 1602 is accomplished as follows. By visualizing the markers 1624 under fluoroscopy, the physician can rotate the catheter tube 1602 until the steering wire anchor point 1630 (shown in phantom) is facing the direction in which the physician desires to steer the distal tip of the catheter tube 1602. The physician can then a pull the steering wire 1628 (shown in phantom), thereby deflecting the distal tip of the catheter tube 1602 from the axis of the catheter tube 1602 in the direction in which the steering wire anchor point 1630 faces (see FIG. 95). The physician can rotate the steering wire anchor point 1630 and pull the steering wire 1628 to deflect the distal tip of the catheter tube 1602 in a different direction. Through this manipulation, the physician can place the distal tip of the catheter tube 1602 into the pulmonary vein 182.

After proper location of the body 1604 within the pulmonary vein 182, the physician then operates the RF generator to deliver RF energy to the conductive shell 1620. In turn, RF energy is emitted from the conductive shell 1620 into the tissue in contact therewith, which returns to an external electrode (unipolar mode), thereby ablating a circumferential lesion 1638 adjacent to the opening 188 inside and outside of the pulmonary vein 182, as depicted in FIG. 94.

Subsequent to the ablation procedure on the pulmonary vein 182, the physician may opt to repeat the ablation procedure on another pulmonary vein. If so, the physician can retract the distal tip and electrode carrying structure 1603 from the pulmonary vein 182. The distal tip and body 1604 can then be steered into another pulmonary vein until the electrode carrying structure 1003 properly engages the tissue around the opening of that pulmonary vein. RF energy is then conveyed to the conductive shell 1620 for further ablation treatment. When the ablation procedure is fully completed, the physician can convey the liquid inflation medium from the body 1604 through the venting lumen 1610 and port 1615, respectively, to place the body 1604 in its collapsed geometry. The catheter tube 1602 can then be removed from the patient's body through the guide sheath (138).

Figure 96:
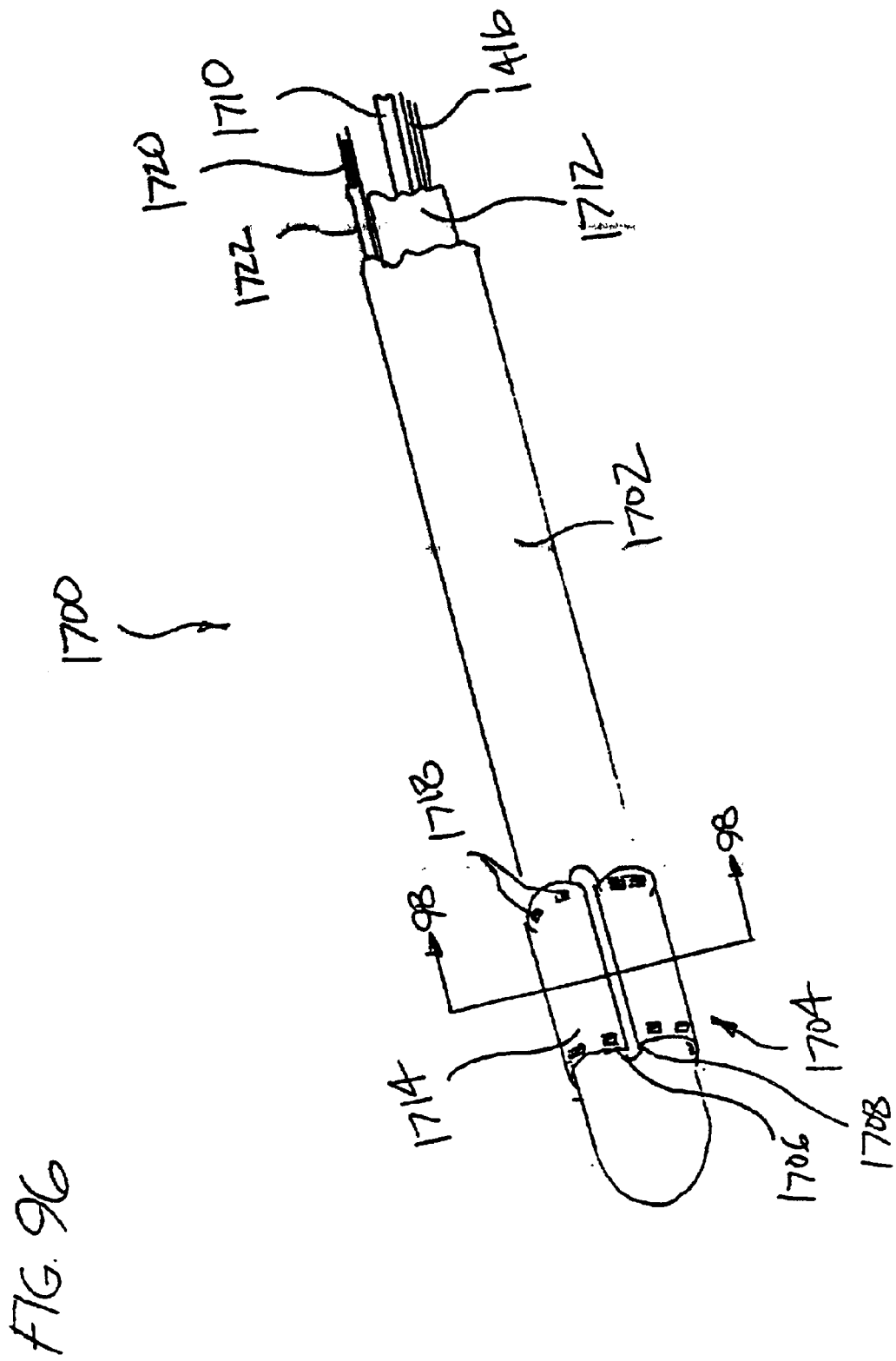
FIG. 96 is a partially cut-away perspective view of yet another preferred tissue ablation catheter assembly, including a still further preferred electrode carrying structure that can be expanded with a rotatable torque shaft depicted in a collapsed geometry.
Figure 97:
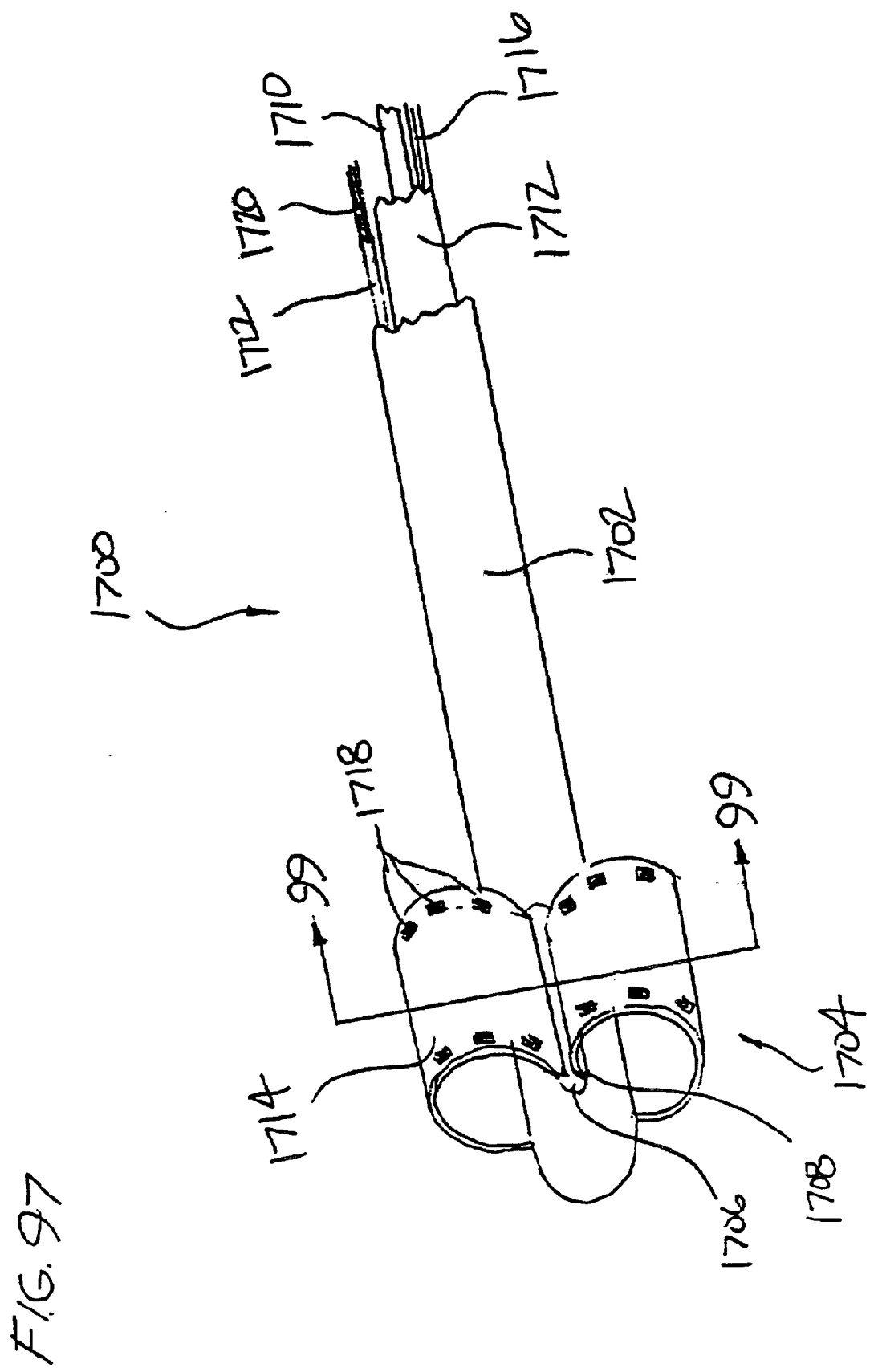
FIG. 97 is a partially cut-away perspective view of the electrode carrying structure of FIG. 96 depicted in an expanded geometry.

Referring to FIGS. 96 and 97, a still further preferred catheter assembly 1700 is configured to create lesions in the pulmonary veins of a patient by employing a flexible catheter tube 1702 having an open proximal end connected to a handle (not shown) and a closed distal end having a preferred electrode carrying structure 1704 disposed thereabout.

In particular, the catheter tube 1702 is made of a polymeric, electrically nonconductive material, like polyethylene, polyurethane, or PEBAX®. The electrode carrying structure 1704 is made of a generally resilient, inert ribbon, such as nickel titanium (commercially available as Nitinol material), stainless steel 17-7, or thermoplastic material. The catheter tube includes a main lumen 1712, in which a rotatable torque shaft 1710 is disposed.

Figure 98:
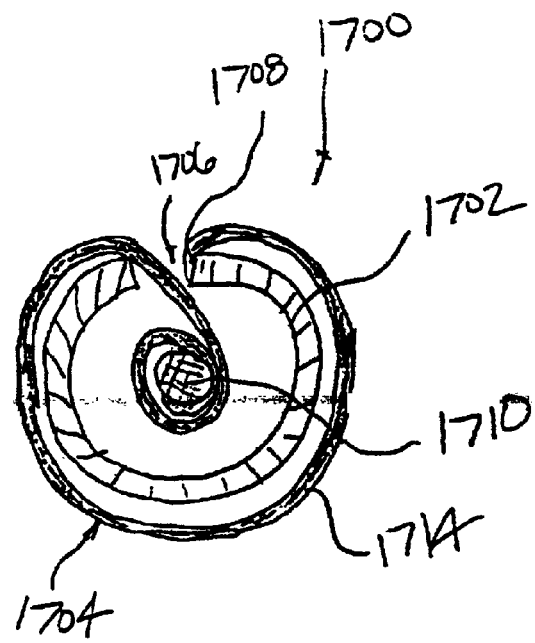
FIG. 98 is a cross-sectional view of the catheter assembly of FIG. 96 taken at the line 98—98.

As best seen in FIG. 98, the catheter tube 1702 includes a slot 1706 formed in the wall of the catheter tube 1702. The electrode carrying structure 1704 is suitably anchored to an edge 1708 adjacent to the slot 1706.

Figure 99:
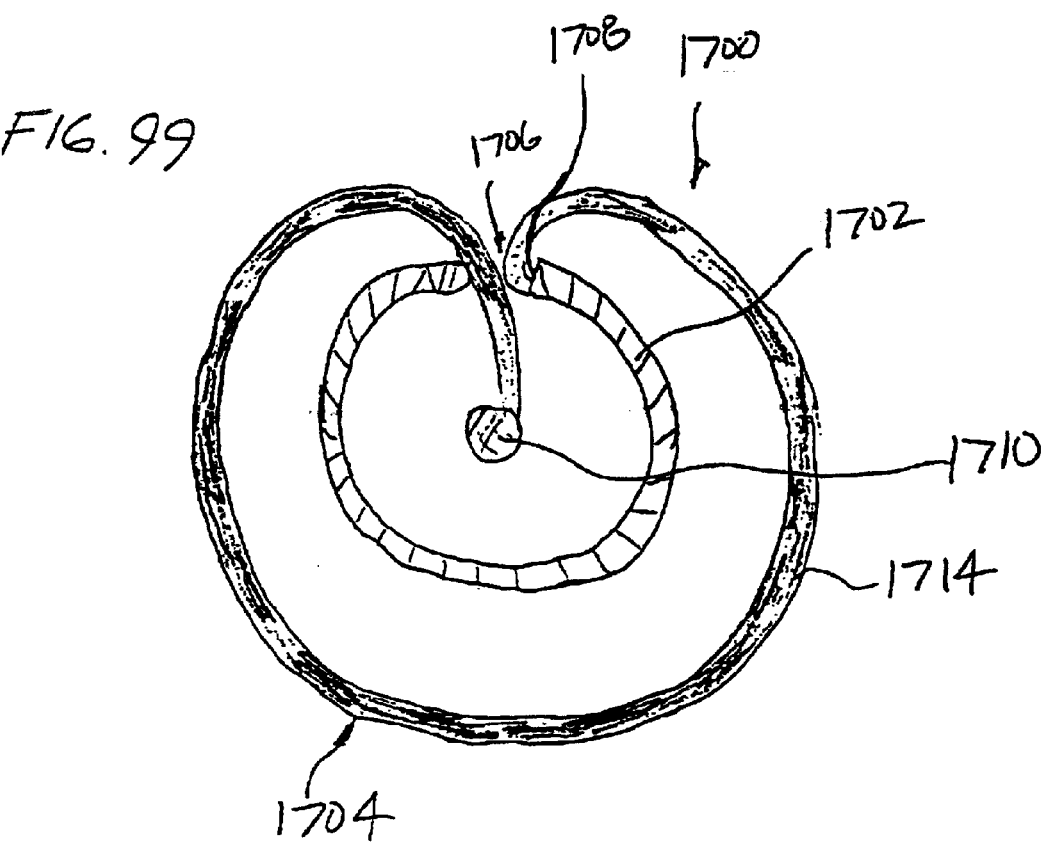
FIG. 99 is a cross-sectional view of the catheter assembly of FIG. 97 taken at the line 99—99.

A first end of the electrode carrying structure 1704 is disposed about the distal end of the catheter tube 1702 adjacent the slot 1706. The other end of the electrode carrying structure 1704 is disposed through the slot 1706 and suitably anchored to a rotatable torque shaft 1710. Rotation of the torque shaft 1710 in alternate directions will accordingly wind the electrode carrying structure 1704, thereby effectively collapsing the electrode carrying structure 1704 (see FIGS. 96 and 98), and unwind the electrode carrying structure 1704, thereby expanding the electrode carrying structure 1704 (see FIGS. 97 and 99).

The electrode carrying structure 1704 includes an electrode 1714 that can be variously created depending upon the underlying material of the electrode carrying structure 1704 itself. For example, if the electrode carrying structure 1704 is made of an electrically conductive material, such as Nitinol, the electrodes 1714 can be made of the Nitinol material itself. To improve the conductive properties and bio-compatibility of the electrode 1714, flexible coil electrodes can be suitably bonded to the electrode carrying structure 1704, or the exterior surface of the electrode carrying structure 1704 can be coated with an electrically conducting material using ion beam deposition or equivalent techniques. Materials possessing these characteristics include, among others, gold, platinum, platinum/iridium, or a combination thereof. In particular, noble metals are preferred.

Alternately, the electrode 1714 may be formed by using conductive, flexible ink, covered by a layer of protective regenerated cellulose, as is disclosed and described in the above-incorporated U.S. application Ser. No. 08/879,343.

If the electrode carrying structure 1704 is made of an electrically non-conducting material, such as plastic with elastic memory, the electrodes 1714 are formed on electrode carrying structure 1704 by suitably bonding flexible coil electrodes on the electrode carrying structure 1704, or coating the exterior surface of the electrode carrying structure 1704 with an electrically conducting material, as described above.

The electrode 1414 is electrically coupled to at least one ablation signal wire 1416 that extends through the main lumen 1712 of the catheter tube 1702 into the handle (not shown), which is electrically coupled to an RF generator (not shown).

Temperature sensing elements 1718, such as thermistors or thermocouples, can be suitably mounted to the electrode 1714 for more controlled lesion creation. The temperature sensing elements 1718 are coupled to a controller (not shown) through temperature sensing element wires 1720 extending through a temperature sensing element wire lumen 1722 carried within the catheter tube 1702. Preferably, the temperature sensing element wires 1722 are shielded to block RF interference emitted by the ablation signal wire 1716. Preferably, the temperature sensors 1718 are located at the edges of the electrode 1714 where the highest current density is found.

Manipulation of the electrode carrying structure 1704 can be accomplished using the various afore-described steering or guide wire arrangements, such as, e.g., the steering wire configurations discussed with respect to previous preferred catheter assemblies shown in FIG. 59 and FIG. 89, or the guide wire configurations discussed in conjunction with FIG. 82 or FIG. 84.

Figure 100:
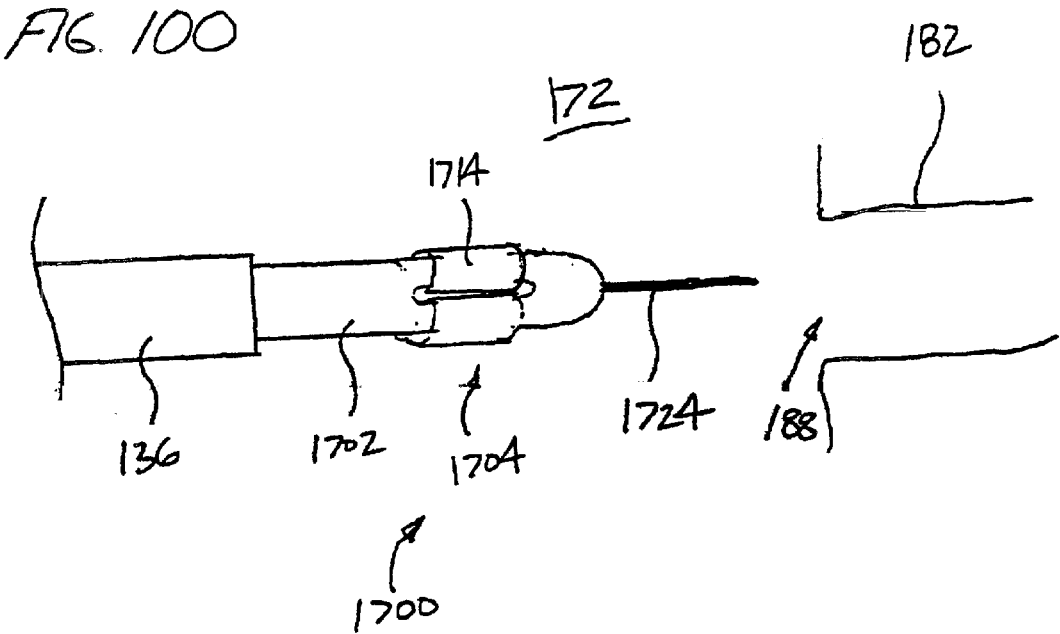
FIG. 100 is a side view of the electrode carrying structure of FIG. 97 disposed in the left atrium of the heart via a guide sheath, wherein the electrode carrying structure is in a collapsed geometry.
Figure 101:
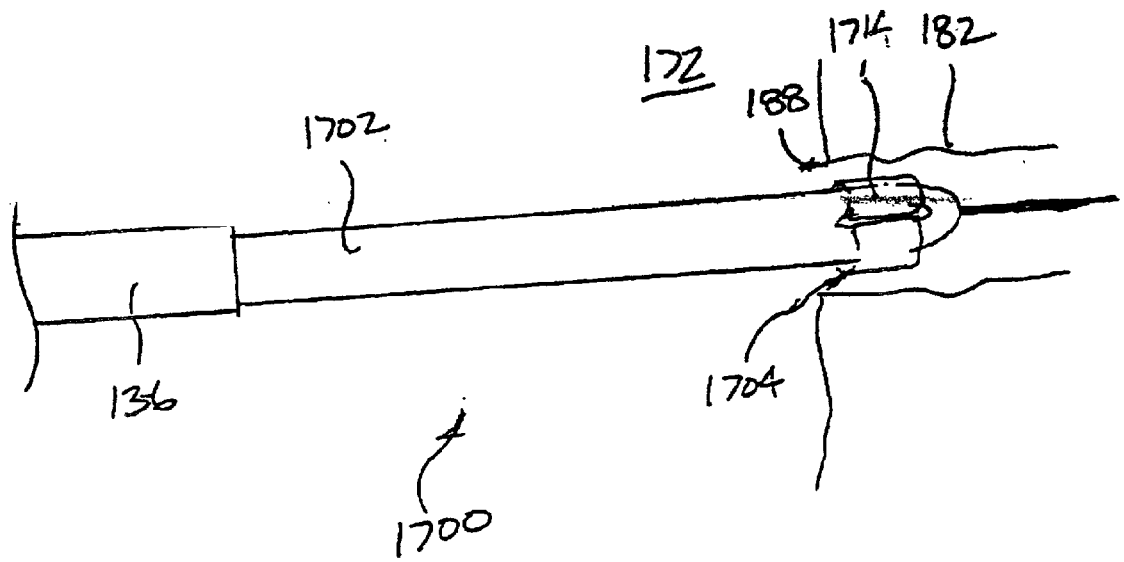
FIG. 101 depicts the electrode carrying structure of FIG. 100, wherein the electrode carrying structure is guided into a pulmonary vein via a guide wire.
Figure 102:
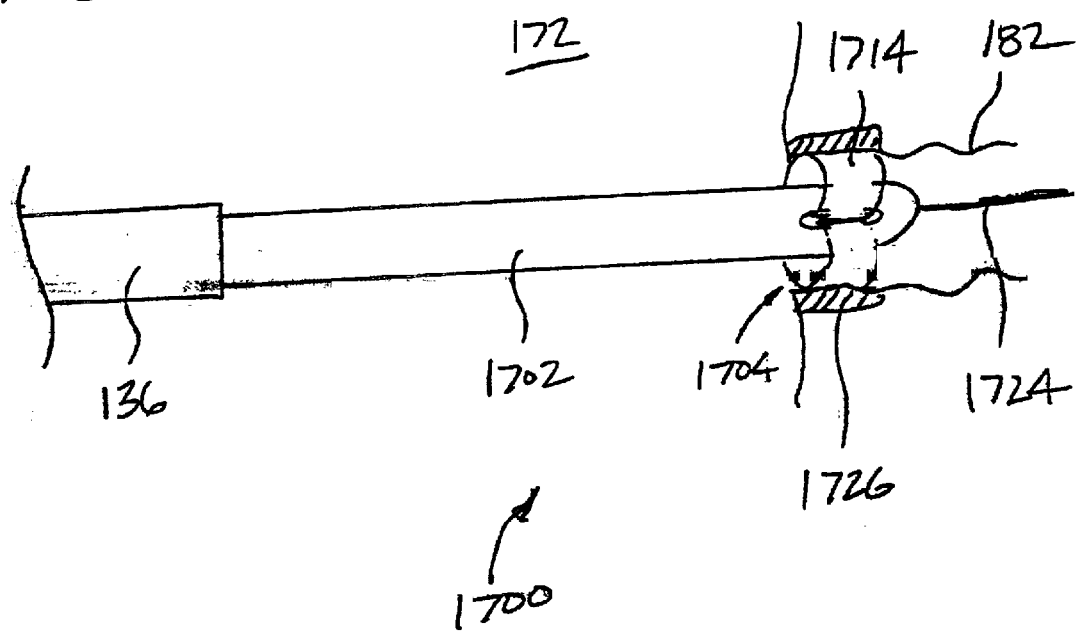
FIG. 102 depicts the electrode carrying structure of FIG. 101, wherein the electrode carrying structure is in an expanded geometry in a pulmonary vein.

Referring to FIGS. 100–102, the catheter assembly 1700 can be employed to create a lesion within the desired pulmonary vein. As depicted in FIGS. 100–102, a guide wire 1724 is employed to manipulate the electrode carrying structure 1704 of the catheter assembly 1700. Other aforementioned methods, however, can be employed to manipulate the electrode carrying structure 1704. The physician can introduce the guide wire 1212 into the left atrium 172 via a guide sheath (e.g., guide sheath 138) through the afore-described retrograde or transeptal approaches. At the physician's option, the electrode carrying structure 1704 can be introduced into the left atrium 172, either concurrently with or subsequent to the location of the guide wire 1724 within the left atrium 172 (see FIG. 100).

The guide wire is manipulated through the opening 188 and into the pulmonary vein 182 for delivery of the electrode carrying structure 1704 therein. While in a low profile geometry (i.e., the collapsed geometry), the electrode carrying structure 1704 is then guided via the guide wire 1724 into the desired region of pulmonary vein 182 adjacent to the opening 188 (see FIG. 101). The physician can then rotate the torque shaft 1710, so that the electrode carrying structure 1704 is expanded and contacts the wall of the pulmonary vein 182 (see FIG. 102).

The physician then causes RF energy to be conveyed from the generator to the electrode 1714 in a unipolar arrangement, thereby creating a lesion 1726 covering a circumferential region of the pulmonary vein 182 adjacent the opening 188.

Following the ablation process, the physician causes the electrode carrying structure 1704 to return to its collapsed geometry—i.e., by rotating the torque shaft 1710 in the opposite direction from that used to expand the electrode carrying structure 1704. The physician can then extract the electrode carrying structure 1704 from the pulmonary vein 182, after which it can be repositioned inside another pulmonary vein for continued ablation therapy or extracted altogether from the patient.

Figure 103:
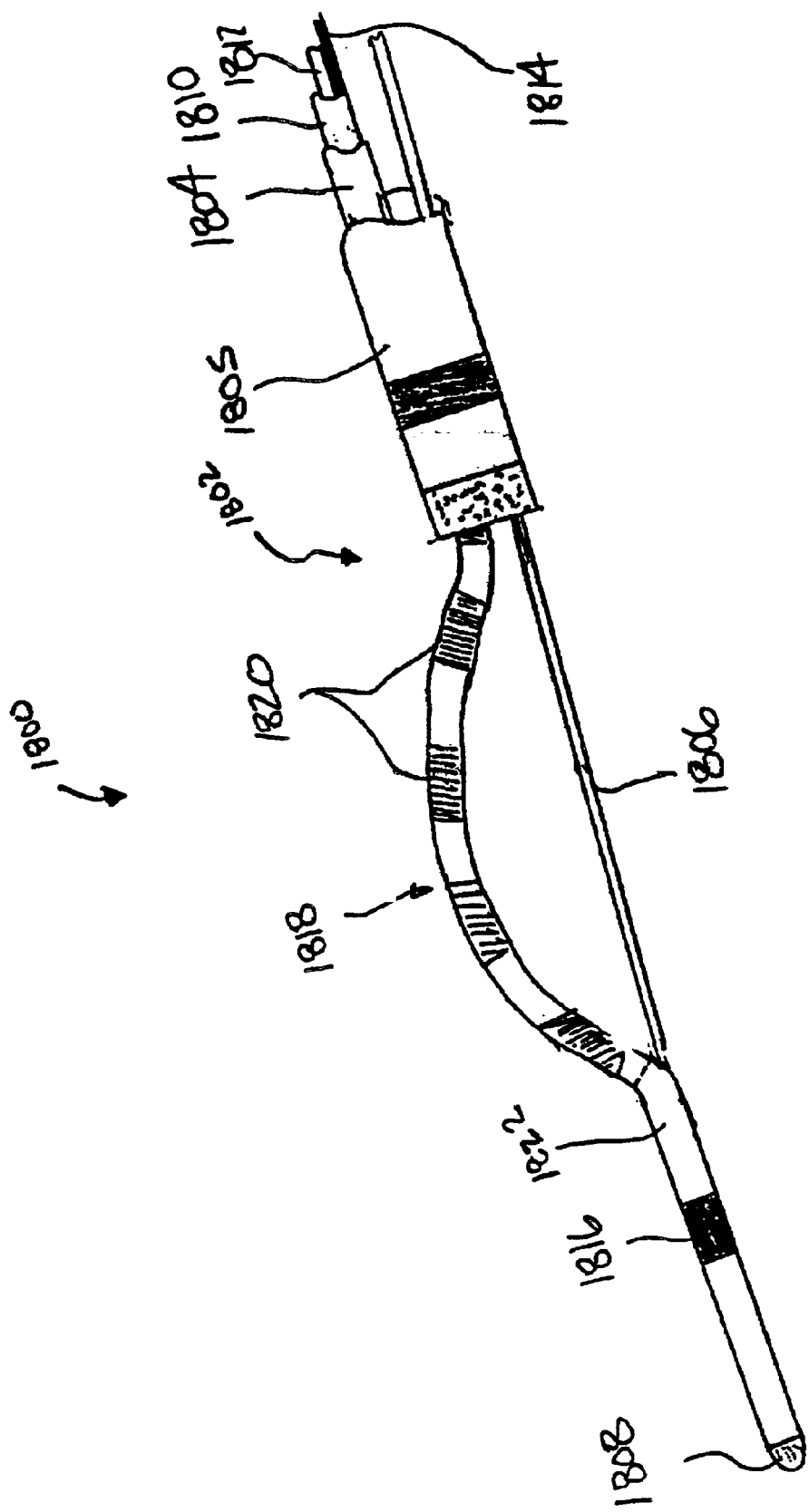
FIG. 103 is a partially cut-away perspective view of the distal end of yet another preferred tissue ablation catheter assembly and electrode carrying structure.

Referring to FIG. 103, a still further preferred catheter assembly 1800 is configured to create a series of lesions around anatomical structures, and particularly around pulmonary veins of the heart, by employing an ablation catheter 1802 with a rigid pull wire 1806, which is disposed in a guide sheath 1805. As with the previously described preferred embodiments, a handle with a guide wire port (not shown) (e.g., such as the respective handle 1408 and port 1410 shown in FIG. 81), are employed to manipulate the ablation catheter 1802.

In particular, the ablation catheter 1802 comprises a flexible catheter tube 1804 made of a polymeric, electrically nonconductive material, like polyethylene, polyurethane, or PEBAX®. The catheter tube 1804 carries a main lumen 1810 used to house a center support 1812 and signal wires 1814, respectively. The center support 1812 is preferably made from resilient, inert wire, such as nickel titanium (commercially available as Nitinol material), stainless steel 17-7, or a thermoplastic material, and is preferably rectilinear in cross-section for radially stability.

The distal end of the catheter tube 1804 forms a preferred electrode carrying structure 1818, about which multiple electrodes 1820 are disposed. As with the above-described preferred embodiments, the electrodes 1820 can be assembled onto the electrode carrying structure 1818 in various ways, e.g., as conductive material or ink coated on, closely wound spiral coils wrapped about, or solid rings having an interference fit with, respectively, the catheter tube 1804. In alternative embodiments, the distal tip 1808 may form a singular electrode. As described in greater detail below, the pull wire 1806 is anchored to the ablation catheter 1802 just distally of the electrode carrying structure 1818.

The electrodes 1820 are electrically coupled to an RF generator (e.g., such as the previously described generator 128) by ablation signal wires 1814 that pass through the main lumen 1810 of the catheter tube 1804, and can be operated in either a unipolar or a bipolar mode as hereinbefore described. The size and spacing of the electrodes 1820 must be optimized to provide contiguous lesions within the ablation area.

The ablation catheter 1802 further includes a tubular distal section 1822 adjoined to the catheter tube 1804 distal to the electrode carrying structure 1818. The tubular distal section 1822 has an open distal end suitably bonded to a closed platinum distal tip 1808, wherein radiopaque markers 1816 is placed near the distal tip 1808 for visualization under fluoroscopy.

The pull wire 1806 is made from resilient, inert wire, such as nickel titanium (commercially available as Nitinol material), stainless steel 17-7, or a thermoplastic material. The proximal end of the pull wire 1806 extends through a guide wire insertion port of the handle (not shown), in a manner such as described above in conjunction with the catheter assembly 1400.

Referring to FIG. 104, the distal section 1822 is adjoined to the catheter tube 1804 distal to the electrode carrying structure 1818 via a tubular bonding insert 1824. In particular, the inner circumferential wall of the distal end of the electrode carrying structure 1818 is disposed about, and bonded to, the outer circumferential surface of a proximal portion of the bonding insert 1824; the inner circumferential wall of the proximal end of the tubular distal section 1822 is disposed about, and bonded to, the outer circumferential surface distal portion of the bonding insert 1824; and the proximal edge of the distal section 1822 is suitably bonded to the distal edge of the electrode carrying structure 1818, forming a joint 1826.

The distal section 1822 generally comprises an anchoring tip portion 1828 and a hinge portion 1830. The anchoring tip 1828 comprises the far distal end of the catheter 1802, and includes a inner stiffening tube 1834. The outer circumferential surface of the inner stiffening tube 1834 is suitably bonded to the inner circumferential wall of the distal section 1822, and the distal end of the inner stiffening tube 1834 is suitably bonded to the distal tip 1808.

The hinge portion 1830 is formed between the inner stiffening tube 1834 and electrode carrying structure 1818. In particular, the hinge portion 1830 has a lesser durometer rating than that of the anchoring section 1830, thereby allowing the electrode carrying structure 1818 to flex with respect to the anchoring tip 1828 (and visa-versa) as shown in FIG. 103.

The distal end of the pull wire 1806 is attached to a slotted stainless steel crimp tube 1836 disposed in the bonding insert 1824, via a pull wire insertion port 1832 formed through the catheter 1802 proximate the bond joint 1826 between the main catheter tube 1804 and the distal section 1822. In particular, the proximal end of the crimp tube 1836 is attached (i.e., "crimped") over the distal end of the center support 1812, and the distal end of the crimp tube is attached over the pull wire 1806. A flattened portion 1838 of the pull wire 1806 (i.e., having a generally rectangular cross-section) extends through the distal end of the crimp tube 1836 and inner stiffening tube 1834, respectively, and is suitably bonded to the inner side of the distal tip 1808. In general, the pull wire 1806 must have sufficient stiffness to push, as well as pull the distal section 1822.

The flattened portion 1838 of the pull wire 1806 disposed in the hinge portion 1830 maintains the flexibility of the hinge portion 1830, while constraining the bending motion of the electrode carrying structure 1818 relative to the anchoring tip 1828 in one direction—i.e., wherein the electrode carrying structure bends in a direction (represented by arrow 1840 in FIG. 104) opposite the pull wire insertion port 1832 and perpendicular to a plane formed by the flattened portion 1838 of the pull wire 1806. The flattened portion 1838 of the pull wire 1806 also provides rotational stability to the electrode carrying structure 1818.

As will be appreciated by those skilled in the art, the flattened portion 1838 of the pull wire 1806 may have any number of alternate, non-circular cross-sectional dimensions (e.g., elliptical or oval), while still allowing for only one direction of bending movement between the respective electrode carrying structure 1818 and anchoring tip 1828.

Referring to FIG. 105, by fixing the pull wire 1806 relative to the guide sheath 1805 and longitudinally displacing the main catheter tube 1804 in a distal direction relative to the guide sheath 1805 (represented by arrow 1842), the electrode carrying structure 1818 moves about the hinge portion 1830 relative to the anchoring tip 1828, forming a first loop formation 1844. The anchoring tip 1828 is shown in an anchored position. As shown in phantom, however, the anchoring tip 1828 will follow the contour of the electrode carrying structure 1818 when the anchoring tip is in a natural position—i.e., when the anchoring tip 1808 is not anchored. Contrariwise, longitudinal displacement of the main catheter tube 1804 in a proximal direction relative to the guide sheath 1805 (represented by arrow 1846) places the electrode carrying structure 1818 in a "low profile" geometry (i.e., axially aligned with the tubular anchoring tip 1828), as shown in FIG. 106.

The respective anchoring tip 1828 and distal tip 1825 of the guide sheath 1805 create a pair of anchor points that facilitate intimate contact between the respective electrodes 1820 located on the electrode carrying structure 1818 and the tissue to be ablated. The size of the loop formed by the electrode carrying structure 1818 and, thus, the formation of the respective electrodes 1820, can be adjusted by varying the longitudinal displacement of the main catheter tube 1804 relative to the guide sheath 1805.

In particular, referring to FIGS. 107 and 108, a radius 1846 of the formed electrode loop can be adjusted by varying the longitudinal displacement (represented by arrow 1848) of the pull wire 1806 relative to the guide sheath 1805. A relatively large distal displacement of the pull wire 1806 relative to the main catheter tube 1804 creates a loop with a large radius 1844 (shown in FIG. 107), and a relatively small distal displacement of the pull wire 1806 relative to the main catheter tube 1804 creates a loop with a small radius 1846. As shown in phantom, the anchoring tip 1808 will follow the contour of the electrode carrying structure 1818 when the anchoring tip 1808 is in a natural position.

Figure 109:
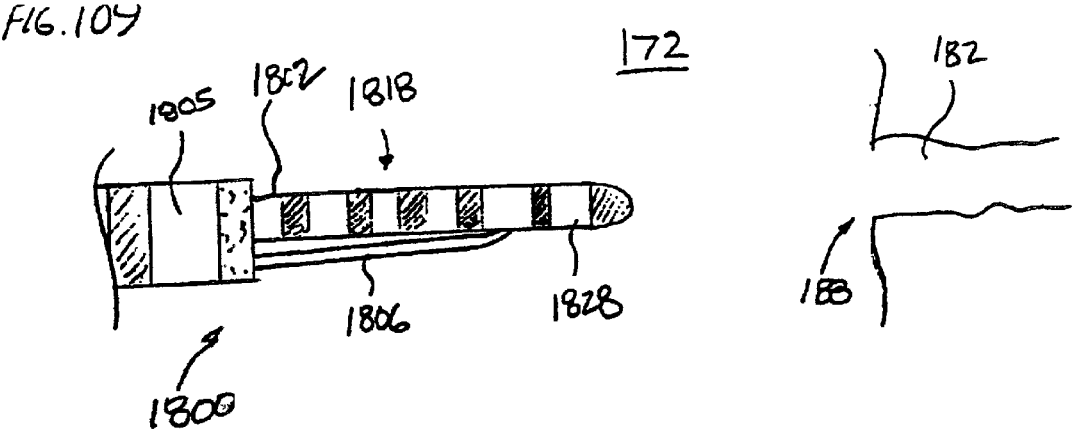
FIG. 109 is a side view of the electrode carrying structure of FIG. 107, disposed in the left atrium of the heart via a guide sheath, and in a low profile geometry.
Figure 110:
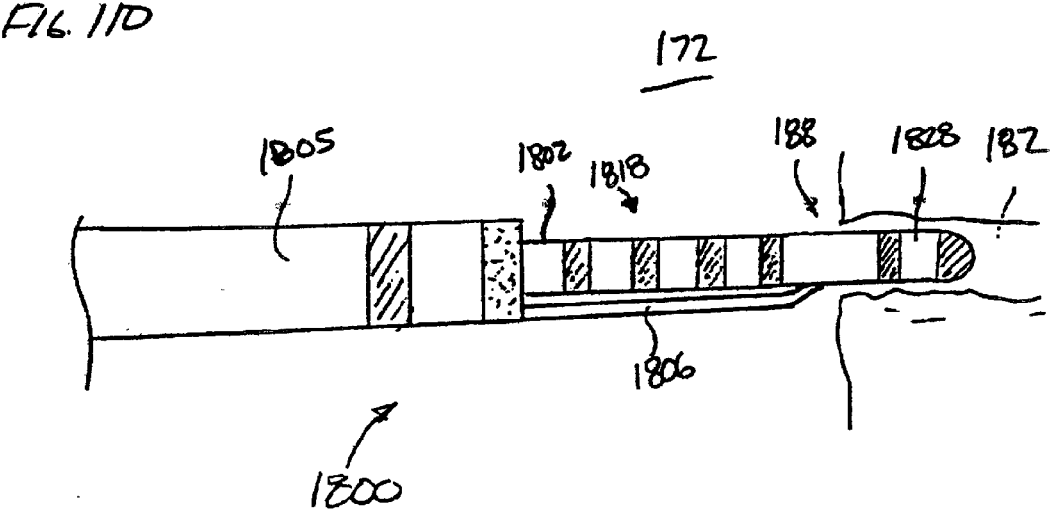
FIG. 110 depicts the electrode carrying structure of FIG. 107, depicting an anchoring end of the ablation catheter is guided into a pulmonary vein via a pull wire.

Referring to FIGS. 109–111, the catheter assembly 1800 can be employed to create linear lesions around an anatomical structure within the heart such as the pulmonary veins. Toward this end, referring specifically to FIG. 109, a physician first introduces the guide sheath 1805 into the left atrium 172 via the aforedescribed retrograde or transeptal approaches. The ablation catheter 1802 and pull wire 1806 are introduced into the guide sheath 1306 and advanced therethrough, until the electrode carrying structure 1818 is disposed in the left atrium 172.

Referring to FIG. 110, the anchoring end 1828 of the ablation catheter 1802 is maneuvered into the opening 188 of the pulmonary vein 182 by manipulating the proximal and (not shown) of the pull wire 1806. The respective ablation catheter 1802 and pull wire 1806 are then longitudinally adjusted relative to the guide sheath 1805, in order to properly set the size and radius of the loop to be formed when the electrode carrying structure 1818 is moved about the hinge portion 1830.

Referring to FIG. 111, the ablation catheter 1802 is axially rotated to locate the pull wire insertion port 1832 directly opposite of the tissue area to be ablated 1850. In the illustrated embodiment, the ablation area 1850 is the region between the pulmonary vein 182 and the mitral valve 176. The proximal end of the ablation catheter 1802 is distally and longitudinally moved relative to the guide sheath 1805, thereby rotating the electrode carrying structure 1818 about the anchoring tip 1828 via the hinge 1830, forming the electrode carrying structure 1818 into a loop and placing the electrodes 1820 into intimate contact with the ablation area 1820. In particular, intimate contact between the electrodes 1820 and the ablation area 1850 is ensured by the anchoring points at the distal end 1825 of the guide sheath 1805 and anchoring tip 1828.

After proper contact is established, a contiguous linear lesion is formed on the ablation area 1850 by applying RF energy to the electrodes 1820, as hereinbefore described. After the lesion in the ablation area 1850 is created, the electrode carrying structure 1818 can be located in another area adjacent to the pulmonary vein 182 by axially rotating the ablation catheter 1802. The size and radius of the loop formed by the electrode carrying structure 1818 can be reset by longitudinally adjusting the ablation catheter 1802 and pull wire 1806 relative to the guide sheath 1805. RF energy is again delivered to the electrodes 1820 to create another lesion adjacent the pulmonary vein 182. If the distal tip 1808 includes a singular electrode, ablation energy can be delivered thereto creating a circumferential lesion within the pulmonary vein 182.

When the ablation procedure is fully completed, the electrode carrying structure 1818 is returned to its low profile geometry by proximally and longitudinally moving the ablation catheter 1802 relative to the guide sheath 1805. The respective ablation catheter 1802 and pull wire 1806 are then removed from the patient's body through the guide sheath 1805.

Although the above-described preferred embodiments have been directed to the creation of lesions in pulmonary veins and surrounding openings of the left atrium of the heart, the various systems, methods and apparatus disclosed and described herein can be used to perform tissue ablation procedures in and around the Inferior Vena Cava, the Superior Vena Cava, and the Sinus Coronary, which are located in the right atrium.

While preferred embodiments have been shown and described, it will be apparent to one of ordinary skill in the art that numerous alterations may be made without departing from the spirit or scope of the invention. Thus, the invention is not to be limited except in accordance with the following claims.

What is claimed:

1. A catheter assembly, comprising:
   an elongate catheter; and
   an expandable electrode body mounted proximate one end of the catheter, the electrode body configured to form a pronounced ring when expanded, the pronounced ring defining a primarily distal facing surface extends along a plan substantially perpendicular to a longitudinal axis of the elongate catheter, and of the electrode body, wherein the distal facing surface includes an area configured to emit radio frequency (RF) energy.

2. The catheter assembly of claim 1, wherein the RF energy emitting area occupies substantially all of the distal facing surface.

3. The catheter assembly of claim 1, wherein the distal facing surface comprises multiple RF energy emitting areas.

4. The catheter assembly of claim 3, wherein each of the RF energy emitting areas composes a conductive substance disposed on the distal facing surface.

5. The catheter assembly of claim 1, wherein the RF energy emitting area comprises a conductive substance disposed on the distal facing surface.

6. The catheter assembly of claim 1, wherein the electrode body comprises a wall enclosing an interior region, the catheter comprises a lumen accessing the interior region, and the RF energy emitting area comprises a microporous section of the wall located in the distal facing surface.

7. The catheter assembly of claim 1, wherein the electrode body comprises a wall enclosing an interior region, the assembly further comprising an interior support structure disposed in the interior region of the electrode body and adapted to urge the electrode body into an expanded geometry to thereby form the enlarged circumferential region.

8. The catheter assembly of claim 1, wherein the pronounced ring further defines a primarily proximal facing surface, and wherein substantially all of the distal facing surface and the distal region is conductive, and wherein substantially all of the proximal facing surface is non-conductive.

9. The catheter assembly of claim 1, wherein the elongate catheter includes a guide wire lumen and a distal guide wire section, the guide wire lumen disposed in the distal guide wire section.

10. The catheter assembly of claim 1, wherein the expandable electrode body further comprises a wall and an interior region, and wherein the elongate catheter comprises an inflation lumen having a distal end and a proximal end, the distal end of the inflation lumen terminating in the interior region.

11. The catheter assembly of claim 10, further comprising:
    a handle having an inflation port, a proximal end of the elongate catheter mounted to the handle, the proximal end of the inflation lumen terminating in said inflation port; and
    RF generator electrically coupled to the RF energy emitting area of the electrode body.

12. The catheter assembly of claim 11, further comprising:
    a temperature sensing element disposed on the expandable electrode body; and
    a controller electrically coupled to the temperature sensing element.

13. A catheter assembly, comprising:
    an elongate catheter; and
    an expandable electrode body mounted proximate one end of the catheter, the electrode body configured to form an enlarged circumferential region and a region distal to the circumferential region when expanded, the circumferential region having a maximum circumference greater than a maximum circumference of the distal region, the circumferential region defining a primarily distal facing surface of the electrode body, wherein the distal facing surface extends along a plan substantially perpendicular to a longitudinal axis of the elongate catheter, and includes an area configured to emit radio frequency (RF) energy.

14. The catheter assembly of claim 13, wherein the RF energy emitting area substantially all of the distal facing surface.

15. The catheter assembly of claim 13, wherein the distal facing surface comprises multiple RF energy emitting areas.

16. The catheter assembly of claim 15, wherein each of the RF energy emitting areas comprises a conductive substance disposed on the distal facing surface.

17. The catheter assembly of claim 13, wherein the RF energy emitting area comprises a conductive substance disposed on the distal facing surface.

18. The catheter assembly of claim 13, wherein the electrode body comprises a wall enclosing an interior region, the catheter comprises a lumen accessing the interior region, and the RF energy emitting area comprises a microporous section of the wall located in the distal facing surface.

19. The catheter assembly of claim 13, wherein the electrode body comprises a wall enclosing an interior region, the assembly further comprising an interior support structure disposed in the interior region of the electrode body and adapted to urge the electrode body into an expanded geometry to thereby form the enlarged circumferential region.

20. The catheter assembly of claim 13, wherein the enlarged circumferential region further defines a primarily proximal facing surface, and wherein substantially all of the distal facing surface and the distal region is conductive, and wherein substantially all of the proximal facing surface is non-conductive.

21. The catheter assembly of claim 13, wherein the elongate catheter includes a guide wire lumen and a distal guide wire section, the guide wire lumen disposed in the distal guide wire section.

22. The catheter assembly of claim 13, wherein the expandable electrode body further comprises a wall and an interior region, and wherein the elongate catheter comprises an inflation lumen having a distal end and a proximal end, the distal end of the inflation lumen terminating in the interior region.

23. The catheter assembly of claim 22, further comprising:
a handle having an inflation port, a proximal end of the elongate catheter mounted to the handle, the proximal end of the inflation lumen terminating in said inflation port; and
an RF generator electrically coupled to the RF energy emitting area of the electrode body.

24. The catheter assembly of claim 13, further comprising:
a temperature sensing element disposed on the expandable electrode body; and
a controller electrically coupled to the temperature sensing element.

25. The catheter assembly of claim 13, wherein the expandable electrode body is configured for ablating tissue outside of a vessel opening, and wherein the distal region and distal facing surface of the enlarged circumferential region are respectively configured to simultaneously engage the tissue inside and the tissue outside of the vessel opening.

26. The catheter assembly of claim 25, wherein the vessel opening is a pulmonary vein opening.

27. The catheter assembly of claim 13, wherein the expandable electrode body is configured for ablating tissue inside and outside of a vessel opening, and wherein the distal region and distal facing surface of the enlarged circumferential region are respectively configured to simultaneously engage the tissue inside and the tissue outside of the vessel opening.

28. The catheter assembly of claim 27, wherein the vessel opening is a pulmonary vein opening.

29. A catheter assembly, comprising:
an elongate catheter; and
an expandable electrode body mounted proximate one end of the catheter, the electrode body configured to form a pronounced ring and a region distal to the pronounced ring when expanded, the pronounced ring defining a primarily distal facing surface of the electrode body, wherein the distal facing surface extends along a plan substantially perpendicular to a longitudinal axis of the elongate catheter, and includes an area configured to emit radio frequency (RF) energy.

30. The catheter assembly of claim 29, wherein the RF energy emitting area occupies substantially all of the distal facing surface.

31. The catheter assembly of claim 29, wherein the distal facing surface comprises multiple RF energy emitting areas.

32. The catheter assembly of claim 31, wherein each of the RF energy emitting areas comprises a conductive substance disposed on the distal facing surface.

33. The catheter assembly of claim 29, wherein the RF energy emitting area comprises a conductive substance disposed on the distal facing surface.

34. The catheter assembly of claim 29, wherein the electrode body comprises a wall enclosing an interior region, the catheter comprises a lumen accessing the interior region, and the RF energy emitting area comprises a microporous section of the wall located in the distal facing surface.

35. The catheter assembly of claim 29, wherein the electrode body comprises a wall enclosing an interior region, the assembly further comprising an interior support structure disposed in the interior region of the electrode body and adapted to urge the electrode body into an expanded geometry to thereby form the pronounced ring.

36. The catheter assembly of claim 29, wherein the pronounced ring further defines a primarily proximal facing surface, and wherein substantially all of the distal facing surface and the distal region is conductive, and wherein substantially all of the proximal facing surface is non-conductive.

37. The catheter assembly of claim 29, wherein the elongate catheter includes a guide wire lumen and a distal guide wire section, the guide wire lumen disposed in the distal guide wire section.

38. The catheter assembly of claim 29, wherein the expandable electrode body further comprises a wall and an interior region, and wherein the elongate catheter comprises an inflation lumen having a distal end and a proximal end, the distal end of the inflation lumen terminating in the interior region.

39. The catheter assembly of claim 38, wherein comprising:
a handle having an inflation port, a proximal end of the elongate catheter mounted to the handle, the proximal end of the inflation lumen terminating in said inflation port; and
an RF generator electrically coupled to the RF energy emitting area of the electrode body.

40. The catheter assembly of claim 29, wherein comprising:
a temperature sensing element disposed on the expandable electrode body; and
a controller electrically coupled to the temperature sensing element.

41. The catheter assembly of claim 29, wherein the expandable electrode body is configured for ablating tissue outside of a vessel opening, and wherein the distal region and distal facing surface of the pronounced ring are respectively configured to simultaneously engage the tissue inside and the tissue outside of the vessel opening.

42. The catheter assembly of claim 41, wherein the vessel opening is a pulmonary vein opening.

43. The catheter assembly of claim 29, wherein the expandable electrode body is configured for ablating tissue inside and outside of a vessel opening, and wherein the distal region and distal facing surface of the pronounced ring are respectively configured to simultaneously engage the tissue inside and the tissue outside of the vessel opening.

44. The catheter assembly of claim 43, wherein the vessel opening is a pulmonary vein opening.

* * * * *

UNITED STATES PATENT AND TRADEMARK OFFICE
CERTIFICATE OF CORRECTION

PATENT NO. : 6,917,834 B2  
DATED : July 12, 2005  
INVENTOR(S) : Josef V. Koblish et al.

Page 1 of 1

It is certified that error appears in the above-identified patent and that said Letters Patent is hereby corrected as shown below:

Column 28,  
Line 58, replace "shwon" with -- shown --.

Column 29,  
Line 54, add -- ) -- between "33" and ".".  
Line 61, replace "1106" with -- 1108 --.

Column 32,  
Line 64, delete "." after "the".

Column 34,  
Line 16, replace "At" with -- at --.

Column 41,  
Line 58, replace "The" with -- the --.

Column 46,  
Line 47, replace "and" with -- end --.

Column 50,  
Lines 34 and 42, replace "wherein" with -- further --.

Signed and Sealed this

Sixteenth Day of May, 2006

JON W. DUDAS  
*Director of the United States Patent and Trademark Office*